United States Patent
Tsuchiya

(10) Patent No.: US 7,052,873 B2
(45) Date of Patent: May 30, 2006

(54) NATURAL HUMAN ANTIBODY

(75) Inventor: Masayuki Tsuchiya, Gotenba (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 0 days.

(21) Appl. No.: 09/509,098

(22) PCT Filed: Oct. 2, 1998

(86) PCT No.: PCT/JP98/04469

§ 371 (c)(1),
(2), (4) Date: Mar. 22, 2000

(87) PCT Pub. No.: WO99/18212

PCT Pub. Date: Apr. 15, 1999

(65) Prior Publication Data

US 2003/0103970 A1    Jun. 5, 2003

(30) Foreign Application Priority Data

Oct. 3, 1997 (JP) .................................. 9-271726

(51) Int. Cl.
C12N 15/00 (2006.01)

(52) U.S. Cl. ................. 435/69.6; 530/387.1; 530/387.3
(58) Field of Classification Search ............... 435/69.6; 530/357.1, 387.3
See application file for complete search history.

(56) References Cited

FOREIGN PATENT DOCUMENTS

WO   WO 90/07861   7/1990
WO   WO 91/09967   7/1991

OTHER PUBLICATIONS

Rudikoff et al (Proc Natl Acad Sci USA 1982 vol. 79 p. 1979.*
Tetsuya Goto et al., "A Novel Membrane Antigen Selectively Expressed on Terminally Defferentiated Human B Cells.", Blood, vol. 84, No. 6, pp. 1922-1930, Sep. 15, 1994.
Peter T. Jones et al., "Replacing the complementarity-determining regions in a human antibody with those from a mouse.", Nature, vol. 321, pp. 522-525, May 29, 1986.
Catherine A. Kettleborough et al., "Humanization of a mouse monoclonal antibody by CDR-grafting: the importance of framework residues on loop conformation.", Protein Entineering, vol. 4, No. 7, pp. 773-783, 1991.
Cary Queen et al., "A humanized antibody that binds to the interleukin 2 receptor.", Proceedings of the National Academy of Science, vol. 86, pp. 10029-10033, Dec. 1989.
Lutz Riechmann et al., "Reshaping human antibodies for therapy.", Nature, vol. 332, pp. 323-327, Mar. 24, 1988.
Koh Sato et al., "Humanization of a Mouse Anti-Human Interleukin-6 Receptor Antibody Comparing Two Methods for Selecting Human Framework Regions.", Molecular Immunology, vol. 31, No. 5, pp. 371-381, 1994.
Man Sung Co et al., "Humanized antibodies for antiviral therapy.", Proceedings of the National Academy of Science, vol. 88, pp. 2869-2873, Apr. 1991.
Martine Verhoeyen et al., "Reshaping Human Antibodies: Grafting an Antilysozyme Activity.", Science, vol. 239, pp. 1534-1536, Mar. 25, 1988.
M.A. Roguska et al., "A comparison of two murine monoclonal antibodies humanized by CDR-grafting and Variable domain resurfacing", Protein Engineering, vol. 9, No. 10, pp. 895-904, (1996).
J.T. Pedersen et al., "Comparison of suface accessible residues in human and murine immunoglobulin Fv domains", J. Mol. Biol., vol. 235, pp. 959-973, (1994).
M.A. Roguska et al., "Humanization of murine monoclonal antibodies through variable domain resurfacing", Proc. Natl. Acad. Sci. USA, vol. 91, pp. 969-973, (1994).
Ohtomo, Toshihiko, et al., "Humanization of Mouse ONS-M21 Antibody with the Aid of Hybrid Variable Regions", Molecular Immunology, vol. 32, No. 6, Apr. 1995, pp. 407-416.
Ono, Koichiro, et al., "The Humanized Anti-HM1.24 Antibody Effective Kills Multiple Myeloma Cells by Human Effector Cell-Mediated Cytotoxicity", Molecular Immunology, vol. 36, No. 6, Apr. 1999, pp. 387-395.

* cited by examiner

Primary Examiner—Larry R. Helms
(74) Attorney, Agent, or Firm—Foley & Lardner LLP

(57) ABSTRACT

A reshaped human anti-HM1.24 antibody comprising:
(A) L chains each comprising (1) a constant region of a human L chain, and (2) FRs of a human L chain, and CDRs of L chain of mouse anti-HM1.24 monoclonal antibody; and
(B) H chains each comprising (2) a constant region of a human H chain, and (2) FRs of a human H chain, and CDRs of H chain of mouse anti-HM1.24 monoclonal antibody. Since the majority of the reshaped human antibody is derived from human antibody and the CDR has a low antigenicity, the reshaped human antibody of the present invention has low antigenicity and therefore is very promising in medical and therapeutic applications.

8 Claims, 33 Drawing Sheets

Fig.6
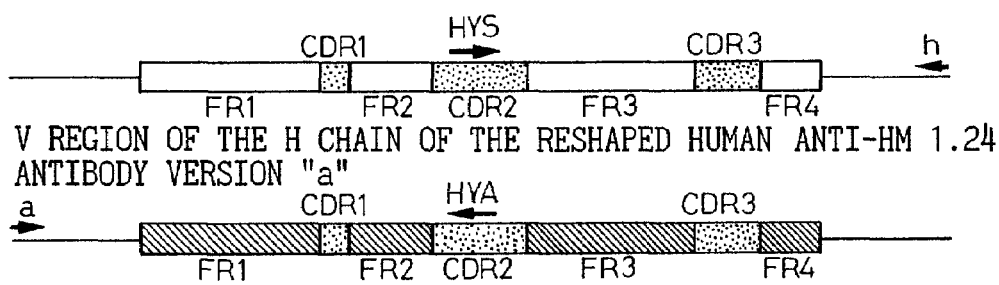
V REGION OF THE MOUSE ANTI-HM 1.24 ANTIBODY
V REGION OF THE H CHAIN OF THE RESHAPED HUMAN ANTI-HM 1.24 ANTIBODY VERSION "a"
↓
FIRST PCR
↓
(a-HYA)    (HYS-h)
↓
ASSEMBLY
↓
SECOND PCR
↓
V REGION OF H CHAIN OF HUMAN MOUSE HYBRID

Fig. 7
V REGION OF THE MOUSE ANTI-HM 1.24 ANTIBODY
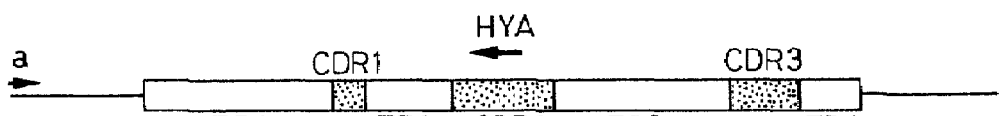
V REGION OF THE H CHAIN OF THE RESHAPED HUMAN ANTI-HM 1.24 ANTIBODY VERSION "a"
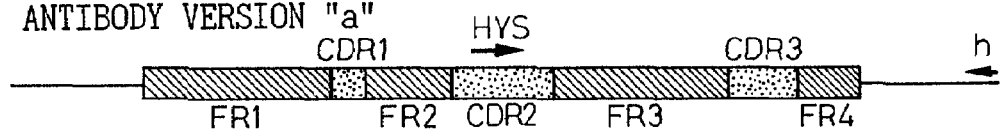
↓
FIRST PCR
↓
(a-HYA)          (HYS-h)
↓
ASSEMBLY
↓
SECOND PCR
a →
          ← h
↓
V REGION OF H CHAIN OF MOUSE HUMAN HYBRID
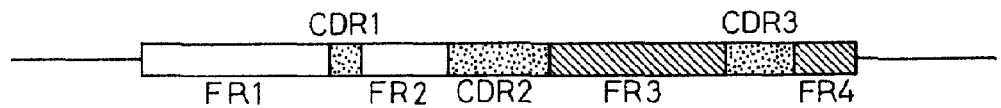

SEQUENCE LISTING

<160> NUMBER OF SEQ ID NOS: 203

<210> SEQ ID NO 1
<211> LENGTH: 394
<212> TYPE: DNA
<213> ORGANISM: Murine sp.
<220> FEATURE:
<221> NAME/KEY: sig_peptide
<222> LOCATION: (1)..(72)
<221> NAME/KEY: mat_peptide
<222> LOCATION: (73)..(393)
<221> NAME/KEY: CDS
<222> LOCATION: (1)..(393)
<223> OTHER INFORMATION: Description of Artificial Sequence: cDNA coding
      for L chain V region of anti-HM1.24 antibody

<400> SEQUENCE: 1

```
atg ggc ttc aag atg gag tca cat ttt ctg gtc ttt gta ttc gtg ttt      48
Met Gly Phe Lys Met Glu Ser His Phe Leu Val Phe Val Phe Val Phe
            -20                 -15                 -10 ctc tgg ttg tct ggt gtt gac gga gac att gtg atg acc cag tct cac      96
Leu Trp Leu Ser Gly Val Asp Gly Asp Ile Val Met Thr Gln Ser His
         -5                  -1   1                   5 aaa ttc atg tcc aca tca gta gga gac agg gtc agc atc acc tgc aag     144
Lys Phe Met Ser Thr Ser Val Gly Asp Arg Val Ser Ile Thr Cys Lys
     10                  15                  20 gcc agt cag gat gtg aat act gct gta gcc tgg tat caa caa aaa cca     192
Ala Ser Gln Asp Val Asn Thr Ala Val Ala Trp Tyr Gln Gln Lys Pro
 25                  30                  35                  40 gga caa tcg cct aaa cta ctg att tac tcg gca tcc aac cgg tac act     240
Gly Gln Ser Pro Lys Leu Leu Ile Tyr Ser Ala Ser Asn Arg Tyr Thr
                 45                  50                  55 gga gtc cct gat cgc atc act ggc agt gga tct ggg acg gat ttc act     288
Gly Val Pro Asp Arg Ile Thr Gly Ser Gly Ser Gly Thr Asp Phe Thr
             60                  65                  70 ttc acc atc agc agt gtg cag gcg gaa gac ctg gca ctt tat tac tgt     336
Phe Thr Ile Ser Ser Val Gln Ala Glu Asp Leu Ala Leu Tyr Tyr Cys
         75                  80                  85 cag caa cat tat agt act cca ttc acg ttc ggc tcg ggg aca aag ttg     384
Gln Gln His Tyr Ser Thr Pro Phe Thr Phe Gly Ser Gly Thr Lys Leu
     90                  95                 100 gaa ata aaa c                                                        394
Glu Ile Lys
105
```

<210> SEQ ID NO 2
<211> LENGTH: 131
<212> TYPE: PRT
<213> ORGANISM: Murine sp.
<220> FEATURE:
<223> OTHER INFORMATION: Description of Artificial Sequence: Amino acid
      sequence of L chain V region of mouse anti-HM1.24
      antibody

<400> SEQUENCE: 2

```
Met Gly Phe Lys Met Glu Ser His Phe Leu Val Phe Val Phe Val Phe
            -20                 -15                 -10

Leu Trp Leu Ser Gly Val Asp Gly Asp Ile Val Met Thr Gln Ser His
         -5                  -1   1                   5

Lys Phe Met Ser Thr Ser Val Gly Asp Arg Val Ser Ile Thr Cys Lys
     10                  15                  20

Ala Ser Gln Asp Val Asn Thr Ala Val Ala Trp Tyr Gln Gln Lys Pro
```

```
              25                  30                  35                  40
Gly Gln Ser Pro Lys Leu Leu Ile Tyr Ser Ala Ser Asn Arg Tyr Thr
                45                  50                  55

Gly Val Pro Asp Arg Ile Thr Gly Ser Gly Ser Gly Thr Asp Phe Thr
            60                  65                  70

Phe Thr Ile Ser Ser Val Gln Ala Glu Asp Leu Ala Leu Tyr Tyr Cys
        75                  80                  85

Gln Gln His Tyr Ser Thr Pro Phe Thr Phe Gly Ser Gly Thr Lys Leu
    90                  95                 100

Glu Ile Lys
105

<210> SEQ ID NO 3
<211> LENGTH: 418
<212> TYPE: DNA
<213> ORGANISM: Murine sp.
<220> FEATURE:
<221> NAME/KEY: sig_peptide
<222> LOCATION: (1)..(57)
<221> NAME/KEY: mat_peptide
<222> LOCATION: (58)..(417)
<221> NAME/KEY: CDS
<222> LOCATION: (1)..(417)
<223> OTHER INFORMATION: Description of Artificial Sequence: cDNA coding
      for H chain V region of mouse anti-HM1.24
      antibody

<400> SEQUENCE: 3 atg gaa tgt aac tgg ata ctt cct ttt att ctg tca gta act tca ggt         48
Met Glu Cys Asn Trp Ile Leu Pro Phe Ile Leu Ser Val Thr Ser Gly
                -15                 -10                  -5 gcc tac tca cag gtt caa ctc cag cag tct ggg gct gag ctg gca aga         96
Ala Tyr Ser Gln Val Gln Leu Gln Gln Ser Gly Ala Glu Leu Ala Arg
         -1   1                   5                  10 cct ggg gct tca gtg aag ttg tcc tgc aag gct tct ggc tac acc ttt        144
Pro Gly Ala Ser Val Lys Leu Ser Cys Lys Ala Ser Gly Tyr Thr Phe
     15                  20                  25 act ccc tac tgg atg cag tgg gta aaa cag agg cct gga cag ggt ctg        192
Thr Pro Tyr Trp Met Gln Trp Val Lys Gln Arg Pro Gly Gln Gly Leu
 30                  35                  40                  45 gaa tgg att ggg tct att ttt cct gga gat ggt gat act agg tac agt        240
Glu Trp Ile Gly Ser Ile Phe Pro Gly Asp Gly Asp Thr Arg Tyr Ser
                 50                  55                  60 cag aag ttc aag ggc aag gcc aca ttg act gca gat aaa tcc tcc agt        288
Gln Lys Phe Lys Gly Lys Ala Thr Leu Thr Ala Asp Lys Ser Ser Ser
             65                  70                  75 aca gcc tac atg caa ctc agc atc ttg gca ttt gag gac tct gcg gtc        336
Thr Ala Tyr Met Gln Leu Ser Ile Leu Ala Phe Glu Asp Ser Ala Val
         80                  85                  90 tat tac tgt gca aga gga tta cga cga ggg ggg tac tac ttt gac tac        384
Tyr Tyr Cys Ala Arg Gly Leu Arg Arg Gly Gly Tyr Tyr Phe Asp Tyr
     95                 100                 105 tgg ggc caa ggc acc act ctc aca gtc tcc tca g                          418
Trp Gly Gln Gly Thr Thr Leu Thr Val Ser Ser
110                 115                 120

<210> SEQ ID NO 4
<211> LENGTH: 139
<212> TYPE: PRT
<213> ORGANISM: Murine sp.
<220> FEATURE:
<223> OTHER INFORMATION: Description of Artificial Sequence: Amino acid
      sequence of H chain V region of mouse anti-
```

HM1.24 antibody

<400> SEQUENCE: 4

```
Met Glu Cys Asn Trp Ile Leu Pro Phe Ile Leu Ser Val Thr Ser Gly
              -15                 -10                 -5
Ala Tyr Ser Gln Val Gln Leu Gln Gln Ser Gly Ala Glu Leu Ala Arg
         -1   1               5                  10
Pro Gly Ala Ser Val Lys Leu Ser Cys Lys Ala Ser Gly Tyr Thr Phe
         15                  20                  25
Thr Pro Tyr Trp Met Gln Trp Val Lys Gln Arg Pro Gly Gln Gly Leu
 30                  35                  40                  45
Glu Trp Ile Gly Ser Ile Phe Pro Gly Asp Gly Asp Thr Arg Tyr Ser
                 50                  55                  60
Gln Lys Phe Lys Gly Lys Ala Thr Leu Thr Ala Asp Lys Ser Ser Ser
             65                  70                  75
Thr Ala Tyr Met Gln Leu Ser Ile Leu Ala Phe Glu Asp Ser Ala Val
             80                  85                  90
Tyr Tyr Cys Ala Arg Gly Leu Arg Arg Gly Gly Tyr Tyr Phe Asp Tyr
 95                 100                 105
Trp Gly Gln Gly Thr Thr Leu Thr Val Ser Ser
110                 115                 120
```

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: CDR (1)
      of L chain V region of anti-HM1.24 antibody

<400> SEQUENCE: 5

```
Lys Ala Ser Gln Asp Val Asn Thr Ala Val Ala
 1               5                  10
```

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: CDR (2)
      of L chain V region of anti-HM1.24 antibody

<400> SEQUENCE: 6

```
Ser Ala Ser Asn Arg Tyr Thr
 1               5
```

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: CDR (3)
      of L chain V region of anti-HM1.24 antibody

<400> SEQUENCE: 7

```
Gln Gln His Tyr Ser Thr Pro Phe Thr
 1               5
```

<210> SEQ ID NO 8
<211> LENGTH: 5
<212> TYPE: PRT
<213> ORGANISM: Artificial Sequence
<220> FEATURE:

-continued

<223> OTHER INFORMATION: Description of Artificial Sequence: CDR (1)
      of H chain V region of anti-HM1.24 antibody

<400> SEQUENCE: 8

Pro Tyr Trp Met Gln
  1               5

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: CDR (2)
      of H chain V region of anti-HM1.24 antibody

<400> SEQUENCE: 9

Ser Ile Phe Gly Asp Gly Asp Thr Arg Tyr Ser Gln Lys Phe Lys Gly
  1               5                  10                  15

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: CDR (3)
      of H chain V region of anti-HM1.24 antibody

<400> SEQUENCE: 10

Gly Leu Arg Arg Gly Gly Tyr Tyr Phe Asp Tyr
  1               5                  10

<210> SEQ ID NO 11
<211> LENGTH: 379
<212> TYPE: DNA
<213> ORGANISM: Artificial Sequence
<220> FEATURE:
<223> OTHER INFORMATION: Description of Artificial Sequence: DNA coding
      for humanized L chain V region of anti-HM1.24 antibody
<221> NAME/KEY: sig_peptide
<222> LOCATION: (1)..(57)
<221> NAME/KEY: mat_peptide
<222> LOCATION: (58)..(378)
<221> NAME/KEY: CDS
<222> LOCATION: (1)..(378)

<400> SEQUENCE: 11

```
atg gga tgg agc tgt atc atc ctc tcc ttg gta gca aca gct aca ggt       48
Met Gly Trp Ser Cys Ile Ile Leu Ser Leu Val Ala Thr Ala Thr Gly
            -15                 -10                  -5 gtc cac tcc gac atc cag atg acc cag agc cca agc agc ctg agc gcc       96
Val His Ser Asp Ile Gln Met Thr Gln Ser Pro Ser Ser Leu Ser Ala
     -1   1               5                  10 agc gtg ggt gac aga gtg acc atc acc tgt aag gct agt cag gat gtg      144
Ser Val Gly Asp Arg Val Thr Ile Thr Cys Lys Ala Ser Gln Asp Val
         15                  20                  25 aat act gct gta gcc tgg tac cag cag aag cca gga aag gct cca aag      192
Asn Thr Ala Val Ala Trp Tyr Gln Gln Lys Pro Gly Lys Ala Pro Lys
     30                  35                  40                  45 ctg ctg atc tac tcg gca tcc aac cgg tac act ggt gtg cca agc aga      240
Leu Leu Ile Tyr Ser Ala Ser Asn Arg Tyr Thr Gly Val Pro Ser Arg
                 50                  55                  60 ttc agc ggt agc ggt agc ggt acc gac ttc acc ttc acc atc agc agc      288
Phe Ser Gly Ser Gly Ser Gly Thr Asp Phe Thr Phe Thr Ile Ser Ser
             65                  70                  75 ctc cag cca gag gac atc gct acc tac tac tgc cag caa cat tat agt      336
Leu Gln Pro Glu Asp Ile Ala Thr Tyr Tyr Cys Gln Gln His Tyr Ser
```

-continued

```
                  80                  85                  90
act cca ttc acg ttc ggc caa ggg acc aag gtg gaa atc aaa c              379
Thr Pro Phe Thr Phe Gly Gln Gly Thr Lys Val Glu Ile Lys
         95                 100                 105

<210> SEQ ID NO 12
<211> LENGTH: 126
<212> TYPE: PRT
<213> ORGANISM: Artificial Sequence
<220> FEATURE:
<223> OTHER INFORMATION: Description of Artificial Sequence: Humanized L
      chain V region of anti-HM1.24 antibody

<400> SEQUENCE: 12

Met Gly Trp Ser Cys Ile Ile Leu Ser Leu Val Ala Thr Ala Thr Gly
              -15                 -10                  -5

Val His Ser Asp Ile Gln Met Thr Gln Ser Pro Ser Ser Leu Ser Ala
         -1   1                   5                  10

Ser Val Gly Asp Arg Val Thr Ile Thr Cys Lys Ala Ser Gln Asp Val
         15                  20                  25

Asn Thr Ala Val Ala Trp Tyr Gln Gln Lys Pro Gly Lys Ala Pro Lys
 30                  35                  40                  45

Leu Leu Ile Tyr Ser Ala Ser Asn Arg Tyr Thr Gly Val Pro Ser Arg
             50                  55                  60

Phe Ser Gly Ser Gly Ser Gly Thr Asp Phe Thr Phe Thr Ile Ser Ser
             65                  70                  75

Leu Gln Pro Glu Asp Ile Ala Thr Tyr Tyr Cys Gln Gln His Tyr Ser
         80                  85                  90

Thr Pro Phe Thr Phe Gly Gln Gly Thr Lys Val Glu Ile Lys
         95                 100                 105

<210> SEQ ID NO 13
<211> LENGTH: 379
<212> TYPE: DNA
<213> ORGANISM: Artificial Sequence
<220> FEATURE:
<223> OTHER INFORMATION: Description of Artificial Sequence: DNA coding
      for humanized L chain V region of anti-HM1.24 antibody
<221> NAME/KEY: sig_peptide
<222> LOCATION: (1)..(57)
<221> NAME/KEY: mat_peptide
<222> LOCATION: (58)..(378)
<221> NAME/KEY: CDS
<222> LOCATION: (1)..(378)

<400> SEQUENCE: 13 atg gga tgg agc tgt atc atc ctc tcc ttg gta gca aca gct aca ggt       48
Met Gly Trp Ser Cys Ile Ile Leu Ser Leu Val Ala Thr Ala Thr Gly
              -15                 -10                  -5 gtc cac tcc gac atc cag atg acc cag agc cca agc agc ctg agc gcc       96
Val His Ser Asp Ile Gln Met Thr Gln Ser Pro Ser Ser Leu Ser Ala
         -1   1                   5                  10 agc gtg ggt gac aga gtg acc atc acc tgt aag gct agt cag gat gtg      144
Ser Val Gly Asp Arg Val Thr Ile Thr Cys Lys Ala Ser Gln Asp Val
         15                  20                  25 aat act gct gta gcc tgg tac cag cag aag cca gga aag gct cca aag      192
Asn Thr Ala Val Ala Trp Tyr Gln Gln Lys Pro Gly Lys Ala Pro Lys
 30                  35                  40                  45 ctg ctg atc tac tcg gca tcc aac cgg tac act ggt gtg cca agc aga      240
Leu Leu Ile Tyr Ser Ala Ser Asn Arg Tyr Thr Gly Val Pro Ser Arg
             50                  55                  60 ttc agc ggt agc ggt agt ggt acc gac tac acc ttc acc atc agc agc      288
```

```
Phe Ser Gly Ser Gly Ser Gly Thr Asp Tyr Thr Phe Thr Ile Ser Ser
            65                  70                  75 ctc cag cca gag gac atc gct acc tac tac tgc cag caa cat tat agt     336
Leu Gln Pro Glu Asp Ile Ala Thr Tyr Tyr Cys Gln Gln His Tyr Ser
        80                  85                  90 act cca ttc acg ttc ggc caa ggg acc aag gtg gaa atc aaa c           379
Thr Pro Phe Thr Phe Gly Gln Gly Thr Lys Val Glu Ile Lys
        95                 100                 105

<210> SEQ ID NO 14
<211> LENGTH: 126
<212> TYPE: PRT
<213> ORGANISM: Artificial Sequence
<220> FEATURE:
<223> OTHER INFORMATION: Description of Artificial Sequence: Humanized
      L chain V region of anti-HM1.24 antibody

<400> SEQUENCE: 14

Met Gly Trp Ser Cys Ile Ile Leu Ser Leu Val Ala Thr Ala Thr Gly
                -15                 -10                  -5

Val His Ser Asp Ile Gln Met Thr Gln Ser Pro Ser Ser Leu Ser Ala
         -1   1                   5                  10

Ser Val Gly Asp Arg Val Thr Ile Thr Cys Lys Ala Ser Gln Asp Val
        15                  20                  25

Asn Thr Ala Val Ala Trp Tyr Gln Gln Lys Pro Gly Lys Ala Pro Lys
 30                  35                  40                  45

Leu Leu Ile Tyr Ser Ala Ser Asn Arg Tyr Thr Gly Val Pro Ser Arg
                50                  55                  60

Phe Ser Gly Ser Gly Ser Gly Thr Asp Tyr Thr Phe Thr Ile Ser Ser
            65                  70                  75

Leu Gln Pro Glu Asp Ile Ala Thr Tyr Tyr Cys Gln Gln His Tyr Ser
        80                  85                  90

Thr Pro Phe Thr Phe Gly Gln Gly Thr Lys Val Glu Ile Lys
        95                 100                 105

<210> SEQ ID NO 15
<211> LENGTH: 418
<212> TYPE: DNA
<213> ORGANISM: Artificial Sequence
<220> FEATURE:
<223> OTHER INFORMATION: Description of Artificial Sequence: DNA coding
      for humanized H chain V region (version a) of anti-HM1.24 antibody
<221> NAME/KEY: sig_peptide
<222> LOCATION: (1)..(57)
<221> NAME/KEY: mat_peptide
<222> LOCATION: (58)..(417)
<221> NAME/KEY: CDS
<222> LOCATION: (1)..(417)

<400> SEQUENCE: 15 atg gac tgg acc tgg agg gtc ttc ttc ttg ctg gct gta gct cca ggt    48
Met Asp Trp Thr Trp Arg Val Phe Phe Leu Leu Ala Val Ala Pro Gly
                -15                 -10                  -5 gct cac tcc cag gtg cag ctg gtg cag tct ggg gct gag gtg aag aag    96
Ala His Ser Gln Val Gln Leu Val Gln Ser Gly Ala Glu Val Lys Lys
         -1   1                   5                  10 cct ggg gcc tca gtg aag gtt tcc tgc aag gca tct gga tac acc ttc    144
Pro Gly Ala Ser Val Lys Val Ser Cys Lys Ala Ser Gly Tyr Thr Phe
        15                  20                  25 act ccc tac tgg atg cag tgg gtg cga cag gcc cct gga caa ggg ctt    192
Thr Pro Tyr Trp Met Gln Trp Val Arg Gln Ala Pro Gly Gln Gly Leu
 30                  35                  40                  45
```

```
gag tgg atg gga tct att ttt cct gga gat ggt gat act agg tac agt      240
Glu Trp Met Gly Ser Ile Phe Pro Gly Asp Gly Asp Thr Arg Tyr Ser
            50                  55                  60 cag aag ttc aag ggc aga gtc acc atg acc gca gac acg tcc acg agc      288
Gln Lys Phe Lys Gly Arg Val Thr Met Thr Ala Asp Thr Ser Thr Ser
        65                  70                  75 aca gtc tac atg gag ctg agc agc ctg aga tct gag gac acg gcc gtg      336
Thr Val Tyr Met Glu Leu Ser Ser Leu Arg Ser Glu Asp Thr Ala Val
    80                  85                  90 tat tac tgt gcg aga gga tta cga cga ggg ggg tac tac ttt gac tac      384
Tyr Tyr Cys Ala Arg Gly Leu Arg Arg Gly Gly Tyr Tyr Phe Asp Tyr
95                  100                 105 tgg ggg caa ggg acc acg gtc acc gtc tcc tca g                        418
Trp Gly Gln Gly Thr Thr Val Thr Val Ser Ser
110                 115                 120

<210> SEQ ID NO 16
<211> LENGTH: 139
<212> TYPE: PRT
<213> ORGANISM: Artificial Sequence
<220> FEATURE:
<223> OTHER INFORMATION: Description of Artificial Sequence: Humanized
      H chain V region (version a) of anti-HM1.24 antibody

<400> SEQUENCE: 16

Met Asp Trp Thr Trp Arg Val Phe Phe Leu Leu Ala Val Ala Pro Gly
            -15                 -10                 -5

Ala His Ser Gln Val Gln Leu Val Gln Ser Gly Ala Glu Val Lys Lys
        -1  1                   5                   10

Pro Gly Ala Ser Val Lys Val Ser Cys Lys Ala Ser Gly Tyr Thr Phe
    15                  20                  25

Thr Pro Tyr Trp Met Gln Trp Val Arg Gln Ala Pro Gly Gln Gly Leu
30                  35                  40                  45

Glu Trp Met Gly Ser Ile Phe Pro Gly Asp Gly Asp Thr Arg Tyr Ser
            50                  55                  60

Gln Lys Phe Lys Gly Arg Val Thr Met Thr Ala Asp Thr Ser Thr Ser
        65                  70                  75

Thr Val Tyr Met Glu Leu Ser Ser Leu Arg Ser Glu Asp Thr Ala Val
    80                  85                  90

Tyr Tyr Cys Ala Arg Gly Leu Arg Arg Gly Gly Tyr Tyr Phe Asp Tyr
95                  100                 105

Trp Gly Gln Gly Thr Thr Val Thr Val Ser Ser
110                 115                 120

<210> SEQ ID NO 17
<211> LENGTH: 418
<212> TYPE: DNA
<213> ORGANISM: Artificial Sequence
<220> FEATURE:
<223> OTHER INFORMATION: Description of Artificial Sequence: DNA coding
      for humanized H chain V region (version b) of anti-HM1.24 antibody
<221> NAME/KEY: sig_peptide
<222> LOCATION: (1)..(57)
<221> NAME/KEY: mat_peptide
<222> LOCATION: (58)..(417)
<221> NAME/KEY: CDS
<222> LOCATION: (1)..(417)

<400> SEQUENCE: 17 atg gac tgg acc tgg agg gtc ttc ttc ttg ctg gct gta gct cca ggt       48
Met Asp Trp Thr Trp Arg Val Phe Phe Leu Leu Ala Val Ala Pro Gly
            -15                 -10                 -5
```

```
gct cac tcc cag gtg cag ctg gtg cag tct ggg gct gag gtg aag aag      96
Ala His Ser Gln Val Gln Leu Val Gln Ser Gly Ala Glu Val Lys Lys
        -1  1               5                  10 cct ggg gcc tca gtg aag gtt tcc tgc aag gca tct gga tac acc ttc     144
Pro Gly Ala Ser Val Lys Val Ser Cys Lys Ala Ser Gly Tyr Thr Phe
        15                  20                  25 act ccc tac tgg atg cag tgg gtg cga cag gcc cct gga caa ggg ctt     192
Thr Pro Tyr Trp Met Gln Trp Val Arg Gln Ala Pro Gly Gln Gly Leu
30                  35                  40                  45 gag tgg atg gga tct att ttt cct gga gat ggt gat act agg tac agt     240
Glu Trp Met Gly Ser Ile Phe Pro Gly Asp Gly Asp Thr Arg Tyr Ser
                50                  55                  60 cag aag ttc aag ggc aaa gtc acc atg acc gca gac acg tcc acg agc     288
Gln Lys Phe Lys Gly Lys Val Thr Met Thr Ala Asp Thr Ser Thr Ser
                    65                  70                  75 aca gtc tac atg gag ctg agc agc ctg aga tct gag gac acg gcc gtg     336
Thr Val Tyr Met Glu Leu Ser Ser Leu Arg Ser Glu Asp Thr Ala Val
                80                  85                  90 tat tac tgt gcg aga gga tta cga cga ggg ggg tac tac ttt gac tac     384
Tyr Tyr Cys Ala Arg Gly Leu Arg Arg Gly Gly Tyr Tyr Phe Asp Tyr
            95                  100                 105 tgg ggg caa ggg acc acg gtc acc gtc tcc tca g                       418
Trp Gly Gln Gly Thr Thr Val Thr Val Ser Ser
110                 115                 120

<210> SEQ ID NO 18
<211> LENGTH: 139
<212> TYPE: PRT
<213> ORGANISM: Artificial Sequence
<220> FEATURE:
<223> OTHER INFORMATION: Description of Artificial Sequence: Humanized
      H chain V region (version b) of anti-HM1.24 antibody

<400> SEQUENCE: 18

Met Asp Trp Thr Trp Arg Val Phe Phe Leu Leu Ala Val Ala Pro Gly
                -15                 -10                  -5

Ala His Ser Gln Val Gln Leu Val Gln Ser Gly Ala Glu Val Lys Lys
        -1   1               5                  10

Pro Gly Ala Ser Val Lys Val Ser Cys Lys Ala Ser Gly Tyr Thr Phe
        15                  20                  25

Thr Pro Tyr Trp Met Gln Trp Val Arg Gln Ala Pro Gly Gln Gly Leu
30                  35                  40                  45

Glu Trp Met Gly Ser Ile Phe Pro Gly Asp Gly Asp Thr Arg Tyr Ser
                50                  55                  60

Gln Lys Phe Lys Gly Lys Val Thr Met Thr Ala Asp Thr Ser Thr Ser
                    65                  70                  75

Thr Val Tyr Met Glu Leu Ser Ser Leu Arg Ser Glu Asp Thr Ala Val
                80                  85                  90

Tyr Tyr Cys Ala Arg Gly Leu Arg Arg Gly Gly Tyr Tyr Phe Asp Tyr
            95                  100                 105

Trp Gly Gln Gly Thr Thr Val Thr Val Ser Ser
110                 115                 120

<210> SEQ ID NO 19
<211> LENGTH: 418
<212> TYPE: DNA
<213> ORGANISM: Artificial Sequence
<220> FEATURE:
<223> OTHER INFORMATION: Description of Artificial Sequence: DNA coding
      for humanized H chain V region (version c) of anti-HM1.24 antibody
<221> NAME/KEY: sig_peptide
```

```
<222> LOCATION: (1)..(57)
<221> NAME/KEY: mat_peptide
<222> LOCATION: (58)..(417)
<221> NAME/KEY: CDS
<222> LOCATION: (1)..(417)

<400> SEQUENCE: 19 atg gac tgg acc tgg agg gtc ttc ttc ttg ctg gct gta gct cca ggt    48
Met Asp Trp Thr Trp Arg Val Phe Phe Leu Leu Ala Val Ala Pro Gly
            -15                 -10                 -5 gct cac tcc cag gtg cag ctg gtg cag tct ggg gct gag gtg aag aag    96
Ala His Ser Gln Val Gln Leu Val Gln Ser Gly Ala Glu Val Lys Lys
        -1   1               5                  10 cct ggg gcc tca gtg aag gtt tcc tgc aag gca tct gga tac acc ttc   144
Pro Gly Ala Ser Val Lys Val Ser Cys Lys Ala Ser Gly Tyr Thr Phe
         15                  20                  25 act ccc tac tgg atg cag tgg gtg cga cag gcc cct gga caa ggg ctt   192
Thr Pro Tyr Trp Met Gln Trp Val Arg Gln Ala Pro Gly Gln Gly Leu
 30                  35                  40                  45 gag tgg atg gga tct att ttt cct gga gat ggt gat act agg tac agt   240
Glu Trp Met Gly Ser Ile Phe Pro Gly Asp Gly Asp Thr Arg Tyr Ser
                 50                  55                  60 cag aag ttc aag ggc aga gtc act atg acc gca gac aag tcc acg agc   288
Gln Lys Phe Lys Gly Arg Val Thr Met Thr Ala Asp Lys Ser Thr Ser
             65                  70                  75 aca gtc tac atg gag ctg agc agc ctg aga tct gag gac acg gcc gtg   336
Thr Val Tyr Met Glu Leu Ser Ser Leu Arg Ser Glu Asp Thr Ala Val
             80                  85                  90 tat tac tgt gcg aga gga tta cga cga ggg ggg tac tac ttt gac tac   384
Tyr Tyr Cys Ala Arg Gly Leu Arg Arg Gly Gly Tyr Tyr Phe Asp Tyr
     95                 100                 105 tgg ggg caa ggg acc acg gtc acc gtc tcc tca g                     418
Trp Gly Gln Gly Thr Thr Val Thr Val Ser Ser
110                 115                 120

<210> SEQ ID NO 20
<211> LENGTH: 139
<212> TYPE: PRT
<213> ORGANISM: Artificial Sequence
<220> FEATURE:
<223> OTHER INFORMATION: Description of Artificial Sequence: H chain V
      region (version c) of anti-HM1.24 antibody

<400> SEQUENCE: 20

Met Asp Trp Thr Trp Arg Val Phe Phe Leu Leu Ala Val Ala Pro Gly
            -15                 -10                 -5

Ala His Ser Gln Val Gln Leu Val Gln Ser Gly Ala Glu Val Lys Lys
        -1   1               5                  10

Pro Gly Ala Ser Val Lys Val Ser Cys Lys Ala Ser Gly Tyr Thr Phe
         15                  20                  25

Thr Pro Tyr Trp Met Gln Trp Val Arg Gln Ala Pro Gly Gln Gly Leu
 30                  35                  40                  45

Glu Trp Met Gly Ser Ile Phe Pro Gly Asp Gly Asp Thr Arg Tyr Ser
                 50                  55                  60

Gln Lys Phe Lys Gly Arg Val Thr Met Thr Ala Asp Lys Ser Thr Ser
             65                  70                  75

Thr Val Tyr Met Glu Leu Ser Ser Leu Arg Ser Glu Asp Thr Ala Val
             80                  85                  90

Tyr Tyr Cys Ala Arg Gly Leu Arg Arg Gly Gly Tyr Tyr Phe Asp Tyr
     95                 100                 105
```

```
Trp Gly Gln Gly Thr Thr Val Thr Val Ser Ser
110             115             120
```

<210> SEQ ID NO 21
<211> LENGTH: 418
<212> TYPE: DNA
<213> ORGANISM: Artificial Sequence
<220> FEATURE:
<223> OTHER INFORMATION: Description of Artificial Sequence: DNA coding
      for humanized H chain V region (version d) of anti-HM1.24 antibody
<221> NAME/KEY: sig_peptide
<222> LOCATION: (1)..(57)
<221> NAME/KEY: mat_peptide
<222> LOCATION: (58)..(417)
<221> NAME/KEY: CDS
<222> LOCATION: (1)..(417)

<400> SEQUENCE: 21

```
atg gac tgg acc tgg agg gtc ttc ttc ttg ctg gct gta gct cca ggt      48
Met Asp Trp Thr Trp Arg Val Phe Phe Leu Leu Ala Val Ala Pro Gly
            -15                 -10                 -5 gct cac tcc cag gtg cag ctg gtg cag tct ggg gct gag gtg aag aag      96
Ala His Ser Gln Val Gln Leu Val Gln Ser Gly Ala Glu Val Lys Lys
        -1   1               5                  10 cct ggg gcc tca gtg aag gtt tcc tgc aag gca tct gga tac acc ttc     144
Pro Gly Ala Ser Val Lys Val Ser Cys Lys Ala Ser Gly Tyr Thr Phe
 15                  20                  25 act ccc tac tgg atg cag tgg gtg cga cag gcc cct gga caa ggg ctt     192
Thr Pro Tyr Trp Met Gln Trp Val Arg Gln Ala Pro Gly Gln Gly Leu
 30                  35                  40                  45 gag tgg atg gga tct att ttt cct gga gat ggt gat act agg tac agt     240
Glu Trp Met Gly Ser Ile Phe Pro Gly Asp Gly Asp Thr Arg Tyr Ser
                 50                  55                  60 cag aag ttc aag ggc aaa gtc acc atg acc gca gac aag tcc acg agc     288
Gln Lys Phe Lys Gly Lys Val Thr Met Thr Ala Asp Lys Ser Thr Ser
             65                  70                  75 aca gtc tac atg gag ctg agc agc ctg aga tct gag gac acg gcc gtg     336
Thr Val Tyr Met Glu Leu Ser Ser Leu Arg Ser Glu Asp Thr Ala Val
         80                  85                  90 tat tac tgt gcg aga gga tta cga cga ggg ggg tac tac ttt gac tac     384
Tyr Tyr Cys Ala Arg Gly Leu Arg Arg Gly Gly Tyr Tyr Phe Asp Tyr
     95                 100                 105 tgg ggg caa ggg acc acg gtc acc gtc tcc tca g                        418
Trp Gly Gln Gly Thr Thr Val Thr Val Ser Ser
110                 115                 120
```

<210> SEQ ID NO 22
<211> LENGTH: 139
<212> TYPE: PRT
<213> ORGANISM: Artificial Sequence
<220> FEATURE:
<223> OTHER INFORMATION: Description of Artificial Sequence: H chain V
      region (version d) of anti-HM1.24 antibody

<400> SEQUENCE: 22

```
Met Asp Trp Thr Trp Arg Val Phe Phe Leu Leu Ala Val Ala Pro Gly
            -15                 -10                 -5

Ala His Ser Gln Val Gln Leu Val Gln Ser Gly Ala Glu Val Lys Lys
        -1   1               5                  10

Pro Gly Ala Ser Val Lys Val Ser Cys Lys Ala Ser Gly Tyr Thr Phe
 15                  20                  25

Thr Pro Tyr Trp Met Gln Trp Val Arg Gln Ala Pro Gly Gln Gly Leu
 30                  35                  40                  45
```

```
Glu Trp Met Gly Ser Ile Phe Pro Gly Asp Gly Asp Thr Arg Tyr Ser
            50                  55                  60

Gln Lys Phe Lys Gly Lys Val Thr Met Thr Ala Asp Lys Ser Thr Ser
        65                  70                  75

Thr Val Tyr Met Glu Leu Ser Ser Leu Arg Ser Glu Asp Thr Ala Val
            80                  85                  90

Tyr Tyr Cys Ala Arg Gly Leu Arg Arg Gly Gly Tyr Tyr Phe Asp Tyr
        95                  100                 105

Trp Gly Gln Gly Thr Thr Val Thr Val Ser Ser
110             115                 120

<210> SEQ ID NO 23
<211> LENGTH: 418
<212> TYPE: DNA
<213> ORGANISM: Artificial Sequence
<220> FEATURE:
<223> OTHER INFORMATION: Description of Artificial Sequence: DNA coding
      for humanized H chain V region (version e) of anti-HM1.24 antibody
<221> NAME/KEY: sig_peptide
<222> LOCATION: (1)..(57)
<221> NAME/KEY: mat_peptide
<222> LOCATION: (58)..(417)
<221> NAME/KEY: CDS
<222> LOCATION: (1)..(417)

<400> SEQUENCE: 23 atg gac tgg acc tgg agg gtc ttc ttc ttg ctg gct gta gct cca ggt         48
Met Asp Trp Thr Trp Arg Val Phe Phe Leu Leu Ala Val Ala Pro Gly
            -15                 -10                 -5 gct cac tcc cag gtg cag ctg gtg cag tct ggg gct gag gtg aag aag         96
Ala His Ser Gln Val Gln Leu Val Gln Ser Gly Ala Glu Val Lys Lys
      -1  1                 5                   10 cct ggg gcc tca gtg aag gtt tcc tgc aag gca tct gga tac acc ttc        144
Pro Gly Ala Ser Val Lys Val Ser Cys Lys Ala Ser Gly Tyr Thr Phe
        15                  20                  25 act ccc tac tgg atg cag tgg gtg cga cag gcc cct gga caa ggg ctt        192
Thr Pro Tyr Trp Met Gln Trp Val Arg Gln Ala Pro Gly Gln Gly Leu
30                  35                  40                  45 gag tgg atg gga tct att ttt cct gga gat ggt gat act agg tac agt        240
Glu Trp Met Gly Ser Ile Phe Pro Gly Asp Gly Asp Thr Arg Tyr Ser
            50                  55                  60 cag aag ttc aag ggc aga gcc acc ctg acc gca gac acg tcc acg agc        288
Gln Lys Phe Lys Gly Arg Ala Thr Leu Thr Ala Asp Thr Ser Thr Ser
        65                  70                  75 aca gtc tac atg gag ctg agc agc ctg aga tct gag gac acg gcc gtg        336
Thr Val Tyr Met Glu Leu Ser Ser Leu Arg Ser Glu Asp Thr Ala Val
            80                  85                  90 tat tac tgt gcg aga gga tta cga cga ggg ggg tac tac ttt gac tac        384
Tyr Tyr Cys Ala Arg Gly Leu Arg Arg Gly Gly Tyr Tyr Phe Asp Tyr
        95                  100                 105 tgg ggg caa ggg acc acg gtc acc gtc tcc tca g                          418
Trp Gly Gln Gly Thr Thr Val Thr Val Ser Ser
110             115                 120

<210> SEQ ID NO 24
<211> LENGTH: 139
<212> TYPE: PRT
<213> ORGANISM: Artificial Sequence
<220> FEATURE:
<223> OTHER INFORMATION: Description of Artificial Sequence: H chain V
      region (version e) of anti-HM1.24 antibody

<400> SEQUENCE: 24
```

```
Met Asp Trp Thr Trp Arg Val Phe Phe Leu Leu Ala Val Ala Pro Gly
            -15                 -10                  -5

Ala His Ser Gln Val Gln Leu Val Gln Ser Gly Ala Glu Val Lys Lys
         -1   1              5                  10

Pro Gly Ala Ser Val Lys Val Ser Cys Lys Ala Ser Gly Tyr Thr Phe
         15              20                  25

Thr Pro Tyr Trp Met Gln Trp Val Arg Gln Ala Pro Gly Gln Gly Leu
 30              35                  40                      45

Glu Trp Met Gly Ser Ile Phe Pro Gly Asp Gly Asp Thr Arg Tyr Ser
             50                      55                  60

Gln Lys Phe Lys Gly Arg Ala Thr Leu Thr Ala Asp Thr Ser Thr Ser
             65                  70                  75

Thr Val Tyr Met Glu Leu Ser Ser Leu Arg Ser Glu Asp Thr Ala Val
         80                  85                  90

Tyr Tyr Cys Ala Arg Gly Leu Arg Arg Gly Gly Tyr Tyr Phe Asp Tyr
 95                      100                     105

Trp Gly Gln Gly Thr Thr Val Thr Val Ser Ser
110                 115                 120
```

<210> SEQ ID NO 25
<211> LENGTH: 418
<212> TYPE: DNA
<213> ORGANISM: Artificial Sequence
<220> FEATURE:
<223> OTHER INFORMATION: Description of Artificial Sequence: DNA coding
      for humanized H chain V region (version f) of anti-HM1.24 antibody
<221> NAME/KEY: sig_peptide
<222> LOCATION: (1)..(57)
<221> NAME/KEY: mat_peptide
<222> LOCATION: (58)..(417)
<221> NAME/KEY: CDS
<222> LOCATION: (1)..(417)

<400> SEQUENCE: 25

```
atg gac tgg acc tgg agg gtc ttc ttc ttg ctg gct gta gct cca ggt      48
Met Asp Trp Thr Trp Arg Val Phe Phe Leu Leu Ala Val Ala Pro Gly
            -15                 -10                  -5 gct cac tcc cag gtg cag ctg gtg cag tct ggg gct gag gtg aag aag      96
Ala His Ser Gln Val Gln Leu Val Gln Ser Gly Ala Glu Val Lys Lys
         -1   1              5                  10 cct ggg gcc tca gtg aag gtt tcc tgc aag gca tct gga tac acc ttc     144
Pro Gly Ala Ser Val Lys Val Ser Cys Lys Ala Ser Gly Tyr Thr Phe
         15              20                  25 act ccc tac tgg atg cag tgg gtg cga cag gcc cct gga caa ggg ctt     192
Thr Pro Tyr Trp Met Gln Trp Val Arg Gln Ala Pro Gly Gln Gly Leu
 30              35                  40                      45 gag tgg atg gga tct att ttt cct gga gat ggt gat act agg tac agt     240
Glu Trp Met Gly Ser Ile Phe Pro Gly Asp Gly Asp Thr Arg Tyr Ser
             50                      55                  60 cag aag ttc aag ggc aga gcc acc ctg act gca gac acg tcg agc         288
Gln Lys Phe Lys Gly Arg Ala Thr Leu Thr Ala Asp Thr Ser Ser Ser
             65                  70                  75 aca gcc tac atg gag ctg agc agc ctg aga tct gag gac acg gcc gtg     336
Thr Ala Tyr Met Glu Leu Ser Ser Leu Arg Ser Glu Asp Thr Ala Val
         80                  85                  90 tat tac tgt gcg aga gga tta cga cga ggg ggg tac tac ttt gac tac     384
Tyr Tyr Cys Ala Arg Gly Leu Arg Arg Gly Gly Tyr Tyr Phe Asp Tyr
 95                      100                     105 tgg ggg caa ggg acc acg gtc acc gtc tcc tca g                       418
Trp Gly Gln Gly Thr Thr Val Thr Val Ser Ser
110                 115                 120
```

<210> SEQ ID NO 26
<211> LENGTH: 139
<212> TYPE: PRT
<213> ORGANISM: Artificial Sequence
<220> FEATURE:
<223> OTHER INFORMATION: Description of Artificial Sequence: Humanizaed
      H chain V region (version f) of anti-HM1.24 antibody

<400> SEQUENCE: 26

Met Asp Trp Thr Trp Arg Val Phe Phe Leu Leu Ala Val Ala Pro Gly
            -15                 -10                 -5

Ala His Ser Gln Val Gln Leu Val Gln Ser Gly Ala Glu Val Lys Lys
         -1  1               5                  10

Pro Gly Ala Ser Val Lys Val Ser Cys Lys Ala Ser Gly Tyr Thr Phe
     15                  20                  25

Thr Pro Tyr Trp Met Gln Trp Val Arg Gln Ala Pro Gly Gln Gly Leu
 30              35                  40                  45

Glu Trp Met Gly Ser Ile Phe Pro Gly Asp Gly Asp Thr Arg Tyr Ser
                 50                  55                  60

Gln Lys Phe Lys Gly Arg Ala Thr Leu Thr Ala Asp Thr Ser Ser Ser
             65                  70                  75

Thr Ala Tyr Met Glu Leu Ser Ser Leu Arg Ser Glu Asp Thr Ala Val
             80                  85                  90

Tyr Tyr Cys Ala Arg Gly Leu Arg Arg Gly Gly Tyr Tyr Phe Asp Tyr
 95                 100                 105

Trp Gly Gln Gly Thr Thr Val Thr Val Ser Ser
110                 115                 120

<210> SEQ ID NO 27
<211> LENGTH: 418
<212> TYPE: DNA
<213> ORGANISM: Artificial Sequence
<220> FEATURE:
<223> OTHER INFORMATION: Description of Artificial Sequence: DNA coding
      for humanized H chain V region (version g) of anti-HM1.24 antibody
<221> NAME/KEY: sig_peptide
<222> LOCATION: (1)..(57)
<221> NAME/KEY: mat_peptide
<222> LOCATION: (58)..(417)
<221> NAME/KEY: CDS
<222> LOCATION: (1)..(417)

<400> SEQUENCE: 27 atg gac tgg acc tgg agg gtc ttc ttc ttg ctg gct gta gct cca ggt      48
Met Asp Trp Thr Trp Arg Val Phe Phe Leu Leu Ala Val Ala Pro Gly
            -15                 -10                 -5 gct cac tcc cag gtg cag ctg gtg cag tct ggg gct gag gtg aag aag      96
Ala His Ser Gln Val Gln Leu Val Gln Ser Gly Ala Glu Val Lys Lys
         -1  1               5                  10 cct ggg gcc tca gtg aag gtt tcc tgc aag gca tct gga tac acc ttc     144
Pro Gly Ala Ser Val Lys Val Ser Cys Lys Ala Ser Gly Tyr Thr Phe
     15                  20                  25 act ccc tac tgg atg cag tgg gtg cga cag cgc cct gga caa ggg ctt     192
Thr Pro Tyr Trp Met Gln Trp Val Arg Gln Arg Pro Gly Gln Gly Leu
 30              35                  40                  45 gag tgg atg gga tct att ttt cct gga gat ggt gat act agg tac agt     240
Glu Trp Met Gly Ser Ile Phe Pro Gly Asp Gly Asp Thr Arg Tyr Ser
                 50                  55                  60 cag aag ttc aag ggc aga gtc acc atg acc gca gac acg tcc acg agc     288
Gln Lys Phe Lys Gly Arg Val Thr Met Thr Ala Asp Thr Ser Thr Ser
             65                  70                  75

```
aca gtc tac atg gag ctg agc agc ctg aga tct gag gac acg gcc gtg      336
Thr Val Tyr Met Glu Leu Ser Ser Leu Arg Ser Glu Asp Thr Ala Val
        80                  85                  90 tat tac tgt gcg aga gga tta cga cga ggg ggg tac tac ttt gac tac      384
Tyr Tyr Cys Ala Arg Gly Leu Arg Arg Gly Gly Tyr Tyr Phe Asp Tyr
        95                 100                 105 tgg ggg caa ggg acc acg gtc acc gtc tcc tca g                        418
Trp Gly Gln Gly Thr Thr Val Thr Val Ser Ser
110                 115                 120

<210> SEQ ID NO 28
<211> LENGTH: 139
<212> TYPE: PRT
<213> ORGANISM: Artificial Sequence
<220> FEATURE:
<223> OTHER INFORMATION: Description of Artificial Sequence: Humanized
      H chain V region (version g) of anti-HM1.24 antibody

<400> SEQUENCE: 28

Met Asp Trp Thr Trp Arg Val Phe Phe Leu Leu Ala Val Ala Pro Gly
            -15                 -10                  -5

Ala His Ser Gln Val Gln Leu Val Gln Ser Gly Ala Glu Val Lys Lys
         -1   1               5                  10

Pro Gly Ala Ser Val Lys Val Ser Cys Lys Ala Ser Gly Tyr Thr Phe
         15                  20                  25

Thr Pro Tyr Trp Met Gln Trp Val Arg Gln Arg Pro Gly Gln Gly Leu
 30                  35                  40                  45

Glu Trp Met Gly Ser Ile Phe Pro Gly Asp Gly Asp Thr Arg Tyr Ser
                 50                  55                  60

Gln Lys Phe Lys Gly Arg Val Thr Met Thr Ala Asp Thr Ser Thr Ser
                 65                  70                  75

Thr Val Tyr Met Glu Leu Ser Ser Leu Arg Ser Glu Asp Thr Ala Val
        80                  85                  90

Tyr Tyr Cys Ala Arg Gly Leu Arg Arg Gly Gly Tyr Tyr Phe Asp Tyr
        95                 100                 105

Trp Gly Gln Gly Thr Thr Val Thr Val Ser Ser
110                 115                 120

<210> SEQ ID NO 29
<211> LENGTH: 418
<212> TYPE: DNA
<213> ORGANISM: Artificial Sequence
<220> FEATURE:
<223> OTHER INFORMATION: Description of Artificial Sequence: DNA coding
      for humanized H chain V region (version h) of anti-HM1.24 antibody
<221> NAME/KEY: sig_peptide
<222> LOCATION: (1)..(57)
<221> NAME/KEY: mat_peptide
<222> LOCATION: (58)..(417)
<221> NAME/KEY: CDS
<222> LOCATION: (1)..(417)

<400> SEQUENCE: 29 atg gac tgg acc tgg agg gtc ttc ttc ttg ctg gct gta gct cca ggt       48
Met Asp Trp Thr Trp Arg Val Phe Phe Leu Leu Ala Val Ala Pro Gly
            -15                 -10                  -5 gct cac tcc cag gtg cag ctg gtg cag tct ggg gct gag gtg aag aag       96
Ala His Ser Gln Val Gln Leu Val Gln Ser Gly Ala Glu Val Lys Lys
         -1   1               5                  10 cct ggg gcc tca gtg aag gtt tcc tgc aag gca tct gga tac acc ttc      144
Pro Gly Ala Ser Val Lys Val Ser Cys Lys Ala Ser Gly Tyr Thr Phe
         15                  20                  25
```

```
act ccc tac tgg atg cag tgg gtg cga cag gcc cct gga caa ggg ctt        192
Thr Pro Tyr Trp Met Gln Trp Val Arg Gln Ala Pro Gly Gln Gly Leu
 30              35                  40                  45 gag tgg atg gga tct att ttt cct gga gat ggt gat act agg tac agt        240
Glu Trp Met Gly Ser Ile Phe Pro Gly Asp Gly Asp Thr Arg Tyr Ser
                 50                  55                  60 cag aag ttc aag ggc aaa gtc acc atg acc gca gac acg tcc tcg agc        288
Gln Lys Phe Lys Gly Lys Val Thr Met Thr Ala Asp Thr Ser Ser Ser
             65                  70                  75 aca gcc tac atg gag ctg agc agc ctg aga tct gag gac acg gcc gtg        336
Thr Ala Tyr Met Glu Leu Ser Ser Leu Arg Ser Glu Asp Thr Ala Val
         80                  85                  90 tat tac tgt gcg aga gga tta cga cga ggg ggg tac tac ttt gac tac        384
Tyr Tyr Cys Ala Arg Gly Leu Arg Arg Gly Gly Tyr Tyr Phe Asp Tyr
     95                 100                 105 tgg ggg caa ggg acc acg gtc acc gtc tcc tca g                          418
Trp Gly Gln Gly Thr Thr Val Thr Val Ser Ser
110                 115                 120

<210> SEQ ID NO 30
<211> LENGTH: 139
<212> TYPE: PRT
<213> ORGANISM: Artificial Sequence
<220> FEATURE:
<223> OTHER INFORMATION: Description of Artificial Sequence: Humanized
      H chain V region (version h) of anti-HM1.24 antibody

<400> SEQUENCE: 30

Met Asp Trp Thr Trp Arg Val Phe Phe Leu Leu Ala Val Ala Pro Gly
                -15                 -10                  -5

Ala His Ser Gln Val Gln Leu Val Gln Ser Gly Ala Glu Val Lys Lys
         -1   1               5                  10

Pro Gly Ala Ser Val Lys Val Ser Cys Lys Ala Ser Gly Tyr Thr Phe
     15                  20                  25

Thr Pro Tyr Trp Met Gln Trp Val Arg Gln Ala Pro Gly Gln Gly Leu
 30              35                  40                  45

Glu Trp Met Gly Ser Ile Phe Pro Gly Asp Gly Asp Thr Arg Tyr Ser
                 50                  55                  60

Gln Lys Phe Lys Gly Lys Val Thr Met Thr Ala Asp Thr Ser Ser Ser
             65                  70                  75

Thr Ala Tyr Met Glu Leu Ser Ser Leu Arg Ser Glu Asp Thr Ala Val
         80                  85                  90

Tyr Tyr Cys Ala Arg Gly Leu Arg Arg Gly Gly Tyr Tyr Phe Asp Tyr
     95                 100                 105

Trp Gly Gln Gly Thr Thr Val Thr Val Ser Ser
110                 115                 120

<210> SEQ ID NO 31
<211> LENGTH: 418
<212> TYPE: DNA
<213> ORGANISM: Artificial Sequence
<220> FEATURE:
<223> OTHER INFORMATION: Description of Artificial Sequence: DNA coding
      for humanized H chain V region (version i) of anti-HM1.24 antibody
<221> NAME/KEY: sig_peptide
<222> LOCATION: (1)..(57)
<221> NAME/KEY: mat_peptide
<222> LOCATION: (58)..(417)
<221> NAME/KEY: CDS
<222> LOCATION: (1)..(417)

<400> SEQUENCE: 31
```

```
atg gac tgg acc tgg agg gtc ttc ttc ttg ctg gct gta gct cca ggt      48
Met Asp Trp Thr Trp Arg Val Phe Phe Leu Leu Ala Val Ala Pro Gly
            -15                 -10                 -5 gct cac tcc cag gtg cag ctg gtg cag tct ggg gct gag gtg aag aag      96
Ala His Ser Gln Val Gln Leu Val Gln Ser Gly Ala Glu Val Lys Lys
        -1   1               5                  10 cct ggg gcc tca gtg aag gtt tcc tgc aag gca tct gga tac acc ttc     144
Pro Gly Ala Ser Val Lys Val Ser Cys Lys Ala Ser Gly Tyr Thr Phe
 15              20                  25 act ccc tac tgg atg cag tgg gtg cga cag gcc cct gga caa ggg ctt     192
Thr Pro Tyr Trp Met Gln Trp Val Arg Gln Ala Pro Gly Gln Gly Leu
 30              35                  40                  45 gag tgg atg gga tct att ttt cct gga gat ggt gat act agg tac agt     240
Glu Trp Met Gly Ser Ile Phe Pro Gly Asp Gly Asp Thr Arg Tyr Ser
                 50                  55                  60 cag aag ttc aag ggc aaa gtc acc atg acc gca gac acg tcc tcg agc     288
Gln Lys Phe Lys Gly Lys Val Thr Met Thr Ala Asp Thr Ser Ser Ser
 65                  70                  75 aca gcc tac atg gag ctg agc agc ctg gca ttt gag gac acg gcc gtg     336
Thr Ala Tyr Met Glu Leu Ser Ser Leu Ala Phe Glu Asp Thr Ala Val
 80                  85                  90 tat tac tgt gcg aga gga tta cga cga ggg ggg tac tac ttt gac tac     384
Tyr Tyr Cys Ala Arg Gly Leu Arg Arg Gly Gly Tyr Tyr Phe Asp Tyr
 95                 100                 105 tgg ggg caa ggg acc acg gtc acc gtc tcc tca g                        418
Trp Gly Gln Gly Thr Thr Val Thr Val Ser Ser
110                 115                 120

<210> SEQ ID NO 32
<211> LENGTH: 139
<212> TYPE: PRT
<213> ORGANISM: Artificial Sequence
<220> FEATURE:
<223> OTHER INFORMATION: Description of Artificial Sequence: Humanizaed
      H chain V region (version i) of anti-HM1.24 antibody

<400> SEQUENCE: 32

Met Asp Trp Thr Trp Arg Val Phe Phe Leu Leu Ala Val Ala Pro Gly
            -15                 -10                 -5

Ala His Ser Gln Val Gln Leu Val Gln Ser Gly Ala Glu Val Lys Lys
        -1   1               5                  10

Pro Gly Ala Ser Val Lys Val Ser Cys Lys Ala Ser Gly Tyr Thr Phe
 15                  20                  25

Thr Pro Tyr Trp Met Gln Trp Val Arg Gln Ala Pro Gly Gln Gly Leu
 30                  35                  40                  45

Glu Trp Met Gly Ser Ile Phe Pro Gly Asp Gly Asp Thr Arg Tyr Ser
                 50                  55                  60

Gln Lys Phe Lys Gly Lys Val Thr Met Thr Ala Asp Thr Ser Ser Ser
 65                  70                  75

Thr Ala Tyr Met Glu Leu Ser Ser Leu Ala Phe Glu Asp Thr Ala Val
 80                  85                  90

Tyr Tyr Cys Ala Arg Gly Leu Arg Arg Gly Gly Tyr Tyr Phe Asp Tyr
 95                 100                 105

Trp Gly Gln Gly Thr Thr Val Thr Val Ser Ser
110                 115                 120

<210> SEQ ID NO 33
<211> LENGTH: 418
<212> TYPE: DNA
```

<210> SEQ ID NO 33
<211> LENGTH: 418
<212> TYPE: DNA
<213> ORGANISM: Artificial Sequence
<220> FEATURE:
<223> OTHER INFORMATION: Description of Artificial Sequence: DNA coding
for humanizaed H chain V region (version j) of anti-HM1.24
antibody
<221> NAME/KEY: sig_peptide
<222> LOCATION: (1)..(57)
<221> NAME/KEY: mat_peptide
<222> LOCATION: (58)..(417)
<221> NAME/KEY: CDS
<222> LOCATION: (1)..(417)

<400> SEQUENCE: 33

```
atg gac tgg acc tgg agg gtc ttc ttc ttg ctg gct gta gct cca ggt      48
Met Asp Trp Thr Trp Arg Val Phe Phe Leu Leu Ala Val Ala Pro Gly
            -15                 -10                  -5 gct cac tcc cag gtg cag ctg gtg cag tct ggg gct gag gtg aag aag      96
Ala His Ser Gln Val Gln Leu Val Gln Ser Gly Ala Glu Val Lys Lys
        -1   1               5                  10 cct ggg gcc tca gtg aag gtt tcc tgc aag gca tct gga tac acc ttc     144
Pro Gly Ala Ser Val Lys Val Ser Cys Lys Ala Ser Gly Tyr Thr Phe
    15                  20                  25 act ccc tac tgg atg cag tgg gtg cga cag gcc cct gga caa ggg ctt     192
Thr Pro Tyr Trp Met Gln Trp Val Arg Gln Ala Pro Gly Gln Gly Leu
30                  35                  40                  45 gag tgg atg gga tct att ttt cct gga gat ggt gat act agg tac agt     240
Glu Trp Met Gly Ser Ile Phe Pro Gly Asp Gly Asp Thr Arg Tyr Ser
                50                  55                  60 cag aag ttc aag ggc aaa gcc acc ctg act gca gac acg tcc tcg agc     288
Gln Lys Phe Lys Gly Lys Ala Thr Leu Thr Ala Asp Thr Ser Ser Ser
            65                  70                  75 aca gcc tac atg gag ctg agc agc ctg aga tct gag gac acg gcc gtg     336
Thr Ala Tyr Met Glu Leu Ser Ser Leu Arg Ser Glu Asp Thr Ala Val
        80                  85                  90 tat tac tgt gcg aga gga tta cga cga ggg ggg tac tac ttt gac tac     384
Tyr Tyr Cys Ala Arg Gly Leu Arg Arg Gly Gly Tyr Tyr Phe Asp Tyr
    95                 100                 105 tgg ggg caa ggg acc acg gtc acc gtc tcc tca g                       418
Trp Gly Gln Gly Thr Thr Val Thr Val Ser Ser
110                 115                 120
```

<210> SEQ ID NO 34
<211> LENGTH: 139
<212> TYPE: PRT
<213> ORGANISM: Artificial Sequence
<220> FEATURE:
<223> OTHER INFORMATION: Description of Artificial Sequence: Humanizaed
H chain V region (version j) of anti-HM1.24 antibody

<400> SEQUENCE: 34

```
Met Asp Trp Thr Trp Arg Val Phe Phe Leu Leu Ala Val Ala Pro Gly
            -15                 -10                  -5

Ala His Ser Gln Val Gln Leu Val Gln Ser Gly Ala Glu Val Lys Lys
        -1   1               5                  10

Pro Gly Ala Ser Val Lys Val Ser Cys Lys Ala Ser Gly Tyr Thr Phe
    15                  20                  25

Thr Pro Tyr Trp Met Gln Trp Val Arg Gln Ala Pro Gly Gln Gly Leu
30                  35                  40                  45

Glu Trp Met Gly Ser Ile Phe Pro Gly Asp Gly Asp Thr Arg Tyr Ser
                50                  55                  60

Gln Lys Phe Lys Gly Lys Ala Thr Leu Thr Ala Asp Thr Ser Ser Ser
            65                  70                  75
```

```
Thr Ala Tyr Met Glu Leu Ser Ser Leu Arg Ser Glu Asp Thr Ala Val
         80                  85                  90

Tyr Tyr Cys Ala Arg Gly Leu Arg Arg Gly Gly Tyr Tyr Phe Asp Tyr
     95                 100                 105

Trp Gly Gln Gly Thr Thr Val Thr Val Ser Ser
110                 115                 120

<210> SEQ ID NO 35
<211> LENGTH: 418
<212> TYPE: DNA
<213> ORGANISM: Artificial Sequence
<220> FEATURE:
<223> OTHER INFORMATION: Description of Artificial Sequence: DNA coding
      for H chain V region (version k) of anti-HM1.24antibody
<221> NAME/KEY: sig_peptide
<222> LOCATION: (1)..(57)
<221> NAME/KEY: mat_peptide
<222> LOCATION: (58)..(417)
<221> NAME/KEY: CDS
<222> LOCATION: (1)..(417)

<400> SEQUENCE: 35 atg gac tgg acc tgg agg gtc ttc ttc ttg ctg gct gta gct cca ggt     48
Met Asp Trp Thr Trp Arg Val Phe Phe Leu Leu Ala Val Ala Pro Gly
            -15                 -10                 -5 gct cac tcc cag gtg cag ctg gtg cag tct ggg gct gag gtg aag aag     96
Ala His Ser Gln Val Gln Leu Val Gln Ser Gly Ala Glu Val Lys Lys
         -1   1                   5                  10 cct ggg gcc tca gtg aag gtt tcc tgc aag gca tct gga tac acc ttc    144
Pro Gly Ala Ser Val Lys Val Ser Cys Lys Ala Ser Gly Tyr Thr Phe
     15                  20                  25 act ccc tac tgg atg cag tgg gtg cga cag gcc cct gga caa ggg ctt    192
Thr Pro Tyr Trp Met Gln Trp Val Arg Gln Ala Pro Gly Gln Gly Leu
 30                  35                  40                  45 gag tgg atg gga tct att ttt cct gga gat ggt gat act agg tac agt    240
Glu Trp Met Gly Ser Ile Phe Pro Gly Asp Gly Asp Thr Arg Tyr Ser
                 50                  55                  60 cag aag ttc aag ggc aaa gtc acc atg acc gca gac acg tcc tcg agc    288
Gln Lys Phe Lys Gly Lys Val Thr Met Thr Ala Asp Thr Ser Ser Ser
             65                  70                  75 aca gcc tac atg cag ctg agc agc cta aga tct gag gac acg gcc gtg    336
Thr Ala Tyr Met Gln Leu Ser Ser Leu Arg Ser Glu Asp Thr Ala Val
         80                  85                  90 tat tac tgt gcg aga gga tta cga cga ggg ggg tac tac ttt gac tac    384
Tyr Tyr Cys Ala Arg Gly Leu Arg Arg Gly Gly Tyr Tyr Phe Asp Tyr
     95                 100                 105 tgg ggg caa ggg acc acg gtc acc gtc tcc tca g                      418
Trp Gly Gln Gly Thr Thr Val Thr Val Ser Ser
110                 115                 120

<210> SEQ ID NO 36
<211> LENGTH: 139
<212> TYPE: PRT
<213> ORGANISM: Artificial Sequence
<220> FEATURE:
<223> OTHER INFORMATION: Description of Artificial Sequence: Humanized
      H chain V region (version k) of anti-HM1.24 antibody

<400> SEQUENCE: 36

Met Asp Trp Thr Trp Arg Val Phe Phe Leu Leu Ala Val Ala Pro Gly
            -15                 -10                 -5

Ala His Ser Gln Val Gln Leu Val Gln Ser Gly Ala Glu Val Lys Lys
         -1   1                   5                  10
```

```
            Pro Gly Ala Ser Val Lys Val Ser Cys Lys Ala Ser Gly Tyr Thr Phe
                15                  20                  25

Thr Pro Tyr Trp Met Gln Trp Val Arg Gln Ala Pro Gly Gln Gly Leu
            30                  35                  40                  45

Glu Trp Met Gly Ser Ile Phe Pro Gly Asp Gly Asp Thr Arg Tyr Ser
                            50                  55                  60

Gln Lys Phe Lys Gly Lys Val Thr Met Thr Ala Asp Thr Ser Ser Ser
                        65                  70                  75

Thr Ala Tyr Met Gln Leu Ser Ser Leu Arg Ser Glu Asp Thr Ala Val
                    80                  85                  90

Tyr Tyr Cys Ala Arg Gly Leu Arg Arg Gly Gly Tyr Tyr Phe Asp Tyr
                95                  100                 105

Trp Gly Gln Gly Thr Thr Val Thr Val Ser Ser
            110                 115                 120

<210> SEQ ID NO 37
<211> LENGTH: 418
<212> TYPE: DNA
<213> ORGANISM: Artificial Sequence
<220> FEATURE:
<223> OTHER INFORMATION: Description of Artificial Sequence: DNA coding
      for humanized H chain V region (version 1) of anti-HM1.24 antibody
<221> NAME/KEY: sig_peptide
<222> LOCATION: (1)..(57)
<221> NAME/KEY: mat_peptide
<222> LOCATION: (58)..(417)
<221> NAME/KEY: CDS
<222> LOCATION: (1)..(417)

<400> SEQUENCE: 37 atg gac tgg acc tgg agg gtc ttc ttc ttg ctg gct gta gct cca ggt       48
Met Asp Trp Thr Trp Arg Val Phe Phe Leu Leu Ala Val Ala Pro Gly
            -15                 -10                 -5 gct cac tcc cag gtg cag ctg gtg cag tct ggg gct gag gtg aag aag       96
Ala His Ser Gln Val Gln Leu Val Gln Ser Gly Ala Glu Val Lys Lys
        -1  1               5                   10 cct ggg gcc tca gtg aag gtt tcc tgc aag gca tct gga tac acc ttc      144
Pro Gly Ala Ser Val Lys Val Ser Cys Lys Ala Ser Gly Tyr Thr Phe
            15                  20                  25 act ccc tac tgg atg cag tgg gtg cga cag gcc cct gga caa ggg ctt      192
Thr Pro Tyr Trp Met Gln Trp Val Arg Gln Ala Pro Gly Gln Gly Leu
30                  35                  40                  45 gag tgg atg gga tct att ttt cct gga gat ggt gat act agg tac agt      240
Glu Trp Met Gly Ser Ile Phe Pro Gly Asp Gly Asp Thr Arg Tyr Ser
                50                  55                  60 cag aag ttc aag ggc aaa gtc acc atg acc gca gac acg tcc tcg agc      288
Gln Lys Phe Lys Gly Lys Val Thr Met Thr Ala Asp Thr Ser Ser Ser
            65                  70                  75 aca gcc tac atg cag ctg agc atc ctg aga tct gag gac acg gcc gtg      336
Thr Ala Tyr Met Gln Leu Ser Ile Leu Arg Ser Glu Asp Thr Ala Val
        80                  85                  90 tat tac tgt gcg aga gga tta cga cga ggg ggg tac tac ttt gac tac      384
Tyr Tyr Cys Ala Arg Gly Leu Arg Arg Gly Gly Tyr Tyr Phe Asp Tyr
    95                  100                 105 tgg ggg caa ggg acc acg gtc acc gtc tcc tca g                        418
Trp Gly Gln Gly Thr Thr Val Thr Val Ser Ser
110                 115                 120

<210> SEQ ID NO 38
<211> LENGTH: 139
<212> TYPE: PRT
<213> ORGANISM: Artificial Sequence
```

```
<220> FEATURE:
<223> OTHER INFORMATION: Description of Artificial Sequence: Humanized
      H chain V region (version 1) of anti-HM1.24 antibody

<400> SEQUENCE: 38

Met Asp Trp Thr Trp Arg Val Phe Phe Leu Leu Ala Val Ala Pro Gly
            -15                 -10                 -5

Ala His Ser Gln Val Gln Leu Val Gln Ser Gly Ala Glu Val Lys Lys
        -1  1                   5                   10

Pro Gly Ala Ser Val Lys Val Ser Cys Lys Ala Ser Gly Tyr Thr Phe
            15                  20                  25

Thr Pro Tyr Trp Met Gln Trp Val Arg Gln Ala Pro Gly Gln Gly Leu
30              35                  40                  45

Glu Trp Met Gly Ser Ile Phe Pro Gly Asp Gly Asp Thr Arg Tyr Ser
                50                  55                  60

Gln Lys Phe Lys Gly Lys Val Thr Met Thr Ala Asp Thr Ser Ser Ser
65                  70                  75

Thr Ala Tyr Met Gln Leu Ser Ile Leu Arg Ser Glu Asp Thr Ala Val
        80                  85                  90

Tyr Tyr Cys Ala Arg Gly Leu Arg Arg Gly Gly Tyr Tyr Phe Asp Tyr
    95                  100                 105

Trp Gly Gln Gly Thr Thr Val Thr Val Ser Ser
110             115                 120

<210> SEQ ID NO 39
<211> LENGTH: 418
<212> TYPE: DNA
<213> ORGANISM: Artificial Sequence
<220> FEATURE:
<223> OTHER INFORMATION: Description of Artificial Sequence: DNA coding
      for humanized H chain V region (version m) of anti-HM1.24 antibody
<221> NAME/KEY: sig_peptide
<222> LOCATION: (1)..(57)
<221> NAME/KEY: mat_peptide
<222> LOCATION: (58)..(417)
<221> NAME/KEY: CDS
<222> LOCATION: (1)..(417)

<400> SEQUENCE: 39 atg gac tgg acc tgg agg gtc ttc ttc ttg ctg gct gta gct cca ggt     48
Met Asp Trp Thr Trp Arg Val Phe Phe Leu Leu Ala Val Ala Pro Gly
            -15                 -10                 -5 gct cac tcc cag gtg cag ctg gtg cag tct ggg gct gag gtg aag aag     96
Ala His Ser Gln Val Gln Leu Val Gln Ser Gly Ala Glu Val Lys Lys
        -1  1                   5                   10 cct ggg gcc tca gtg aag gtt tcc tgc aag gca tct gga tac acc ttc    144
Pro Gly Ala Ser Val Lys Val Ser Cys Lys Ala Ser Gly Tyr Thr Phe
            15                  20                  25 act ccc tac tgg atg cag tgg gtg cga cag gcc cct gga caa ggg ctt    192
Thr Pro Tyr Trp Met Gln Trp Val Arg Gln Ala Pro Gly Gln Gly Leu
30              35                  40                  45 gag tgg atg gga tct att ttt cct gga gat ggt gat act agg tac agt    240
Glu Trp Met Gly Ser Ile Phe Pro Gly Asp Gly Asp Thr Arg Tyr Ser
                50                  55                  60 cag aag ttc aag ggc aaa gtc acc atg acc gca gac acg tcc tcg agc    288
Gln Lys Phe Lys Gly Lys Val Thr Met Thr Ala Asp Thr Ser Ser Ser
65                  70                  75 aca gcc tac atg cag ctg agc atc ctg aga tct gag gac tcg gcc gtg    336
Thr Ala Tyr Met Gln Leu Ser Ile Leu Arg Ser Glu Asp Ser Ala Val
        80                  85                  90 tat tac tgt gcg aga gga tta cga cga ggg ggg tac tac ttt gac tac    384
```

-continued

```
Tyr Tyr Cys Ala Arg Gly Leu Arg Arg Gly Gly Tyr Tyr Phe Asp Tyr
        95                 100                 105 tgg ggg caa ggg acc acg gtc acc gtc tcc tca g                              418
Trp Gly Gln Gly Thr Thr Val Thr Val Ser Ser
110                 115                 120
```

<210> SEQ ID NO 40
<211> LENGTH: 139
<212> TYPE: PRT
<213> ORGANISM: Artificial Sequence
<220> FEATURE:
<223> OTHER INFORMATION: Description of Artificial Sequence: Humanized
      H chain V region (version m) of anti-HM1.24 antibody

<400> SEQUENCE: 40

```
Met Asp Trp Thr Trp Arg Val Phe Phe Leu Leu Ala Val Ala Pro Gly
                -15                 -10                  -5

Ala His Ser Gln Val Gln Leu Val Gln Ser Gly Ala Glu Val Lys Lys
         -1   1                   5                  10

Pro Gly Ala Ser Val Lys Val Ser Cys Lys Ala Ser Gly Tyr Thr Phe
     15                  20                  25

Thr Pro Tyr Trp Met Gln Trp Val Arg Gln Ala Pro Gly Gln Gly Leu
 30                  35                  40                  45

Glu Trp Met Gly Ser Ile Phe Pro Gly Asp Gly Asp Thr Arg Tyr Ser
                 50                  55                  60

Gln Lys Phe Lys Gly Lys Val Thr Met Thr Ala Asp Thr Ser Ser Ser
             65                  70                  75

Thr Ala Tyr Met Gln Leu Ser Ile Leu Arg Ser Glu Asp Ser Ala Val
         80                  85                  90

Tyr Tyr Cys Ala Arg Gly Leu Arg Arg Gly Gly Tyr Tyr Phe Asp Tyr
     95                 100                 105

Trp Gly Gln Gly Thr Thr Val Thr Val Ser Ser
110                 115                 120
```

<210> SEQ ID NO 41
<211> LENGTH: 418
<212> TYPE: DNA
<213> ORGANISM: Artificial Sequence
<220> FEATURE:
<223> OTHER INFORMATION: Description of Artificial Sequence: DNA coding
      for humanized H chain V region (version n) of anti- HM1.24
      antibody
<221> NAME/KEY: sig_peptide
<222> LOCATION: (1)..(57)
<221> NAME/KEY: mat_peptide
<222> LOCATION: (58)..(417)
<221> NAME/KEY: CDS
<222> LOCATION: (1)..(417)

<400> SEQUENCE: 41

```
atg gac tgg acc tgg agg gtc ttc ttc ttg ctg gct gta gct cca ggt        48
Met Asp Trp Thr Trp Arg Val Phe Phe Leu Leu Ala Val Ala Pro Gly
                -15                 -10                  -5 gct cac tcc cag gtg cag ctg gtg cag tct ggg gct gag gtg aag aag        96
Ala His Ser Gln Val Gln Leu Val Gln Ser Gly Ala Glu Val Lys Lys
         -1   1                   5                  10 cct ggg gcc tca gtg aag gtt tcc tgc aag gca tct gga tac acc ttc       144
Pro Gly Ala Ser Val Lys Val Ser Cys Lys Ala Ser Gly Tyr Thr Phe
     15                  20                  25 act ccc tac tgg atg cag tgg gtg cga cag gcc cct gga caa ggg ctt       192
Thr Pro Tyr Trp Met Gln Trp Val Arg Gln Ala Pro Gly Gln Gly Leu
 30                  35                  40                  45
```

```
gag tgg atg gga tct att ttt cct gga gat ggt gat act agg tac agt      240
Glu Trp Met Gly Ser Ile Phe Pro Gly Asp Gly Asp Thr Arg Tyr Ser
            50                  55                  60 cag aag ttc aag ggc aaa gtc acc atg acc gca gac acg tcc tcg agc      288
Gln Lys Phe Lys Gly Lys Val Thr Met Thr Ala Asp Thr Ser Ser Ser
        65                  70                  75 aca gcc tac atg gag ctg agc atc ctg aga tct gag gac acg gcc gtg      336
Thr Ala Tyr Met Glu Leu Ser Ile Leu Arg Ser Glu Asp Thr Ala Val
        80                  85                  90 tat tac tgt gcg aga gga tta cga cga ggg ggg tac tac ttt gac tac      384
Tyr Tyr Cys Ala Arg Gly Leu Arg Arg Gly Gly Tyr Tyr Phe Asp Tyr
    95                  100                 105 tgg ggg caa ggg acc acg gtc acc gtc tcc tca g                        418
Trp Gly Gln Gly Thr Thr Val Thr Val Ser Ser
110                 115                 120

<210> SEQ ID NO 42
<211> LENGTH: 139
<212> TYPE: PRT
<213> ORGANISM: Artificial Sequence
<220> FEATURE:
<223> OTHER INFORMATION: Description of Artificial Sequence: Humanized
      H chain V region (version n) of anti-HM1.24 antibody

<400> SEQUENCE: 42

Met Asp Trp Thr Trp Arg Val Phe Phe Leu Leu Ala Val Ala Pro Gly
            -15                 -10                 -5

Ala His Ser Gln Val Gln Leu Val Gln Ser Gly Ala Glu Val Lys Lys
        -1  1                   5                   10

Pro Gly Ala Ser Val Lys Val Ser Cys Lys Ala Ser Gly Tyr Thr Phe
        15                  20                  25

Thr Pro Tyr Trp Met Gln Trp Val Arg Gln Ala Pro Gly Gln Gly Leu
30                  35                  40                  45

Glu Trp Met Gly Ser Ile Phe Pro Gly Asp Gly Asp Thr Arg Tyr Ser
            50                  55                  60

Gln Lys Phe Lys Gly Lys Val Thr Met Thr Ala Asp Thr Ser Ser Ser
        65                  70                  75

Thr Ala Tyr Met Glu Leu Ser Ile Leu Arg Ser Glu Asp Thr Ala Val
        80                  85                  90

Tyr Tyr Cys Ala Arg Gly Leu Arg Arg Gly Gly Tyr Tyr Phe Asp Tyr
    95                  100                 105

Trp Gly Gln Gly Thr Thr Val Thr Val Ser Ser
110                 115                 120

<210> SEQ ID NO 43
<211> LENGTH: 418
<212> TYPE: DNA
<213> ORGANISM: Artificial Sequence
<220> FEATURE:
<223> OTHER INFORMATION: Description of Artificial Sequence: DNA coding
      for humanized H chain V region (version o) of anti-HM1.24 antibody
<221> NAME/KEY: sig_peptide
<222> LOCATION: (1)..(57)
<221> NAME/KEY: mat_peptide
<222> LOCATION: (58)..(417)
<221> NAME/KEY: CDS
<222> LOCATION: (1)..(417)

<400> SEQUENCE: 43 atg gac tgg acc tgg agg gtc ttc ttc ttg ctg gct gta gct cca ggt       48
Met Asp Trp Thr Trp Arg Val Phe Phe Leu Leu Ala Val Ala Pro Gly
            -15                 -10                 -5
```

```
gct cac tcc cag gtg cag ctg gtg cag tct ggg gct gag gtg aag aag        96
Ala His Ser Gln Val Gln Leu Val Gln Ser Gly Ala Glu Val Lys Lys
        -1  1               5                      10 cct ggg gcc tca gtg aag gtt tcc tgc aag gca tct gga tac acc ttc       144
Pro Gly Ala Ser Val Lys Val Ser Cys Lys Ala Ser Gly Tyr Thr Phe
 15              20                      25 act ccc tac tgg atg cag tgg gtg cga cag gcc cct gga caa ggg ctt       192
Thr Pro Tyr Trp Met Gln Trp Val Arg Gln Ala Pro Gly Gln Gly Leu
 30              35                      40                   45 gag tgg atg gga tct att ttt cct gga gat ggt gat act agg tac agt       240
Glu Trp Met Gly Ser Ile Phe Pro Gly Asp Gly Asp Thr Arg Tyr Ser
                 50                      55                  60 cag aag ttc aag ggc aaa gtc acc atg acc gca gac acg tcc tcg agc       288
Gln Lys Phe Lys Gly Lys Val Thr Met Thr Ala Asp Thr Ser Ser Ser
             65                      70                  75 aca gcc tac atg gag ctg agc agc ctg aga tct gag gac tcg gcc gta       336
Thr Ala Tyr Met Glu Leu Ser Ser Leu Arg Ser Glu Asp Ser Ala Val
         80                      85                  90 tat tac tgt gcg aga gga tta cga cga ggg ggg tac tac ttt gac tac       384
Tyr Tyr Cys Ala Arg Gly Leu Arg Arg Gly Gly Tyr Tyr Phe Asp Tyr
     95                     100                     105 tgg ggg caa ggg acc acg gtc acc gtc tcc tca g                         418
Trp Gly Gln Gly Thr Thr Val Thr Val Ser Ser
110             115                 120
```

<210> SEQ ID NO 44
<211> LENGTH: 139
<212> TYPE: PRT
<213> ORGANISM: Artificial Sequence
<220> FEATURE:
<223> OTHER INFORMATION: Description of Artificial Sequence: Humanized
      H chain V region (version o) of anti-HM1.24 antibody

<400> SEQUENCE: 44

```
Met Asp Trp Thr Trp Arg Val Phe Phe Leu Leu Ala Val Ala Pro Gly
                -15                 -10                  -5

Ala His Ser Gln Val Gln Leu Val Gln Ser Gly Ala Glu Val Lys Lys
        -1   1               5                      10

Pro Gly Ala Ser Val Lys Val Ser Cys Lys Ala Ser Gly Tyr Thr Phe
 15              20                      25

Thr Pro Tyr Trp Met Gln Trp Val Arg Gln Ala Pro Gly Gln Gly Leu
 30              35                      40                   45

Glu Trp Met Gly Ser Ile Phe Pro Gly Asp Gly Asp Thr Arg Tyr Ser
                 50                      55                  60

Gln Lys Phe Lys Gly Lys Val Thr Met Thr Ala Asp Thr Ser Ser Ser
             65                      70                  75

Thr Ala Tyr Met Glu Leu Ser Ser Leu Arg Ser Glu Asp Ser Ala Val
         80                      85                  90

Tyr Tyr Cys Ala Arg Gly Leu Arg Arg Gly Gly Tyr Tyr Phe Asp Tyr
     95                     100                     105

Trp Gly Gln Gly Thr Thr Val Thr Val Ser Ser
110             115                 120
```

<210> SEQ ID NO 45
<211> LENGTH: 418
<212> TYPE: DNA
<213> ORGANISM: Artificial Sequence
<220> FEATURE:
<223> OTHER INFORMATION: Description of Artificial Sequence: DNA coding
      for humanized H chain V region (version p) of anti-HM1.24 antibody
<221> NAME/KEY: sig_peptide

```
<222> LOCATION: (1)..(57)
<221> NAME/KEY: mat_peptide
<222> LOCATION: (58)..(417)
<221> NAME/KEY: CDS
<222> LOCATION: (1)..(417)

<400> SEQUENCE: 45 atg gac tgg acc tgg agg gtc ttc ttc ttg ctg gct gta gct cca ggt       48
Met Asp Trp Thr Trp Arg Val Phe Phe Leu Leu Ala Val Ala Pro Gly
            -15                 -10                 -5 gct cac tcc cag gtg cag ctg gtg cag tct ggg gct gag gtg aag aag       96
Ala His Ser Gln Val Gln Leu Val Gln Ser Gly Ala Glu Val Lys Lys
        -1  1               5                   10 cct ggg gcc tca gtg aag gtt tcc tgc aag gca tct gga tac acc ttc      144
Pro Gly Ala Ser Val Lys Val Ser Cys Lys Ala Ser Gly Tyr Thr Phe
    15                  20                  25 act ccc tac tgg atg cag tgg gtg cga cag gcc cct gga caa ggg ctt      192
Thr Pro Tyr Trp Met Gln Trp Val Arg Gln Ala Pro Gly Gln Gly Leu
30                  35                  40                  45 gag tgg atg gga tct att ttt cct gga gat ggt gat act agg tac agt      240
Glu Trp Met Gly Ser Ile Phe Pro Gly Asp Gly Asp Thr Arg Tyr Ser
                50                  55                  60 cag aag ttc aag ggc aga gtc acc atg acc gca gac acg tcc acg agc      288
Gln Lys Phe Lys Gly Arg Val Thr Met Thr Ala Asp Thr Ser Thr Ser
            65                  70                  75 aca gcc tac atg gag ctg agc agc ctg aga tct gag gac acg gcc gtg      336
Thr Ala Tyr Met Glu Leu Ser Ser Leu Arg Ser Glu Asp Thr Ala Val
        80                  85                  90 tat tac tgt gcg aga gga tta cga cga ggg ggg tac tac ttt gac tac      384
Tyr Tyr Cys Ala Arg Gly Leu Arg Arg Gly Gly Tyr Tyr Phe Asp Tyr
    95                  100                 105 tgg ggg caa ggg acc acg gtc acc gtc tcc tca g                        418
Trp Gly Gln Gly Thr Thr Val Thr Val Ser Ser
110                 115                 120

<210> SEQ ID NO 46
<211> LENGTH: 139
<212> TYPE: PRT
<213> ORGANISM: Artificial Sequence
<220> FEATURE:
<223> OTHER INFORMATION: Description of Artificial Sequence: Humanized
      H chain V region (version p) of anti-HM1.24 antibody

<400> SEQUENCE: 46

Met Asp Trp Thr Trp Arg Val Phe Phe Leu Leu Ala Val Ala Pro Gly
            -15                 -10                 -5

Ala His Ser Gln Val Gln Leu Val Gln Ser Gly Ala Glu Val Lys Lys
        -1  1               5                   10

Pro Gly Ala Ser Val Lys Val Ser Cys Lys Ala Ser Gly Tyr Thr Phe
    15                  20                  25

Thr Pro Tyr Trp Met Gln Trp Val Arg Gln Ala Pro Gly Gln Gly Leu
30                  35                  40                  45

Glu Trp Met Gly Ser Ile Phe Pro Gly Asp Gly Asp Thr Arg Tyr Ser
                50                  55                  60

Gln Lys Phe Lys Gly Arg Val Thr Met Thr Ala Asp Thr Ser Thr Ser
            65                  70                  75

Thr Ala Tyr Met Glu Leu Ser Ser Leu Arg Ser Glu Asp Thr Ala Val
        80                  85                  90

Tyr Tyr Cys Ala Arg Gly Leu Arg Arg Gly Gly Tyr Tyr Phe Asp Tyr
    95                  100                 105
```

-continued

```
Trp Gly Gln Gly Thr Thr Val Thr Val Ser Ser
110             115             120

<210> SEQ ID NO 47
<211> LENGTH: 418
<212> TYPE: DNA
<213> ORGANISM: Artificial Sequence
<220> FEATURE:
<223> OTHER INFORMATION: Description of Artificial Sequence: DNA coding
      for humanized H chain V region (version p) of anti-HM1.24 antibody
<221> NAME/KEY: sig_peptide
<222> LOCATION: (1)..(57)
<221> NAME/KEY: mat_peptide
<222> LOCATION: (58)..(417)
<221> NAME/KEY: CDS
<222> LOCATION: (1)..(417)

<400> SEQUENCE: 47 atg gac tgg acc tgg agg gtc ttc ttc ttg ctg gct gta gct cca ggt      48
Met Asp Trp Thr Trp Arg Val Phe Phe Leu Leu Ala Val Ala Pro Gly
            -15                 -10                  -5 gct cac tcc cag gtg cag ctg gtg cag tct ggg gct gag gtg aag aag      96
Ala His Ser Gln Val Gln Leu Val Gln Ser Gly Ala Glu Val Lys Lys
        -1  1               5                   10 cct ggg gcc tca gtg aag gtt tcc tgc aag gca tct gga tac acc ttc     144
Pro Gly Ala Ser Val Lys Val Ser Cys Lys Ala Ser Gly Tyr Thr Phe
        15                  20                  25 act ccc tac tgg atg cag tgg gtg cga cag gcc cct gga caa ggg ctt     192
Thr Pro Tyr Trp Met Gln Trp Val Arg Gln Ala Pro Gly Gln Gly Leu
    30              35                  40                  45 gag tgg atg gga tct att ttt cct gga gat ggt gat act agg tac agt     240
Glu Trp Met Gly Ser Ile Phe Pro Gly Asp Gly Asp Thr Arg Tyr Ser
                50                  55                  60 cag aag ttc aag ggc aga gtc acc atg acc gca gac acg tcc tcg agc     288
Gln Lys Phe Lys Gly Arg Val Thr Met Thr Ala Asp Thr Ser Ser Ser
                65                  70                  75 aca gtc tac atg gag ctg agc agc ctg aga tct gag gac acg gcc gtg     336
Thr Val Tyr Met Glu Leu Ser Ser Leu Arg Ser Glu Asp Thr Ala Val
            80                  85                  90 tat tac tgt gcg aga gga tta cga cga ggg ggg tac tac ttt gac tac     384
Tyr Tyr Cys Ala Arg Gly Leu Arg Arg Gly Gly Tyr Tyr Phe Asp Tyr
        95                  100                 105 tgg ggg caa ggg acc acg gtc acc gtc tcc tca g                       418
Trp Gly Gln Gly Thr Thr Val Thr Val Ser Ser
110             115             120

<210> SEQ ID NO 48
<211> LENGTH: 139
<212> TYPE: PRT
<213> ORGANISM: Artificial Sequence
<220> FEATURE:
<223> OTHER INFORMATION: Description of Artificial Sequence: Humanizaed
      H chain V region (version p) of anti-HM1.24 antibody

<400> SEQUENCE: 48

Met Asp Trp Thr Trp Arg Val Phe Phe Leu Leu Ala Val Ala Pro Gly
            -15                 -10                  -5

Ala His Ser Gln Val Gln Leu Val Gln Ser Gly Ala Glu Val Lys Lys
        -1  1               5                   10

Pro Gly Ala Ser Val Lys Val Ser Cys Lys Ala Ser Gly Tyr Thr Phe
        15                  20                  25

Thr Pro Tyr Trp Met Gln Trp Val Arg Gln Ala Pro Gly Gln Gly Leu
    30              35                  40                  45
```

```
Glu Trp Met Gly Ser Ile Phe Pro Gly Asp Gly Asp Thr Arg Tyr Ser
            50                  55                  60

Gln Lys Phe Lys Gly Arg Val Thr Met Thr Ala Asp Thr Ser Ser Ser
            65                  70                  75

Thr Val Tyr Met Glu Leu Ser Ser Leu Arg Ser Glu Asp Thr Ala Val
            80                  85                  90

Tyr Tyr Cys Ala Arg Gly Leu Arg Arg Gly Gly Tyr Tyr Phe Asp Tyr
            95                  100                 105

Trp Gly Gln Gly Thr Thr Val Thr Val Ser Ser
110             115                 120

<210> SEQ ID NO 49
<211> LENGTH: 418
<212> TYPE: DNA
<213> ORGANISM: Artificial Sequence
<220> FEATURE:
<223> OTHER INFORMATION: Description of Artificial Sequence: DNA coding
      for humanized H chain V region (version r) of anti-HM1.24 antibody
<221> NAME/KEY: sig_peptide
<222> LOCATION: (1)..(57)
<221> NAME/KEY: mat_peptide
<222> LOCATION: (58)..(417)
<221> NAME/KEY: CDS
<222> LOCATION: (1)..(417)

<400> SEQUENCE: 49 atg gac tgg acc tgg agg gtc ttc ttc ttg ctg gct gta gct cca ggt      48
Met Asp Trp Thr Trp Arg Val Phe Phe Leu Leu Ala Val Ala Pro Gly
            -15                 -10                 -5 gct cac tcc cag gtg cag ctg gtg cag tct ggg gct gag gtg aag aag      96
Ala His Ser Gln Val Gln Leu Val Gln Ser Gly Ala Glu Val Lys Lys
        -1  1               5                   10 cct ggg gcc tca gtg aag gtt tcc tgc aag gca tct gga tac acc ttc     144
Pro Gly Ala Ser Val Lys Val Ser Cys Lys Ala Ser Gly Tyr Thr Phe
        15                  20                  25 act ccc tac tgg atg cag tgg gtg cga cag gcc cct gga caa ggg ctt     192
Thr Pro Tyr Trp Met Gln Trp Val Arg Gln Ala Pro Gly Gln Gly Leu
30                  35                  40                  45 gag tgg atg gga tct att ttt cct gga gat ggt gat act agg tac agt     240
Glu Trp Met Gly Ser Ile Phe Pro Gly Asp Gly Asp Thr Arg Tyr Ser
            50                  55                  60 cag aag ttc aag ggc aga gtc acc atg acc gca gac aag tcc acg agc     288
Gln Lys Phe Lys Gly Arg Val Thr Met Thr Ala Asp Lys Ser Thr Ser
            65                  70                  75 aca gcc tac atg gag ctg agc agc ctg aga tct gag gac acg gcc gtg     336
Thr Ala Tyr Met Glu Leu Ser Ser Leu Arg Ser Glu Asp Thr Ala Val
            80                  85                  90 tat tac tgt gcg aga gga tta cga cga ggg ggg tac tac ttt gac tac     384
Tyr Tyr Cys Ala Arg Gly Leu Arg Arg Gly Gly Tyr Tyr Phe Asp Tyr
            95                  100                 105 tgg ggg caa ggg acc acg gtc acc gtc tcc tca g                       418
Trp Gly Gln Gly Thr Thr Val Thr Val Ser Ser
110             115                 120

<210> SEQ ID NO 50
<211> LENGTH: 139
<212> TYPE: PRT
<213> ORGANISM: Artificial Sequence
<220> FEATURE:
<223> OTHER INFORMATION: Description of Artificial Sequence: Humanized
      H chain V region (version r) of anti-HM1.24 antibody

<400> SEQUENCE: 50
```

```
Met Asp Trp Thr Trp Arg Val Phe Phe Leu Leu Ala Val Ala Pro Gly
            -15                 -10                  -5

Ala His Ser Gln Val Gln Leu Val Gln Ser Gly Ala Glu Val Lys Lys
         -1   1              5                  10

Pro Gly Ala Ser Val Lys Val Ser Cys Lys Ala Ser Gly Tyr Thr Phe
     15              20                  25

Thr Pro Tyr Trp Met Gln Trp Val Arg Gln Ala Pro Gly Gln Gly Leu
 30              35                  40                      45

Glu Trp Met Gly Ser Ile Phe Pro Gly Asp Gly Asp Thr Arg Tyr Ser
             50                  55                  60

Gln Lys Phe Lys Gly Arg Val Thr Met Thr Ala Asp Lys Ser Thr Ser
             65                  70                  75

Thr Ala Tyr Met Glu Leu Ser Ser Leu Arg Ser Glu Asp Thr Ala Val
             80                  85                  90

Tyr Tyr Cys Ala Arg Gly Leu Arg Arg Gly Tyr Tyr Phe Asp Tyr
 95             100                 105

Trp Gly Gln Gly Thr Thr Val Thr Val Ser Ser
110             115                 120

<210> SEQ ID NO 51
<211> LENGTH: 40
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 51
actagtcgac atgaagttgc ctgttaggct gttggtgctg                    40

<210> SEQ ID NO 52
<211> LENGTH: 39
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 52
actagtcgac atggagwcag acacactcct gytatgggt                     39

<210> SEQ ID NO 53
<211> LENGTH: 40
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 53
actagtcgac atgagtgtgc tcactcaggt cctggsgttg                    40

<210> SEQ ID NO 54
<211> LENGTH: 43
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 54
actagtcgac atgaggrccc ctgctcagwt tyttggmwtc ttg                43
```

<210> SEQ ID NO 55
<211> LENGTH: 40
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 55
actagtcgac atggatttwc aggtgcagat twtcagcttc                                  40

<210> SEQ ID NO 56
<211> LENGTH: 37
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 56
actagtcgac atgaggtkcy ytgytsagyt yctgrgg                                     37

<210> SEQ ID NO 57
<211> LENGTH: 41
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 57
actagtcgac atgggcwtca agatggagtc acakwyycwg g                                41

<210> SEQ ID NO 58
<211> LENGTH: 41
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 58
actagtcgac atgtggggay ctktttycmm tttttcaatt g                                41

<210> SEQ ID NO 59
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 59
actagtcgac atggtrtccw casctcagtt ccttg                                       35

<210> SEQ ID NO 60
<211> LENGTH: 37
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 60
actagtcgac atgtatatat gtttgttgtc tatttct                                     37

<210> SEQ ID NO 61
<211> LENGTH: 38
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 61
actagtcgac atggaagccc cagctcagct tctcttcc                              38

<210> SEQ ID NO 62
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 62
ggatcccggg tggatggtgg gaagatg                                          27

<210> SEQ ID NO 63
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 63
tagagtcacc gaggagccag ttgta                                            25

<210> SEQ ID NO 64
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 64
ggatcccggg agtggataga ccgatg                                           26

<210> SEQ ID NO 65
<211> LENGTH: 34
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 65
gataagcttc caccatgggc ttcaagatgg agtc                                  34

<210> SEQ ID NO 66
<211> LENGTH: 34
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 66
gataagcttc caccatggaa tgtaactgga tact                                  34

<210> SEQ ID NO 67

```
<211> LENGTH: 34
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 67
ggcggatcca ctcacgtttt atttccaact ttgt                                34

<210> SEQ ID NO 68
<211> LENGTH: 34
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 68
ggcggatcca ctcacctgag gagactgtga gagt                                34

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 69
cagacagtgg ttcaaagt                                                  18

<210> SEQ ID NO 70
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 70
gaattcggat ccactcacgt ttgatt                                         26

<210> SEQ ID NO 71
<211> LENGTH: 48
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 71
agtcaggatg tgaatactgc tgtagcctgg taccagcaga agccagga                 48

<210> SEQ ID NO 72
<211> LENGTH: 39
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 72
gcatccaacc ggtacactgg tgtgccaagc agattcagc                           39

<210> SEQ ID NO 73
<211> LENGTH: 45
```

<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 73
caacattata gtactccatt cacgttcggc caagggacca aggtg                45

<210> SEQ ID NO 74
<211> LENGTH: 47
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 74
gcagtattca catcctgact ggccttacag gtgatggtca ctctgtc             47

<210> SEQ ID NO 75
<211> LENGTH: 38
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 75
acaccagtgt accggttgga tgccgagtag atcagcag                       38

<210> SEQ ID NO 76
<211> LENGTH: 41
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 76
gtgaatggag tactataatg ttgctggcag tagtaggtag c                   41

<210> SEQ ID NO 77
<211> LENGTH: 31
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 77
ggtaccgact acaccttcac catcagcagc c                              31

<210> SEQ ID NO 78
<211> LENGTH: 31
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 78
ggtgaaggtg tagtcggtac cgctaccgct a                              31

<210> SEQ ID NO 79
<211> LENGTH: 144
<212> TYPE: DNA

```
<213> ORGANISM: Artificial Sequence
<220> FEATURE:
<223> OTHER INFORMATION: Description of Artificial Sequence: Synthetic
      DNA Primer

<400> SEQUENCE: 79
atgccttgca ggaaaccttc actgaggccc caggcttctt cacctcagcc ccagactgca      60
ccagctgcac ctgggagtga gcacctggag ctacagccag caagaagaag accctccagg     120
tccagtccat ggtggaagct tatc                                             144

<210> SEQ ID NO 80
<211> LENGTH: 130
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 80
tcagtgaagg tttcctgcaa ggcatctgga tacaccttca ctccctactg gatgcagtgg      60
gtgcgacagg cccctggaca agggcttgag tggatgggat ctattttcc tggagatggt     120 gatactaggt                                                             130

<210> SEQ ID NO 81
<211> LENGTH: 131
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 81
aatacacggc cgtgtcctca gatctcaggc tgctcagctc catgtagact gtgctcgtgg      60
acgtgtctgc ggtcatggtg actctgccct tgaacttctg actgtaccta gtatcaccat     120
ctccaggaaa a                                                           131

<210> SEQ ID NO 82
<211> LENGTH: 119
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 82
gagatctgag gacacggccg tgtattactg tgcgagagga ttacgacgag gggggtacta      60
ctttgactac tggggcaag ggaccacggt caccgtctcc tcaggtgagt ggatccgac       119

<210> SEQ ID NO 83
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 83
gataagcttc caccatggac tggac                                            25

<210> SEQ ID NO 84
<211> LENGTH: 25
<212> TYPE: DNA
```

```
<213> ORGANISM: Artificial Sequence
<220> FEATURE:
<223> OTHER INFORMATION: Description of Artificial Sequence: Synthetic
      DNA Primer

<400> SEQUENCE: 84
gtcggatcca ctcacctgag gagac                                          25

<210> SEQ ID NO 85
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 85
aagttcaagg gcaaagtcac catgac                                         26

<210> SEQ ID NO 86
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 86
gtcatggtga ctttgccctt gaactt                                         26

<210> SEQ ID NO 87
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 87
atgaccgcag acaagtccac gagcac                                         26

<210> SEQ ID NO 88
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 88
gtgctcgtgg acttgtctgc ggtcat                                         26

<210> SEQ ID NO 89
<211> LENGTH: 47
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 89
aagttcaagg gcaaagtcac catgaccgca gacaagtcca cgagcac                  47

<210> SEQ ID NO 90
<211> LENGTH: 47
<212> TYPE: DNA
<213> ORGANISM: Artificial Sequence
```

```
<220> FEATURE:
<223> OTHER INFORMATION: Description of Artificial Sequence: Synthetic
      DNA Primer

<400> SEQUENCE: 90
gtgctcgtgg acttgtctgc ggtcatggtg actttgccct tgaactt                    47

<210> SEQ ID NO 91
<211> LENGTH: 38
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 91
aagttcaagg gcagagccac cctgaccgca gacacgtc                              38

<210> SEQ ID NO 92
<211> LENGTH: 38
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 92
gacgtgtctg cggtcagggt ggctctgccc ttgaactt                              38

<210> SEQ ID NO 93
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 93
cagacagtgg ttcaaagt                                                    18

<210> SEQ ID NO 94
<211> LENGTH: 17
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 94
gccccaaagc caaggtc                                                     17

<210> SEQ ID NO 95
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 95
atttttcctg gagatggtga tac                                              23

<210> SEQ ID NO 96
<211> LENGTH: 23
<212> TYPE: DNA
<213> ORGANISM: Artificial Sequence
<220> FEATURE:
```

<223> OTHER INFORMATION: Description of Artificial Sequence: Synthetic
       DNA Primer

<400> SEQUENCE: 96
gtatcaccat ctccaggaaa tat                                              23

<210> SEQ ID NO 97
<211> LENGTH: 418
<212> TYPE: DNA
<213> ORGANISM: Artificial Sequence
<220> FEATURE:
<223> OTHER INFORMATION: Description of Artificial Sequence: DNA coding
       for humanized H chain V region (native/version a mix)of anti-
       HM1.24antibody
<221> NAME/KEY: sig_peptide
<222> LOCATION: (1)..(57)
<221> NAME/KEY: mat_peptide
<222> LOCATION: (58)..(417)
<221> NAME/KEY: CDS
<222> LOCATION: (1)..(417)

<400> SEQUENCE: 97

```
atg gaa tgt aac tgg ata ctt cct ttt att ctg tca gta act tca ggt      48
Met Glu Cys Asn Trp Ile Leu Pro Phe Ile Leu Ser Val Thr Ser Gly
            -15                 -10                 -5 gcc tac tca cag gtt caa ctc cag cag tct ggg gct gag ctg gca aga      96
Ala Tyr Ser Gln Val Gln Leu Gln Gln Ser Gly Ala Glu Leu Ala Arg
        -1   1               5                  10 cct ggg gct tca gtg aag ttg tcc tgc aag gct tct ggc tac acc ttt     144
Pro Gly Ala Ser Val Lys Leu Ser Cys Lys Ala Ser Gly Tyr Thr Phe
     15                  20                  25 act ccc tac tgg atg cag tgg gta aaa cag agg cct gga cag ggt ctg     192
Thr Pro Tyr Trp Met Gln Trp Val Lys Gln Arg Pro Gly Gln Gly Leu
 30              35                  40                  45 gaa tgg att ggg tct att ttt cct gga gat ggt gat act agg tac agt     240
Glu Trp Ile Gly Ser Ile Phe Pro Gly Asp Gly Asp Thr Arg Tyr Ser
                 50                  55                  60 cag aag ttc aag ggc aga gtc acc atg acc gca gac acg tcc acg agc     288
Gln Lys Phe Lys Gly Arg Val Thr Met Thr Ala Asp Thr Ser Thr Ser
             65                  70                  75 aca gtc tac atg gag ctg agc agc ctg aga tct gag gac acg gcc gtg     336
Thr Val Tyr Met Glu Leu Ser Ser Leu Arg Ser Glu Asp Thr Ala Val
         80                  85                  90 tat tac tgt gcg aga gga tta cga cga ggg ggg tac tac ttt gac tac     384
Tyr Tyr Cys Ala Arg Gly Leu Arg Arg Gly Gly Tyr Tyr Phe Asp Tyr
     95                 100                 105 tgg ggg caa ggg acc acg gtc acc gtc tcc tca g                       418
Trp Gly Gln Gly Thr Thr Val Thr Val Ser Ser
110             115                 120
```

<210> SEQ ID NO 98
<211> LENGTH: 139
<212> TYPE: PRT
<213> ORGANISM: Artificial Sequence
<220> FEATURE:
<223> OTHER INFORMATION: Description of Artificial Sequence: Humanized
       H chain V region (native/version a mix) of anti-HM1.24 antibody

<400> SEQUENCE: 98

Met Glu Cys Asn Trp Ile Leu Pro Phe Ile Leu Ser Val Thr Ser Gly
            -15                 -10                 -5

Ala Tyr Ser Gln Val Gln Leu Gln Gln Ser Gly Ala Glu Leu Ala Arg
        -1   1               5                  10

Pro Gly Ala Ser Val Lys Leu Ser Cys Lys Ala Ser Gly Tyr Thr Phe

```
                 15                  20                  25
Thr Pro Tyr Trp Met Gln Trp Val Lys Gln Arg Pro Gly Gln Gly Leu
 30                  35                  40                  45

Glu Trp Ile Gly Ser Ile Phe Pro Gly Asp Gly Asp Thr Arg Tyr Ser
                 50                  55                  60

Gln Lys Phe Lys Gly Arg Val Thr Met Thr Ala Asp Thr Ser Thr Ser
             65                  70                  75

Thr Val Tyr Met Glu Leu Ser Ser Leu Arg Ser Glu Asp Thr Ala Val
         80                  85                  90

Tyr Tyr Cys Ala Arg Gly Leu Arg Arg Gly Gly Tyr Tyr Phe Asp Tyr
     95                 100                 105

Trp Gly Gln Gly Thr Thr Val Thr Val Ser Ser
110                 115                 120

<210> SEQ ID NO 99
<211> LENGTH: 418
<212> TYPE: DNA
<213> ORGANISM: Artificial Sequence
<220> FEATURE:
<223> OTHER INFORMATION: Description of Artificial Sequence: DNA coding
      for humanized C chain V region (native/version a mix)of anti-
      HM1.24 antibody
<221> NAME/KEY: sig_peptide
<222> LOCATION: (1)..(57)
<221> NAME/KEY: mat_peptide
<222> LOCATION: (58)..(417)
<221> NAME/KEY: CDS
<222> LOCATION: (1)..(417)

<400> SEQUENCE: 99 atg gac tgg acc tgg agg gtc ttc ttc ttg ctg gct gta gct cca ggt        48
Met Asp Trp Thr Trp Arg Val Phe Phe Leu Leu Ala Val Ala Pro Gly
            -15                 -10                  -5 gct cac tcc cag gtg cag ctg gtg cag tct ggg gct gag gtg aag aag        96
Ala His Ser Gln Val Gln Leu Val Gln Ser Gly Ala Glu Val Lys Lys
         -1   1                   5                  10 cct ggg gcc tca gtg aag gtt tcc tgc aag gca tct gga tac acc ttc       144
Pro Gly Ala Ser Val Lys Val Ser Cys Lys Ala Ser Gly Tyr Thr Phe
 15                  20                  25 act ccc tac tgg atg cag tgg gtg cga cag gcc cct gga caa ggg ctt       192
Thr Pro Tyr Trp Met Gln Trp Val Arg Gln Ala Pro Gly Gln Gly Leu
 30                  35                  40                  45 gag tgg atg gga tct att ttt cct gga gat ggt gat act agg tac agt       240
Glu Trp Met Gly Ser Ile Phe Pro Gly Asp Gly Asp Thr Arg Tyr Ser
                 50                  55                  60 cag aag ttc aag ggc aag gcc aca ttg act gca gat aaa tcc tcc agt       288
Gln Lys Phe Lys Gly Lys Ala Thr Leu Thr Ala Asp Lys Ser Ser Ser
             65                  70                  75 aca gcc tac atg caa ctc agc atc ttg gca ttt gag gac tct gcg gtc       336
Thr Ala Tyr Met Gln Leu Ser Ile Leu Ala Phe Glu Asp Ser Ala Val
         80                  85                  90 tat tac tgt gca aga gga tta cga cga ggg ggg tac tac ttt gac tac       384
Tyr Tyr Cys Ala Arg Gly Leu Arg Arg Gly Gly Tyr Tyr Phe Asp Tyr
     95                 100                 105 tgg ggc caa ggc acc act ctc aca gtc tcc tca g                         418
Trp Gly Gln Gly Thr Thr Leu Thr Val Ser Ser
110                 115                 120

<210> SEQ ID NO 100
<211> LENGTH: 139
<212> TYPE: PRT
<213> ORGANISM: Artificial Sequence
```

<220> FEATURE:
<223> OTHER INFORMATION: Description of Artificial Sequence: Humanized
     C chain V region (native/version a mix) of anti-HM1.24 antibody

<400> SEQUENCE: 100

```
Met Asp Trp Thr Trp Arg Val Phe Phe Leu Leu Ala Val Ala Pro Gly
            -15                 -10                 -5

Ala His Ser Gln Val Gln Leu Val Gln Ser Gly Ala Glu Val Lys Lys
     -1   1               5                  10

Pro Gly Ala Ser Val Lys Val Ser Cys Lys Ala Ser Gly Tyr Thr Phe
         15                  20                  25

Thr Pro Tyr Trp Met Gln Trp Val Arg Gln Ala Pro Gly Gln Gly Leu
 30              35                  40                      45

Glu Trp Met Gly Ser Ile Phe Pro Gly Asp Gly Asp Thr Arg Tyr Ser
             50                  55                  60

Gln Lys Phe Lys Gly Lys Ala Thr Leu Thr Ala Asp Lys Ser Ser Ser
             65                  70                  75

Thr Ala Tyr Met Gln Leu Ser Ile Leu Ala Phe Glu Asp Ser Ala Val
             80                  85                  90

Tyr Tyr Cys Ala Arg Gly Leu Arg Arg Gly Gly Tyr Tyr Phe Asp Tyr
     95                 100                 105

Trp Gly Gln Gly Thr Thr Leu Thr Val Ser Ser
110             115                 120
```

<210> SEQ ID NO 101
<211> LENGTH: 38
<212> TYPE: DNA
<213> ORGANISM: Artificial Sequence
<220> FEATURE:
<223> OTHER INFORMATION: Description of Artificial Sequence: Synthetic
     DNA Primer

<400> SEQUENCE: 101
ctggttcggc ccacctctga aggttccaga atcgatag                        38

<210> SEQ ID NO 102
<211> LENGTH: 35
<212> TYPE: DNA
<213> ORGANISM: Artificial Sequence
<220> FEATURE:
<223> OTHER INFORMATION: Description of Artificial Sequence: Synthetic
     DNA Primer

<400> SEQUENCE: 102
gcagacacgt cctcgagcac agcctacatg gagct                           35

<210> SEQ ID NO 103
<211> LENGTH: 35
<212> TYPE: DNA
<213> ORGANISM: Artificial Sequence
<220> FEATURE:
<223> OTHER INFORMATION: Description of Artificial Sequence: Synthetic
     DNA Primer

<400> SEQUENCE: 103
agctccatgt aggctgtgct cgaggacgtg tctgc                           35

<210> SEQ ID NO 104
<211> LENGTH: 26
<212> TYPE: DNA
<213> ORGANISM: Artificial Sequence
<220> FEATURE:
<223> OTHER INFORMATION: Description of Artificial Sequence: Synthetic DNA Primer

<400> SEQUENCE: 104
tgggtgcgac agcgccctgg acaagg                                              26

<210> SEQ ID NO 105
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 105
ccttgtccag ggcgctgtcg caccca                                              26

<210> SEQ ID NO 106
<211> LENGTH: 41
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 106
tacatggagc tgagcagcct ggcatttgag gacacggccg t                             41

<210> SEQ ID NO 107
<211> LENGTH: 41
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 107
acggccgtgt cctcaaatgc caggctgctc agctccatgt a                             41

<210> SEQ ID NO 108
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 108
aagttcaagg gcaaagccac cctgac                                              26

<210> SEQ ID NO 109
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 109
gtcagggtgg ctttgccctt gaactt                                              26

<210> SEQ ID NO 110
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA Primer

```
<400> SEQUENCE: 110
gcctacatgc agctgagcag cct                                              23

<210> SEQ ID NO 111
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 111
aggctgctca gctgcatgta ggc                                              23

<210> SEQ ID NO 112
<211> LENGTH: 38
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 112
gcctacatgc agctgagcat cctgagatct gaggacac                              38

<210> SEQ ID NO 113
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 113
gatctcagga tgctcagctg catgtaggct gtgct                                 35

<210> SEQ ID NO 114
<211> LENGTH: 50
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 114
gcctacatgc agctgagcat cctgagatct gaggactcgg ccgtgtatta                 50

<210> SEQ ID NO 115
<211> LENGTH: 50
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 115
acggccgagt cctcagatct caggatgctc agctgcatgt aggctgtgct                 50

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA Primer
```

```
<400> SEQUENCE: 116
gagctgagca tcctgagatc                                               20

<210> SEQ ID NO 117
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 117
gatctcagga tgctcagctc catgta                                        26

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 118
agatctgagg actcggccgt                                               20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 119
acggccgagt cctcagatct                                               20

<210> SEQ ID NO 120
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 120
gcagacacgt ccacgagcac agcctacatg gagct                              35

<210> SEQ ID NO 121
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 121
agctccatgt aggctgtgct cgtggacgtg tctgc                              35

<210> SEQ ID NO 122
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 122
```

-continued

```
gcagacacgt cctcgagcac agtctacatg gagct                                35

<210> SEQ ID NO 123
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 123
agctccatgt agactgtgct cgaggacgtg tctgc                                35

<210> SEQ ID NO 124
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 124
agagtcacca tcaccgcaga caagtc                                          26

<210> SEQ ID NO 125
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 125
gacttgtctg cggtgatggt gactct                                          26

<210> SEQ ID NO 126
<211> LENGTH: 418
<212> TYPE: DNA
<213> ORGANISM: Artificial Sequence
<220> FEATURE:
<223> OTHER INFORMATION: Description of Artificial Sequence: DNA coding
      for humanized H chain V region (version s) of HM1.24antibody
<221> NAME/KEY: sig_peptide
<222> LOCATION: (1)..(57)
<221> NAME/KEY: mat_peptide
<222> LOCATION: (58)..(417)
<221> NAME/KEY: CDS
<222> LOCATION: (1)..(417)

<400> SEQUENCE: 126 atg gac tgg acc tgg agg gtc ttc ttc ttg ctg gct gta gct cca ggt       48
Met Asp Trp Thr Trp Arg Val Phe Phe Leu Leu Ala Val Ala Pro Gly
            -15                 -10                 -5 gct cac tcc cag gtg cag ctg gtg cag tct ggg gct gag gtg aag aag       96
Ala His Ser Gln Val Gln Leu Val Gln Ser Gly Ala Glu Val Lys Lys
        -1   1               5                  10 cct ggg gcc tca gtg aag gtt tcc tgc aag gca tct gga tac acc ttc      144
Pro Gly Ala Ser Val Lys Val Ser Cys Lys Ala Ser Gly Tyr Thr Phe
         15                  20                  25 act ccc tac tgg atg cag tgg gtg cga cag gcc cct gga caa ggg ctt      192
Thr Pro Tyr Trp Met Gln Trp Val Arg Gln Ala Pro Gly Gln Gly Leu
 30                  35                  40                  45 gag tgg atg gga tct att ttt cct gga gat ggt gat act agg tac agt      240
Glu Trp Met Gly Ser Ile Phe Pro Gly Asp Gly Asp Thr Arg Tyr Ser
                 50                  55                  60
```

-continued

```
cag aag ttc aag ggc aga gtc acc atc acc gca gac aag tcc acg agc        288
Gln Lys Phe Lys Gly Arg Val Thr Ile Thr Ala Asp Lys Ser Thr Ser
            65                  70                  75 aca gcc tac atg gag ctg agc agc ctg aga tct gag gac acg gcc gtg        336
Thr Ala Tyr Met Glu Leu Ser Ser Leu Arg Ser Glu Asp Thr Ala Val
        80                  85                  90 tat tac tgt gcg aga gga tta cga cga ggg ggg tac tac ttt gac tac        384
Tyr Tyr Cys Ala Arg Gly Leu Arg Arg Gly Gly Tyr Tyr Phe Asp Tyr
    95                 100                 105 tgg ggg caa ggg acc acg gtc acc gtc tcc tca g                          418
Trp Gly Gln Gly Thr Thr Val Thr Val Ser Ser
110                 115                 120
```

<210> SEQ ID NO 127
<211> LENGTH: 139
<212> TYPE: PRT
<213> ORGANISM: Artificial Sequence
<220> FEATURE:
<223> OTHER INFORMATION: Description of Artificial Sequence: Humanized
      H chain V region (version s) of HM1.24 antibody

<400> SEQUENCE: 127

```
Met Asp Trp Thr Trp Arg Val Phe Phe Leu Leu Ala Val Ala Pro Gly
            -15                 -10                  -5

Ala His Ser Gln Val Gln Leu Val Gln Ser Gly Ala Glu Val Lys Lys
     -1   1               5                  10

Pro Gly Ala Ser Val Lys Val Ser Cys Lys Ala Ser Gly Tyr Thr Phe
        15                  20                  25

Thr Pro Tyr Trp Met Gln Trp Val Arg Gln Ala Pro Gly Gln Gly Leu
 30                  35                  40                  45

Glu Trp Met Gly Ser Ile Phe Pro Gly Asp Gly Asp Thr Arg Tyr Ser
                50                  55                  60

Gln Lys Phe Lys Gly Arg Val Thr Ile Thr Ala Asp Lys Ser Thr Ser
            65                  70                  75

Thr Ala Tyr Met Glu Leu Ser Ser Leu Arg Ser Glu Asp Thr Ala Val
        80                  85                  90

Tyr Tyr Cys Ala Arg Gly Leu Arg Arg Gly Gly Tyr Tyr Phe Asp Tyr
    95                 100                 105

Trp Gly Gln Gly Thr Thr Val Thr Val Ser Ser
110                 115                 120
```

<210> SEQ ID NO 128
<211> LENGTH: 1013
<212> TYPE: DNA
<213> ORGANISM: Homo sapiens
<220> FEATURE:
<221> NAME/KEY: CDS
<222> LOCATION: (23)..(562)
<223> OTHER INFORMATION: DNA coding for HM1.24 antigenic protein

<400> SEQUENCE: 128

```
gaattcggca cgagggatct gg atg gca tct act tcg tat gac tat tgc aga        52
                        Met Ala Ser Thr Ser Tyr Asp Tyr Cys Arg
                         1               5                  10 gtg ccc atg gaa gac ggg gat aag cgc tgt aag ctt ctg ctg ggg ata       100
Val Pro Met Glu Asp Gly Asp Lys Arg Cys Lys Leu Leu Leu Gly Ile
                15                  20                  25 gga att ctg gtg ctc ctg atc atc gtg att ctg ggg gtg ccc ttg att       148
Gly Ile Leu Val Leu Leu Ile Ile Val Ile Leu Gly Val Pro Leu Ile
        30                  35                  40 atc ttc acc atc aag gcc aac agc gag gcc tgc cgg gac ggc ctt cgg       196
```

| | | |
|---|---|---|
| Ile Phe Thr Ile Lys Ala Asn Ser Glu Ala Cys Arg Asp Gly Leu Arg<br>            45                    50                    55 | | |
| gca gtg atg gag tgt cgc aat gtc acc cat ctc ctg caa caa gag ctg<br>Ala Val Met Glu Cys Arg Asn Val Thr His Leu Leu Gln Gln Glu Leu<br> 60                      65                      70 | 244 | |
| acc gag gcc cag aag ggc ttt cag gat gtg gag gcc cag gcc gcc acc<br>Thr Glu Ala Gln Lys Gly Phe Gln Asp Val Glu Ala Gln Ala Ala Thr<br> 75                      80                    85                    90 | 292 | |
| tgc aac cac act gtg atg gcc cta atg gct tcc ctg gat gca gag aag<br>Cys Asn His Thr Val Met Ala Leu Met Ala Ser Leu Asp Ala Glu Lys<br>            95                    100                   105 | 340 | |
| gcc caa gga caa aag aaa gtg gag gag ctt gag gga gag atc act aca<br>Ala Gln Gly Gln Lys Lys Val Glu Glu Leu Glu Gly Glu Ile Thr Thr<br>            110                   115                  120 | 388 | |
| tta aac cat aag ctt cag gac gcg tct gca gag gtg gag cga ctg aga<br>Leu Asn His Lys Leu Gln Asp Ala Ser Ala Glu Val Glu Arg Leu Arg<br>            125                   130                  135 | 436 | |
| aga gaa aac cag gtc tta agc gtg aga atc gcg gac aag aag tac tac<br>Arg Glu Asn Gln Val Leu Ser Val Arg Ile Ala Asp Lys Lys Tyr Tyr<br> 140                      145                   150 | 484 | |
| ccc agc tcc cag gac tcc agc tcc gct gcg gcg ccc cag ctg ctg att<br>Pro Ser Ser Gln Asp Ser Ser Ser Ala Ala Ala Pro Gln Leu Leu Ile<br>155                      160                    165                   170 | 532 | |
| gtg ctg ctg ggc ctc agc gct ctg ctg cag tgagatccca ggaagctggc<br>Val Leu Leu Gly Leu Ser Ala Leu Leu Gln<br>            175                   180 | 582 | |
| acatcttgga aggtccgtcc tgctcggctt ttcgcttgaa cattcccttg atctcatcag | 642 | |
| ttctgagcgg tcatggggc aacacggtta gcggggagag cacgggtag ccggagaagg | 702 | |
| gcctctggac aggtctgga ggggccatgg ggcagtcctg ggtctgggga cacagtcggg | 762 | |
| ttgacccagg gctgtctccc tccagagcct ccctccggac aatgagtccc cctcttgtc | 822 | |
| tcccaccctg agattgggca tggggtgcgg tgtgggggc atgtgctgcc tgttgttatg | 882 | |
| ggttttttt gcgggggggg ttgctttttt ctgggtcctt tgagctccaa aaaataaac | 942 | |
| acttcctttg agggagagca caccttaaaa aaaaaaaaa aaaaaaaaa aaaaaaattc | 1002 | |
| gggcggccgc c | 1013 | |

```
<210> SEQ ID NO 129
<211> LENGTH: 180
<212> TYPE: PRT
<213> ORGANISM: Homo sapiens
<220> FEATURE:
<223> OTHER INFORMATION: HM1.24 antigenic protein

<400> SEQUENCE: 129
```

Met Ala Ser Thr Ser Tyr Asp Tyr Cys Arg Val Pro Met Glu Asp Gly
  1               5                  10                  15

Asp Lys Arg Cys Lys Leu Leu Leu Gly Ile Gly Ile Leu Val Leu Leu
             20                  25                  30

Ile Ile Val Ile Leu Gly Val Pro Leu Ile Ile Phe Thr Ile Lys Ala
         35                  40                  45

Asn Ser Glu Ala Cys Arg Asp Gly Leu Arg Ala Val Met Glu Cys Arg
     50                  55                  60

Asn Val Thr His Leu Leu Gln Gln Glu Leu Thr Glu Ala Gln Lys Gly
 65                  70                  75                  80

Phe Gln Asp Val Glu Ala Gln Ala Ala Thr Cys Asn His Thr Val Met
                 85                  90                  95

```
Ala Leu Met Ala Ser Leu Asp Ala Glu Lys Ala Gln Gly Gln Lys Lys
            100                 105                 110

Val Glu Glu Leu Glu Gly Glu Ile Thr Thr Leu Asn His Lys Leu Gln
        115                 120                 125

Asp Ala Ser Ala Glu Val Glu Arg Leu Arg Arg Glu Asn Gln Val Leu
    130                 135                 140

Ser Val Arg Ile Ala Asp Lys Lys Tyr Tyr Pro Ser Ser Gln Asp Ser
145                 150                 155                 160

Ser Ser Ala Ala Ala Pro Gln Leu Leu Ile Val Leu Leu Gly Leu Ser
                165                 170                 175

Ala Leu Leu Gln
            180

<210> SEQ ID NO 130
<211> LENGTH: 107
<212> TYPE: PRT
<213> ORGANISM: Artificial Sequence
<220> FEATURE:
<223> OTHER INFORMATION: Description of Artificial Sequence: Amino acid
      sequence of the L chain V region of AHM

<400> SEQUENCE: 130

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Ile Thr Gly
    50                  55                  60

Ser Gly Ser Gly Thr Asp Phe Thr Phe Thr Ile Ser Ser Val Gln Ala
65                  70                  75                  80

Glu Asp Leu Ala Leu Tyr Tyr Cys Gln Gln His Tyr Ser Thr Pro Phe
                85                  90                  95

Thr Phe Gly Ser Gly Thr Lys Leu Glu Ile Lys
            100                 105

<210> SEQ ID NO 131
<211> LENGTH: 80
<212> TYPE: PRT
<213> ORGANISM: Artificial Sequence
<220> FEATURE:
<223> OTHER INFORMATION: Description of Artificial Sequence: Amino acid
      sequence of the L chain V region of HuSG I

<400> SEQUENCE: 131

Asp Ile Gln Met Thr Gln Ser Pro Ser Ser Leu Ser Ala Ser Val Gly
1               5                   10                  15

Asp Arg Val Thr Ile Thr Cys Trp Tyr Gln Gln Lys Pro Gly Lys Ala
            20                  25                  30

Pro Lys Leu Leu Ile Tyr Gly Val Pro Ser Arg Phe Ser Gly Ser Gly
        35                  40                  45

Ser Gly Thr Asp Phe Thr Leu Thr Ile Ser Ser Leu Gln Pro Glu Asp
    50                  55                  60

Phe Ala Thr Tyr Tyr Cys Phe Gly Gln Gly Thr Lys Val Glu Ile Lys
65                  70                  75                  80

<210> SEQ ID NO 132
<211> LENGTH: 80
```

-continued

```
<212> TYPE: PRT
<213> ORGANISM: Artificial Sequence
<220> FEATURE:
<223> OTHER INFORMATION: Description of Artificial Sequence: Amino acid
      sequence of the L chain V region of REI

<400> SEQUENCE: 132

Asp Ile Gln Met Thr Gln Ser Pro Ser Ser Leu Ser Ala Ser Val Gly
 1               5                  10                  15

Asp Arg Val Thr Ile Thr Cys Trp Tyr Gln Gln Lys Pro Gly Lys Ala
             20                  25                  30

Pro Lys Leu Leu Ile Tyr Gly Val Pro Ser Arg Phe Ser Gly Ser Gly
         35                  40                  45

Ser Gly Thr Asp Phe Thr Phe Thr Ile Ser Ser Leu Gln Pro Glu Asp
     50                  55                  60

Ile Ala Thr Tyr Tyr Cys Phe Gly Gln Gly Thr Lys Val Glu Ile Lys
 65                  70                  75                  80

<210> SEQ ID NO 133
<211> LENGTH: 106
<212> TYPE: PRT
<213> ORGANISM: Artificial Sequence
<220> FEATURE:
<223> OTHER INFORMATION: Description of Artificial Sequence: Amino acid
      sequence of the L chain V region of RVLa

<400> SEQUENCE: 133

Asp Ile Val Met Thr Gln Ser His Lys Phe Met Ser Thr Ser Val Gly
 1               5                  10                  15

Asp Arg Val Ser Ile Thr Cys Lys Ala Ser Gln Asp Val Asn Thr Ala
             20                  25                  30

Val Ala Trp Tyr Gln Gln Lys Pro Gly Gln Ser Pro Lys Leu Leu Ile
         35                  40                  45

Tyr Ser Ala Ser Asn Arg Tyr Thr Gly Val Pro Asp Arg Ile Thr Gly
     50                  55                  60

Ser Gly Ser Gly Thr Asp Phe Thr Phe Thr Ile Ser Ser Val Gln Ala
 65                  70                  75                  80

Glu Asp Leu Ala Leu Tyr Tyr Cys Gln Gln His Tyr Ser Thr Pro Phe
                 85                  90                  95

Thr Gly Gln Gly Thr Lys Val Glu Ile Lys
            100                 105

<210> SEQ ID NO 134
<211> LENGTH: 107
<212> TYPE: PRT
<213> ORGANISM: Artificial Sequence
<220> FEATURE:
<223> OTHER INFORMATION: Description of Artificial Sequence: Amino acid
      sequence of the L chain V region of RVLb

<400> SEQUENCE: 134

Asp Ile Val Met Thr Gln Ser His Lys Phe Met Ser Thr Ser Val Gly
 1               5                  10                  15

Asp Arg Val Ser Ile Thr Cys Lys Ala Ser Gln Asp Val Asn Thr Ala
             20                  25                  30

Val Ala Trp Tyr Gln Gln Lys Pro Gly Gln Ser Pro Lys Leu Leu Ile
         35                  40                  45

Tyr Ser Ala Ser Asn Arg Tyr Thr Gly Val Pro Asp Arg Ile Thr Gly
     50                  55                  60

Ser Gly Ser Gly Thr Asp Tyr Thr Phe Thr Ile Ser Ser Val Gln Ala
```

-continued

```
                65                  70                  75                  80
Glu Asp Leu Ala Leu Tyr Tyr Cys Gln Gln His Tyr Ser Thr Pro Phe
                        85                  90                  95
Thr Phe Gly Gln Gly Thr Lys Val Glu Ile Lys
            100                 105

<210> SEQ ID NO 135
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (1) AHM

<400> SEQUENCE: 135

Gln Val Gln Leu Gln Gln Ser Gly Ala Glu Leu Ala Arg Pro Gly Ala
 1               5                  10                  15

Ser Val Lys Leu Ser Cys Lys Ala Ser Gly Tyr Thr Phe Thr Pro Tyr
            20                  25                  30

Trp Met Gln Trp Val Lys Gln Arg Pro Gly Gln Gly Leu Glu Trp Ile
        35                  40                  45

Gly

<210> SEQ ID NO 136
<211> LENGTH: 44
<212> TYPE: PRT
<213> ORGANISM: Artificial Sequence
<220> FEATURE:
<223> OTHER INFORMATION: Description of Artificial Sequence: Amino acid
      sequence of the H chain V region (1) HuSGI
<221> NAME/KEY: MOD_RES
<222> LOCATION: (16)
<223> OTHER INFORMATION: Any, other or unknown amino acid
<221> NAME/KEY: MOD_RES
<222> LOCATION: (19)
<223> OTHER INFORMATION: Any, other or unknown amino acid
<221> NAME/KEY: MOD_RES
<222> LOCATION: (38)
<223> OTHER INFORMATION: Any, other or unknown amino acid

<400> SEQUENCE: 136

Glu Val Gln Leu Val Gln Ser Gly Ala Asp Val Lys Lys Pro Gly Xaa
 1               5                  10                  15

Ser Val Xaa Val Ser Cys Lys Ala Ser Gly Tyr Thr Phe Ser Trp Val
            20                  25                  30

Arg Gln Ala Pro Gly Xaa Gly Leu Asp Trp Val Gly
        35                  40

<210> SEQ ID NO 137
<211> LENGTH: 44
<212> TYPE: PRT
<213> ORGANISM: Artificial Sequence
<220> FEATURE:
<223> OTHER INFORMATION: Description of Artificial Sequence: Amino acid
      sequence of the H chain V region (1) HG3

<400> SEQUENCE: 137

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Asn Trp Val
            20                  25                  30

Arg Gln Ala Pro Gly Gln Gly Leu Glu Trp Met Gly
        35                  40
```

<210> SEQ ID NO 138
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (1) RVHa

<400> SEQUENCE: 138

Gln Val Gln Leu Gln Gln Ser Gly Ala Glu Leu Ala Arg Pro Gly Ala
 1               5                  10                  15

Ser Val Lys Leu Ser Cys Lys Ala Ser Gly Tyr Thr Phe Thr Pro Tyr
            20                  25                  30

Trp Met Gln Trp Val Lys Gln Arg Pro Gly Gln Gly Leu Glu Trp Ile
        35                  40                  45

Gly

<210> SEQ ID NO 139
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (1) RVHb

<400> SEQUENCE: 139

Gln Val Gln Leu Gln Gln Ser Gly Ala Glu Leu Ala Arg Pro Gly Ala
 1               5                  10                  15

Ser Val Lys Leu Ser Cys Lys Ala Ser Gly Tyr Thr Phe Thr Pro Tyr
            20                  25                  30

Trp Met Gln Trp Val Lys Gln Arg Pro Gly Gln Gly Leu Glu Trp Ile
        35                  40                  45

Gly

<210> SEQ ID NO 140
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (1) RVHc

<400> SEQUENCE: 140

Gln Val Gln Leu Gln Gln Ser Gly Ala Glu Leu Ala Arg Pro Gly Ala
 1               5                  10                  15

Ser Val Lys Leu Ser Cys Lys Ala Ser Gly Tyr Thr Phe Thr Pro Tyr
            20                  25                  30

Trp Met Gln Trp Val Lys Gln Arg Pro Gly Gln Gly Leu Glu Trp Ile
        35                  40                  45

Gly

<210> SEQ ID NO 141
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (1) RVHd

<400> SEQUENCE: 141

Gln Val Gln Leu Gln Gln Ser Gly Ala Glu Leu Ala Arg Pro Gly Ala
 1               5                  10                  15

Ser Val Lys Leu Ser Cys Lys Ala Ser Gly Tyr Thr Phe Thr Pro Tyr
            20                  25                  30

Trp Met Gln Trp Val Lys Gln Arg Pro Gly Gln Gly Leu Glu Trp Ile
        35                  40                  45

Gly

<210> SEQ ID NO 142
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (1) RVHe

<400> SEQUENCE: 142

Gln Val Gln Leu Gln Gln Ser Gly Ala Glu Leu Ala Arg Pro Gly Ala
 1               5                   10                  15

Ser Val Lys Leu Ser Cys Lys Ala Ser Gly Tyr Thr Phe Thr Pro Tyr
            20                  25                  30

Trp Met Gln Trp Val Lys Gln Arg Pro Gly Gln Gly Leu Glu Trp Ile
        35                  40                  45

Gly

<210> SEQ ID NO 143
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (1) RVHf

<400> SEQUENCE: 143

Gln Val Gln Leu Gln Gln Ser Gly Ala Glu Leu Ala Arg Pro Gly Ala
 1               5                   10                  15

Ser Val Lys Leu Ser Cys Lys Ala Ser Gly Tyr Thr Phe Thr Pro Tyr
            20                  25                  30

Trp Met Gln Trp Val Lys Gln Arg Pro Gly Gln Gly Leu Glu Trp Ile
        35                  40                  45

Gly

<210> SEQ ID NO 144
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (1) RVHg

<400> SEQUENCE: 144

Gln Val Gln Leu Gln Gln Ser Gly Ala Glu Leu Ala Arg Pro Gly Ala
 1               5                   10                  15

Ser Val Lys Leu Ser Cys Lys Ala Ser Gly Tyr Thr Phe Thr Pro Tyr
            20                  25                  30

Trp Met Gln Trp Val Lys Gln Arg Pro Gly Gln Gly Leu Glu Trp Ile
        35                  40                  45

Gly

<210> SEQ ID NO 145
<211> LENGTH: 49
<212> TYPE: PRT

```
<213> ORGANISM: Artificial Sequence
<220> FEATURE:
<223> OTHER INFORMATION: Description of Artificial Sequence: Amino acid
      sequence of the H chain V region (1) RVHh

<400> SEQUENCE: 145

Gln Val Gln Leu Gln Gln Ser Gly Ala Glu Leu Ala Arg Pro Gly Ala
 1               5                  10                  15

Ser Val Lys Leu Ser Cys Lys Ala Ser Gly Tyr Thr Phe Thr Pro Tyr
            20                  25                  30

Trp Met Gln Trp Val Lys Gln Arg Pro Gly Gln Gly Leu Glu Trp Ile
        35                  40                  45

Gly

<210> SEQ ID NO 146
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (1) RVHi

<400> SEQUENCE: 146

Gln Val Gln Leu Gln Gln Ser Gly Ala Glu Leu Ala Arg Pro Gly Ala
 1               5                  10                  15

Ser Val Lys Leu Ser Cys Lys Ala Ser Gly Tyr Thr Phe Thr Pro Tyr
            20                  25                  30

Trp Met Gln Trp Val Lys Gln Arg Pro Gly Gln Gly Leu Glu Trp Ile
        35                  40                  45

Gly

<210> SEQ ID NO 147
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (1) RVHj

<400> SEQUENCE: 147

Gln Val Gln Leu Gln Gln Ser Gly Ala Glu Leu Ala Arg Pro Gly Ala
 1               5                  10                  15

Ser Val Lys Leu Ser Cys Lys Ala Ser Gly Tyr Thr Phe Thr Pro Tyr
            20                  25                  30

Trp Met Gln Trp Val Lys Gln Arg Pro Gly Gln Gly Leu Glu Trp Ile
        35                  40                  45

Gly

<210> SEQ ID NO 148
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (1) RVHk

<400> SEQUENCE: 148

Gln Val Gln Leu Gln Gln Ser Gly Ala Glu Leu Ala Arg Pro Gly Ala
 1               5                  10                  15

Ser Val Lys Leu Ser Cys Lys Ala Ser Gly Tyr Thr Phe Thr Pro Tyr
            20                  25                  30
```

-continued

```
Trp Met Gln Trp Val Lys Gln Arg Pro Gly Gln Gly Leu Glu Trp Ile
        35                  40                  45

Gly

<210> SEQ ID NO 149
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (1) RVHl

<400> SEQUENCE: 149

Gln Val Gln Leu Gln Gln Ser Gly Ala Glu Leu Ala Arg Pro Gly Ala
  1               5                  10                  15

Ser Val Lys Leu Ser Cys Lys Ala Ser Gly Tyr Thr Phe Thr Pro Tyr
                 20                  25                  30

Trp Met Gln Trp Val Lys Gln Arg Pro Gly Gln Gly Leu Glu Trp Ile
        35                  40                  45

Gly

<210> SEQ ID NO 150
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (1) RVHm

<400> SEQUENCE: 150

Gln Val Gln Leu Gln Gln Ser Gly Ala Glu Leu Ala Arg Pro Gly Ala
  1               5                  10                  15

Ser Val Lys Leu Ser Cys Lys Ala Ser Gly Tyr Thr Phe Thr Pro Tyr
                 20                  25                  30

Trp Met Gln Trp Val Lys Gln Arg Pro Gly Gln Gly Leu Glu Trp Ile
        35                  40                  45

Gly

<210> SEQ ID NO 151
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (1) RVHn

<400> SEQUENCE: 151

Gln Val Gln Leu Gln Gln Ser Gly Ala Glu Leu Ala Arg Pro Gly Ala
  1               5                  10                  15

Ser Val Lys Leu Ser Cys Lys Ala Ser Gly Tyr Thr Phe Thr Pro Tyr
                 20                  25                  30

Trp Met Gln Trp Val Lys Gln Arg Pro Gly Gln Gly Leu Glu Trp Ile
        35                  40                  45

Gly

<210> SEQ ID NO 152
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (1) RVHo
```

-continued

<400> SEQUENCE: 152

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Pro Tyr
            20                  25                  30

Trp Met Gln Trp Val Lys Gln Arg Pro Gly Gln Gly Leu Glu Trp Ile
        35                  40                  45

Gly

<210> SEQ ID NO 153
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (1) RVHp

<400> SEQUENCE: 153

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Pro Tyr
            20                  25                  30

Trp Met Gln Trp Val Lys Gln Arg Pro Gly Gln Gly Leu Glu Trp Ile
        35                  40                  45

Gly

<210> SEQ ID NO 154
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (1) RVHq

<400> SEQUENCE: 154

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Pro Tyr
            20                  25                  30

Trp Met Gln Trp Val Lys Gln Arg Pro Gly Gln Gly Leu Glu Trp Ile
        35                  40                  45

Gly

<210> SEQ ID NO 155
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (1) RVHr

<400> SEQUENCE: 155

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Pro Tyr
            20                  25                  30

Trp Met Gln Trp Val Lys Gln Arg Pro Gly Gln Gly Leu Glu Trp Ile
        35                  40                  45

Gly

<210> SEQ ID NO 156
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (2) AHM

<400> SEQUENCE: 156

Ser Ile Phe Pro Gly Asp Gly Asp Thr Arg Tyr Ser Gln Lys Phe Lys
 1               5                  10                  15

Gly Lys Ala Thr Leu Thr Ala Asp Lys Ser Ser Ser Thr Ala Tyr Met
                20                  25                  30

Gln Leu Ser Ile Leu Ala Phe Glu Asp Ser Ala Val Tyr Tyr Cys Ala
         35                  40                  45

Arg

<210> SEQ ID NO 157
<211> LENGTH: 32
<212> TYPE: PRT
<213> ORGANISM: Artificial Sequence
<220> FEATURE:
<223> OTHER INFORMATION: Description of Artificial Sequence: Amino acid
      sequence of the H chain V region (2) HuSGI
<221> NAME/KEY: MOD_RES
<222> LOCATION: (4)
<223> OTHER INFORMATION: Any, other or unknown amino acid
<221> NAME/KEY: MOD_RES
<222> LOCATION: (6)
<223> OTHER INFORMATION: Any, other or unknown amino acid
<221> NAME/KEY: MOD_RES
<222> LOCATION: (8)
<223> OTHER INFORMATION: Any, other or unknown amino acid
<221> NAME/KEY: MOD_RES
<222> LOCATION: (10)
<223> OTHER INFORMATION: Any, other or unknown amino acid

<400> SEQUENCE: 157

Arg Val Thr Xaa Thr Xaa Asp Xaa Ser Xaa Asn Thr Ala Tyr Met Glu
 1               5                  10                  15

Leu Ser Ser Leu Arg Ser Glu Asp Thr Ala Val Tyr Tyr Cys Ala Arg
                20                  25                  30

<210> SEQ ID NO 158
<211> LENGTH: 32
<212> TYPE: PRT
<213> ORGANISM: Artificial Sequence
<220> FEATURE:
<223> OTHER INFORMATION: Description of Artificial Sequence: Amino acid
      sequence of the H chain V region (2) HG3

<400> SEQUENCE: 158

Arg Val Thr Met Thr Arg Asp Thr Ser Thr Ser Thr Val Tyr Met Glu
 1               5                  10                  15

Leu Ser Ser Leu Arg Ser Glu Asp Thr Ala Val Tyr Tyr Cys Ala Arg
                20                  25                  30

<210> SEQ ID NO 159
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (2) RVHa

<400> SEQUENCE: 159

-continued

Ser Ile Phe Pro Gly Asp Gly Asp Thr Arg Tyr Ser Gln Lys Phe Lys
1               5                   10                  15

Gly Lys Ala Thr Leu Thr Ala Asp Lys Ser Ser Ser Thr Ala Tyr Met
            20                  25                  30

Gln Leu Ser Ile Leu Ala Phe Glu Asp Ser Ala Val Tyr Tyr Cys Ala
        35                  40                  45

Arg

<210> SEQ ID NO 160
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (2) RVHb

<400> SEQUENCE: 160

Ser Ile Phe Pro Gly Asp Gly Asp Thr Arg Tyr Ser Gln Lys Phe Lys
1               5                   10                  15

Gly Lys Ala Thr Leu Thr Ala Asp Lys Ser Ser Ser Thr Ala Tyr Met
            20                  25                  30

Gln Leu Ser Ile Leu Ala Phe Glu Asp Ser Ala Val Tyr Tyr Cys Ala
        35                  40                  45

Arg

<210> SEQ ID NO 161
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (2) RVHc

<400> SEQUENCE: 161

Ser Ile Phe Pro Gly Asp Gly Asp Thr Arg Tyr Ser Gln Lys Phe Lys
1               5                   10                  15

Gly Lys Ala Thr Leu Thr Ala Asp Lys Ser Ser Ser Thr Ala Tyr Met
            20                  25                  30

Gln Leu Ser Ile Leu Ala Phe Glu Asp Ser Ala Val Tyr Tyr Cys Ala
        35                  40                  45

Arg

<210> SEQ ID NO 162
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (2) RVHd

<400> SEQUENCE: 162

Ser Ile Phe Pro Gly Asp Gly Asp Thr Arg Tyr Ser Gln Lys Phe Lys
1               5                   10                  15

Gly Lys Ala Thr Leu Thr Ala Asp Lys Ser Ser Ser Thr Ala Tyr Met
            20                  25                  30

Gln Leu Ser Ile Leu Ala Phe Glu Asp Ser Ala Val Tyr Tyr Cys Ala
        35                  40                  45

Arg

<210> SEQ ID NO 163
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (2) RVHe

<400> SEQUENCE: 163

Ser Ile Phe Pro Gly Asp Gly Asp Thr Arg Tyr Ser Gln Lys Phe Lys
  1               5                  10                  15

Gly Lys Ala Thr Leu Thr Ala Asp Lys Ser Ser Ser Thr Ala Tyr Met
             20                  25                  30

Gln Leu Ser Ile Leu Ala Phe Glu Asp Ser Ala Val Tyr Tyr Cys Ala
         35                  40                  45

Arg

<210> SEQ ID NO 164
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (2) RVHf

<400> SEQUENCE: 164

Ser Ile Phe Pro Gly Asp Gly Asp Thr Arg Tyr Ser Gln Lys Phe Lys
  1               5                  10                  15

Gly Lys Ala Thr Leu Thr Ala Asp Lys Ser Ser Ser Thr Ala Tyr Met
             20                  25                  30

Gln Leu Ser Ile Leu Ala Phe Glu Asp Ser Ala Val Tyr Tyr Cys Ala
         35                  40                  45

Arg

<210> SEQ ID NO 165
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (2) RVHg

<400> SEQUENCE: 165

Ser Ile Phe Pro Gly Asp Gly Asp Thr Arg Tyr Ser Gln Lys Phe Lys
  1               5                  10                  15

Gly Lys Ala Thr Leu Thr Ala Asp Lys Ser Ser Ser Thr Ala Tyr Met
             20                  25                  30

Gln Leu Ser Ile Leu Ala Phe Glu Asp Ser Ala Val Tyr Tyr Cys Ala
         35                  40                  45

Arg

<210> SEQ ID NO 166
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (2) RVHh

<400> SEQUENCE: 166

Ser Ile Phe Pro Gly Asp Gly Asp Thr Arg Tyr Ser Gln Lys Phe Lys
  1               5                  10                  15

```
Gly Lys Ala Thr Leu Thr Ala Asp Lys Ser Ser Ser Thr Ala Tyr Met
            20                  25                  30

Gln Leu Ser Ile Leu Ala Phe Glu Asp Ser Ala Val Tyr Tyr Cys Ala
        35                  40                  45

Arg

<210> SEQ ID NO 167
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (2) RVHi

<400> SEQUENCE: 167

Ser Ile Phe Pro Gly Asp Gly Asp Thr Arg Tyr Ser Gln Lys Phe Lys
 1               5                  10                  15

Gly Lys Ala Thr Leu Thr Ala Asp Lys Ser Ser Ser Thr Ala Tyr Met
            20                  25                  30

Gln Leu Ser Ile Leu Ala Phe Glu Asp Ser Ala Val Tyr Tyr Cys Ala
        35                  40                  45

Arg

<210> SEQ ID NO 168
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (2) RVHj

<400> SEQUENCE: 168

Ser Ile Phe Pro Gly Asp Gly Asp Thr Arg Tyr Ser Gln Lys Phe Lys
 1               5                  10                  15

Gly Lys Ala Thr Leu Thr Ala Asp Lys Ser Ser Ser Thr Ala Tyr Met
            20                  25                  30

Gln Leu Ser Ile Leu Ala Phe Glu Asp Ser Ala Val Tyr Tyr Cys Ala
        35                  40                  45

Arg

<210> SEQ ID NO 169
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (2) RVHk

<400> SEQUENCE: 169

Ser Ile Phe Pro Gly Asp Gly Asp Thr Arg Tyr Ser Gln Lys Phe Lys
 1               5                  10                  15

Gly Lys Ala Thr Leu Thr Ala Asp Lys Ser Ser Ser Thr Ala Tyr Met
            20                  25                  30

Gln Leu Ser Ile Leu Ala Phe Glu Asp Ser Ala Val Tyr Tyr Cys Ala
        35                  40                  45

Arg

<210> SEQ ID NO 170
<211> LENGTH: 49
<212> TYPE: PRT
<213> ORGANISM: Artificial Sequence
```

```
<220> FEATURE:
<223> OTHER INFORMATION: Description of Artificial Sequence: Amino acid
      sequence of the H chain V region (2) RVHl

<400> SEQUENCE: 170

Ser Ile Phe Pro Gly Asp Gly Asp Thr Arg Tyr Ser Gln Lys Phe Lys
  1               5                  10                  15

Gly Lys Ala Thr Leu Thr Ala Asp Lys Ser Ser Ser Thr Ala Tyr Met
             20                  25                  30

Gln Leu Ser Ile Leu Ala Phe Glu Asp Ser Ala Val Tyr Tyr Cys Ala
         35                  40                  45

Arg

<210> SEQ ID NO 171
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (2) RVHm

<400> SEQUENCE: 171

Ser Ile Phe Pro Gly Asp Gly Asp Thr Arg Tyr Ser Gln Lys Phe Lys
  1               5                  10                  15

Gly Lys Ala Thr Leu Thr Ala Asp Lys Ser Ser Ser Thr Ala Tyr Met
             20                  25                  30

Gln Leu Ser Ile Leu Ala Phe Glu Asp Ser Ala Val Tyr Tyr Cys Ala
         35                  40                  45

Arg

<210> SEQ ID NO 172
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (2) RVHn

<400> SEQUENCE: 172

Ser Ile Phe Pro Gly Asp Gly Asp Thr Arg Tyr Ser Gln Lys Phe Lys
  1               5                  10                  15

Gly Lys Ala Thr Leu Thr Ala Asp Lys Ser Ser Ser Thr Ala Tyr Met
             20                  25                  30

Gln Leu Ser Ile Leu Ala Phe Glu Asp Ser Ala Val Tyr Tyr Cys Ala
         35                  40                  45

Arg

<210> SEQ ID NO 173
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (2) RVHo

<400> SEQUENCE: 173

Ser Ile Phe Pro Gly Asp Gly Asp Thr Arg Tyr Ser Gln Lys Phe Lys
  1               5                  10                  15

Gly Lys Ala Thr Leu Thr Ala Asp Lys Ser Ser Ser Thr Ala Tyr Met
             20                  25                  30

Gln Leu Ser Ile Leu Ala Phe Glu Asp Ser Ala Val Tyr Tyr Cys Ala
```

```
            35                  40                  45

Arg

<210> SEQ ID NO 174
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (2) RVHp

<400> SEQUENCE: 174

Ser Ile Phe Pro Gly Asp Gly Asp Thr Arg Tyr Ser Gln Lys Phe Lys
 1               5                  10                  15

Gly Lys Ala Thr Leu Thr Ala Asp Lys Ser Ser Ser Thr Ala Tyr Met
            20                  25                  30

Gln Leu Ser Ile Leu Ala Phe Glu Asp Ser Ala Val Tyr Tyr Cys Ala
        35                  40                  45

Arg

<210> SEQ ID NO 175
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (2) RVHq

<400> SEQUENCE: 175

Ser Ile Phe Pro Gly Asp Gly Asp Thr Arg Tyr Ser Gln Lys Phe Lys
 1               5                  10                  15

Gly Lys Ala Thr Leu Thr Ala Asp Lys Ser Ser Ser Thr Ala Tyr Met
            20                  25                  30

Gln Leu Ser Ile Leu Ala Phe Glu Asp Ser Ala Val Tyr Tyr Cys Ala
        35                  40                  45

Arg

<210> SEQ ID NO 176
<211> LENGTH: 49
<212> TYPE: PRT
<213> ORGANISM: Artificial Sequence
<220> FEATURE:
<223> OTHER INFORMATION: Description of Artificial Sequence: Amino acid
      sequence of the H chain V region (2) RVHr

<400> SEQUENCE: 176

Ser Ile Phe Pro Gly Asp Gly Asp Thr Arg Tyr Ser Gln Lys Phe Lys
 1               5                  10                  15

Gly Lys Ala Thr Leu Thr Ala Asp Lys Ser Ser Ser Thr Ala Tyr Met
            20                  25                  30

Gln Leu Ser Ile Leu Ala Phe Glu Asp Ser Ala Val Tyr Tyr Cys Ala
        35                  40                  45

Arg

<210> SEQ ID NO 177
<211> LENGTH: 22
<212> TYPE: PRT
<213> ORGANISM: Artificial Sequence
<220> FEATURE:
<223> OTHER INFORMATION: Description of Artificial Sequence: Amino acid
      sequence of the H chain V region AHM
```

```
<400> SEQUENCE: 177

Gly Leu Arg Arg Gly Gly Tyr Tyr Phe Asp Tyr Trp Gly Gln Gly Thr
  1               5                  10                  15

Thr Leu Thr Val Ser Ser
            20

<210> SEQ ID NO 178
<211> LENGTH: 11
<212> TYPE: PRT
<213> ORGANISM: Artificial Sequence
<220> FEATURE:
<223> OTHER INFORMATION: Description of Artificial Sequence: Amino acid
      sequence of the H chain V region HuSGI

<400> SEQUENCE: 178

Trp Gly Gln Gly Thr Leu Val Thr Val Ser Ser
  1               5                  10

<210> SEQ ID NO 179
<211> LENGTH: 11
<212> TYPE: PRT
<213> ORGANISM: Artificial Sequence
<220> FEATURE:
<223> OTHER INFORMATION: Description of Artificial Sequence: Amino acid
      sequence of the H chain V region JH6

<400> SEQUENCE: 179

Trp Gly Gln Gly Thr Thr Val Thr Val Ser Ser
  1               5                  10

<210> SEQ ID NO 180
<211> LENGTH: 22
<212> TYPE: PRT
<213> ORGANISM: Artificial Sequence
<220> FEATURE:
<223> OTHER INFORMATION: Description of Artificial Sequence: Amino acid
      sequence of the H chain V region RVHa

<400> SEQUENCE: 180

Gly Leu Arg Arg Gly Gly Tyr Tyr Phe Asp Tyr Trp Gly Gln Gly Thr
  1               5                  10                  15

Thr Leu Thr Val Ser Ser
            20

<210> SEQ ID NO 181
<211> LENGTH: 22
<212> TYPE: PRT
<213> ORGANISM: Artificial Sequence
<220> FEATURE:
<223> OTHER INFORMATION: Description of Artificial Sequence: Amino acid
      sequence of the H chain V region RVHb

<400> SEQUENCE: 181

Gly Leu Arg Arg Gly Gly Tyr Tyr Phe Asp Tyr Trp Gly Gln Gly Thr
  1               5                  10                  15

Thr Leu Thr Val Ser Ser
            20

<210> SEQ ID NO 182
<211> LENGTH: 22
<212> TYPE: PRT
<213> ORGANISM: Artificial Sequence
<220> FEATURE:
<223> OTHER INFORMATION: Description of Artificial Sequence: Amino acid
      sequence of the H chain V region RVHc
```

<400> SEQUENCE: 182

Gly Leu Arg Arg Gly Gly Tyr Tyr Phe Asp Tyr Trp Gly Gln Gly Thr
1               5                   10                  15

Thr Leu Thr Val Ser Ser
            20

<210> SEQ ID NO 183
<211> LENGTH: 22
<212> TYPE: PRT
<213> ORGANISM: Artificial Sequence
<220> FEATURE:
<223> OTHER INFORMATION: Description of Artificial Sequence: Amino acid
      sequence of the H chain V region RVHd

<400> SEQUENCE: 183

Gly Leu Arg Arg Gly Gly Tyr Tyr Phe Asp Tyr Trp Gly Gln Gly Thr
1               5                   10                  15

Thr Leu Thr Val Ser Ser
            20

<210> SEQ ID NO 184
<211> LENGTH: 22
<212> TYPE: PRT
<213> ORGANISM: Artificial Sequence
<220> FEATURE:
<223> OTHER INFORMATION: Description of Artificial Sequence: Amino acid
      sequence of the H chain V region RVHe

<400> SEQUENCE: 184

Gly Leu Arg Arg Gly Gly Tyr Tyr Phe Asp Tyr Trp Gly Gln Gly Thr
1               5                   10                  15

Thr Leu Thr Val Ser Ser
            20

<210> SEQ ID NO 185
<211> LENGTH: 22
<212> TYPE: PRT
<213> ORGANISM: Artificial Sequence
<220> FEATURE:
<223> OTHER INFORMATION: Description of Artificial Sequence: Amino acid
      sequence of the H chain V region RVHf

<400> SEQUENCE: 185

Gly Leu Arg Arg Gly Gly Tyr Tyr Phe Asp Tyr Trp Gly Gln Gly Thr
1               5                   10                  15

Thr Leu Thr Val Ser Ser
            20

<210> SEQ ID NO 186
<211> LENGTH: 22
<212> TYPE: PRT
<213> ORGANISM: Artificial Sequence
<220> FEATURE:
<223> OTHER INFORMATION: Description of Artificial Sequence: Amino acid
      sequence of the H chain V region RVHg

<400> SEQUENCE: 186

Gly Leu Arg Arg Gly Gly Tyr Tyr Phe Asp Tyr Trp Gly Gln Gly Thr
1               5                   10                  15

Thr Leu Thr Val Ser Ser
            20

<210> SEQ ID NO 187
<211> LENGTH: 22

```
<212> TYPE: PRT
<213> ORGANISM: Artificial Sequence
<220> FEATURE:
<223> OTHER INFORMATION: Description of Artificial Sequence: Amino acid
      sequence of the H chain V region RVHh

<400> SEQUENCE: 187

Gly Leu Arg Arg Gly Gly Tyr Tyr Phe Asp Tyr Trp Gly Gln Gly Thr
 1               5                  10                  15

Thr Leu Thr Val Ser Ser
            20

<210> SEQ ID NO 188
<211> LENGTH: 22
<212> TYPE: PRT
<213> ORGANISM: Artificial Sequence
<220> FEATURE:
<223> OTHER INFORMATION: Description of Artificial Sequence: Amino acid
      sequence of the H chain V region RVHi

<400> SEQUENCE: 188

Gly Leu Arg Arg Gly Gly Tyr Tyr Phe Asp Tyr Trp Gly Gln Gly Thr
 1               5                  10                  15

Thr Leu Thr Val Ser Ser
            20

<210> SEQ ID NO 189
<211> LENGTH: 22
<212> TYPE: PRT
<213> ORGANISM: Artificial Sequence
<220> FEATURE:
<223> OTHER INFORMATION: Description of Artificial Sequence: Amino acid
      sequence of the H chain V region RVHj

<400> SEQUENCE: 189

Gly Leu Arg Arg Gly Gly Tyr Tyr Phe Asp Tyr Trp Gly Gln Gly Thr
 1               5                  10                  15

Thr Leu Thr Val Ser Ser
            20

<210> SEQ ID NO 190
<211> LENGTH: 22
<212> TYPE: PRT
<213> ORGANISM: Artificial Sequence
<220> FEATURE:
<223> OTHER INFORMATION: Description of Artificial Sequence: Amino acid
      sequence of the H chain V region RVHk

<400> SEQUENCE: 190

Gly Leu Arg Arg Gly Gly Tyr Tyr Phe Asp Tyr Trp Gly Gln Gly Thr
 1               5                  10                  15

Thr Leu Thr Val Ser Ser
            20

<210> SEQ ID NO 191
<211> LENGTH: 22
<212> TYPE: PRT
<213> ORGANISM: Artificial Sequence
<220> FEATURE:
<223> OTHER INFORMATION: Description of Artificial Sequence: Amino acid
      sequence of the H chain V region RVHl

<400> SEQUENCE: 191

Gly Leu Arg Arg Gly Gly Tyr Tyr Phe Asp Tyr Trp Gly Gln Gly Thr
 1               5                  10                  15
```

Thr Leu Thr Val Ser Ser
            20

<210> SEQ ID NO 192
<211> LENGTH: 22
<212> TYPE: PRT
<213> ORGANISM: Artificial Sequence
<220> FEATURE:
<223> OTHER INFORMATION: Description of Artificial Sequence: Amino acid
      sequence of the H chain V region RVHm

<400> SEQUENCE: 192

Gly Leu Arg Arg Gly Gly Tyr Tyr Phe Asp Tyr Trp Gly Gln Gly Thr
1               5                   10                  15

Thr Leu Thr Val Ser Ser
            20

<210> SEQ ID NO 193
<211> LENGTH: 22
<212> TYPE: PRT
<213> ORGANISM: Artificial Sequence
<220> FEATURE:
<223> OTHER INFORMATION: Description of Artificial Sequence: Amino acid
      sequence of the H chain V region RVHn

<400> SEQUENCE: 193

Gly Leu Arg Arg Gly Gly Tyr Tyr Phe Asp Tyr Trp Gly Gln Gly Thr
1               5                   10                  15

Thr Leu Thr Val Ser Ser
            20

<210> SEQ ID NO 194
<211> LENGTH: 22
<212> TYPE: PRT
<213> ORGANISM: Artificial Sequence
<220> FEATURE:
<223> OTHER INFORMATION: Description of Artificial Sequence: Amino acid
      sequence of the H chain V region RVHo

<400> SEQUENCE: 194

Gly Leu Arg Arg Gly Gly Tyr Tyr Phe Asp Tyr Trp Gly Gln Gly Thr
1               5                   10                  15

Thr Leu Thr Val Ser Ser
            20

<210> SEQ ID NO 195
<211> LENGTH: 22
<212> TYPE: PRT
<213> ORGANISM: Artificial Sequence
<220> FEATURE:
<223> OTHER INFORMATION: Description of Artificial Sequence: Amino acid
      sequence of the H chain V region RVHp

<400> SEQUENCE: 195

Gly Leu Arg Arg Gly Gly Tyr Tyr Phe Asp Tyr Trp Gly Gln Gly Thr
1               5                   10                  15

Thr Leu Thr Val Ser Ser
            20

<210> SEQ ID NO 196
<211> LENGTH: 22
<212> TYPE: PRT
<213> ORGANISM: Artificial Sequence
<220> FEATURE:
<223> OTHER INFORMATION: Description of Artificial Sequence: Amino acid
      sequence of the H chain V region RVHq

```
<400> SEQUENCE: 196

Gly Leu Arg Arg Gly Gly Tyr Tyr Phe Asp Tyr Trp Gly Gln Gly Thr
 1               5                  10                  15

Thr Leu Thr Val Ser Ser
            20

<210> SEQ ID NO 197
<211> LENGTH: 22
<212> TYPE: PRT
<213> ORGANISM: Artificial Sequence
<220> FEATURE:
<223> OTHER INFORMATION: Description of Artificial Sequence: Amino acid
      sequence of the H chain V region RVHr

<400> SEQUENCE: 197

Gly Leu Arg Arg Gly Gly Tyr Tyr Phe Asp Tyr Trp Gly Gln Gly Thr
 1               5                  10                  15

Thr Leu Thr Val Ser Ser
            20

<210> SEQ ID NO 198
<211> LENGTH: 120
<212> TYPE: PRT
<213> ORGANISM: Artificial Sequence
<220> FEATURE:
<223> OTHER INFORMATION: Description of Artificial Sequence: Design of V
      region of Natural Humanized Antibody (HM1.24 )

<400> SEQUENCE: 198

Gln Val Gln Leu Gln Gln Ser Gly Ala Glu Leu Ala Arg Pro Gly Ala
 1               5                  10                  15

Ser Val Lys Leu Ser Cys Lys Ala Ser Gly Tyr Thr Phe Thr Pro Tyr
            20                  25                  30

Trp Met Gln Trp Val Lys Gln Arg Pro Gly Gln Gly Leu Glu Trp Ile
        35                  40                  45

Gly Ser Ile Phe Pro Gly Asp Gly Asp Thr Arg Tyr Ser Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ile Leu Ala Phe Glu Asp Ser Ala Val Tyr Tyr Cys
                85                  90                  95

Ala Arg Gly Leu Arg Arg Gly Gly Tyr Tyr Phe Asp Tyr Trp Gly Gln
            100                 105                 110

Gly Thr Thr Leu Thr Val Ser Ser
        115                 120

<210> SEQ ID NO 199
<211> LENGTH: 87
<212> TYPE: PRT
<213> ORGANISM: Artificial Sequence
<220> FEATURE:
<223> OTHER INFORMATION: Description of Artificial Sequence: Design of V
      region of Natural Humanized Antibody (HuSGI)
<221> NAME/KEY: MOD_RES
<222> LOCATION: (16)
<223> OTHER INFORMATION: Any, other or unknown amino acid
<221> NAME/KEY: MOD_RES
<222> LOCATION: (19)
<223> OTHER INFORMATION: Any, other or unknown amino acid
<221> NAME/KEY: MOD_RES
<222> LOCATION: (38)
<223> OTHER INFORMATION: Any, other or unknown amino acid
```

```
<400> SEQUENCE: 199

Glu Val Gln Leu Val Gln Ser Gly Ala Asp Val Lys Lys Pro Gly Xaa
 1               5                  10                  15

Ser Val Xaa Val Ser Cys Lys Ala Ser Gly Tyr Thr Phe Ser Trp Val
            20                  25                  30

Arg Gln Ala Pro Gly Xaa Gly Leu Asp Trp Val Gly Arg Val Thr Xaa
        35                  40                  45

Thr Xaa Asp Xaa Ser Xaa Asn Thr Ala Tyr Met Glu Leu Ser Ser Leu
    50                  55                  60

Arg Ser Glu Asp Thr Ala Val Tyr Tyr Cys Ala Arg Trp Gly Gln Gly
65                  70                  75                  80

Thr Leu Val Thr Val Ser Ser
                85

<210> SEQ ID NO 200
<211> LENGTH: 87
<212> TYPE: PRT
<213> ORGANISM: Artificial Sequence
<220> FEATURE:
<223> OTHER INFORMATION: Description of Artificial Sequence: Design of V
      region of Natural Humanized Antibody (HG3)

<400> SEQUENCE: 200

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Asn Trp Val
            20                  25                  30

Arg Gln Ala Pro Gly Gln Gly Leu Glu Trp Met Gly Arg Val Thr Met
        35                  40                  45

Thr Arg Asp Thr Ser Thr Ser Thr Val Tyr Met Glu Leu Ser Ser Leu
    50                  55                  60

Arg Ser Glu Asp Thr Ala Val Tyr Tyr Cys Ala Arg Trp Gly Gln Gly
65                  70                  75                  80

Thr Thr Val Thr Val Ser Ser
                85

<210> SEQ ID NO 201
<211> LENGTH: 120
<212> TYPE: PRT
<213> ORGANISM: Artificial Sequence
<220> FEATURE:
<223> OTHER INFORMATION: Description of Artificial Sequence: Design of V
      region of Natural Humanized Antibody (RVHr)

<400> SEQUENCE: 201

Gln Val Gln Leu Gln Gln Ser Gly Ala Glu Leu Ala Arg Pro Gly Ala
 1               5                  10                  15

Ser Val Lys Leu Ser Cys Lys Ala Ser Gly Tyr Thr Phe Thr Pro Tyr
            20                  25                  30

Trp Met Gln Trp Val Lys Gln Arg Pro Gly Gln Gly Leu Glu Trp Ile
        35                  40                  45

Gly Ser Ile Phe Pro Gly Asp Gly Asp Thr Arg Tyr Ser Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ile Leu Ala Phe Glu Asp Ser Ala Val Tyr Tyr Cys
                85                  90                  95

Ala Arg Gly Leu Arg Arg Gly Gly Tyr Tyr Phe Asp Tyr Trp Gly Gln
```

```
                100             105             110

Gly Thr Thr Leu Thr Val Ser Ser
        115                 120

<210> SEQ ID NO 202
<211> LENGTH: 120
<212> TYPE: PRT
<213> ORGANISM: Artificial Sequence
<220> FEATURE:
<223> OTHER INFORMATION: Description of Artificial Sequence: Design of V
      region of Natural Humanized Antibody (2ndRVH)

<400> SEQUENCE: 202

Gln Val Gln Leu Gln Gln Ser Gly Ala Glu Leu Ala Arg Pro Gly Ala
  1               5                  10                  15

Ser Val Lys Leu Ser Cys Lys Ala Ser Gly Tyr Thr Phe Thr Pro Tyr
             20                  25                  30

Trp Met Gln Trp Val Lys Gln Arg Pro Gly Gln Gly Leu Glu Trp Ile
         35                  40                  45

Gly Ser Ile Phe Pro Gly Asp Gly Asp Thr Arg Tyr Ser Gln Lys Phe
 50                  55                  60

Lys Gly Lys Ala Thr Ile Thr Ala Asp Lys Ser Ser Ser Thr Ala Tyr
 65                  70                  75                  80

Met Gln Leu Ser Ile Leu Ala Phe Glu Asp Ser Ala Val Tyr Tyr Cys
                 85                  90                  95

Ala Arg Gly Leu Arg Arg Gly Gly Tyr Tyr Phe Asp Tyr Trp Gly Gln
            100                 105                 110

Gly Thr Thr Leu Thr Val Ser Ser
        115                 120

<210> SEQ ID NO 203
<211> LENGTH: 94
<212> TYPE: PRT
<213> ORGANISM: Artificial Sequence
<220> FEATURE:
<223> OTHER INFORMATION: Description of Artificial Sequence: Primary
      design antibody

<400> SEQUENCE: 203

Arg Tyr Thr Met Thr Ala Asp Lys Ser Thr Ser Thr Ala Tyr Met Glu
  1               5                  10                  15

Leu Ser Ser Leu Arg Ser Glu Asp Thr Ala Val Tyr Tyr Cys Ala Arg
             20                  25                  30

Val Arg Gln Ala Pro Gly Gln Gly Leu Glu Trp Met Gly Arg Ile Ile
         35                  40                  45

Pro Ile Leu Gly Ile Ala Asn Tyr Ala Gln Lys Phe Gln Gly Arg Val
 50                  55                  60

Thr Ile Thr Ala Asp Lys Ser Thr Ser Thr Ala Tyr Met Glu Leu Ser
 65                  70                  75                  80

Ser Leu Arg Ser Glu Asp Thr Ala Val Tyr Tyr Cys Ala Arg
                 85                  90
```

NATURAL HUMAN ANTIBODY

This application is a 35 U.S.C. §371 filing of PCT/J98/04469, filed on Oct. 2, 1998.

TECHNICAL FIELD

The present invention relates to a method of preparing natural humanized antibody and the natural humanized antibody obtained by said method of preparation. The present invention also relates to DNA encoding natural humanized antibody, an expression vector comprising said DNA, a host comprising said DNA, and a method of preparing natural humanized antibody from cells into which said DNA has been introduced.

BACKGROUND ART

Mouse monoclonal antibodies can be relatively easily isolated by the widely used hybridoma technology (Kohler, G. and Milstein, C. Nature (1975) 256, 495–497). On the other hand, a similar technique for human hybridoma has yet to be widespread though it is expected to become so. Furthermore, there is a need for antibodies to human antigens in clinical applications, and therefore the generation of mouse monoclonal antibodies is indispensable for the development of antibody pharmaceuticals.

In fact, a number of monoclonal antibodies have been isolated against tumor cells and viruses, and have been studied in clinical applications. It has been revealed, however, that mouse antibodies, which are a foreign substances to humans, induce HAMA (human anti-mouse antibody) due to the potent antigenicity, and that it is extremely unsuitable for clinical applications because of such problems as a weak activity of inducing ADCC (Schroff, R. W., Cancer Res. (1985) 45, 879–885; Shawler, D. L., et al, J. Immunol. (1985) 135, 1530–1535).

In order to solve this problem, chimeric antibody was created (Neuberger, M. S. et al., Nature (1984) 312, 604–608; Boulianne, G. L. et al., Nature (1984) 312, 643–646). Chimeric antibody is made by linking a variable region of a mouse antibody to a constant region of a human antibody, i.e. in chimeric antibody the constant region of the mouse antibody which is responsible for a particularly potent antigenicity has been replaced with a human counterpart. This is expected to enable a physiological binding with a human Fc receptor and to induce Fc-mediated functions. In fact, marked decreases in antigenicity has been reported in a clinical study using chimeric antibodies (LoBuglio, A. F. et al., Proc. Natl. Acad. Sci. U.S.A. (1989) 86, 4220–4224). However, trouble-causing cases were reported that developed HAMA against mouse variable regions (LoBuglio, A. F. et al., Proc. Natl. Acad. Sci. U.S.A. (1989) 86, 4220–4224).

Accordingly, methods have been developed, though more complicated, for making a humanized antibody which is closer to a human antibody. This is a technique of reconstructing the antigen binding site of a mouse antibody on a human antibody (Jones, P. T. et al., Nature (1986) 321, 5225–525; Verhoeyen, M. et al., Scinece (1988) 239, 1534–1536; Riechmann, L. et al., Nature (1988) 332,323–327)). Thus, a variable region of an antibody, for both of the H chain and the L chain, comprises four framework regions (FRS) and three complementarity determining regions (CDRs) sandwiched between them.

It is known that CDR is mainly responsible for the formation of antigen binding sites and some amino acid residues on the FR are involved therein either directly or indirectly. Since the basic structures of antibodies are similar to each other, it was thought possible to graft an antigen binding site of an antibody to another antibody. The research group led by G. Winter has, in fact, successfully grafted CDRs of a mouse anti-rhizobium antibody to a human antibody (CDR-grafting) thereby obtaining a humanized antibody having a rhizobium binding activity (Jones, P. T. et al., Nature (1986) 321, 522–525).

In some cases, however, humanization by CDR-grafting alone does not provide humanized antibody that has an antigen binding activity similar to the original mouse antibody. Accordingly, as described above, attempts have been made to replace some FR amino acid residues. FR amino acid residues to be replaced are involved in the maintenance of the structure of amino acid residues that constitute the basic structure of an antibody molecule (canonical structure; Chothia, C. et al., Nature (1989) 342, 877–883; Chothia, C. and Lesk, A. M. J. Molec. Biol. (1987) 196, 901–917) or CDRs, or directly interact with antigen molecules.

In fact, amino acid substitution on the FR has been made for most of the humanized antibody, wherein artificial FR sequences that do not naturally occur are formed. At times, too many amino acid substitutions have been made, which makes doubtful the original meaning of CDR-grafting for minimizing the antigenicity of mouse antibody (Queen, C. et al., Proc. Natl. Acad. Sci. U.S.A. (1989) 86, 10029–10033; Co, M. S. et al., Proc. Natl. Acad. Sci. U.S.A. (1991) 88, 2869–2873).

A solution to this problem is to devise methods of selecting human FRS. Thus, the number of FR amino acid residues to be replaced depends on the homology between the FRs of the human antibody selected for CDR-grafting and the FRs of the original mouse antibody. Accordingly, human FRs having a high homology with mouse FRs are usually selected so as to minimize the degree of substitution. However, in many cases even the FRs of humanized antibody thus obtained have amino acid sequences that do not occur naturally, which may present the problem of antigenicity. Thus, there is a need for the technology of constructing humanized antibody that can solve the above problems, have lower probability of inducing antigenicity, and have higher safety.

DISCLOSURE OF THE INVENTION

The present invention is an improvement of the conventional method of constructing humanized antibody, and provides a method of constructing humanized antibody that completely retains the antigen binding activity of the original mouse antibody and that comprises naturally occurring human FRs, in other words a method of constructing humanized antibody that involves no amino acid substitution on the FR.

Thus, the present invention provides a method of preparing a natural humanized antibody which comprises conducting a homology search for the FR of a primary design antibody and selecting a natural human FR retaining the artificial amino acid residues contained in the FR of the primary design antibody and having a homology therewith. As used herein, the primary design antibody is a humanized antibody (also called a reshaped human antibody) prepared by the conventional CDR-grafting.

The present invention also provides a method of preparing a natural humanized antibody which comprises conducting a homology search for the FR of a primary design antibody, selecting a natural human FR retaining the artificial amino acid residues contained in the FR of the primary design antibody and having a homology therewith, and exchanging one or a plurality of different amino acid residues between the FR of the primary design antibody and the selected natural human FR.

Preferably, in the above method of preparation, the primary design antibody comprises the CDRs derived from a first animal species and the FRs derived from a second animal species. More preferably, in the primary design antibody the first animal species is a non-human mammal and the second animal species is human. Examples of the first animal species, i.e. a mammal, include mouse, rat, hamster, rabbit, and monkey.

The present invention also provides a method of preparing a natural humanized antibody which comprises conducting a homology search for the FR of a primary design antibody, selecting a natural human FR retaining the artificial amino acid residues derived from the FR of a non-human antibody contained in the FR of the primary design antibody and having a high homology therewith, and exchanging one or a plurality of different amino acid residues between the FR of the primary design antibody and the selected natural human FR.

The present invention also provides a natural humanized antibody obtained by the above preparation method.

The present invention also provides a natural humanized antibody containing the CDRs derived from a first animal species and the FRS derived from a second animal species characterized in that said FRs comprise an amino acid sequence which is different from the FRs used for CDR-grafting by one or a plurality of amino acid residues and is replaced with the FR derived from the second animal species having the same amino acid residues as said different amino acid residues at the same positions. Preferably the first animal species is a non-human mammal and the second animal species is human. Examples of the first animal species, i.e. a mammal, include mouse, rat, hamster, rabbit, and monkey.

The present invention also provides DNA encoding the above natural humanized antibody.

The present invention also provides an expression vector comprising the above DNA.

The present invention also provides a host comprising the above DNA.

The present invention also provides a method of preparing a natural humanized antibody which comprises culturing cells into which an expression vector comprising the above DNA has been introduced and collecting the desired natural humanized antibody from the culture of said cells.

The present invention also provides a pharmaceutical composition comprising a natural humanized antibody.

BRIEF EXPLANATION OF THE DRAWINGS

FIG. 6 is a diagram showing a method of constructing the H chain V region of human-mouse hybrid anti-HM1.24 antibody.

FIG. 7 is a diagram showing a method of constructing the H chain V region of mouse-human hybrid anti-HM1.24 antibody.

EMBODIMENT FOR CARRYING OUT THE INVENTION

1. Natural FR Sequence

Figure 1:
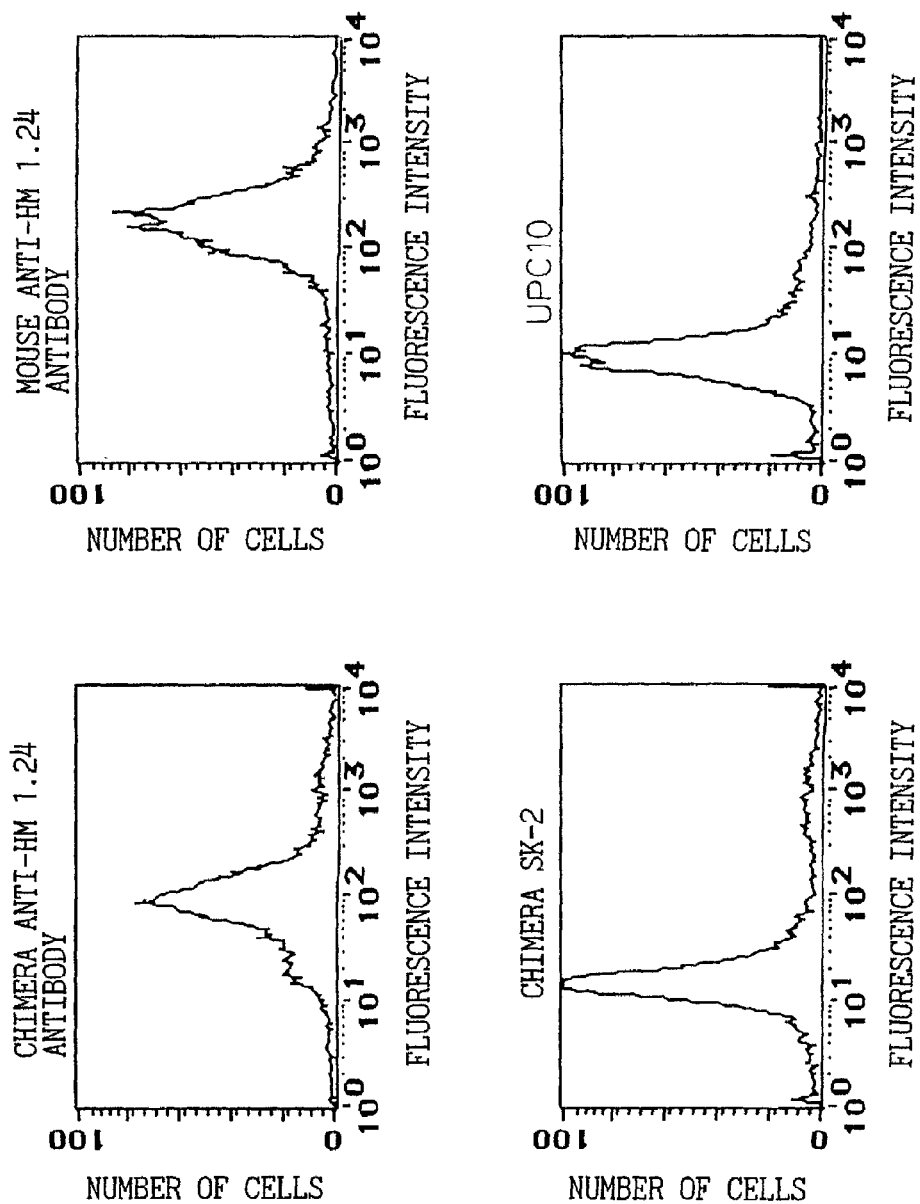
FIG. 1 is a graph showing that the fluorescent intensity of chimeric anti-HM1.24 antibody is shifted similarly to that of mouse anti-HM1.24 antibody as compared to control antibody in the FCM analysis using a human myeloma cell line KPMM2.

In order to produce antibodies to a variety of antigens from the genes comprising limited antibody variable regions, organisms have a mechanism of introducing random gene mutations (called somatic mutations) in the antibody variable regions. In theory this should form extremely diverse FR amino acid sequences, but in practice positions of amino acid residues more prone to the introduction of mutations and the kinds of amino acid residues appear to be limited to a certain degree as determined by structural analysis of many human antibody FRs for which actual structures have been elucidated.

As used herein, the term FR refers to the FR that has been defined in Kabat, E. A. et al., Sequence of Proteins of Immunological Interest (1991). Thus, in the H chain, FR1 is amino acids No. 1 to 30, FR2 is amino acids No. 36 to 49, FR3 is amino acids No. 66 to 94, and FR4 is amino acids No. 103 to 113. On the other hand, in the L chain FR1 is amino acids No. 1 to 23, FR2 is amino acids No. 35 to 49, FR3 is amino acids No. 57 to 88, and FR4 is amino acids No. 98 to 107.

2. From Human FR to Natural Human FR

In many cases, humanized antibodies (also called reshaped human antibody) produced by the conventional CDR-grafting method have FR amino acid sequences that cannot be found in nature. However, because a variety of FR amino acid sequences have already been found by somatic mutation as mentioned above, it is possible that FRs having artificial amino acid residues created by humanization could be converted into human FRs that occur in nature.

The present invention is intended to create humanized antibody comprising naturally occurring human FRs in stead of artificial FRs by further processing humanized antibody that was constructed by the conventional humanization technology. When humanized antibody that underwent amino acid substitution is subjected to homology search using human antibody FRs and known databases such as Swiss Plot (protein sequence database), GenBank (nucleic acid sequence database), PRF (protein sequence database) PIR (protein sequence database), and GenPept (translated protein sequence from GenBank), human FRs having completely matched amino acid sequences or human FRs having homology can be found.

In the former case, FR substitution was carried out when seen from the human FR that was used as the acceptor of CDR-grafting, in which a formed FR that had been presumed to be artificial is present in the natural FR, which can be considered an acceptor, and therefore an FR that underwent no FR substitution can be obtained. In the latter case, by focusing on the amino acid sequence of human FR having a high homology with an artificial FR, it is possible to effect amino acid substitution in the artificial FR that results in returning to a suitable natural human antibody thereby causing a complete match with the natural human FR. This procedure represents humanization on CDR-grafted antibodies.

Since homology search of amino acid sequences between human antibodies is conducted in this case, it is possible to find a human FR that belongs to the same subgroup as the human FR used in CDR-grafting and to find an amino acid sequence having an extremely high homology. Thus, a natural human FR, obtained for each FR, more than satisfies the consensus sequence of the subgroup though it is derived from different antibodies.

3. Natural-Sequence Humanized Antibody

The natural humanized antibody obtained in the present invention comprises human antibody FRs that have been recognized to occur in nature. Though FR1 to FR4 are sometimes derived from different antibodies, homology search between human antibodies permits the selection of the antibodies that only belong to the same subgroup as described above. The FR structure of each antibody in the same subgroup has a structure very similar to another, and in fact humanized antibodies based on consensus sequences in the subgroup have been generated (Kettleborough, C. A. et al., Protein Engng. (1991) 4, 773–783; Satoh, K. et al., Molec. Immun. (1994) 31, 371–381).

It is believed that in antibodies, as described above, extremely diverse amino acid sequences occur naturally through somatic mutation. Only some of the structures have been characterized at present. If the FR sequence of the antibody obtained cannot be found in nature, it is not clear whether the FR is present in nature or not. When antibodies are considered as pharmaceuticals, the construction of CDR-grafting antibody comprising naturally occurring human FRs provides such an antibody that has properties superior to the conventional humanized antibodies from a viewpoint of of the object of the present invention to reduce antigenicity.

4. Method of Constructing Novel Humanized Antibody

The present invention solves the problem associated with humanized antibody constructed by the conventional technique of humanization, that is, it eliminates antigenicity arising from artificial FRs that are not found in nature. Otherwise it is a technology to construct humanized antibody by CDR-grafting composed of human FRs actually found in nature. The amino acid sequences of artificial FRs refer to the amino acid sequences of the FRs which as a whole cannot be found in nature. The artificial amino acid sequences contained in FRs refer to those amino acid sequences that cannot be found in nature in FRs.

As the amino acid sequences of FRs that are not found in nature, there may be mentioned FRs having an amino acid sequence in which human amino acid residues in a FR have returned to amino acid residues found in the FR of antibody derived from a non-human mammal which is a template of humanization in a humanized antibody constructed by the conventional antibody-humanization technology. Alternatively, in a humanized antibody constructed by the conventional antibody-humanization technology, there may be mentioned FRs having an amino acid sequence that are not found in the antibodies derived from human and non-human mammals.

The method of producing the natural humanized antibody of the present invention is described hereinbelow.

First, a FR of the human antibody for use in CDR-grafting is selected by a conventional technique. The FR is subjected to amino acid substitution to construct a humanized antibody having a biological activity equal to or higher than that of mouse antibody. This is considered as an end product of humanized antibody in the conventional method, but in the present invention it is a mere intermediate for construction of natural humanized antibody having a natural sequence. In the present invention it is called the primary design antibody.

Subsequently, homology search is conducted on each of the FRs of the primary design antibody. FRs having a complete match mean that the FRs have already comprised the natural FRs. On the other hand, a series of natural human FRs are listed that belong to the same subgroup as the primary design antibody and having a homology but not a complete match with the primary design antibody. From the list, there may be selected most appropriate natural human FRS that maintain the amino acid residue of the FR derived from a non-human mammal such as mouse which was important in the construction of the primary design antibody, and that has a homology with the primary design antibody.

Homology search of FRS can be conducted using known databases. Examples of such databases include Swiss Plot, GenBank, PRF, PIR, and GenPept. Homology search is conducted using these databases in which "the FR having a homology with the FR of the primary design antibody" listed by homology search refers to the FR having a homology in the amino acid sequence of at least 80%, preferably at least 90%, more preferably at least 91%, more preferably at least 92%, more preferably at least 93%, more preferably at least 94%, more preferably at least 95%, more preferably at least 96% or greater, more preferably at least 97% or greater, more preferably at least 98% or greater, and more preferably at least 99% or greater. The homology of protein can be determined by the algorithm described Wilbur, W. J. and Lipman, D. J. Proc. Natl. Acad. Sci. U.S.A. (1983) 80, 726–730.

Amino acid residues of a non-human mammal which were important for construction of the primary design antibody refers to the amino acid residues derived from a non-human FR contained in an artificial FR. Many such amino acid residues are found in the amino acid residues (canonical structure) responsible for the basic structure of antibody molecule, the amino acid residues involved in the maintenance of the structure of CDRs, or the amino acid residues that directly interact with antigen molecule, and include for example an amino acid at position 71 of the H chain, an amino acid at position 94 of the H chain, and the like, though they may vary depending on the antibody.

As mentioned above, if one or a plurality of amino acid residues different between the FR of the primary design antibody and the natural FR are replaced so as to produce humanized antibody having the amino acid residues of a natural human FR, the humanized antibody (natural humanized antibody; termed the secondary design antibody) thus obtained all comprise natural FRs. In this case all human FRs are preferably human FRs that belong to the same subgroup, and more preferably are derived from the same antibody. Furthermore, all human FRs are not required to belong to the same subgroup, as long as they are reshaped into an antibody and provide certain antigen binding activity, and thereby they are not limited to the human FRS that belong to the same subgroup. According to the present invention, a plurality of amino acid residues mean 2 or more amino acid residues, preferably 2 or more and 10 or less amino acid residues, more preferably 2 or more and 5 or less amino acid residues, more preferably 2 or more and 4 or less amino acid residues, and more preferably 2 or more and 3 or less amino acid residues in the amino acid sequence.

Homology between an artificial FR and a natural human FR is at least 80%, preferably at least 90%, more preferably at least 91%, more preferably at least 92%, more preferably at least 93%, more preferably at least 94%, more preferably at least 95%, more preferably at least 96% or greater, more preferably at least 97% or greater, more preferably at least 98% or greater, and more preferably at least 99% or greater.

Then, the secondary design antibody is allowed to be expressed in a suitable expression system, for example in an animal cell, to evaluate the antigen binding activity, and the like.

Furthermore, the method of preparation of the present invention can be effected even without the actual construction of the primary design antibody. Thus, the primary design antibody is conventionally designed, and without the evaluation thereof the secondary design antibody may be designed, which may be directly evaluated. In fact, however, the identification of important FR residues sometimes involves experiment, and the secondary design antibody is preferably constructed after the conventional primary design antibody has been experimentally constructed.

Specifically, in one aspect of the present invention, the natural humanized antibody of the present invention was produced with mouse anti-HM1.24 antibody (Goto, T. et al., Blood (1994) 84, 1922–1930) as a template.

For natural humanized antibodies designed as mentioned above, the gene encoding them can be obtained by a known method. For example, several oligonucleotides are synthesized that have overlapping ends corresponding to the DNA encoding the amino acid sequence of the designed natural humanized antibody. A PCR method is carried out using these oligonucleotides as primers. Then, a PCR method is carried out using primers that define the both ends of the DNA encoding the amino acid sequence of the designed natural humanized antibody to obtain the gene encoding the desired natural humanized antibody.

Genes encoding a natural humanized antibody constructed as described above may be expressed in a known method so as to obtain the natural humanized antibody. In the case of mammalian cells, expression may be accomplished using a commonly used useful promoter/enhancer, the antibody gene to be expressed, and DNA in which the poly A signal has been operably linked at 3' downstream thereof, or using a vector containing the same. Examples of the promoter/enhancer include human cytomegalovirus immediate early promoter/enhancer.

Additionally, as the promoter/enhancer which can be used for expression of antibody for use in the present invention, there can be used viral promoters/enhancers such as retrovirus, polyoma virus, adenovirus, and simian virus 40 (SV40), and promoters/enhancers derived from mammalian cells such as human elongation factor 1α (HEF1α).

For example, expression may be readily accomplished by the method of Mulligan et al. (Nature (1979) 277, 108) when the SV40 promoter/enhancer is used, or by the method of Mizushima et al. (Nucleic Acids Res. (1990) 18, 5322) when the HEF1α promoter/enhancer is used.

In the case of *Escherichia coli* (*E. coli*), expression may be effected by operably linking a commonly used useful promoter, a signal sequence for antibody secretion, and the antibody gene to be expressed, followed by expression thereof. As the promoter, for example, there can be mentioned the lacz promoter and the araB promoter. The method of Ward et al. (Nature (1098) 341, 544–546; FASEB J. (1992) 6, 2422–2427) may be used when lacz promoter is used, and the method of Better et al. (Science (1988) 240, 1041–1043) may be used when araB promoter is used.

As the signal sequence for antibody secretion, when produced in the periplasm of *E. coli*, the pelB signal sequence (Lei, S. P. et al., J. Bacteriol. (1987) 169, 4379) can be used. After separating the antibody produced in the periplasm, the structure of the antibody is appropriately refolded before use (see, for example, International Patent Publication WO 96/30394, and Japanese Examined Patent Publication (Kokoku) No. 7(1995)-93879).

As the origin of replication, there can be used those derived from SV40, polyoma virus, adenovirus, bovine papilloma virus (BPV) and the like. Furthermore, for the amplification of the gene copy number in the host cell system, expression vectors can include as selectable markers the aminoglycoside transferase (APH) gene, the thymidine kinase (TK) gene, *E. coli* xanthine guaninephosphoribosyl transferase (Ecogpt) gene, the dihydrofolate reductase (dhfr) gene and the like.

For the production of antibody for use in the present invention, any production system can be used. The production system of antibody preparation comprises the in vitro or the in vivo production system. As the in vitro production system, there can be mentioned a production system which employs eukaryotic cells and the production system which employs prokaryotic cells.

When the eukaryotic cells are used, there are the production systems which employ animal cells, plant cells, and fungal cells. Known animal cells include (1) mammalian cells such as CHO cells (J. Exp. Med. (1995) 108, 945), COS cells, myeloma cells, baby hamster kidney (BHK) cells, HeLa cells, and Vero cells, (2) amphibian cells such as Xenopus oosytes (Valle, et al., Nature (1981) 291, 358–340), or (3) insect cells such as sf9, sf21, and Tn5. As CHO cells, preferably dhfr-CHO (Proc. Natl. Acad. Sci. U.S.A. (1980) 77, 4216–4220) that lacks the DHFR gene and CHO K-1 (Proc. Natl. Acad. Sci. U.S.A. (1968) 60, 1275) may be used.

Known plant cells include, for example, those derived from *Nicotiana tabacum*, which is subjected to callus culture. Known fungal cells include yeasts such as the genus *Saccharomyces*, for example *Saccharomyces cereviceae*, or filamentous fungi such as the genus *Aspergillus*, for example *Aspergillus niger*.

When the prokaryotic cells are used, there are the production systems which employ bacterial cells. Known bacterial cells include *Escherichia coli* (*E. coli*), and *Bacillus subtilis*.

By transforming these cells with the gene encoding the natural humanized antibody of the present invention and and culturing the transformed cells in vitro, the natural humanized antibody can be obtained. Culturing is carried out in a known method. For example, as the culture liquid, DMEM, MEM, RPMI1640, and IMDM can be used, and serum supplements such as fetal calf serum (FCS) may be used in combination, or serum-free culture medium may be used. In addition, antibodies may be produced in vivo by implanting cells into which the antibody gene has been introduced into the abdominal cavity of an animal and the like.

As in vivo production systems, there can be mentioned those which employ animals and those which employ plants. The gene of antibody is introduced into an animal or a plant, and the antibody is produced in such an animal or a plant and then collected.

When animals are used, there are the production systems which employ mammals and insects.

As mammals, goats, pigs, sheep, mice, and cattle can be used (Vicki Glaser, SPECTRUM Biotechnology Applications, 1993). When mammals are used, transgenic animals can also be used.

For example, an antibody gene is inserted into a gene encoding protein which is inherently produced in the milk such as goat β casein to prepare fusion genes. DNA fragments containing the fusion gene into which the antibody gene has been inserted are injected into a goat embryo, and the embryo is introduced into a female goat. The desired antibody is obtained from the milk produced by the transgenic goat borne to the goat who received the embryo or offsprings thereof. In order to increase the amount of milk containing the desired antibody produced by the transgenic goat, hormones may be given to the transgenic goat as appropriate (Ebert, K. M. et al., Bio/Technology (1994) 12, 699–702).

When insects are used, silkworms can be used. When silkworms are used, baculovirus into which the desired antibody gene has been inserted is infected to the silkworm, and the desired antibody can be obtained from the body fluid of the silkworm (Susumu, M. et al., Nature (1985) 315, 592–594).

When plants are used, tabacco, for example, can be used. Moreover, when tabacco is used, the desired antibody gene is inserted into an expression vector for plants, for example pMON 530, and then the vector is introduced into a bacterium such as *Agrobacterium tumefaciens*. The bacterium is then infected to tabacco such as *Nicotiana tabacum* to obtain the desired antibody from the leaves of the tabacco (Julian, K. -C. Ma et al., Eur. J. Immunol. (1994) 24, 131–138).

As described above, "hosts" as used herein encompasses animals and plants that produce the desired natural humanized antibody. When antibody is produced in vitro or in vivo production systems, as described above, DNA encoding an H chain or an L chain of an antibody may be separately integrated into an expression vector and a host is transformed simultaneously, or DNA encoding an H chain and DNA encoding an L chain may be integrated into a single expression vector and a host is transformed therewith (see International Patent Publication WO 94-11523).

As method of introducing an expression vector into a host, a known method such as the calcium phosphate method (Virology (1973) 52, 456–467) and the electropolation method (EMBO J. (982) 1, 841–845) and the like can be used.

A natural humanized antibody produced and expressed as described above can be separated from the inside or outside of the cell or from the host and then may be purified to homogeneity. Separation and purification of the natural humanized antibody for use in the present invention may be accomplished by conventional methods of separation and purification used for protein, without any limitation. Separation and purification may be accomplished by combining, as appropriate, chromatography such as affinity chromatography, filtration, ultrafiltration, salting-out, dialysis and the like (Antibodies: A Laboratory Manual, Ed Harlow and David Lane, Cold Spring Harbor Laboratory, 1988).

As the column used for such affinity chromatography, there can be mentioned Protein A column and Protein G column. As carriers for use in the Protein A column there can be mentioned Hyper D, POROS, Sepharose F.F. (Pharmacis) and the like.

Chromatography other than affinity chromatography includes, for example, ion exchange chromatography, hydrophobic chromatography, gel-filtration, reverse-phase chromatography, adsorption chromatography and the like (Strategies for Protein Purification and Characterization: A Laboratory Course Manual. Ed Daniel R. Marshak et al., Cold Spring Harbor Laboratory Press, 1996).

These chromatographies can be carried out using a liquid chromatography such as HPLC, FPLC, and the like.

The concentration of the natural humanized antibody of the present invention can be determined by the measurement of absorbance or by the enzyme-linked immunosorbent assay (ELISA) and the like. Thus, when absorbance measurement is employed, the natural humanized antibody obtained is appropriately diluted with PBS and then the absorbance is measured at 280 nm, followed by calculation using the absorption coefficient of 1.35 OD at 1 mg/ml.

When the ELISA method is used, measurement is conducted as follows. Thus, 100 µl of goat anti-human IgG (manufactured by BIO SOURCE) diluted to 1 mg/ml in 0.1 M bicarbonate buffer, pH 9.6, is added to a 96-well plate (manufactured by Nunc), and is incubated overnight at 4° C. to immobilize the antibody. After blocking, 100 µl each of appropriately diluted natural humanized antibody of the present invention or a sample containing the antibody, or human IgG (manufactured by CAPPEL) of a known concentration as the standard is added, and incubated at room temperature for 1 hour.

After washing, 100 µl of 5000-fold diluted alkaline phosphatase-labeled anti-human IgG antibody (manufactured by BIO SOURCE) is added, and incubated at room temperature for 1 hour. After washing, the substrate solution is added and incubated, followed by the measurement of absorbance at 405 nm using the MICROPLATE READER Model 3550 (manufactured by Bio-Rad) to calculate the concentration of the desired antibody. BIAcore (manufactured by Pharmacia) can be used for the measurement of antibody concentration.

The antigen binding activity, binding inhibition activity, and neutralizing activity of the natural humanized antibody of the present invention can be evaluated by known methods. For example, as methods of determining the activity of the natural humanized antibody of the present invention, there can be mentioned ELISA, EIA (enzymeimmunoassay), RIA (radioimmunoassay), or fluorescent antibody method. For the evaluation of the above antibody, BIAcore (manufactured by Pharmacia) can be used.

The natural humanized antibody of the present invention may be antibody fragments or modified versions thereof. For example, as fragments of antibody, there may be mentioned Fab, F(ab')$_2$, Fv or single-chain Fv (scFv). scFv has a structure in which Fvs of the H chain and the L chain are ligated via a suitable linker.

In order to produce these antibodies, antibodies are treated with an enzyme such as papain or pepsin, or genes encoding these antibody fragments are constructed and then introduced into an expression vector, which is expressed in a suitable host cell to express them (see, for example, Co, M. S. et al., J. Immunol. (1994) 152, 2968–2976; Better, M. and Horwitz, A. H., Methods in Enzymology (1989) 178, 476–496, Academic Press Inc.; Plucktrun, A. and Skerra, A., Methods in Enzymol. (1989) 178, 476–496, Academic Press Inc.; Lamoyi, E., Methods in Enzymol. (1986) 121, 652–663; Rousseaux, J. et al., Methods in Enzymol. (1986) 121, 663–669; Bird, R. E. and Walker, B. W., TIBTECH (1991) 9, 132–137).

scFv can be obtained by ligating the V region of H chain and the V region of L chain of antibody (see, International Patent Publication WO 88-09344). In scFv, the V region of H chain and the V region of L chain are preferably ligated via a linker, preferably a peptide linker (Huston, J. S. et al., Proc. Natl. Acad. Sci. U.S.A. (1988) 85, 5879–5883). The V region of H chain and the V region of L chain in the scFv may be derived from any of the above-mentioned antibodies. As the peptide linker for ligating the V regions, any single-chain peptide comprising, for example, one comprising 12 to 19 amino acid residues may be used (see, U.S. Pat. No. 5,525,491).

DNA encoding scFv can be obtained using DNA encoding the H chain or the H chain V region of the above antibody and DNA encoding the L chain or the L chain V region of the above antibody as the template by amplifying the portion of the DNA encoding the desired amino acid sequence among the above sequences by the PCR technique with the primer pair specifying the both ends thereof, and by further amplifying the combination of DNA encoding the peptide linker portion and the primer pair which defines that both ends of said DNA be ligated to the H chain and the L chain, respectively.

Once DNAs encoding scFv are constructed, an expression vector containing them and a host transformed with said expression vector can be obtained by the conventional methods, and scFv can be obtained using the resultant host by the conventional methods.

These antibody fragments can be produced by obtaining the gene thereof in a similar manner to that mentioned above and by allowing it to be expressed in a host. "Antibody" as used in the claim of the present application encompasses these antibody fragments.

As modified antibodies, antibodies associated with various molecules such as polyethylene glycol (PEG) can be used. "Antibody" as used in the claim of the present application encompasses these modified antibodies. These modified antibodies can be obtained by chemically modifying the antibodies thus obtained. These methods have already been established in the art.

The natural humanized antibody of the present invention may be administered orally or pareterally, either systemically or topically. The parenteral route may be selected from intravenous injection such as drip infusion, intramuscular injection, intraperitoneal injection, and subcutaneous injection, and the method of administration may be chosen, as appropriate, depending on the age and the condition of the patient.

The natural humanized antibody of the present invention may be administered at a dosage that is sufficient to treat or to block at least partially the pathological condition. For example, the effective dosage is chosen from the range of 0.01 mg to 100 mg per kg of body weight per administration. Alternatively, the dosage in the range of 1 to 1000 mg, preferably 5 to 50 mg per patient may be chosen. However, the natural humanized antibody of the present invention is not limited to these dosages.

The natural humanized antibody of the present invention may contain pharmaceutically acceptable carriers or additives depending on the route of administration. Examples of such carriers or additives include water, a pharmaceutical acceptable organic solvent, collagen, polyvinyl alcohol, polyvinylpyrrolidone, a carboxyvinyl polymer, carboxymethyl cellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, propylene glycol, polyethylene glycol, Vaseline, paraffin, stearyl alcohol, searic acid, human serum albumin (HSA), mannitol, sorbitol, lactose, a pharmaceutically acceptable surfactant and the like. Additives used are chosen from, but not limited to, the above or combinations thereof depending on the dosage form.

REFERENCE EXAMPLES

Before explaining the present invention with reference to the working examples, reference examples will be described as the premise thereof.

Reference Example 1

Cloning of cDNA Encoding the Variable Region of a Mouse Anti-HM1.24 Antibody

1. Isolation of Messenger RNA (mRNA)

Using the Fast Track mRNA Isolation Kit Version 3.2 (manufactured by Invitrogen) according to the instruction attached thereto, mRNA was isolated from $2 \times 10^8$ hybridoma cells (FERM BP-5233) that produce a mouse anti-HM1.24 antibody.

2. Amplification of the Gene Encoding the Variable Region of Antibody by the PCR Method PCR was carried out using the amplification Thermal Cycler (manufactured by Perkin Elmer Cetus).

2-1. Amplification and Fragmentation of the Gene Encoding the V Region of a Mouse L Chain From the mRNA thus isolated, single stranded cDNA was synthesized using the AMV Reverse Transcriptase First-strand cDNA Synthesis Kit (manufactured by Life Science) and used for PCR. As primers used for PCR, MKV (Mouse Kappa Variable) primers (Jones, S. T. et al, Bio/Technology, 9, 88–89, (1991)) shown in SEQ ID NO: 29 to 39 that hybridize with the leader sequence of a mouse kappa type L chain were used.

A hundred microliters of the PCR solution containing 10 mM Tris-HCl (pH 8.3), 50 mM KCl, 0.1 mM dNTPS (dATP, dGTP, dCTP, dTTP), 1.5 mM MgCl2, 5 units of DNA polymerase Ampli Taq (manufactured by Perkin Elmer Cetus), 0.25 mM of the MKV primers shown in SEQ ID NO: 29 to 39, 3 mM of the MKC primer shown in SEQ ID NO: 40, and 100 ng of single stranded cDNA was covered with 50 μl of a mineral oil, and then heated at an initial temperature of 94° C. for 3 minutes, and then at 94° C. for 1 minute, at 55° C. for 1 minute, and at 72° C. for 1 minute in this order. After repeating this cycle for 30 times, the reaction mixture was incubated at 72° C. for 10 minutes. The amplified DNA fragment was purified by the low melting point agarose (manufactured by Sigma), and digested with XmaI (manufactured by New England Biolabs) and SalI (manufactured by Takara Shuzo) at 37° C.

2-2. Amplification and Fragmentation of cDNA Encoding the V Region of a Mouse H Chain The gene encoding the V region of a mouse H chain was amplified by the 5'-RACE method (Rapid Amplification of cDNA ends; Frohman, M. A. et al., Proc. Natl. Acad. Sci. USA, 85, 8998–9002, (1988), Edwards, J. B. D. M., et al., Nucleic Acids Res., 19, 5227–5232, (1991)). After cDNA was synthesized using primer P1 (SEQ ID NO: 63) that specifically hybridizes with the constant region of mouse IgG2a, cDNA encoding the V region of a mouse H chain was amplified by the 5'-AmpliFINDER RACE KIT (manufactured by CLONTECH) using the primer MHC 2a (SEQ ID NO: 64) that specifically hybridizes with the constant region of mouse IgG2a and the anchor primer (SEQ ID NO: 101) attached to the kit. The amplified DNA fragment was purified with the low melting point agarose (manufactured by Sigma) and digested with EcoRI (manufactured by Takara) and XmaI (manufactured by New England Biolabs) at 37° C.

3. Linking and Transformation

The DNA fragment comprising the gene encoding the V region of the mouse kappa type L chain prepared as above was ligated to the pUC19 vector prepared by digesting with SalI and XmaI by reacting in a reaction mixture containing 50 mM Tris-HCl (pH 7.6), 10 mM MgCl$_2$, 10 mM dithiothreitol, 1 mM ATP, 50 mg/ml of polyethylene glycol (8000) and one unit of T4 DNA ligase (manufactured by GIBCO-BRL) at 16° C. for 2.5 hours. Similarly, the gene encoding the V region of the mouse H chain was reacted and ligated to pUC19 vector prepared by digesting with EcoRI and XmaI at 16° C. for three hours.

Then 10 μl of the above ligation mixture was added to 50 μl of the competent cells of *Escherichia coli* DH5, which was left on ice for 30 minutes, at 42° C. for one minute, and again on ice for one minute. Subsequently 400 μl of 2×YT medium (Molecular Cloning: A Laboratory Manual, Sambrook et al., Cold Spring Harbor Laboratory Press, (1989)) was added thereto, incubated at 37° C. for one hour, and then the *E. coli* was plated on the 2×YT agar medium (Molecular Cloning: A Laboratory Manual, Sambrook et al., Cold Spring Harbor Laboratory Press, (1989)) containing 50 μg/ml of ampicillin, and then incubated overnight at 37° C. to obtain the *E. coli* transformant.

The transformant was cultured overnight at 37° C. in 10 ml of the 2×YT medium containing 50 μg/ml of ampicillin, and then from this culture plasmid DNA was prepared using the alkali method (Molecular Cloning: A Laboratory Manual, Sambrook et al., Cold Spring Harbor Laboratory Press, (1989)).

The plasmid thus obtained containing the gene encoding the V region of the mouse kappa type L chain derived from the hybridoma that produces the anti-HM1.24 antibody was termed pUCHMVL9. The plasmid obtained in the above-mentioned method containing the gene encoding the V region of the mouse H chain derived from the hybridoma that produces the anti-HM1.24 antibody was termed pUCHMVHR16.

Reference Example 2

Determination of the Nucleotide Sequence of DNA

The nucleotide sequence of the cDNA coding region in the above-mentioned plasmid was determined using the automatic DNA sequencer (manufactured by Applied Biosystem Inc.) and Taq Dye Deoxy Terminator Cycle Sequencing Kit (manufactured by Applied Biosystem Inc.) in the protocol indicated by the manufacturer.

The nucleotide sequence of the gene encoding the V region of the L chain of the mouse anti-HM1.24 antibody contained in the plasmid pUCHMVL9 is shown in SEQ ID NO: 1. The nucleotide sequence of the gene encoding the V region of the H chain of the mouse anti-HM1.24 antibody contained in the plasmid pUCHMVHR16 is shown in SEQ ID NO: 3.

Reference Example 3

Determination of CDR

The overall structures of the V regions of an L chain and an H chain have a similarity with each other in which four framework portions are linked by three hypervariable regions, i.e. complementarity determining regions (CDR). The amino acid sequence of the framework is relatively well conserved but variation in the amino acid sequence is extremely high (Kabat, E. A., et al., "Sequences of Proteins of Immunological Interest", US Dept. Health and Human Services, 1983).

Based on these facts, the amino acid sequence of the variable region of the anti-HM1.24 antibody was fitted to the database of the amino acid sequences of antibodies to investigate homology, and the CDR region was determined as shown in Table 1.

TABLE 1

| Plasmid | Sequence No. | CDR(1) | CDR(2) | CDR(3) |
|---|---|---|---|---|
| pUCHMVL9 | 5 to 7 | 24–34 | 50–56 | 89–97 |
| pUCHMVHR16 | 8 to 10 | 31–35 | 50–66 | 99–109 |

Reference Example 4

Confirmation of Expression of the Cloned cDNA (Construction of the Chimera Anti-HM1.24 Antibody)

1. Construction of an Expression Vector

In order to construct an expression vector that expresses a chimera anti-HM1.24 antibody, cDNA clones pUCHMVL9 and pUCHMVHR16 encoding the V regions of the L chain and the H chain of the mouse anti-HM1.24 antibody, respectively, were modified by the PCR method, and then introduced into the HEF expression vector (International Patent Publication No. WO 92-19759).

The backward primer ONS-L722S (SEQ ID NO: 65) for the V region of an L chain and the backward primer VHR16S (SEQ ID NO: 66) for the V region of an H chain were designed so that they hybridize to the DNA encoding the start of the leader sequence of the V region of each and they have the Kozak consensus sequence (Kozak, M. et al., J. Mol. Biol., 196, 947–950, (1987)) and the recognition site for HindIII restriction enzyme. The forward primer VL9A (SEQ ID NO: 67) for the V region of an L chain and the forward primer VHR16A (SEQ ID NO: 68) for the V region of an H chain were designed so that they hybridize to the DNA sequence encoding the end of the J region and they have a splice donor sequence and the recognition site for BamHI restriction enzyme.

One hundred µl of the PCR reaction mixture containing 10 mM Tris-HCl (pH 8.3), 50 mM KCl, 0.1 mM dNTPs, 1.5 mM $MgCl_2$, 100 pmole each of each primer, 100 ng of template DNA (pUCHMVL9 or pUCHMVHR16), and 5 units of Ampli Taq enzyme was covered with 50 µl of a mineral oil, and then after the initial denaturation at 94° C., heated at 94° C. for 1 minute, at 55° C. for 1 minute and at 72° C. for 1 minute for 30 cycles and finally incubated at 72° C. for 10 minutes.

The PCR product was purified by the low melting point agarose gel, and digested with HindIII and BamHI, and then cloned to HEF-VL-gκ for the V region of the L chain and to HEF-VH-gγ1 for the V region of the H chain. After determination of the DNA sequence, the plasmids containing the DNA fragment that contains the correct DNA sequence were designated as HEF-1.24L-gκ and HEF-1.24H-gγ1, respectively.

The regions encoding the respective variable region from the above plasmids HEF-1.24L-gκ and HEF-1.24H-gγ1 were digested with restriction enzymes HindIII and BamHI to make restriction fragments, which were inserted to the HindIII site and the BamHI sites of plasmid vector pUC19 and they were designated as pUC19-1.24L-gκ and pUC19-1.24H-gγ1, respectively.

*Escherichia coli* containing respective plasmids pUC19-1.24L-gκ and pUC19-1.24H-gγ1 were designated as *Escherichia coli* DH5 (pUC19-1.24L-gκ) and *Escherichia coli* DH5 (pUC19-1.24H-gγ1), and were internationally deposited on Aug. 29, 1996, with the National Institute of Bioscience and Human-Technology, Agency of Industrial Science and Technology, MITI (Higashi 1-Chome 1-3, Tsukuba city, Ibalaki prefecture, Japan) under the accession numbers FERM BP-5646 and FERM BP-5644, respectively, under the provisions of the Budapest Treaty.

2. Transfection into COS-7 Cells

In order to observe the transient expression of the chimera anti-HM1.24 antibody, the above expression vectors were tested in the COS-7 (ATCC CRL-1651) cells. HEF-1.24L-gκ and HEF-1.24H-gγ1 were cotransformed into COS-7 cells by electroporation using the Gene Pulser instrument (manufactured by BioRad). Each DNA (10 µg) was added to 0.8 ml aliquots of $1 \times 10^7$ cells/ml in PBS, and was subjected to pulses at 1500 V and a capacity of 25 µF.

After a recovery period of 10 minutes at room temperature, the electroporated cells were added to 30 ml of the DHEM culture liquid (manufactured by GIBCO) containing 10% γ-globulin-free bovine fetal serum. After incubation of 72 hours in the $CO_2$ incubator BNA120D (manufactured by TABAI), the culture supernatant was collected, the cell debris was removed by centrifugation, and the supernatant was used for the following experiment.

3. FCM Analysis

The antigen binding activity of the chimera anti-HM1.24 antibody was investigated by FCM (flow cytometry) analysis using the KPMM2 cells. After $4.7 \times 10^5$ KPMM2 cells (Japanese Unexamined Patent Publication (Kokai) No. 7(1995)-236475) were washed with PBS(−), 50 µl of the culture of COS-7 cells that produce the above-mentioned chimera anti-HM1.24 antibody and 50 μl of FACS buffer (PBS(−)) containing 2% bovine fetal serum and 0.1% sodium azide), or 5 μl of 500 μg/ml purified mouse anti-HM1.24 antibody and 95 μl of the FACS buffer were added, and incubated at the temperature of ice for one hour.

As a control, 50 μl of 2 μg/ml chimera SK2 (International Patent Publication No. WO 94-28159) and 50 μl of the FACS buffer, or 5 μl of 500 μg/ml purified mouse IgG2aκ (UPC10) (manufactured by CAPPEL) instead of purified mouse anti-HM1.24 antibody, and 95 μl of FACS buffer were added, and similarly incubated. After washing with the FACS buffer, 100 μl of 25 μg/ml FITC-labeled goat anti-human antibody (GAH) (manufactured by CAPPEL) or 10 μg/ml FITC labeled goat anti-mouse antibody (GAM) (manufactured by Becton Dickinson) were added, and incubated at a temperature of ice for 30 minutes. After washing with the FACS buffer, it was suspended in one ml of the FACS buffer, and fluorescence intensity of each cell was measured by the FACScan (manufactured by Becton Dickinson).

As shown in FIG. 1, it was revealed that the chimera anti-HM1.24 antibody bound to the KPMM2 cell because the peak of fluorescence intensity shifted to the right in the chimera anti-HM1.24 antibody-added cells as compared to the control similarly to the case where mouse anti-HM1.24 antibody was added. This confirmed that the cloned cDNA encodes the variable region of the mouse anti-HM1.24 antibody.

Reference Example 5

Establishment of the CHO Cell Line that Stably Produces a Chimera Anti-HM1.24 Antibody 1. Construction of an Expression Vector for the Chimera H Chain By digesting the above plasmid HEF-1.24H-gγ1 with the restriction enzymes PvuI and BamHI, an about 2.8 kbp fragment containing the EF1 promoter and the DNA encoding the V region of the H chain of the mouse anti-HM1.24 antibody was purified using 1.5% low melting point agarose gel. Then, the above DNA fragment was inserted into an about 6 kbp fragment prepared by digesting the expression vector used for a human H chain expression vector, DHFR-ΔE-Rvh-PM1f (see International Patent Publication No. WO 92/19759), containing the DHFR gene and the gene encoding the constant region of a human H chain with PvuI and BamHI to construct an expression vector, DHFR-ΔE-HEF-1.24-H-gγ1, for the H chain of the chimera anti-HM1.24 antibody.

2. Gene Introduction into CHO Cells

In order to establish a stable production system of the chimera anti-HM1.24 antibody, the genes of the above-mentioned expression vectors, HEF-1.24L-gκ and DHFR-ΔE-HEF-1.24H-gγ1, that were linearized by digestion with PvuI were simultaneously introduced into the CHO cell DXBII (donated from the Medical Research Council Collaboration Center) by the electroporation method under the condition similar to the above-mentioned one (the above-mentioned transfection into the COS-7 cells).

3. Gene Amplification by MTX

Among the gene-introduced CHO cells, only those CHO cells in which both of the L chain and the H chain expression vectors have been introduced can survive in the nucleoside-free α-MEM culture liquid (manufactured by GIBCO-BRL) to which 500 μg/ml G418 (manufactured by GIBCO-BRL) and 10% bovine fetal serum were added, and so they were selected. Subsequently, 10 nM MTX (manufactured by Sigma) was added to the above culture liquid. Among the clones that propagated, those that produce the chimera anti-HM1.24 antibody in large amounts were selected. As a result, clones #8 to #13 that exhibited a production efficiency of about 20 μg/ml of the chimera antibody were obtained and termed the chimera anti-HM1.24 antibody-producing cell lines.

Reference Example 6

Construction of the Chimera Anti-HM1.24 Antibody

The chimera anti-HM1.24 antibody was constructed in the following method. The above chimera anti-HM1.24 antibody-producing CHO cells were subjected to continuous culture for 30 days using as the medium Iscove's Modified Dulbecco's Medium (manufactured by GIBCO-BRL) containing 5% γ-globulin-free newborn bovine serum (manufactured by GIBCO-BRL) by the high-density cell culture instrument Verax system 20 (manufactured by CELLEX BIOSCIENCE Inc.).

On day 13, 20, 23, 26, and 30 after starting the culture, the culture liquid was recovered using a pressurized filter unit SARTOBRAN (manufactured by Sartorius), and then the chimera anti-HM1.24 antibody was affinity-purified using a large-volume antibody collection system Afi-Prep System (manufactured by Nippon Gaishi) and Super Protein A column (bed volume: 100 ml, manufactured by Nippon Gaishi) using PBS as the absorption/wash buffer and 0.1 M sodium citrate buffer (pH 3) as the elution buffer according to the attached instructions. The eluted fractions were adjusted to about pH 7.4 by immediately adding 1 M Tris-HCl (pH 8.0). Antibody concentration was measured by absorbance at 280 nm and calculated with 1 μg/ml as 1.35 OD.

Reference Example 7

Determination of Activity of the Chimera Anti-HM1.24 Antibody

Chimera anti-HM1.24 antibody was evaluated by the following binding inhibition activity.

1. Measurement of Binding Inhibition Activity 1-1. Construction of a Biotinylated Anti-HM1.24 Antibody After the mouse anti-HM1.24 antibody was diluted with 0.1 M bicarbonate buffer to 4 mg/ml, 4 μl of 50 mg/ml Biotin-N-hydroxy succinimide (manufactured by EY LABS Inc.) was added and reacted at room temperature for 3 hours. Thereafter, 1.5 ml of 0.2 M glycine solution was added thereto, incubated at room temperature for 30 minutes to stop the reaction, and then the biotinylated IgG fractions were collected using the PD-10 column (manufactured by Pharmacia Biotech).

1-2. Measurement of Binding Inhibition Activity

The binding inhibition activity by the biotin-labeled mouse anti-HM1.24 antibody was measured by the Cell-ELISA using the human amniotic membrane cell line WISH cells (ATCC CCL 25). The Cell-ELISA plates were prepared as follows. To a 96-well plate was added 4×10$^5$ cells/ml prepared with PRMI 1640 medium supplemented with 10% fetal bovine serum, incubated overnight, and after washing twice with PBS(−), were immobilized with 0.1% glutaraldehyde (manufactured by Nacalai Tesque Inc.).

After blocking, 50 μl of serial dilutions of the chimera anti-HM1.24 antibody or the mouse anti-HM1.24 antibody obtained by affinity purification was added to each well and simultaneously 50 μl of 2 μg/ml biotin-labeled mouse anti-HM1.24 antibody was added, incubated at room temperature for two hours, and then the peroxidase-labeled streptavidin (manufactured by DAKO) was added. After incubating at room temperature for one hour and then washing, the substrate solution was added. After stopping the reaction by adding 50 μl of 6N sulfuric acid, absorbance at 490 nm was measured using the MICROPLATE READER Model 3550 (manufactured by Bio-Rad).

Figure 2:
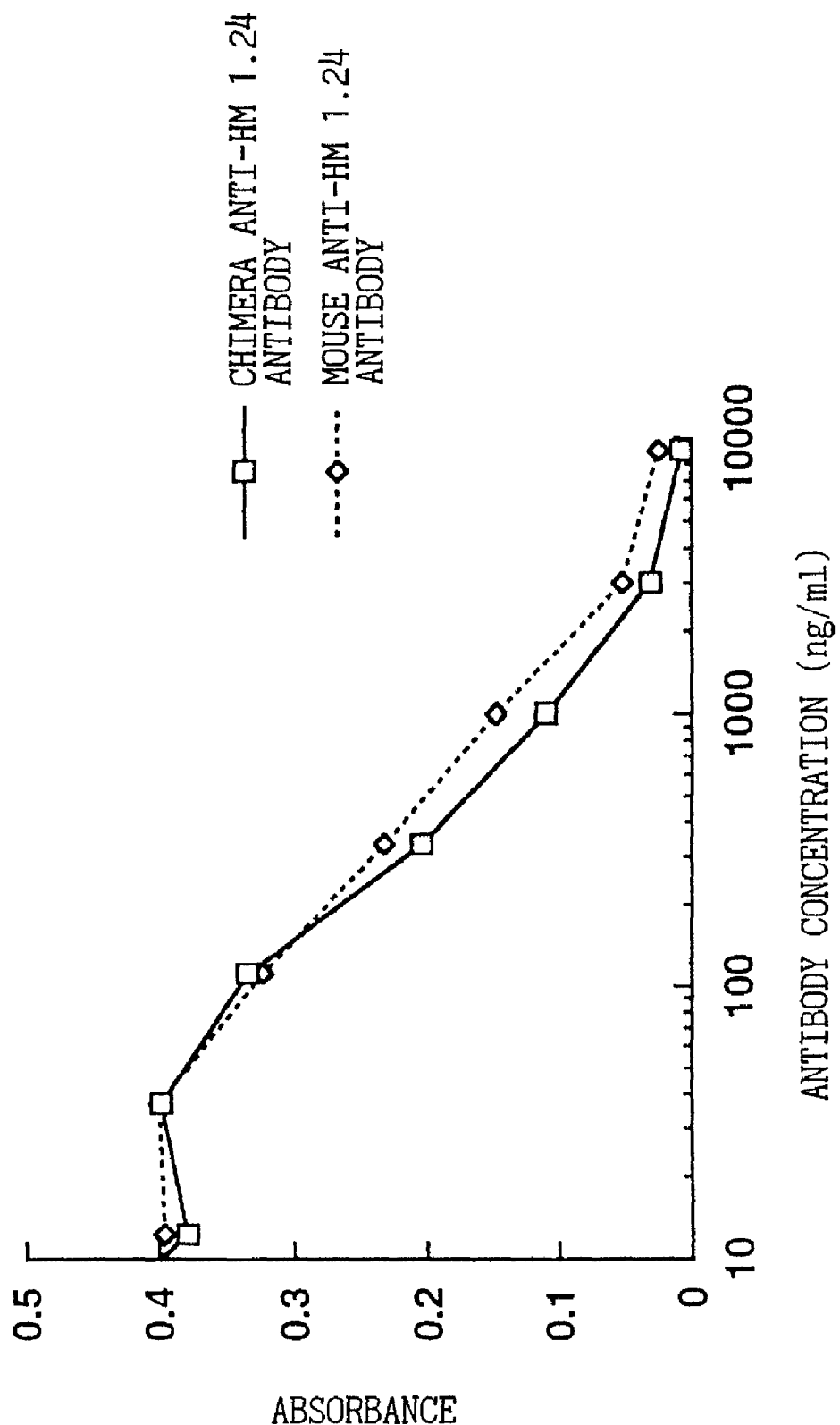
FIG. 2 is a graph showing that chimeric anti-HM1.24 antibody inhibits the binding of biotinylated mouse anti-HM1.24 antibody to the WISH cells in a dose-dependent manner similarly to that of mouse anti-HM1.24 antibody.

The result, as shown in FIG. 2, revealed that the chimera anti-HM1.24 antibody has a similar binding inhibition activity with the mouse anti-HM1.24 antibody as the biotin-labeled mouse anti-HM1.24 antibody. This indicates that the chimera antibody had the same V region as the mouse anti-HM1.24 antibody.

Reference Example 8

Measurement of the ADCC Activity of the Chimera Anti-HM1.24 Antibody

ADCC (Antibody-dependent Cellular Cytotoxicity) activity was measured according to the method as set forth in Current Protocols in Immunology, Chapter 7, Immunologic studies in humans, Editor, Johan E. Coligan et al., John Wiley & Sons, Inc., 1993.

1. Preparation of Effector Cells

Monocytes were separated from the peripheral blood or bone marrow of healthy humans and patients with multiple myeloma by the density centrifugation method. Thus, an equal amount of PBS(−) was added to the peripheral blood and the bone marrow of healthy humans and patients with multiple myeloma, which was layered on Ficoll (manufactured by Pharmacia)-Conrey (manufactured by Daiichi Pharmaceutical Co. Ltd.) (specific gravity, 1.077), and was centrifuged at 400 g for 30 minutes. The monocyte layer was collected, and washed twice with RPMI 1640 (manufactured by Sigma) supplemented with 10% bovine fetal serum (manufactured by Witaker), and prepared at a cell density of $5\times10^6$/ml with the same culture liquid.

2. Preparation of Target Cells

The human myeloma cell line RPMI 8226 (ATCC CCL 155) was radiolabeled by incubating in the RPMI 1640 (manufactured by Sigma) supplemented with 10% bovine fetal serum (manufactured by Witaker) together with 0.1 mCi of $^{51}$Cr-sodium chromate at 37° C. for 60 minutes. After radiolabeling, cells were washed three times with Hanks balanced salt solution (HBSS) and adjusted to a concentration of $2\times10^5$/ml.

3. ADCC Assay

Into a 96-well U-bottomed plate (manufactured by Corning) were added 50 μl of $2\times10^5$ target cells/ml, 1 μg/ml of affinity-purified chimera anti-HM1.24 antibody and mouse anti-HM1.24 antibody, or control human IgG (manufactured by Serotec), and the plate was held at 4° C. for 15 minutes.

Then, 100 μl of $5\times10^5$ effector cells/ml was added thereto, and the result was cultured in a $CO_2$ incubator for 4 hours, whereupon the ratio (E:T) of the effector cells (E) to the target cells (T) was set at 0:1, 5:1, 20:1, or 50:1.

One hundred μl of the supernatant was taken and the radioactivity released into the culture supernatant was measured by a gamma counter (ARC361, manufactured by Aloka). For measurement of the maximum radioactivity, 1% NP-40 (manufactured by BRL) was used. Cytotoxicity (%) was calculated by (A−C)/(B−C)×100, wherein A is radioactivity (cpm) released in the presence of antibody, B is radioactivity (cpm) released by NP-40, and C is radioactivity (cpm) released by the culture liquid alone without antibody.

Figure 3:
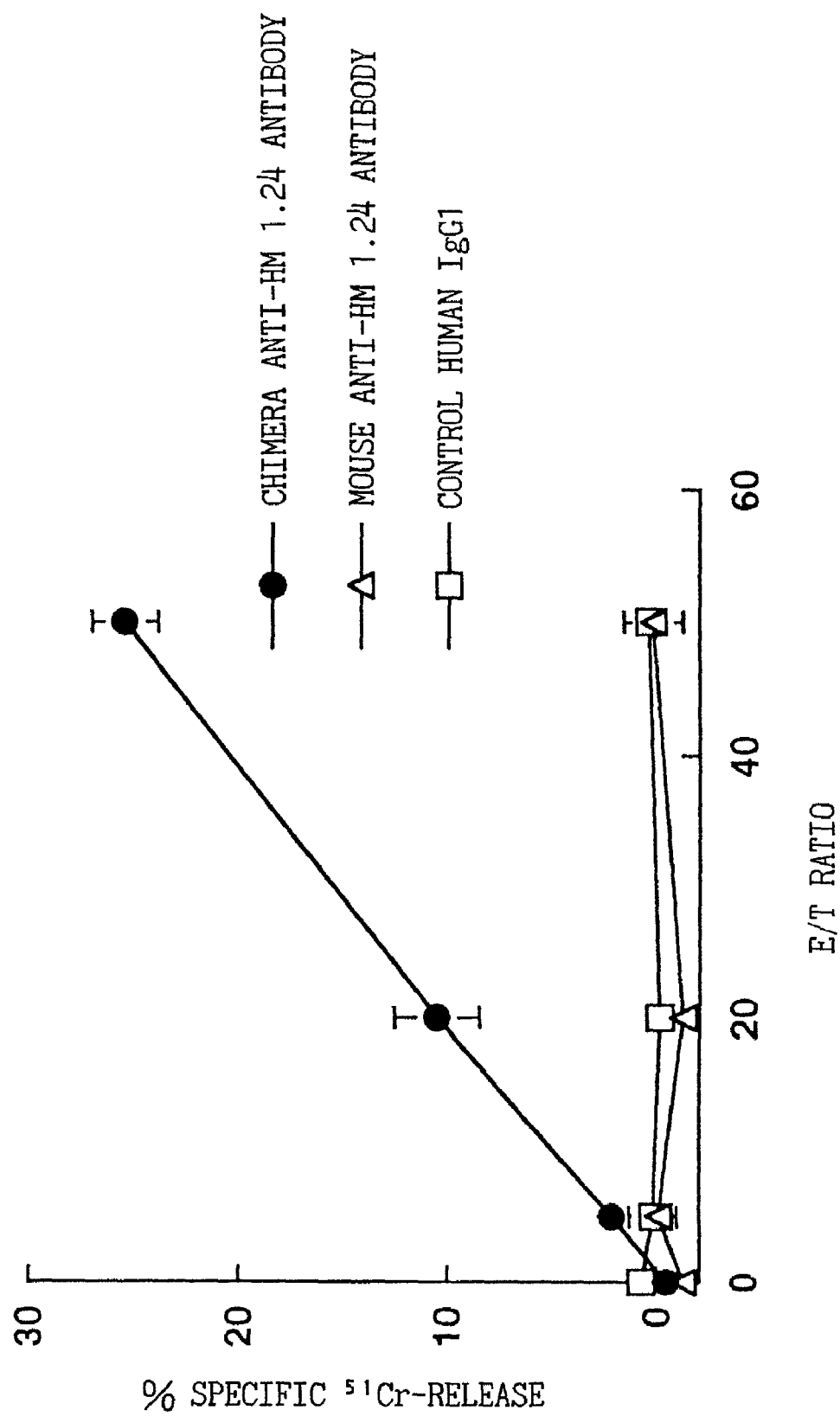
FIG. 3 is a graph showing that chimeric anti-HM1.24 antibody has an increased cytotoxic activity to the RPMI 8226 cells with increasing E/T ratios whereas control IgG1 or mouse anti-HM1.24 antibody has no cytotoxic activity to the RPMI 8226 cells.

As shown in FIG. 3, when the chimera anti-HM1.24 antibody was added as compared to the control IgG1, cytotoxicity increased with the increase in the E:T ratio, which indicated that this chimera anti-HM1.24 antibody has ADCC activity. Furthermore, since there was no cytotoxicity observed even when the mouse anti-HM1.24 antibody was added, it was shown that the Fc portion of human antibody is required to obtain ADCC activity when the effector cell is a human-derived cell.

Reference Example 9

Construction of the Reshaped Human Anti-HM1.24 Antibody

1. Designing of the V Region of the Reshaped Human Anti-HM1.24 Antibody

In order to construct the reshaped human antibody in which the CDR of mouse monoclonal antibody has been transplanted to a human antibody, it is preferred that there is a high homology between the FR of the mouse antibody and the FR of the human antibody. Thus, the V regions of the L chain and the H chain of the mouse anti-HM1.24 antibody were compared to the V regions of all known antibodies whose structure has been elucidated using the Protein Data Bank.

The V region of the L chain of the mouse anti-HM1.24 antibody is most similar to the consensus sequence of the subgroup IV (HSGIV) of the V region of a human L chain with a homology of 66.4%. On the other hand, it has shown a homology of 56.9%, 55.8%, and 61.5% with HSGI, HSGII and HSG III, respectively.

When the V region of the L chain of the mouse anti-HM1.24 antibody is compared to the V region of the L chain of known human antibodies, it has shown a homology of 67.0% with the V region REI of a human L chain, one of the subgroups I of the V region of a human L chain. Thus, the FR of REI was used as the starting material for construction of the V region of the L chain of the reshaped human anti-HM1.24 antibody.

Version a of the L chain V region of the reshaped human anti-HM1.24 antibody was designed. In this version, human FR was made identical with the REI-based FR present in the reshaped human CAMPATH-1H antibody (see Riechmann, L. et al., Nature 322, 21–25, (1988), the FR contained in version a of the V region of the L chain of the reshaped human anti PM-1 antibody described in International Patent Publication No. WO 92-19759), and the mouse CDR was made identical with the CDR in the V region of the L chain of the mouse anti-HM1.24 antibody.

The H chain V region of the mouse anti-HM1.24 antibody is most similar to the consensus sequence of HSGI of the V region of a human H chain with a homology of 54.7%. On the other hand, it shows a homology of 34.6% and 48.1% with HSGII and HSGIII, respectively. When the V region of the H chain of the mouse anti-HM1.24 antibody is compared to the V region of the H chain of known human antibodies, FR1 to FR3 were most similar to the V region of the H chain of the human antibody HG3, one of subgroup I of the V region of a human H chain (Rechavi, G. et al., Proc. Natl. Acad. Sci. USA, 80, 855–859), with a homology of 67.3%.

Therefore, the FR of the human antibody HG3 was used as the starting material for construction of the V region of the H chain of the reshaped human anti-HM1.24 antibody. However, since the amino acid sequence of the FR4 of human HG3 has not been described, the amino acid sequence of the FR4 of the human antibody JH6 (Ravetch, J. V. et al., Cell, 27, 583–591) that shows the highest homology with the FR4 of the H chain of the mouse anti-HM1.24 antibody was used. The FR4 of JH6 has the same amino acid sequence as that of the FR4 of the H chain of the mouse anti-HM1.24 antibody except for one amino acid.

In the first version a of the V region of the H chain of the reshaped human anti-HM1.24 antibody, FR1 to FR3 were made identical with the FR1 to FR3 of human HG3, and the CDR was made identical with the CDR of the V region of the H chain of the mouse anti-HM1.24 antibody, except that the amino acids at position 30 in the human FR1 and position 71 in the human FR3 were made identical with the amino acids in the mouse anti-HM1.24 antibody.

Figure 4:
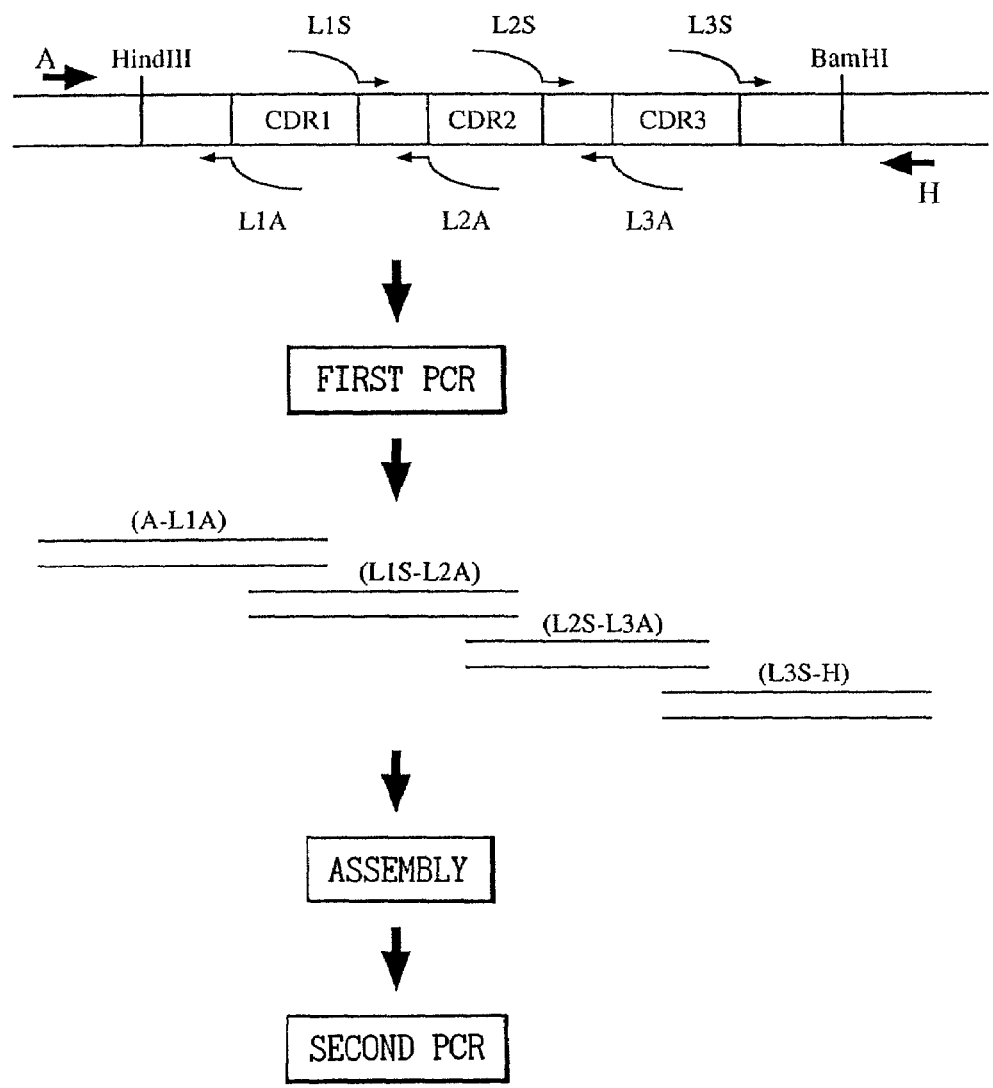
FIG. 4 is a diagram showing a method of constructing the L chain of reshaped human anti-HM1.24 antibody by CDR-grafting using the PCR method.

2. Construction of the V Region of the L Chain of the Reshaped Human Anti-HM1.24 Antibody The L chain of the reshaped human anti-HM1.24 antibody was constructed by the CDR grafting in the PCR method. The method is shown in FIG. 4. Eight PCR primers were used for construction of the reshaped human anti-HM1.24 antibody (version a) having the FR derived from the human antibody REI. The external primers A (SEQ ID NO: 69) and H (SEQ ID NO: 70) were designed to hybridize with the DNA sequence of the expression vector HEF-VL-gκ.

The CDR grafting primers L1S (SEQ ID NO: 71), L2S (SEQ ID NO: 72), and L3S (SEQ ID NO: 73) have the sense DNA sequence. The CDR grafting primers L1A (SEQ ID NO: 74), L2A (SEQ ID NO: 75), and L3A (SEQ ID NO: 76) have the antisense DNA sequence, each having a complementary DNA sequence (20 to 23 bp) to the DNA sequence at the 5'-end of the primers L1S, L2S, and L3S, respectively.

In the first stage of PCR, the four reactions A-L1A, L1S-L2A, L2S-L3A, and L3S-H were conducted to purify each PCR product. The four PCR products from the first PCR were allowed to assemble with one another by their own complementarity (see International Patent Publication No. WO 92-19759). Then, external primers A and H were added to amplify the full-length DNA encoding the V region of the L chain of the reshaped human anti-HM1.24 antibody (the second PCR). In the above-mentioned PCR, the plasmid HEF-RVL-M21a (see International Patent Publication No. WO 95-14041) encoding the version a of the V region of the L chain of the reshaped human ONS-M21 antibody based on the human antibody REI-derived FR was employed as a template.

In the first stage of PCR, the PCR mixture containing 10 mM Tris-HCl (pH 8.3), 50 mM KCl, 0.1 mM dNTPs, 1.5 mM MgCl2, 100 ng of template DNA, 100 pmole of each primer, and 5 u of Ampli Taq was used. Each PCR tube was covered with 50 µl of a mineral oil. Then after it was first denatured by heating at 94° C., it was subjected to a reaction cycle of 94° C. for 1 minute, 55° C. for 1 minute and 72° C. for 1 minute, and then was incubated at 72° C. for 10 minutes.

PCR products A-L1A (215 bp), L1S-L2A (98 bp), L2S-L3A (140 bp), and L3S-H (151 bp) were purified using 1.5% low melting point agarose gel and were assembled in the second PCR. In the second PCR, 98 µl of PCR mixture containing 1 µg each of the first stage PCR products and 5 u of Ample Taq was incubated for 2 cycles of 94° C. for 2 minutes, 55° C. for 2 minutes, and 72° C. for 2 minutes, and then 100 pmole each of the external primers (A and H) was added. The PCR tube was coated with 50 µl of a mineral oil and 30 cycles of PCR were conducted under the same condition as above.

A 516 bp DNA fragment resulting from the second PCR was purified using 1.5% low melting point agarose gel, digested with BamHI and HindIII, and the DNA fragments thus obtained were cloned into the HEF expression vector HEF-VL-gκ. After determining the DNA sequence, the DNA fragment having the correct amino acid sequence of the V region of the L chain of the reshaped human anti-HM1.24 antibody was designated as plasmid HEF-RVLa-AHM-gκ. The amino acid sequence and the nucleotide sequence of the V region of L chain contained in this plasmid HEF-RVLa-AHM-gκ are shown in SEQ ID NO: 11.

The version b of the V region of the L chain of the reshaped human anti-HM1.24 antibody was constructed by mutagenesis using PCR. Mutagen primers FTY-1 (SEQ ID NO: 77) and FTY-2 (SEQ ID NO: 78) were so designed as to mutate phenylalanine at position 71 to tyrosine.

After the above primers were amplified using the plasmid HEF-RVLa-AHM-gκ as a template, the final product was purified by digesting with BamHI and HindIII. The DNA fragments obtained were cloned into the HEF expression vector HEF-VL-gκ to obtain plasmid HEF-RVLb-AHM-gκ. The amino acid sequence and the base sequence of the V region of the L chain contained in this plasmid HEF-RVLb-AHM-gκ are shown in SEQ ID NO: 13.

3. Construction of the H Chain V Region of the Reshaped Human Anti-HM1.24 Antibody 3-1. Construction of Versions a to e of the H Chain V Region of the Reshaped Human Anti-HM1.24 Antibody DNA encoding the V region of the H chain of the reshaped human anti-HM1.24 antibody was designed as follows. By linking the DNA sequence encoding the FR1 to 3 of the human antibody HG3 and the FR4 of the human antibody JH6 to the DNA sequence encoding the CDR of the V region of the H chain of the mouse anti-HM1.24 antibody, the full length DNA encoding the V region of the H chain of the reshaped human anti-HM1.24 antibody was designed.

Then, to the 5'-end and the 3'-end of this DNA sequence the HindIII recognition site/KOZAK consensus sequence and BamHI recognition site/splice donor sequence, respectively, were attached so as to enable insertion of the HEF expression vector.

Figure 5:
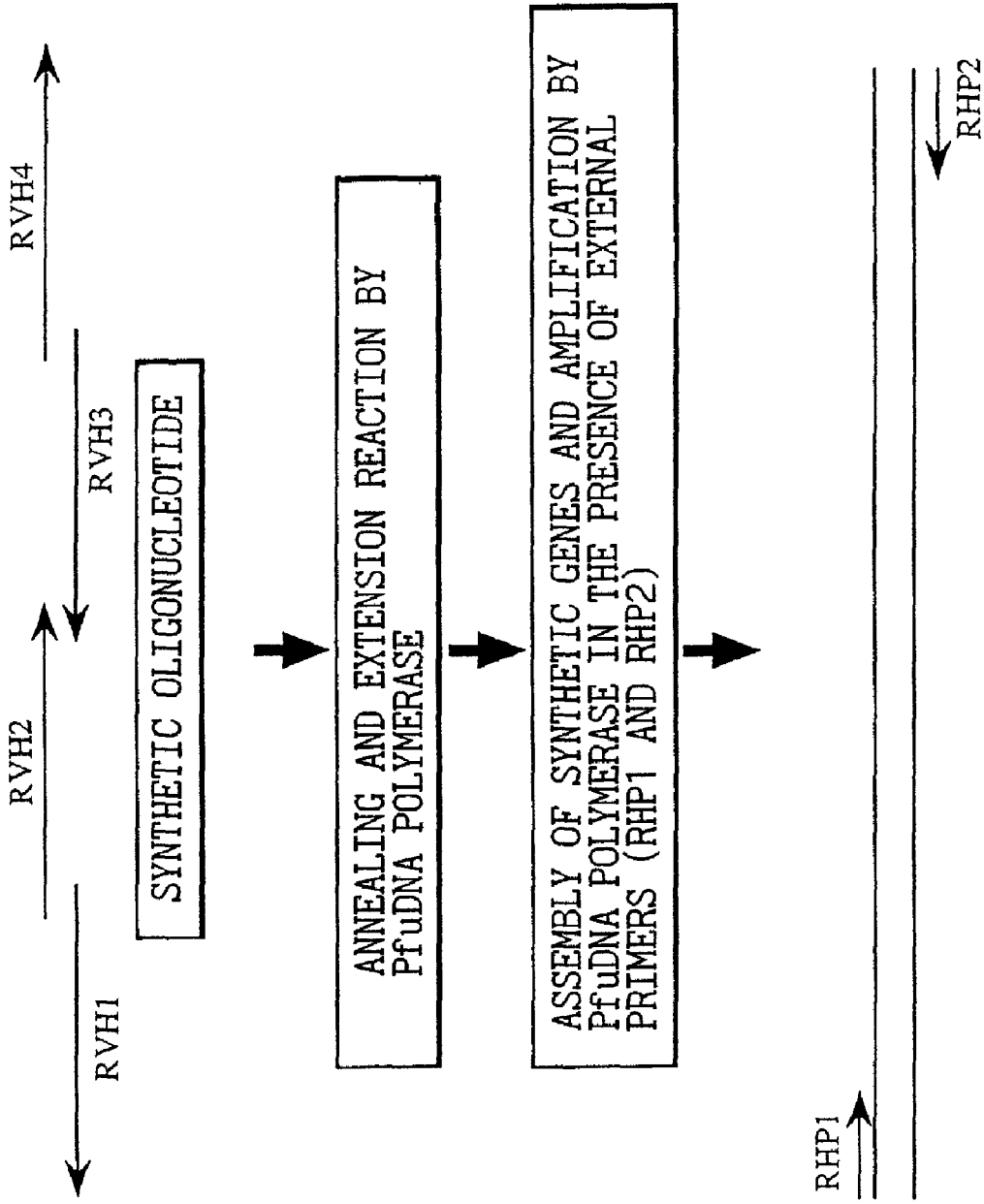
FIG. 5 is a diagram showing a method of constructing the H chain of reshaped human anti-HM1.24 antibody in which oligonucleotides RVH1, RVH2, RVH3, and RVH4 are assembled by the PCR method.

The DNA sequence thus designed was divided into four oligonucleotides. Subsequently, oligonucleotides which potentially hinder assembly of these oligonucleotides were subjected to computer analysis for the secondary structure. The sequences of the four oligonucleotides RVH1 to RVH4 are shown in SEQ ID NO: 79 to 82. These oligonucleotides have a length of 119 to 144 bases and have the 25 to 26 bp overlapping region. Among the oligonucleotides, RVH2 (SEQ ID NO: 80) and RVH4 (SEQ ID NO: 82) have the sense DNA sequence, and RVH1 (SEQ ID NO: 79) and RVH3 (SEQ ID NO: 81) have the antisense DNA sequence. The method for assembling these four oligonucleotides by the PCR method is shown in the figure (see FIG. 5).

The PCR mixture (98 µl) containing 100 ng each of the four oligonucleotides and 5 u of Ampli Taq was first denatured by heating at 94° C. for 2 minutes, and was subjected to two cycles of incubation comprising 94° C. for 2 minutes, 55° C. for 2 minutes and 72° C. for 2 minutes. After 100 pmole each of RHP1 (SEQ ID NO: 83) and RHP2 (SEQ ID NO: 84) were added as the external primer, the PCR tube was coated with 50 μl of a mineral oil. Then it was first denatured by heating at 94° C. for 1 minute, and then was subjected to 38 cycles of 94° C. for 1 minute, 55° C. for 1 minute and 72° C. for 1 minute, and then was incubated at 72° C. for 10 minutes.

The 438 bp DNA fragment was purified using 1.5% low melting point agarose gel, digested with HindIII and BamHI, and then cloned into the HEF expression vector HEF-VH-gγ1. After determination of the base sequence, the plasmid that contains the DNA fragment encoding the amino acid sequence of the correct V region of the H chain was designated as HEF-RVHa-AHM-gγ1. The amino acid sequence and the base sequence of the V region of the H chain contained in this plasmid HEF-RVHa-AHM-gγ1 are shown in SEQ ID NO: 11.

Each of versions b, c, d, and e of the V region of the H chain of the reshaped human anti-HM1.24 antibody was constructed as follows.

Using as the mutagen primer BS (SEQ ID NO: 85) and BA (SEQ ID NO: 86) designed to mutate arginine at position 66 to lysine and, as a template DNA, the plasmid HEF-RVHa-AHM-gγ1 by the PCR method, version b was amplified to obtain plasmid HEF-RVHb-AHM-gγ1. The amino acid sequence and the base sequence of the V region of the H chain contained in this plasmid HEF-RVHb-AHM-gγ1 are shown in SEQ ID NO: 17.

Using as the mutagen primer CS (SEQ ID NO: 87) and CA (SEQ ID NO: 88) designed to mutate threonine at position 73 to lysine and, as a template DNA, the plasmid HEF-RVHa-AHM-gγ1 by the PCR method, version c was amplified to obtain plasmid HEF-RVHc-AHM-gγ1. The amino acid sequence and the base sequence of the V region of the H chain contained in this plasmid HEF-RVHc-AHM-gγ1 are shown in SEQ ID NO: 19.

Using as the mutagen primer DS (SEQ ID NO: 89) and DA (SEQ ID NO: 90) designed to mutate arginine at position 66 to lysine and threonine at position 73 to lysine and as a template DNA the plasmid HEF-RVHa-AHM-gγ1 by the PCR method, version d was amplified to obtain plasmid HEF-RVHd-AHM-gγ1. The amino acid sequence and the base sequence of the V region of the H chain contained in this plasmid HEF-RVHd-AHM-gγ1 are shown in SEQ ID NO: 21.

Using as the mutagen primer ES (SEQ ID NO: 91) and EA (SEQ ID NO: 92) designed to mutate valine at position 67 to alanine and methionine at position 69 to leucine and as a template DNA the plasmid HEF-RVHa-AHM-gγ1, version e was amplified to obtain plasmid HEF-RVHe-AHM-gγ1. The amino acid sequence and the base sequence of the V region of the H chain contained in this plasmid HEF-RVHe-AHM-gγ1 are shown in SEQ ID NO: 23.

3-2. Construction of the H Chain Hybrid V Region

Two H chain hybrid V regions were constructed. One is a mouse-human hybrid anti-HM1.24 antibody in which the amino acid sequences of FR1 and FR2 are derived from the mouse anti-HM1.24 antibody and those of FR3 and FR4 are from version a of the V region of the H chain of the reshaped human anti-HM1.24 antibody, and the other is human-mouse hybrid anti-HM1.24 antibody in which the amino acid sequences of FR1 and FR2 are derived from version a of the V region of the H chain of the reshaped human anti-HM1.24 antibody and those of FR3 and FR4 are from the mouse anti-HM1.24 antibody. The amino acid sequences of the CDR regions are all derived from mouse anti-HM1.24 antibody.

Two H chain hybrid V regions were constructed by the PCR method. The method is schematically shown in FIGS. 6 and 7. For the construction of two H chain hybrid V regions, four primers were used. The external primers a (SEQ ID NO: 93) and h (SEQ ID NO: 94) were designed to hybridize with the DNA sequence of the HEF expression vector HEF-VH-gγ1. The H chain hybrid construction primer HYS (SEQ ID NO: 95) was designed to have the sense DNA sequence and the H chain hybrid primer HYA (SEQ ID NO: 96) to have the antisense DNA sequence so that the DNA sequence are complementary to each other.

For the construction of the H chain hybrid V region in which the amino acid sequences of FR1 and FR2 are derived from the mouse anti-HM1.24 antibody and those of FR3 and FR4 are from version a of the V region of the H chain of the reshaped human anti-HM1.24 antibody, PCR using the plasmid HEF-1.24H-gγl as a template, the external primer a, and the H chain hybrid primer HYA, and PCR using the plasmid HEF-RVLa-AHM-gγ1 as a template, the H chain hybrid primer HYS (SEQ ID NO: 95), and the external primer h (SEQ ID NO: 94) were carried out in the first stage of PCR to purify each PCR product. The two PCR products from the first PCR were allowed to assemble by their own complementarity (see International Patent Publication No. WO 92-19759).

Then, by adding the external primers a (SEQ ID NO: 93) and h (SEQ ID NO: 94) a full-length DNA encoding the H chain hybrid V region in which the amino acid sequences of FR1 and FR2 are derived from the mouse anti-HM1.24 antibody and those of FR3 and FR4 are from version a of the V region of the H chain of the reshaped human anti-HM1.24 antibody was amplified in the second PCR stage.

For the construction of the H chain hybrid V region in which the amino acid sequences of FR1 and FR2 are derived from version a of the V region of the H chain of the reshaped human anti-HM1.24 antibody and those of FR3 and FR4 are from the mouse anti-HM1.24 antibody, PCR using the plasmid HEF-RVHa-AHM-gγ1 as a template, the external primer a, and the H chain hybrid primer HYA, and PCR using the plasmid HEF-1.24H-gγ1 as a template, the H chain hybrid primer HYS, and the external primer h were carried out in the first stage of PCR to purify each PCR product. The two PCR purified products from the first PCR were allowed to assemble by their own complementarity (see International Patent Publication No. WO 92-19759).

Then, by adding the external primers a and h, a full-length DNA encoding the H chain hybrid V region in which the amino acid sequences of FR1 and FR2 are derived from version a of the V region of the H chain of the reshaped human anti-HM1.24 antibody and those of FR3 and FR4 are from the mouse anti-HM1.24 antibody was amplified in the second PCR stage.

The methods of the first PCR, purification of PCR products, assembling, the second PCR, and cloning into the HEF expression vector HEF-VH-gγ1 were carried out according to the methods shown in "Example 9. Construction of the V region of the L chain of the reshaped human anti-HM1.24 antibody".

After sequencing the DNA sequence, the plasmid that contains the DNA fragment encoding the correct amino acid sequence of the H chain hybrid V region in which the amino acid sequences of FR1 and FR2 are derived from the mouse anti-HM1.24 antibody and those of FR3 and FR4 are from version a of the V region of the H chain of the reshaped human anti-HM1.24 antibody was termed HEF-MH-RVH-AHM-gγ1. The amino acid sequence and the base sequence of the V region of the H chain contained in this plasmid HEF-MH-RVH-AHM-gγ1 are shown in SEQ ID NO: 97. Also, the plasmid that contains the DNA fragment encoding the correct amino acid sequence of the H chain hybrid V region in which the amino acid sequences of FR1 and FR2 are derived from version a of the V region of the H chain of the reshaped human anti-HM1.24 antibody and those of FR3 and FR4 are from the mouse anti-HM1.24 antibody was termed HEF-HM-RVH-AHM-gγ1. The amino acid sequence and the base sequence of the V region of the H chain contained in this plasmid HEF-HM-RVH-AHM-gγ1 are shown in SEQ ID NO: 99.

3-3. Construction of Versions f to r of the V Region of the H Chain of the Reshaped Human Anti-HM1.24 Antibody Each of versions f, g, h, i, j, k, l, m, n, o, p, q, and r of the V region of the H chain of the reshaped human anti-HM1.24 antibody were constructed as follows.

Using as the mutagen primer FS (SEQ ID NO: 102) and FA (SEQ ID NO: 103) designed to mutate threonine at position 75 to serine and valine at position 78 to alanine and as a template DNA the plasmid HEF-RVHe-AHM-gγ1 by the PCR method, version f was amplified to obtain plasmid HEF-RVHf-AHM-gγ1. The amino acid sequence and the base sequence of the V region of the H chain contained in this plasmid HEF-RVHf-AHM-gγ1 are shown in SEQ ID NO: 25.

Using as the mutagen primer GS (SEQ ID NO: 104) and GA (SEQ ID NO: 105) designed to mutate alanine at position 40 to arginine and, as a template DNA, the plasmid HEF-RVHa-AHM-gγ1, version g was amplified to obtain plasmid HEF-RVHg-AHM-gγ1. The amino acid sequence and the base sequence of the V region of the H chain contained in this plasmid HEF-RVHg-AHM-gγ1 are shown in SEQ ID NO: 27.

Using as the mutagen primer FS (SEQ ID NO: 102) and FA (SEQ ID NO: 103) and, as a template DNA, the plasmid HEF-RVHb-AHM-gγ1, version h was amplified to obtain plasmid HEF-RVHh-AHM-gγ1. The amino acid sequence and the base sequence of the V region of the H chain contained in this plasmid HEF-RVHh-AHM-gγ1 are shown in SEQ ID NO: 29.

Using as the mutagen primer IS (SEQ ID NO: 106) and IA (SEQ ID NO: 107) designed to mutate arginine at position 83 to alanine and serine at position 84 to phenylalanine and, as a template DNA, the plasmid HEF-RVHh-AHM-gγ1, version i was amplified to obtain plasmid HEF-RVHi-AHM-gγ1. The amino acid sequence and the base sequence of the V region of the H chain contained in this plasmid HEF-RVHi-AHM-gγ1 are shown in SEQ ID NO: 31.

Using as the mutagen primer JS (SEQ ID NO: 108) and JA (SEQ ID NO: 109) designed to mutate arginine at position 66 to lysine and, as a template DNA, the plasmid HEF-RVHf-AHM-gγ1, version j was amplified to obtain plasmid HEF-RVHj-AHM-gγ1. The amino acid sequence and the base sequence of the V region of the H chain contained in this plasmid HEF-RVHj-AHM-gγ1 are shown in SEQ ID NO: 33.

Using as the mutagen primer KS (SEQ ID NO: 110) and KA (SEQ ID NO: 111) designed to mutate glutamic acid at position 81 to glutamine and, as a template DNA, the plasmid HEF-RVHh-AHM-gγ1, version k was amplified to obtain plasmid HEF-RVHk-AHM-gγ1. The amino acid sequence and the base sequence of the V region of the H chain contained in this plasmid HEF-RVHk-AHM-gγ1 are shown in SEQ ID NO: 35.

Using as the mutagen primer LS (SEQ ID NO: 112) and LA (SEQ ID NO: 113) designed to mutate glutamic acid at position 81 to glutamine and serine at position 82B to isoleucine and, as a template DNA, the plasmid HEF-RVHh-AHM-gγ1, version 1 was amplified to obtain plasmid HEF-RVHl-AHM-gγ1. The amino acid sequence and the base sequence of the V region of the H chain contained in this plasmid HEF-RVHl-AHM-gγ1 are shown in SEQ ID NO: 37.

Using as the mutagen primer MS (SEQ ID NO: 114) and MA (SEQ ID NO: 115) designed to mutate glutamic acid at position 81 to glutamine, serine at position 82b to isoleucine, and threonine at position 87 to serine and, as a template DNA, the plasmid HEF-RVHh-AHM-gγ1, version m was amplified to obtain plasmid HEF-RVHm-AHM-gγ1. The amino acid sequence and the base sequence of the V region of the H chain contained in this plasmid HEF-RVHm-AHM-gγ1 are shown in SEQ ID NO: 39.

Using as the mutagen primer NS (SEQ ID NO: 116) and NA (SEQ ID NO: 117) designed to mutate serine at position 82B to isoleucine and, as a template DNA, the plasmid HEF-RVHh-AHM-gγ1, version n was amplified to obtain plasmid HEF-RVHn-AHM-gγ1. The amino acid sequence and the base sequence of the V region of the H chain contained in this plasmid HEF-RVHn-AHM-gγ1 are shown in SEQ ID NO: 41.

Using as the mutagen primer OS (SEQ ID NO: 118) and OA (SEQ ID NO: 119) designed to mutate threonine at position 87 to serine and, as a template DNA, the plasmid HEF-RVHh-AHM-gγ1, version o was amplified to obtain plasmid HEF-RVHo-AHM-gγ1. The amino acid sequence and the base sequence of the V region of the H chain contained in this plasmid HEF-RVHo-AHM-gγ1 are shown in SEQ ID NO: 43.

Using as the mutagen primer PS (SEQ ID NO: 120) and PA (SEQ ID NO: 121) designed to mutate valine at position 78 to alanine and, as a template DNA, the plasmid HEF-RVHa-AHM-gγ1, version p was amplified by the PCR method to obtain plasmid HEF-RVHp-AHM-gγ1. The amino acid sequence and the base sequence of the V region of the H chain contained in this plasmid HEF-RVHp-AHM-gγ1 are shown in SEQ ID NO: 45.

Using as the mutagen primer QS (SEQ ID NO: 122) and QA (SEQ ID NO: 123) designed to mutate threonine at position 75 to serine and, as a template DNA, the plasmid HEF-RVHa-AHM-gγ1, version q was amplified by the PCR method to obtain plasmid HEF-RVHq-AHM-gγ1. The amino acid sequence and the base sequence of the V region of the H chain contained in this plasmid HEF-RVHq-AHM-gγ1 are shown in SEQ ID NO: 47.

Using as the mutagen primer CS (SEQ ID NO: 87) and CA (SEQ ID NO: 88) and, as a template DNA, the plasmid HEF-RVHp-AHM-gγ1, version r was amplified by the PCR method to obtain plasmid HEF-RVHr-AHM-gγ1. The amino acid sequence and the base sequence of the V region of the H chain contained in this plasmid HEF-RVHr-AHM-gγ1 are shown in SEQ ID NO: 49.

The regions encoding the variable region of each of the above-mentioned plasmids HEF-RVLa-AHM-gκ and HEF-RVHr-AHM-gγ1 were digested to make restriction fragments with restriction enzymes HindIII and BamHI. They were inserted into the HindIII and BamHI sites of plasmid vector pUC19. Each plasmid was termed pUC19-RVLa-AHM-gκ and pUC19-RVHr-AHM-gγ1.

The *Escherichia coli* that contain each of the plasmids pUC19-RVLa-AHM-gκ and pUC19-RVHr-AHM-gγ1 was termed *Escherichia coli* DH5α (pUC19-RVLa-AHM-gκ) and *Escherichia coli* DH5α (pUC19-RVHr-AHM-gγ1), respectively, and have been internationally deposited on Aug. 29, 1996, with the National Institute of Bioscience and Human-Technology, Agency of Industrial Science and Technology, MITI (Higashi 1-Chome 1-3, Tsukuba city, Ibalaki prefecture, Japan) under the accession numbers FERM BP-5645 and FERM BP-5643, respectively, under the provisions of the Budapest Treaty.

4. Construction of the Reshaped Human Anti-HM1.24 Antibody, the Chimera Anti-HM1.24 Antibody, and the H Chain Hybrid Antibody In order to evaluate each chain of the reshaped human anti-HM1.24 antibody, the reshaped human anti-HM1.24 antibody and the chimera anti-HM1.24 antibody as a positive control antibody were allowed to express. In constructing each of version b and after of the V region of the H chain of the reshaped human anti-HM1.24 antibody, the H chain hybrid antibody was allowed to express in order to investigate which amino acid sequence in the FR should be substituted. Furthermore, it was expressed in combination with the chimera H chain in order to evaluate version a of L chain of the reshaped human anti-HM1.24 antibody.

4-1. Expression of the Reshaped Human Anti-HM1.24 Antibody

Ten μg each of the expression vector (HEF-RVHa-AHM-gγ1 to HEF-RVHr-AHM-gγ1) for the H chain of the reshaped human anti-HM1.24 antibody and the expression vector (HEF-RVLa-AHM-gκ or HEF-RVLb-AHM-gκ) for the L chain of the reshaped human anti-HM1.24 antibody were cotransformed into COS-7 cells by electroporation using the Gene Pulser instrument (manufactured by Bio-Rad). Each DNA (10 μg) was added to 0.8 ml aliquots of $1\times10^7$ cells/ml in PBS, and was subjected to pulses at 1500 V and a capacity of 25 μF.

After the recovery period of 10 minutes at room temperature, the electroporated cells were added to 30 ml of DHEM culture liquid (manufactured by GIBCO) containing 10% γ-globulin-free bovine fetal serum. After incubation of 72 hours in the $CO_2$ incubator BNA120D (manufactured by TABAI) under the condition of 37° C. and 5% $CO_2$, the culture supernatant was collected, the cell debris was removed by centrifugation at 1000 rpm for 5 minutes in a centrifuge 15PR-22 (manufactured by HITACHI) equipped with a centrifuge rotor 03 (manufactured by HITACHI), and a microconcentrator (Centricon 100, manufactured by Amicon) was ultrafiltrated using a centrifuge J2-21 (manufactured by BECKMAN) equipped with a centrifuge rotor JA-20.1 (manufactured by BECKMAN) at a condition of 2000 rpm, and was used for Cell-ELISA.

4-2. Expression of the Chimera Anti-HM1.24 Antibody

Using ten μg each of the expression vector HEF-1.24H-gγ1 for the H chain of the chimera human anti-HM1.24 antibody and the expression vector HEF-1.24L-gκ for the L chain of the chimera human anti-HM1.24 antibody, the chimera anti-HM1.24 antibody to be used for Cell-ELISA was prepared according to the above-mentioned method for expression of the reshaped human anti-HM1.24 antibody.

4-3. Expression of the Anti-HM1.24 Antibody Comprising Version a of the Humanized L Chain and the Chimera H Chain Using ten μg each of the expression vector HEF-1.24H-gγ1 for the H chain of the chimera human anti-HM1.24 antibody and the expression vector HEF-RVLa-AHM-Gκ for version a of the L chain of the reshaped human anti-HM1.24 antibody, the anti-HM1.24 antibody comprising version a of the humanized L chain and the chimera H chain to be used for Cell-ELISA was prepared according to the above-mentioned method for expression of the reshaped human anti-HM1.24 antibody.

4-4. Expression of the H Chain Hybrid Antibody

Using ten μg each of the expression vector (HEF-MH-RVH-AHM-gγ1 or HEF-HM-RVH-AHM-gγ1) for the V region of the H chain hybrid and the expression vector HEF-RVLa-AHM-gκ for the L chain of the reshaped human anti-HM1.24 antibody, the H chain hybrid antibody to be used for Cell-ELISA was prepared according to the above-mentioned method for expression of the reshaped human anti-HM1.24 antibody.

4-5. Measurement of Antibody Concentration

Concentration of the antibody obtained was measured by ELISA. Each well of a 96-well ELISA plate (Maxisorp, manufactured by NUNC) was immobilized by adding 100 μl of goat anti-human IgG antibody (manufactured by BIO SOURCE) prepared to a concentration of 1 μg/ml with the coating buffer (0.1 M $NaHCO_3$, 0.02% $NaN_3$, pH 9.6) and incubating at room temperature for one hour. After blocking with 100 μl of the dilution buffer (50 mM Tris-HCl, 1 mM $MgCl_2$, 0.15 M NaCl, 0.05% Tween 20, 0.02% $NaN_3$, 1% bovine serum albumin (BSA), pH 8.1), 100 μl each of serial dilutions of the reshaped human anti-HM1.24 antibody, chimera anti-HM1.24 antibody, and the H chain hybrid antibody that were concentrated by ultrafiltration were added to each well and incubated at room temperature for one hour. Then, after washing, 100 μl of alkaline phosphatase-labeled goat anti-human IgG antibody (manufactured by DAKO) was added.

After incubating at room temperature for one hour and washing, 100 μl of 1 μg/ml substrate solution (Sigma104, p-nitrophenyl phosphate, manufactured by SIGMA) dissolved in the substrate buffer (50 mM $NaHCO_3$, 10 mM $MgCl_2$, pH 9.8) was added, and then the absorbance at 405 nm was measured using the MICROPLATE READER Model 3550 (manufactured by Bio Rad). As the standard for the measurement of concentration, human IgG1κ (manufactured by The Binding Site) was used.

5. Establishment of the CHO Cell Line that Stably Produces the Human Anti-HM1.24 Antibody 5-1. Construction of the Expression Vector for the H Chain of the Reshaped Human Anti-HM1.24 Antibody By digesting plasmid HEF-RVHr-AHM-gγ1 with the restriction enzymes PvuI and BamHI, an about 2.8 kbp fragment containing the DNA encoding the EF1 promoter and the V region of the H chain of the reshaped human anti-HM1.24 antibody was purified using 1.5% low melting point agarose gel. Then, the above DNA fragment was inserted into an about 6 kbp fragment that was prepared by digesting the expression vector used for a human H chain expression vector, DHFR-ΔE-RVh-PM1f (International Patent Publication No. WO 92-19759), containing the DHFR gene and the gene encoding the constant region of a human H chain with PvuI and BamHI to construct an expression vector, DHFR-ΔE-HEF-RVHr-AHM-gγ1, for the H chain of the reshaped anti-HM1.24 antibody.

5-2. Gene Introduction into CHO Cells

In order to establish a stable production system of the reshaped anti-HM1.24 antibody, the genes of the above-mentioned expression vectors, DHFR-ΔE-RVHr-AHM-gγ1 and HEF-RVLa-AHM-gκ, that were linearized by digestion with PvuI were simultaneously introduced into the CHO cell DXB-11 by the electroporation method under the condition similar to the above-mentioned one (transfection into the above-mentioned COS-7 cells).

5-3. Gene Amplification by MTX

Among the gene-introduced CHO cells, only those CHO cells in which both of L chain and H chain expression vectors have been introduced can survive in the nucleoside-free α-MEM culture liquid (manufactured by GIBCO-BRL) to which 500 μg/ml G418 (manufactured by GIBCO-BRL) and 10% bovine fetal serum were added, and so they were selected. Subsequently, 10 nM MTX (manufactured by Sigma) was added to the above culture liquid. Among the clones that propagated, those that produce the reshaped anti-HM1.24 antibody in large amounts were selected. As a result, clone #1 that exhibits a production efficiency of about 3 μg/ml of the reshaped anti-HM1.24 antibody was obtained and termed the reshaped anti-HM1.24 antibody-producing cell line.

5-4. Construction of the Reshaped Human Anti-HM1.24 Antibody

The reshaped anti-HM1.24 antibody was constructed in the following method. The above CHO cells that produce the reshaped anti-HM1.24 antibody were cultured for 10 days using as the medium the nucleoside-free α-MEM culture liquid (manufactured by GIBCO-BRL) to which 500 μg/ml G418 (manufactured by GIBCO-BRL) containing 10% γ-globulin-free bovine fetal serum (manufactured by GIBCO-BRL) were added using the $CO_2$ incubator BNAS120D (manufactured by TABAI) under the condition of 37° C. and 5% $CO_2$. On day 8 and 10 after starting the culture the culture liquid was recovered, the cell debris was removed by centrifuging for 10 minutes at 2000 rpm using the centrifuge RL-500SP (manufactured by Tomy Seiko) equipped with the TS-9 rotor, and then filter-sterilized using a bottle top filter (manufactured by FALCON) having a membrane with pores of 0.45 μm in diameter.

After an equal amount of PBS(-) was added to the culture liquid of the CHO cells that produce the reshaped human anti-HM1.24 antibody, then the reshaped anti-HM1.24 antibody was affinity-purified using the high-speed antibody purification system ConSep LC100 (manufactured by MILLIPORE) and Hyper D Protein A column (manufactured by Nippon Gaishi) using PBS(-) as the absorption/wash buffer and 0.1 M sodium citrate buffer (pH 3) as the elution buffer according to the attached instructions. The eluted fractions were adjusted to about pH 7.4 by immediately adding 1 M Tris-HCl (pH 8.0) and then using the centrifuging ultrafiltration concentrator Centriprep 10 (manufactured by MILLIPORE), concentration and substitution to PBS(-) was carried out and filter-sterilized using a membrane filter MILLEX-GV (manufactured by MILLIPORE) with a pore size of 0.22 μm to obtain the purified reshaped human anti-HM1.24 antibody. Antibody concentration was measured by absorbance at 280 nm and calculated with 1 μg/ml as 1.35 OD.

Reference Example 11

Determination of Activity of the Reshaped Anti-HM1.24 Antibody

The reshaped anti-HM1.24 antibody was evaluated for the following antigen binding activity and binding inhibition activity.

1. The Method of Measurement of Antigen Binding Activity and Binding Inhibition Activity 1-1. Measurement of Antigen Binding Activity Antigen binding activity was measured by the Cell-ELISA using WICH cells. Cell-ELISA plates were prepared as described in the above Example 7.1-2.

After blocking, 100 μl of serial dilutions of the reshaped human anti-HM1.24 antibody that was obtained from the concentrate of the culture supernatant of COS-7 cells or purified from the culture supernatant of CHO cells was added to each well. After it was incubated for 2 hours at room temperature and washed, peroxidase-labeled rabbit anti-human IgG antibody (manufactured by DAKO) was added. After incubating for 2 hours at room temperature and washing, the substrate solution was added and incubated. Then the reaction was stopped by adding 50 μl of 6N sulfuric acid, and absorbance at 490 nm was measured using the MICROPLATE READER Model 3550 (manufactured by Bio-Rad).

1-2. Measurement of Binding Inhibition Activity

The binding inhibition activity by the biotin-labeled mouse anti-HM1.24 antibody was measured by the Cell-ELISA using WISH cells. Cell-ELISA plates were prepared as described above. After blocking, 50 μl of serial dilutions of the reshaped human anti-HM1.24 antibody that was obtained from the concentrate of the culture supernatant of COS-7 cells or purified from the culture supernatant of CHO cells was added to each well, and 50 μl of 2 μg/ml biotin-labeled mouse anti-HM1.24 antibody was added simultaneously. After incubating at room temperature for two hours and washing, peroxidase-labeled streptavidin (manufactured by DAKO) was added. After incubating at room temperature for one hour and then washing, the substrate solution was added and incubated. Then the reaction was stopped by adding 50 μl of 6N sulfuric acid, and absorbance at 490 nm was measured using the MICROPLATE READER Model 3550 (manufactured by Bio-Rad).

2. Evaluation of the Reshaped Human Anti-HM1.24 Antibody 2-1. L Chain

Figure 8:
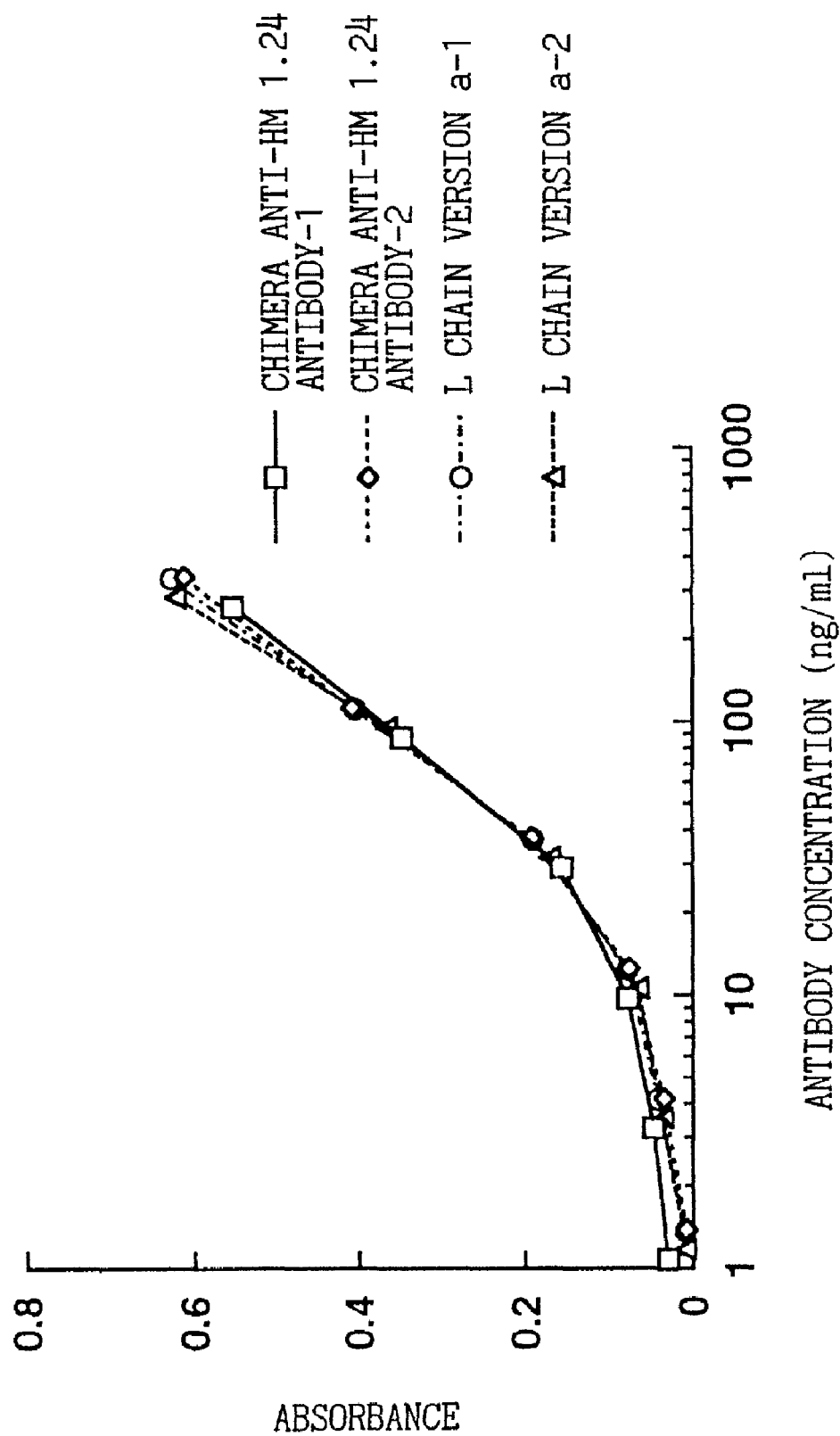
FIG. 8 is a graph showing that the L chain version a of reshaped human anti-HM1.24 antibody has an antigen binding activity of a similar degree to that of chimeric anti-HM1.24 antibody. In the figure, −1 and −2 represent different lots.
Figure 9:
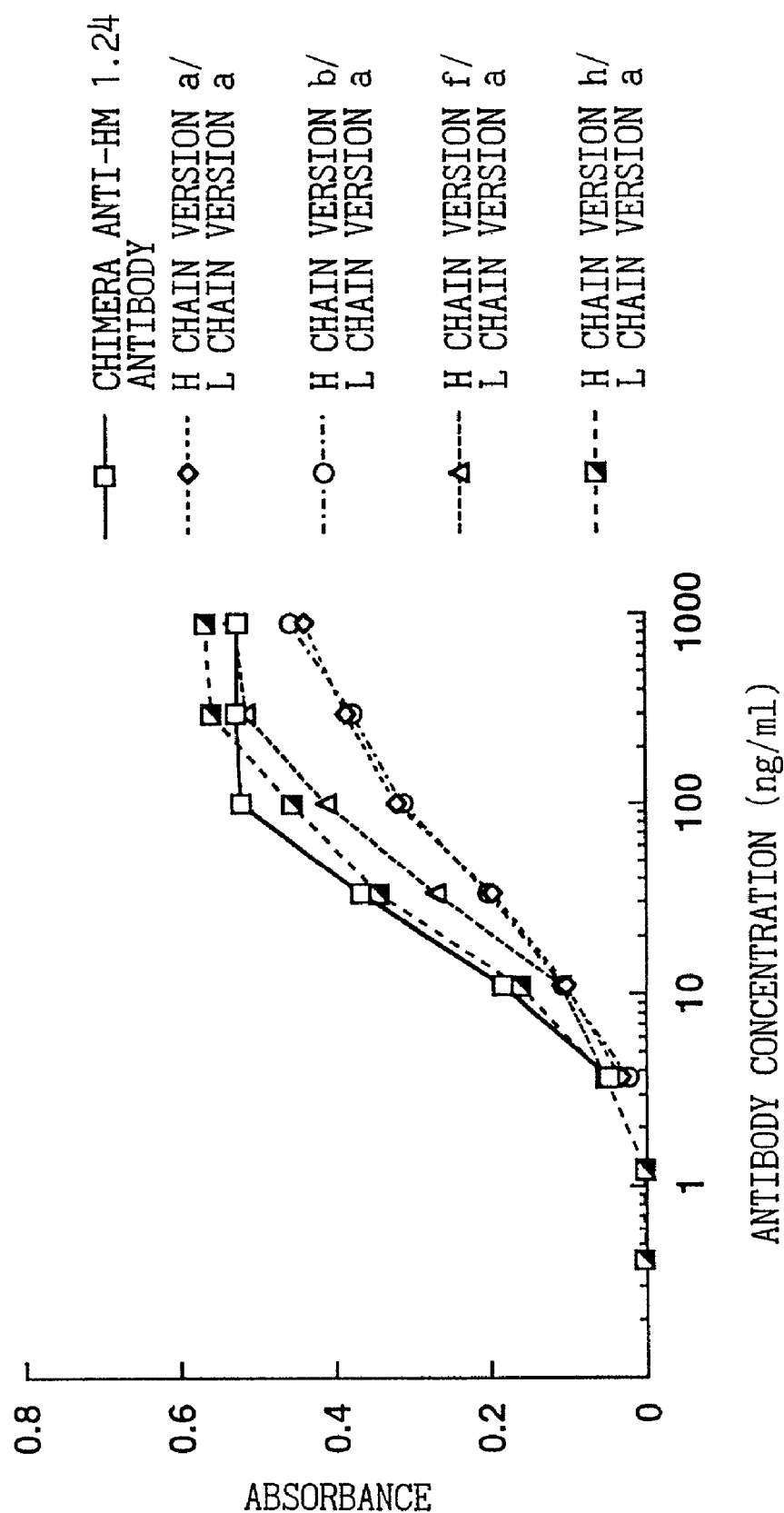
FIG. 9 is a graph showing the antigen binding activity of reshaped human anti-HM1.24 antibody prepared from a combination of the L chain version a and the H chain version a, b, f, or h, and chimeric anti-HM1.24 antibody.
Figure 10:
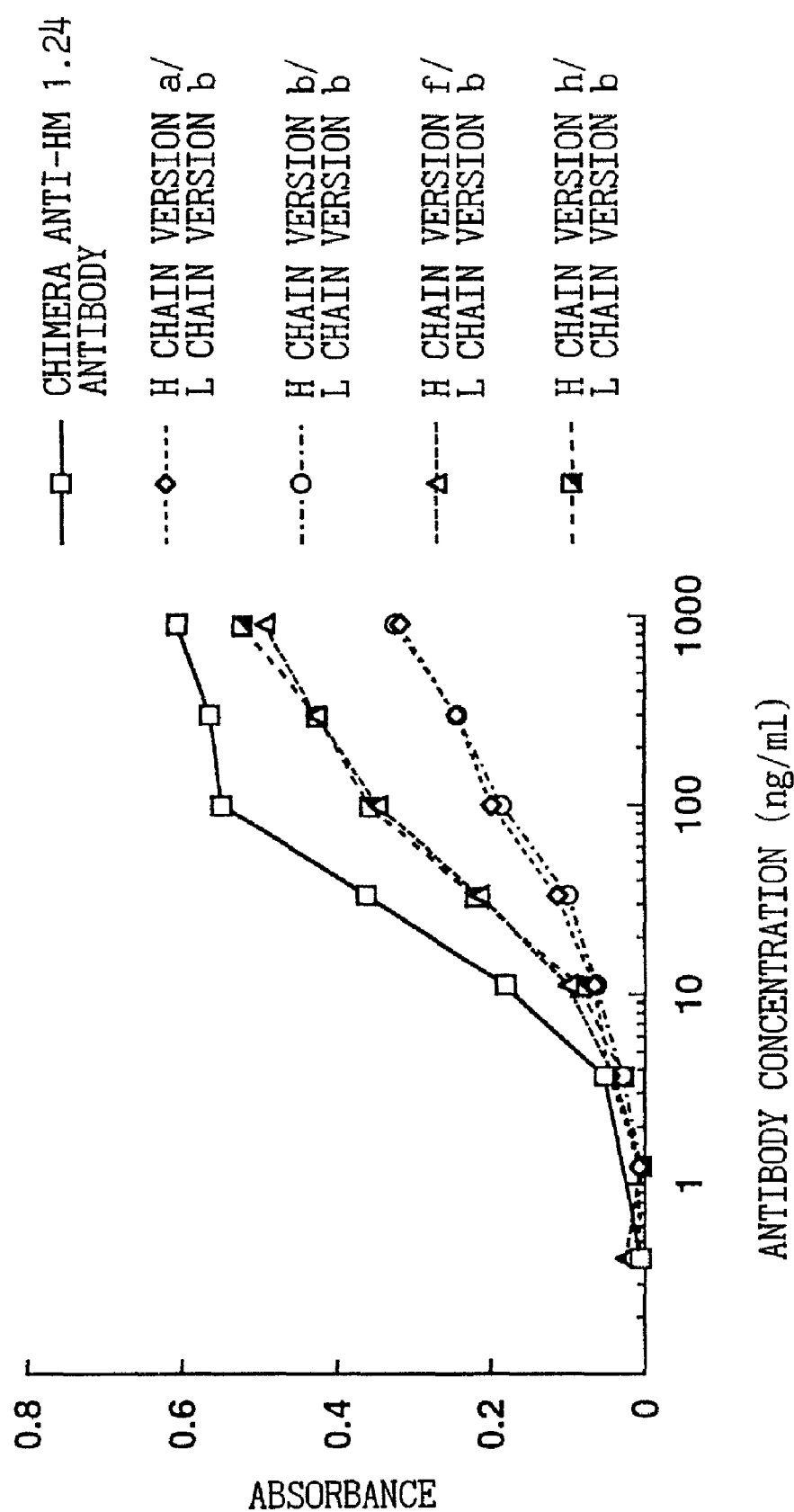
FIG. 10 is a graph showing the antigen binding activity of reshaped human anti-HM1.24 antibody prepared from a combination of the L chain version b and the H chain version a, b, f, or h, and chimeric anti-HM1.24 antibody.
Figure 11:
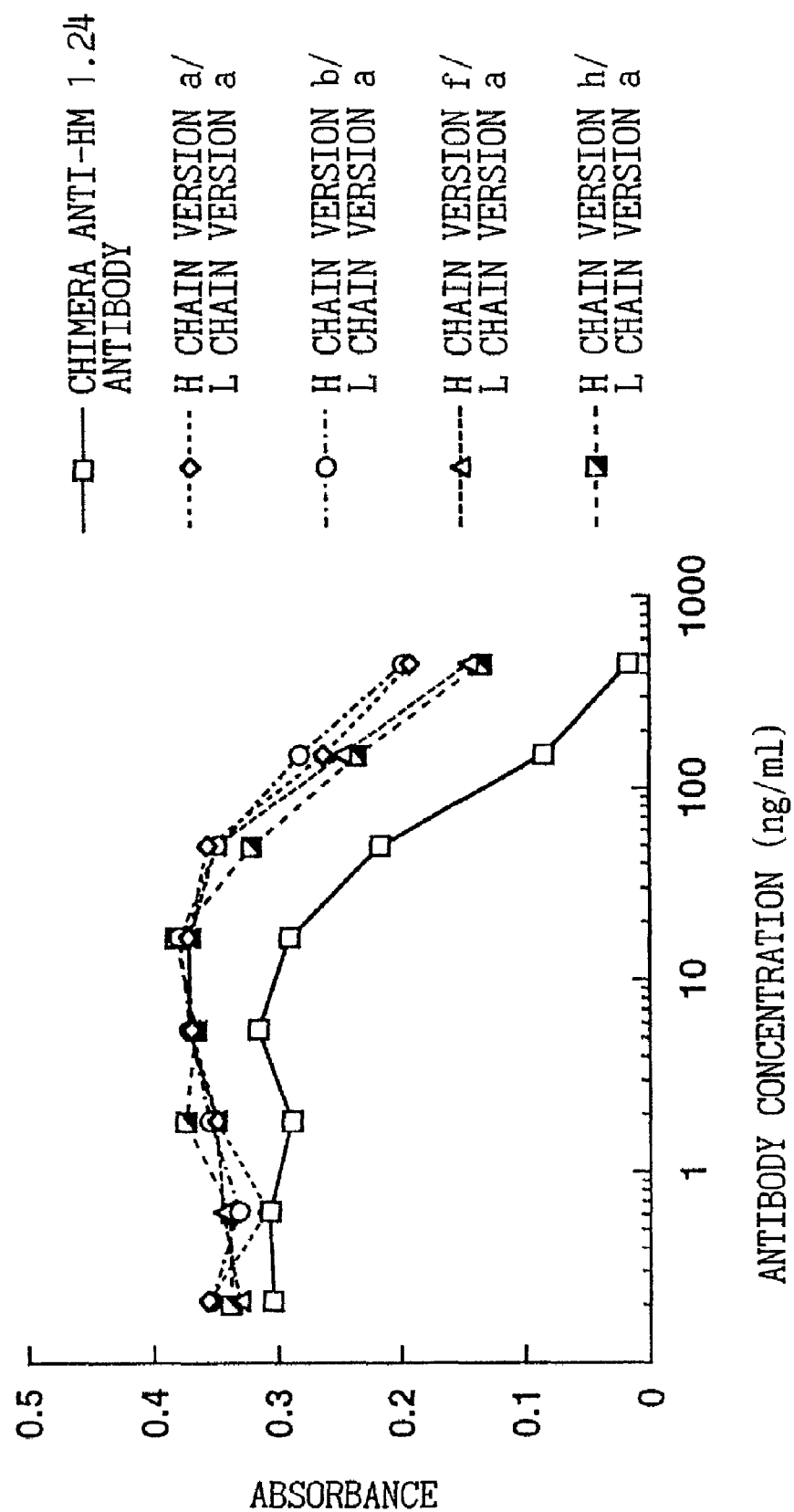
FIG. 11 is a graph showing the binding inhibition activity of reshaped human anti-HM1.24 antibody prepared from a combination of the L chain version a and the H chain version a, b, f, or h, and chimeric anti-HM1.24 antibody.
Figure 12:
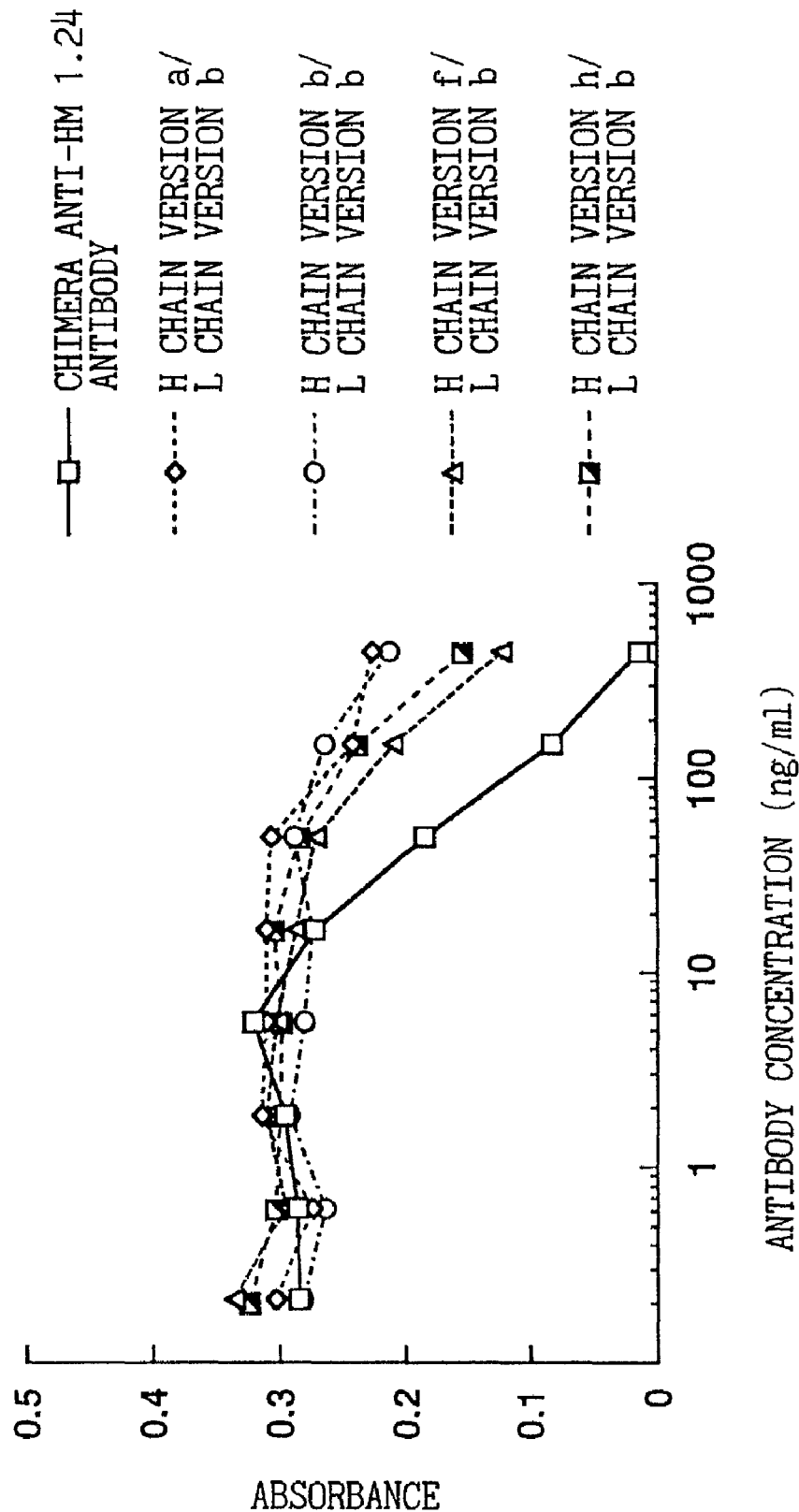
FIG. 12 is a graph showing the binding inhibition activity of reshaped human anti-HM1.24 antibody prepared from a combination of the L chain version b and the H chain version a, b, f, or h, and chimeric anti-HM1.24 antibody.
Figure 13:
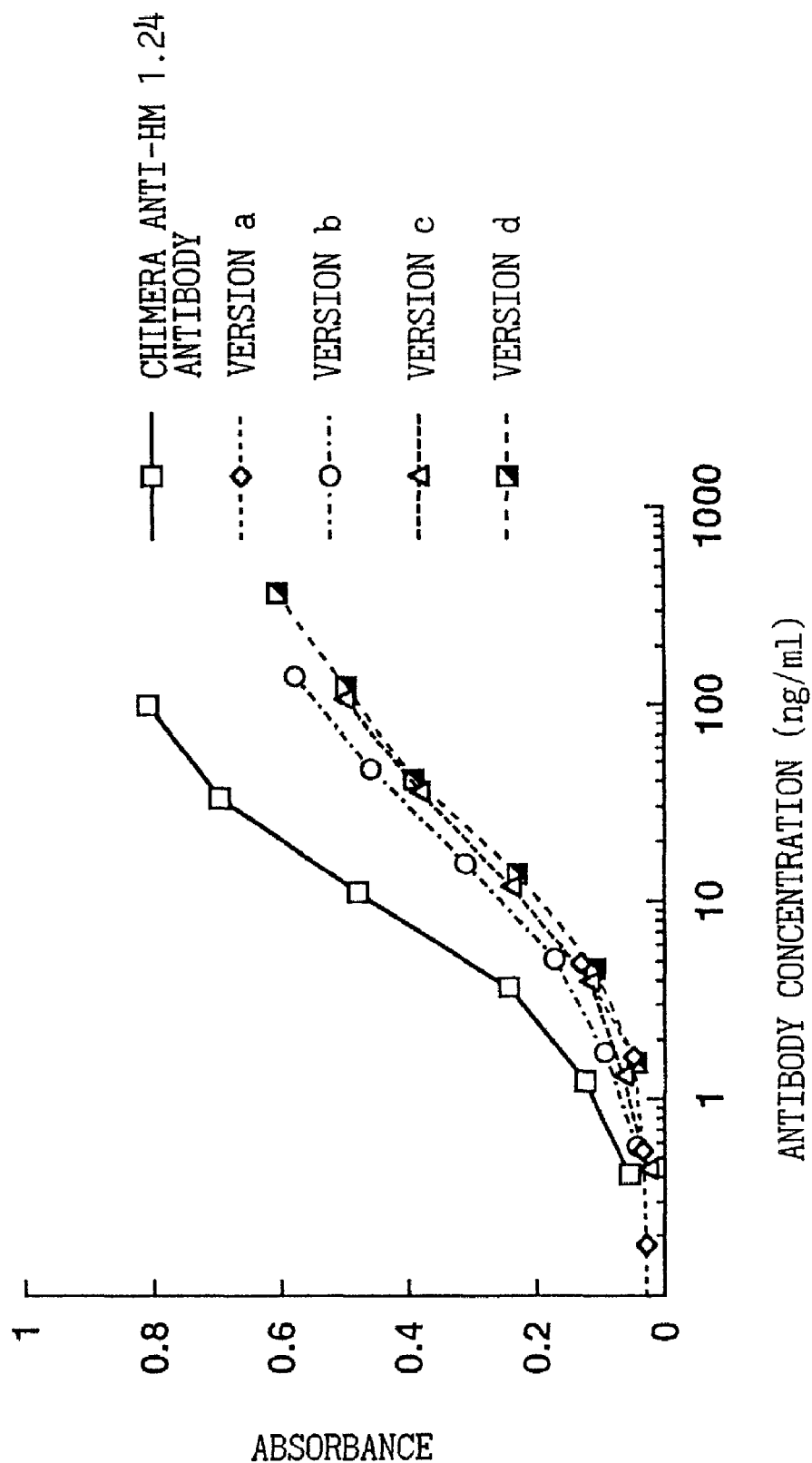
FIG. 13 is a graph showing the antigen binding activity of the H chain versions a, b, c, and d of reshaped human anti-HM1.24 antibody and chimeric anti-HM1.24 antibody.
Figure 14:
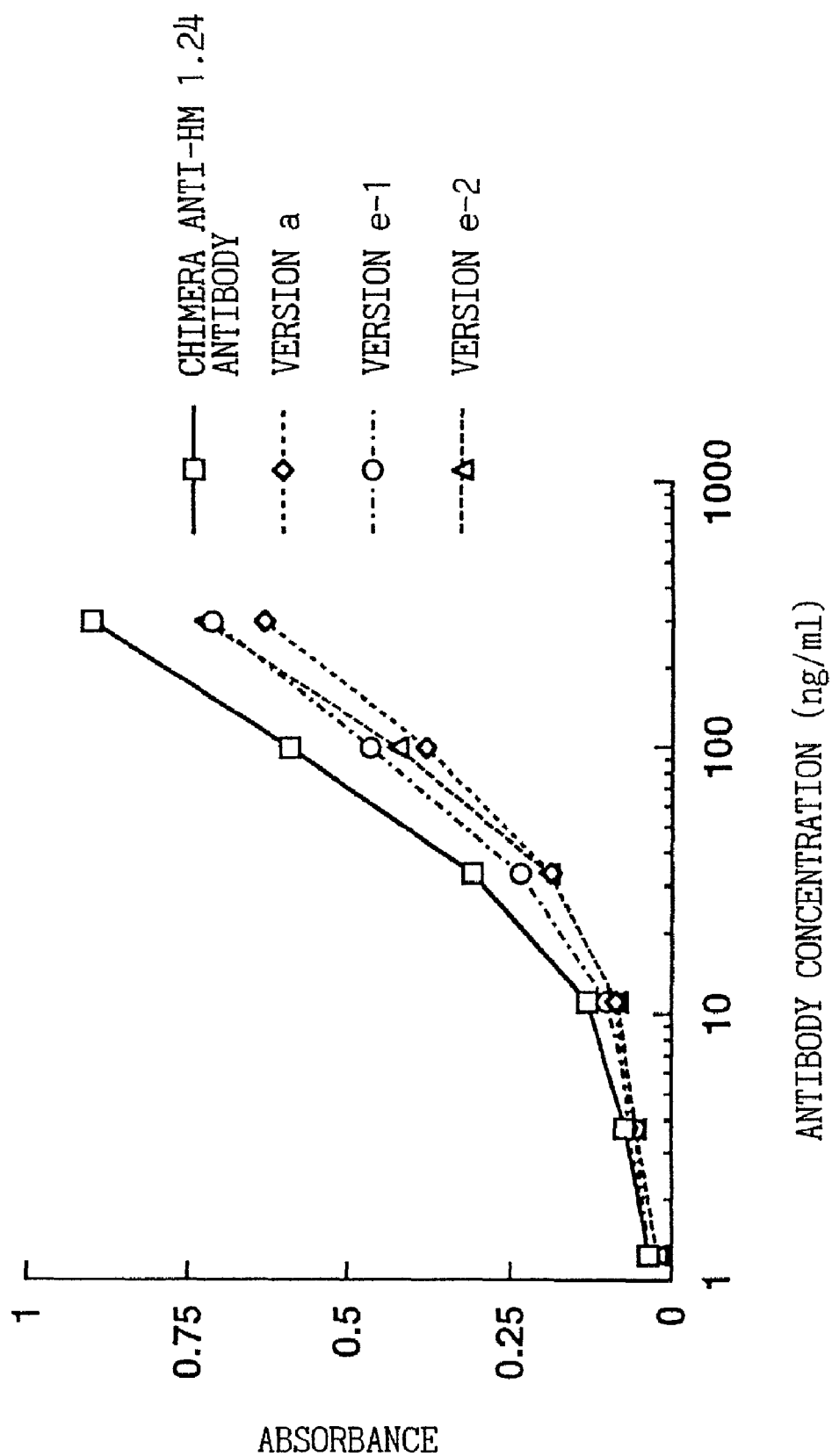
FIG. 14 is a graph showing the antigen binding activity of the H chain versions a and e of reshaped human anti-HM1.24 antibody and chimeric anti-HM1.24 antibody. In the figure, −1 and −2 represent different lots.

Version a of the L chain of the reshaped human anti-HM1.24 antibody was evaluated as mentioned above for measurement of antigen binding activity. As shown in FIG. 8, when version a of the L chain is expressed in combination with the chimera H chain it has shown a similar level of antigen binding activity. However, in consideration of further increase in activity and of compatibility with the H chain, version b of the L chain was constructed. Versions a and b of the L chain were evaluated together for antigen binding activity and of binding inhibition activity when combined with versions a, b, f, or h of the H chain. As shown in FIGS. 9, 10, 11, and 12, version a of the L chain had a higher activity than version b in both activities in all versions a, b, f, and h of the H chain. Therefore, version a of the L chain of the reshaped human anti-HM1.24 antibody was used for the following experiment.

2-2. H Chain Versions a to e

Versions a to e of the H chain of the reshaped human anti-HM1.24 antibody were evaluated in combination with the version a of the L chain as mentioned above for measurement of antigen binding activity and for binding inhibition activity. The result, as shown in FIGS. 11, 13, 14, and 15, indicated that all versions were weaker in both activities as compared to the chimera anti-HM1.24 antibody, suggesting that further amino acid substitution is required.

2-3. The H Chain Hybrid Antibody

Figure 16:
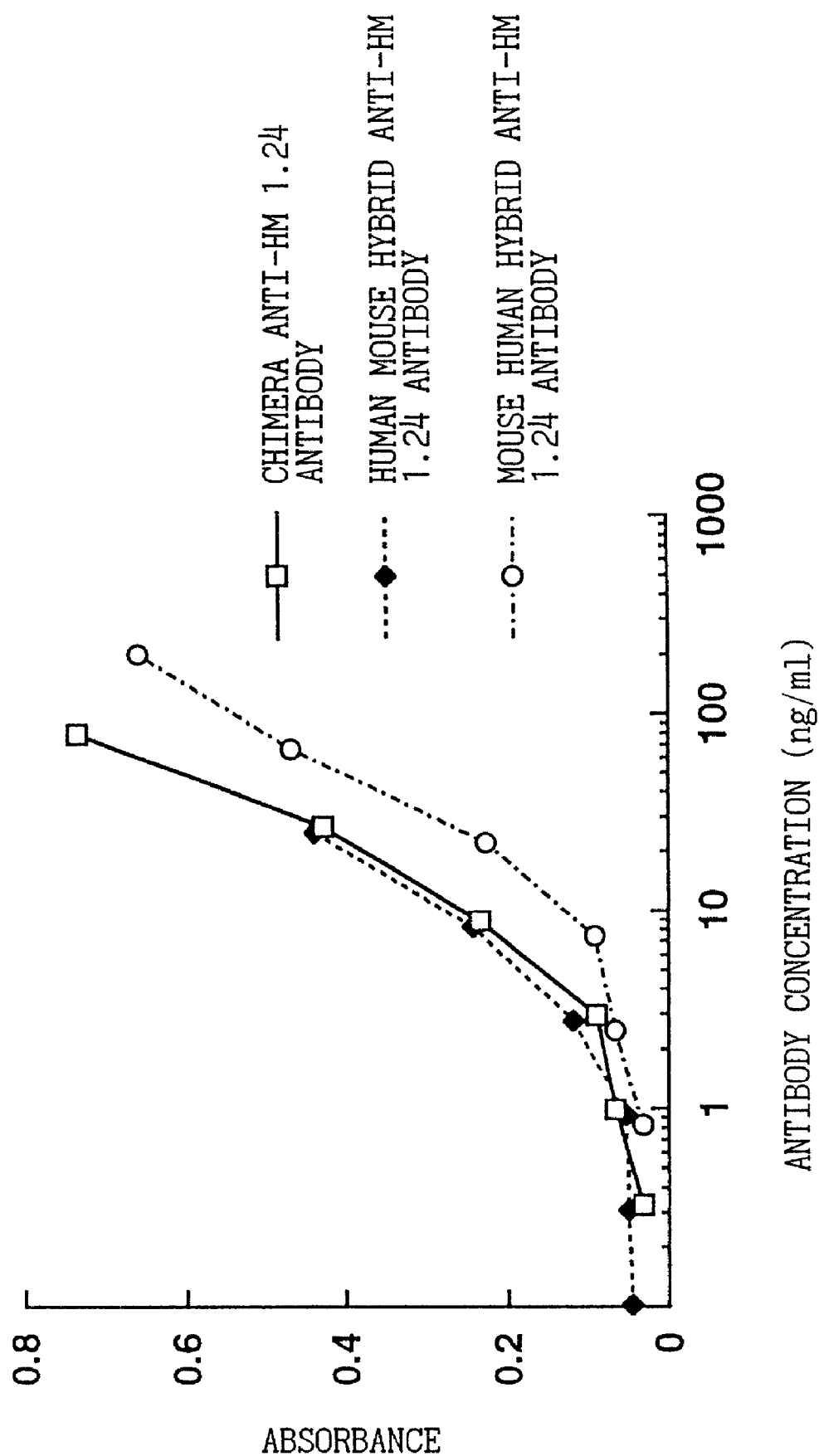
FIG. 16 is a graph showing the antigen binding activity of human-mouse hybrid anti-HM1.24 antibody, mouse-human hybrid anti-HM1.24 antibody and chimeric anti-HM1.24 antibody.

The H chain hybrid antibody was evaluated as mentioned above for measurement of antigen binding activity. The result, as shown in FIG. 16, indicated that the human-mouse hybrid anti-HM1.24 antibody has shown a similar activity to that of the chimera anti-HM1.24 antibody for antigen binding activity, whereas the mouse-human hybrid anti-HM1.24 antibody had a weaker activity than the chimera anti-HM1.24 antibody. This indicated that, in order to construct the reshaped human anti-HM1.24 antibody having the antigen binding activity similar to that of the chimera anti- HM1.24 antibody, it is necessary to convert amino acids included in FR3 or FR4 among those contained the V region of the H chain.

2-4. Versions f to r of the H Chain

Figure 17:
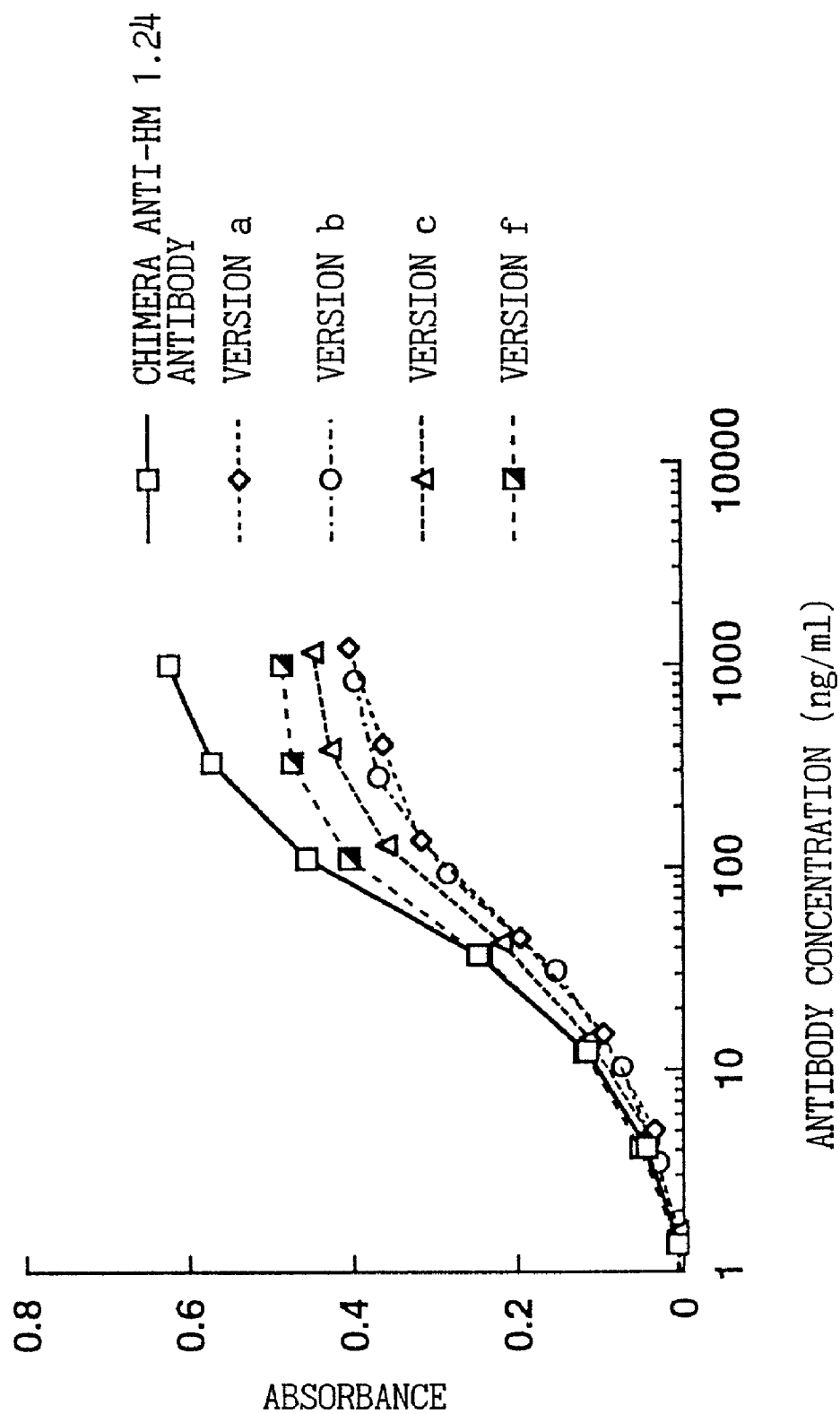
FIG. 17 is a graph showing the antigen binding activity of the H chain version a, b, c, and f of reshaped human anti-HM1.24 antibody and chimeric anti-HM1.24 antibody.

Version f of the H chain of the reshaped human anti-HM1.24 antibody was evaluated as mentioned above for measurement of antigen binding activity. The result, as shown in FIG. 17, indicated that its antigen binding activity is decreased as compared to the chimera anti-HM1.24 antibody, but is increased as compared to the above versions a to c, suggesting that any of the four amino acids at positions 67, 69, 75, and 78 that were newly converted in this version is responsible for the activity of the reshaped human antibody.

Figure 18:
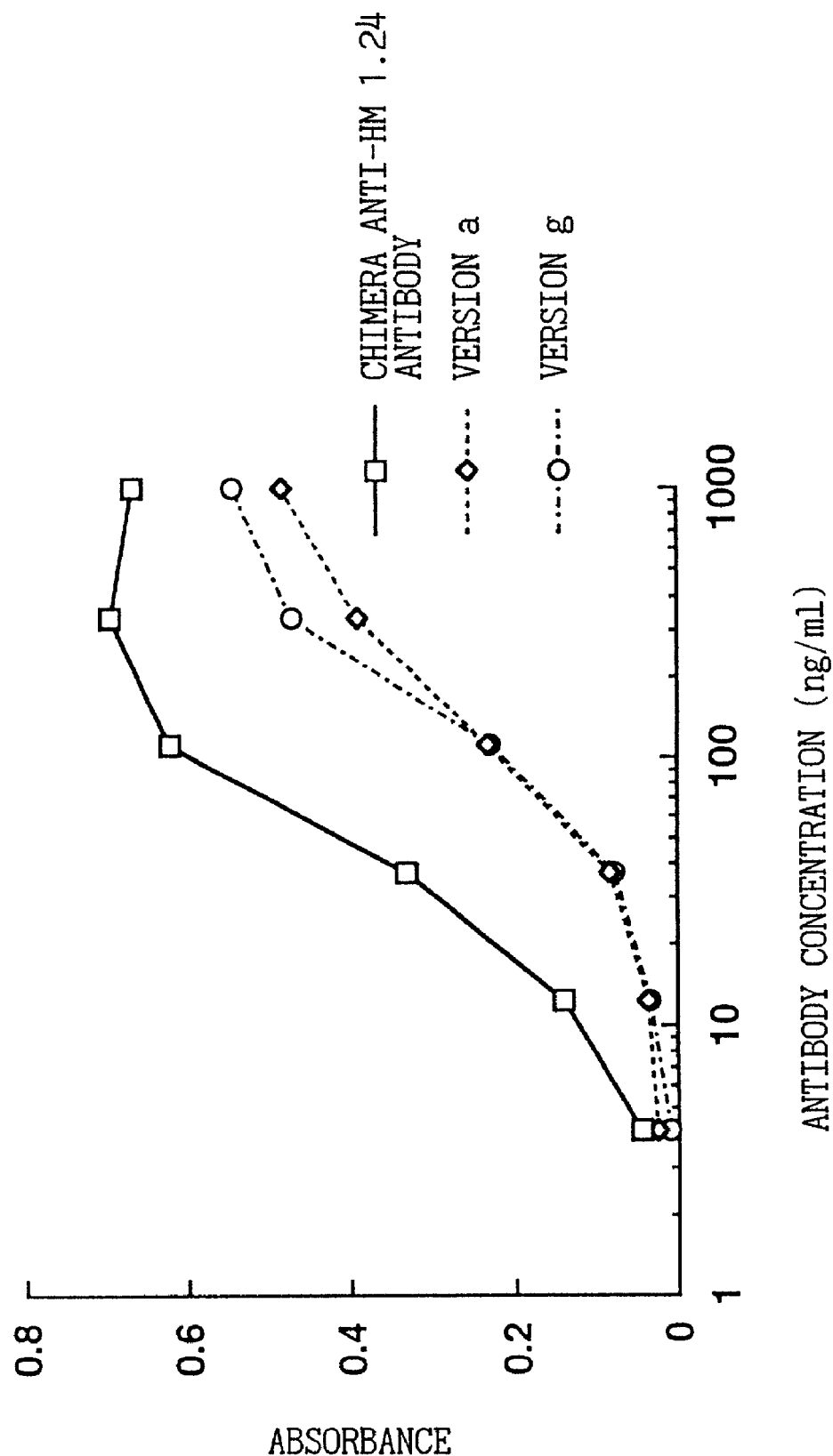
FIG. 18 is a graph showing the antigen binding activity of the H chain versions a and g of reshaped human anti-HM1.24 antibody and chimeric anti-HM1.24 antibody.
Figure 19:
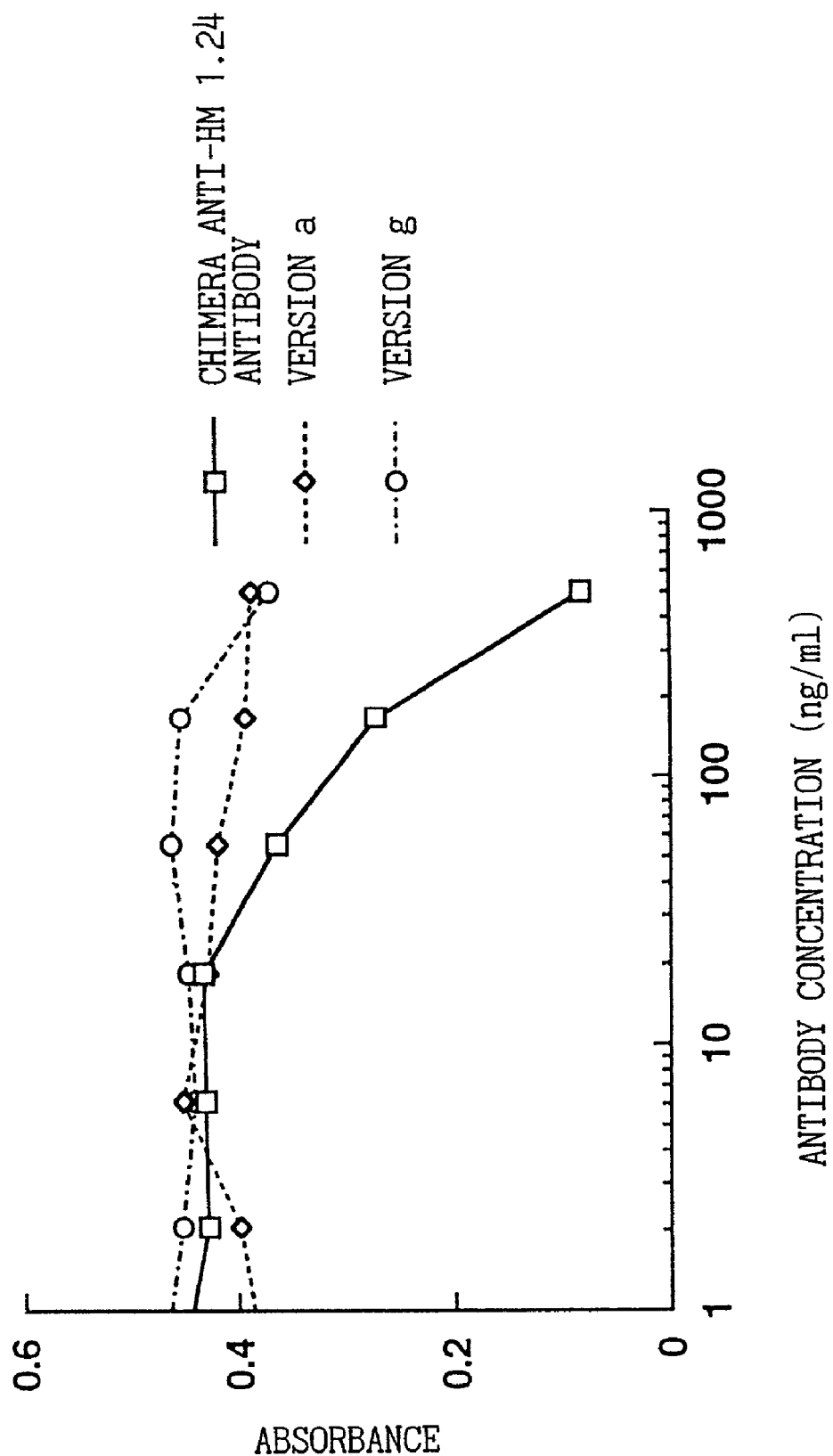
FIG. 19 is a graph showing the binding inhibition activity of the H chain versions a and g of reshaped human anti-HM1.24 antibody and chimeric anti-HM1.24 antibody.
Figure 20:
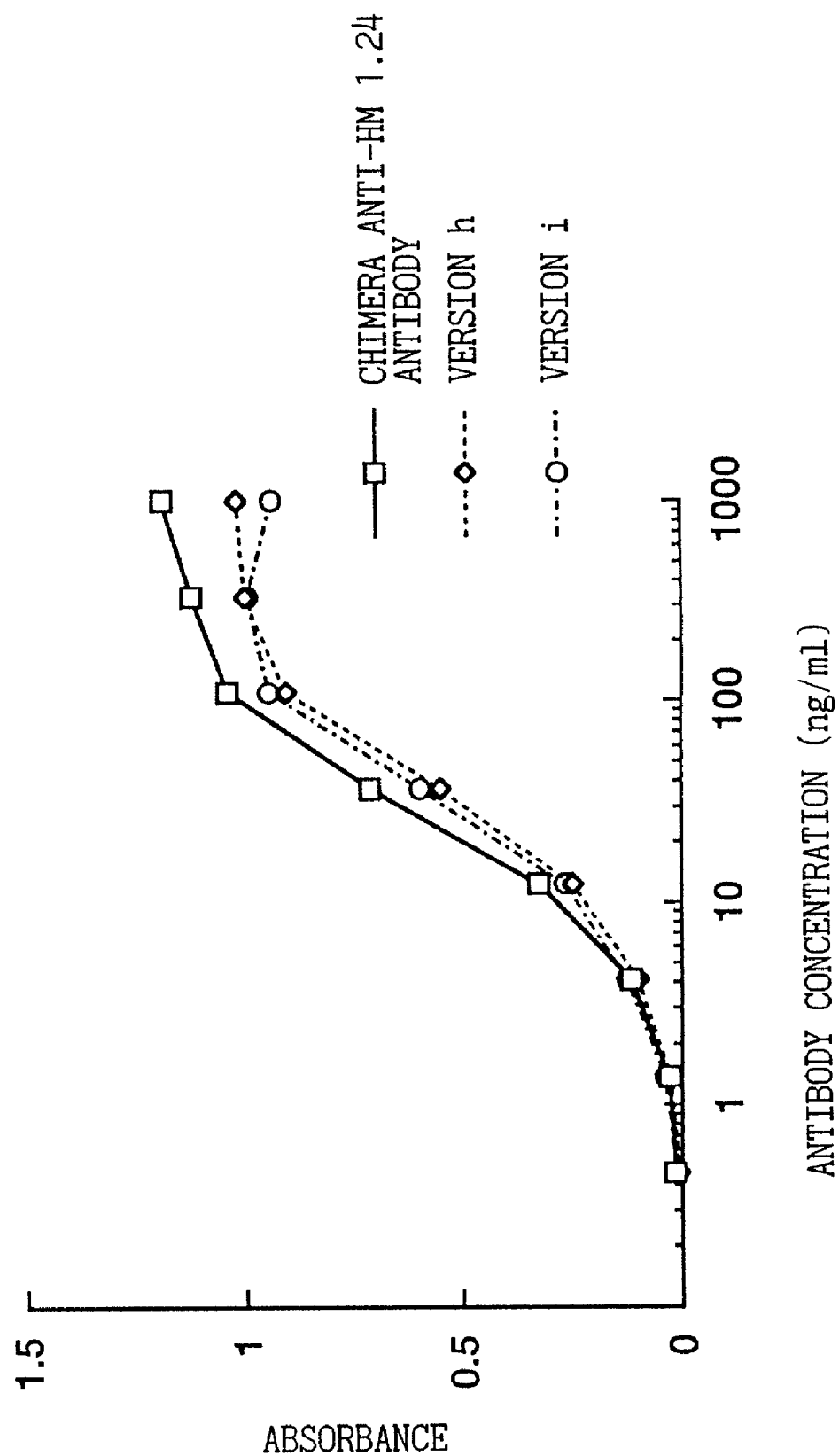
FIG. 20 is a graph showing the antigen binding activity of the H chain versions h and i of reshaped human anti-HM1.24 antibody and chimeric anti-HM1.24 antibody.
Figure 21:
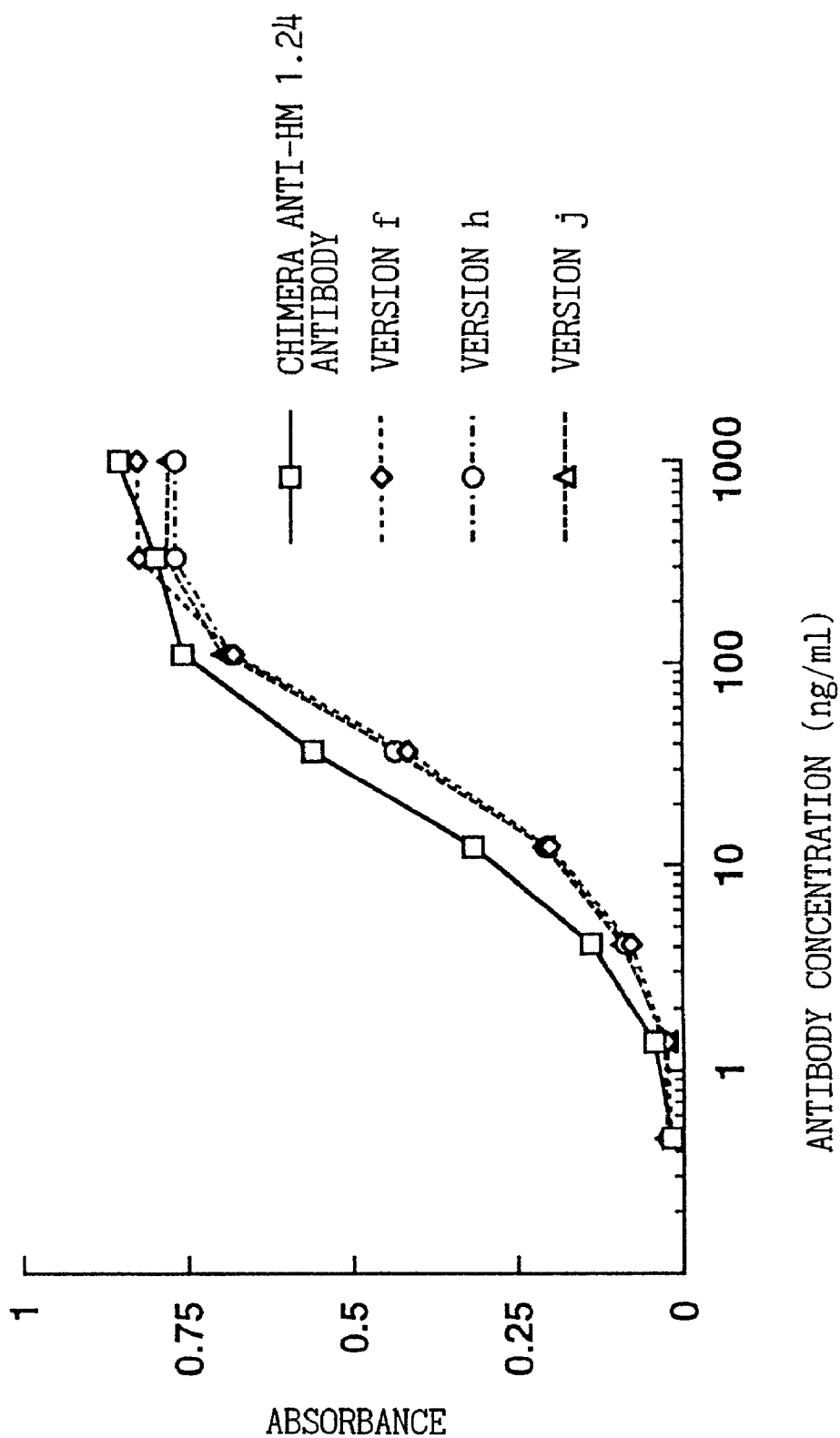
FIG. 21 is a graph showing the antigen binding activity of the H chain versions f, h, and j of reshaped human anti-HM1.24 antibody and chimeric anti-HM1.24 antibody.
Figure 22:
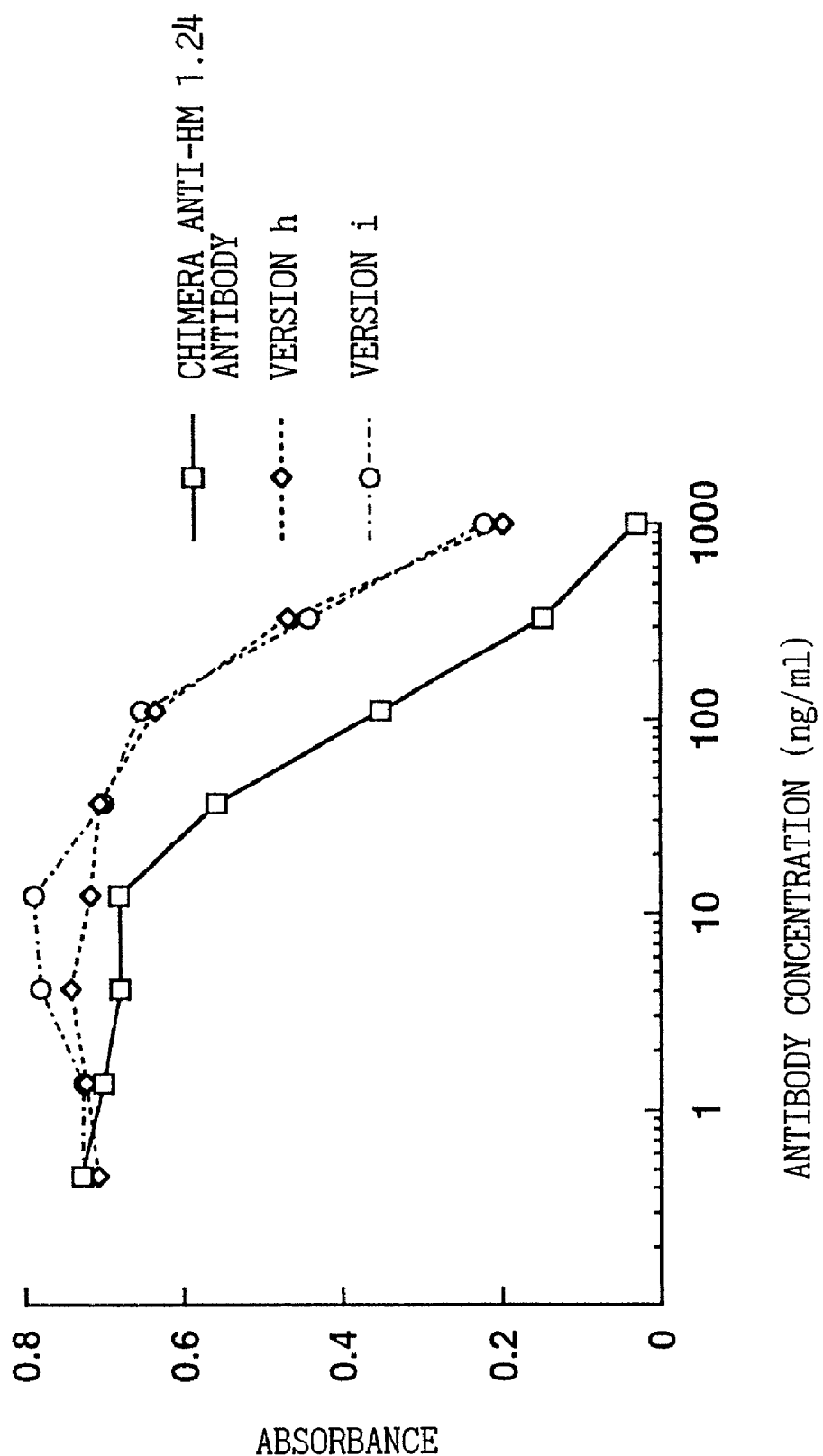
FIG. 22 is a graph showing the binding inhibition activity of the H chain versions h and i of reshaped human anti-HM1.24 antibody and chimeric anti-HM1.24 antibody.
Figure 23:
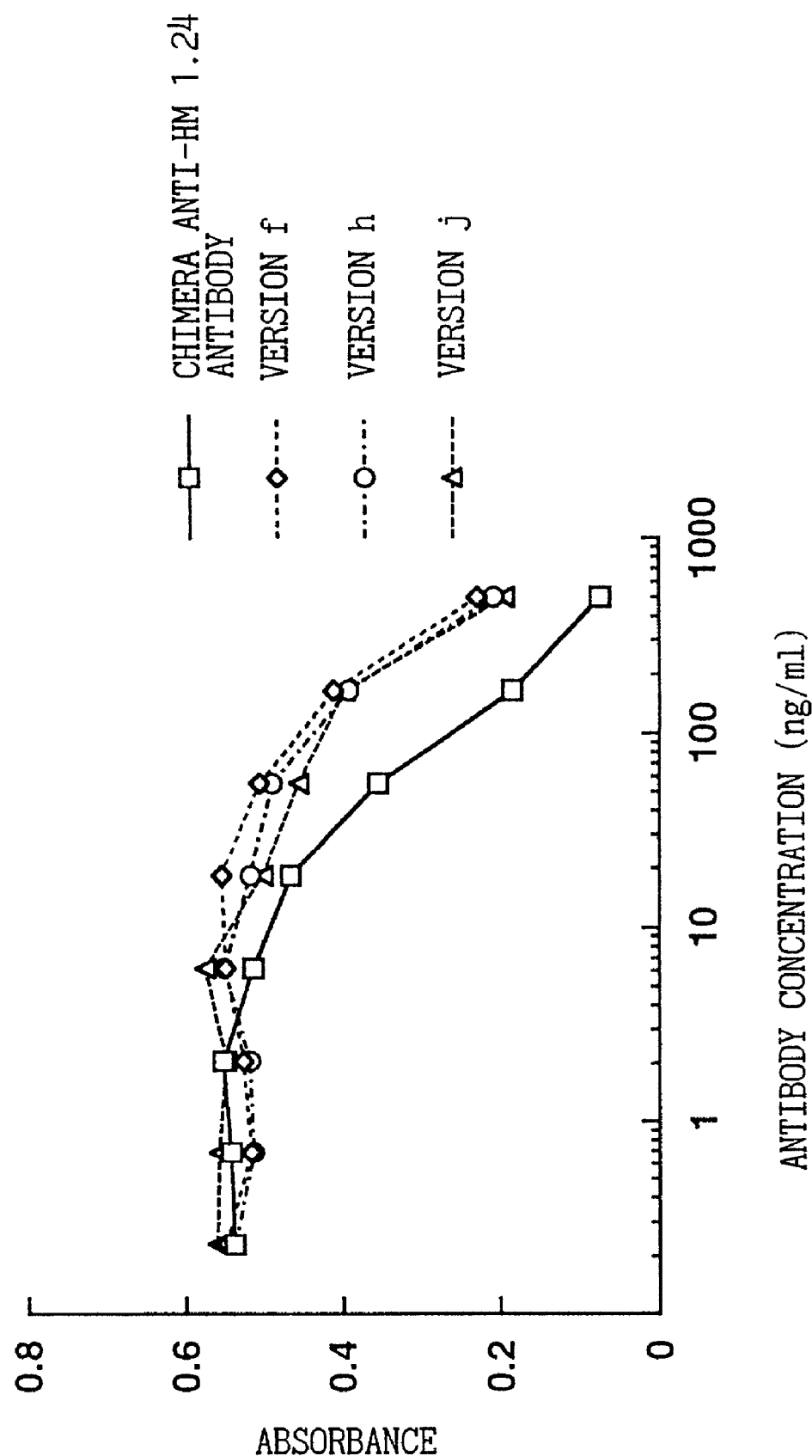
FIG. 23 is a graph showing the binding inhibition activity of the H chain versions f, h, and j of reshaped human anti-HM1.24 antibody and chimeric anti-HM1.24 antibody.
Figure 24:
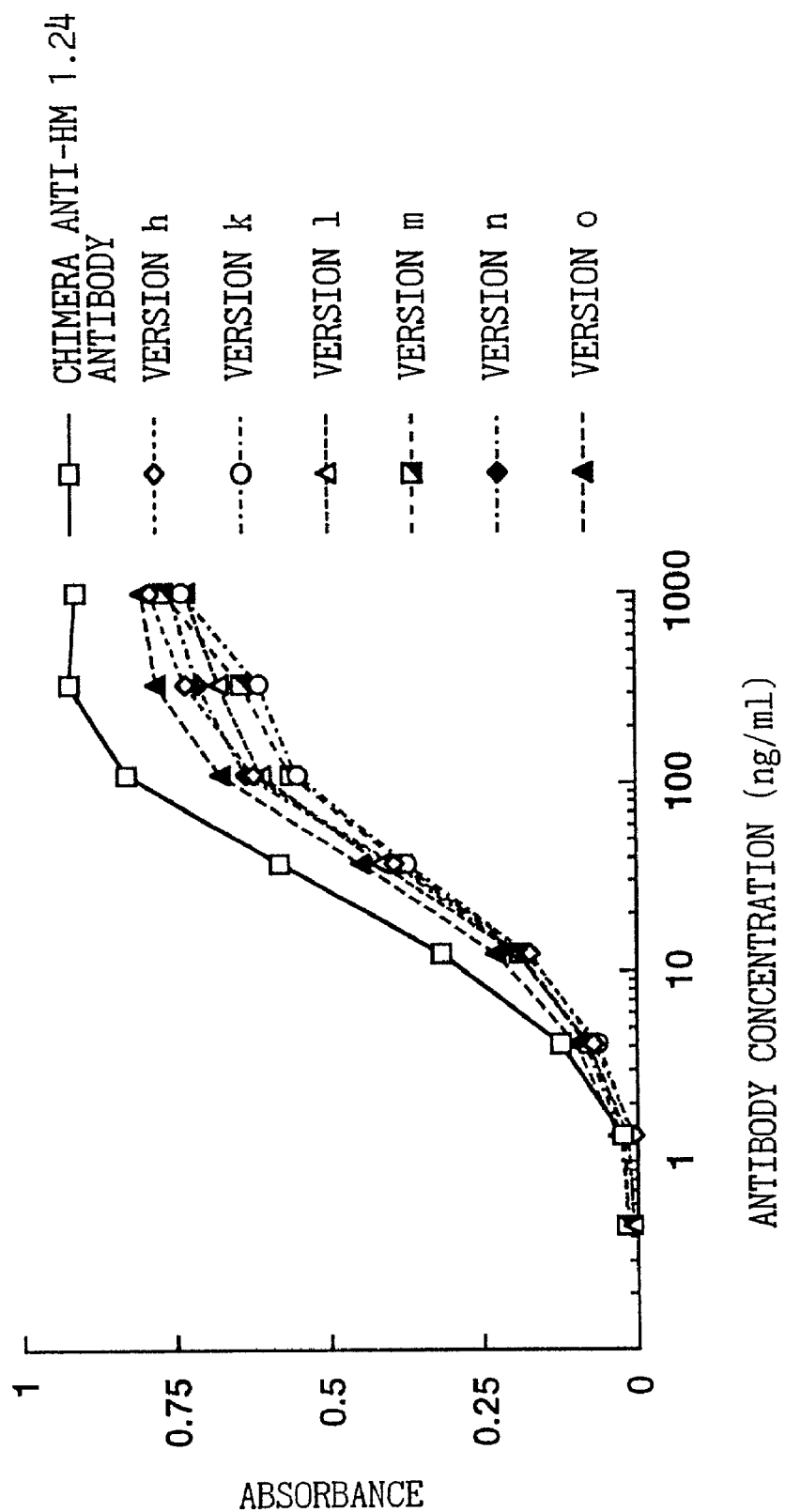
FIG. 24 is a graph showing the antigen binding activity of the H chain versions h, k, l, m, n, and o of reshaped human anti-HM1.24 antibody and chimeric anti-HM1.24 antibody.

Version g of the H chain of the reshaped human anti-HM1.24 antibody was evaluated as mentioned above for measurement of antigen binding activity. The result, as shown in FIGS. 18 and 19, indicated that this version has exhibited a similar level of activity to that of the above version a at most, revealing that, as shown for the above H chain human-mouse hybrid antibody, the amino acid at position 40 that was converted in this version is not responsible for the increase in the activity of the reshaped human antibody.

Versions h to j of the H chain of the reshaped human anti-HM1.24 antibody were evaluated as mentioned above for measurement of antigen binding activity and of binding inhibition activity. The result, as shown in FIGS. 20, 21, 22, and 23, indicated that all versions were weaker for both activities as compared to the chimera anti-HM1.24 antibody and were similar to the above-mentioned f, suggesting that the amino acids at positions 67 and 69 among the four amino acids that were newly converted in version f are not responsible for the increase in the activity of the reshaped human antibody.

Versions k to p of the H chain of the reshaped human anti-HM1.24 antibody were evaluated as mentioned above for measurement of antigen binding activity and of binding inhibition activity. The result, as shown in FIGS. 24, 25, 26, and 27, indicated that all versions were weaker for both activities as compared to the chimera anti-HM1.24 antibody and were similar to the above-mentioned h, suggesting that the amino acids at position 80 and after that were newly converted in these six versions are not responsible for the increase in the activity of the reshaped human antibody.

Figure 25:
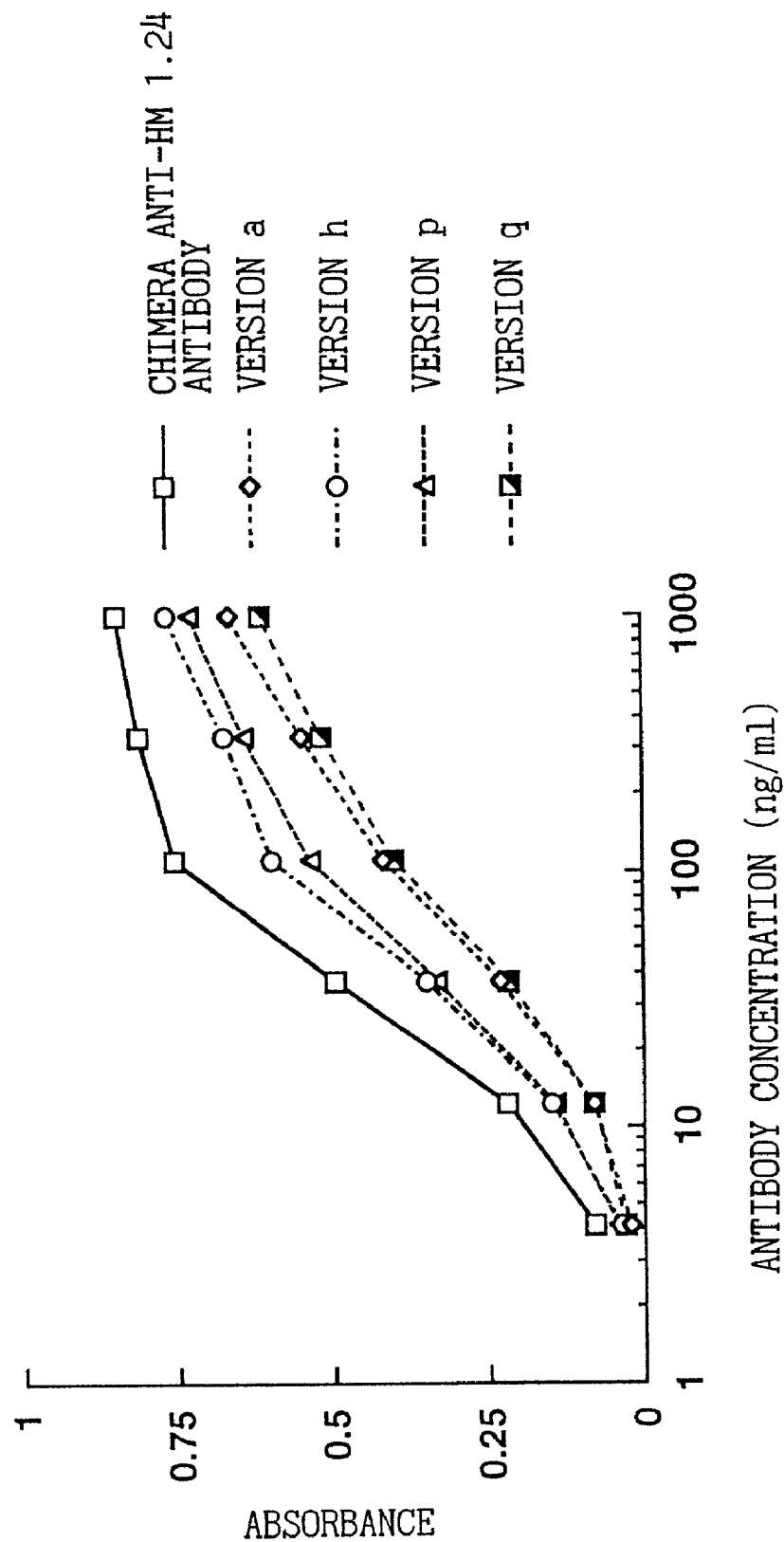
FIG. 25 is a graph showing the antigen binding activity of the H chain versions a, h, p, and q of reshaped human anti-HM1.24 antibody and chimeric anti-HM1.24 antibody.
Figure 26:
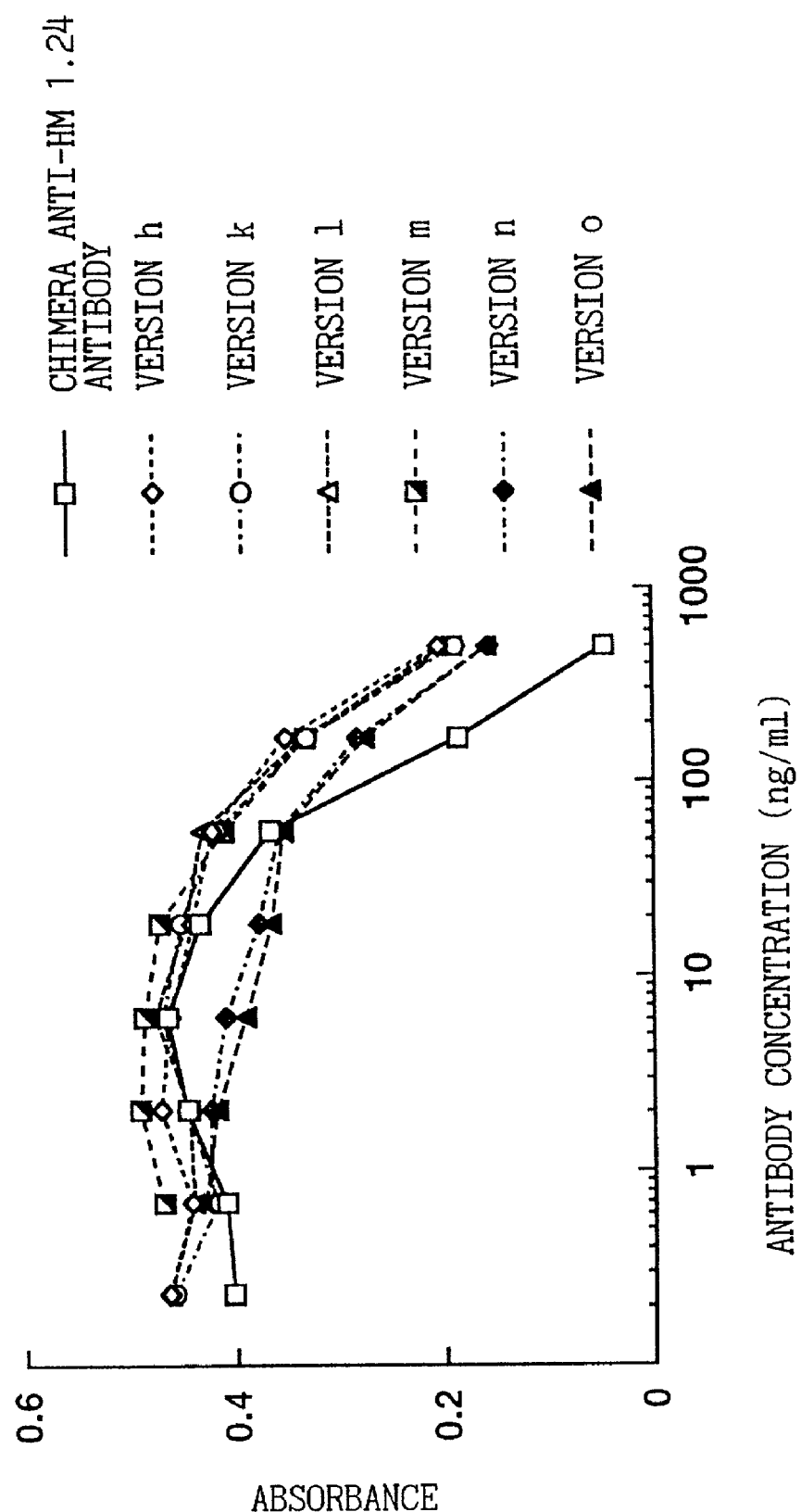
FIG. 26 is a graph showing the binding inhibition activity of the H chain versions h, k, l, m, n, and o of reshaped human anti-HM1.24 antibody and chimeric anti-HM1.24 antibody to the WISH cells.
Figure 27:
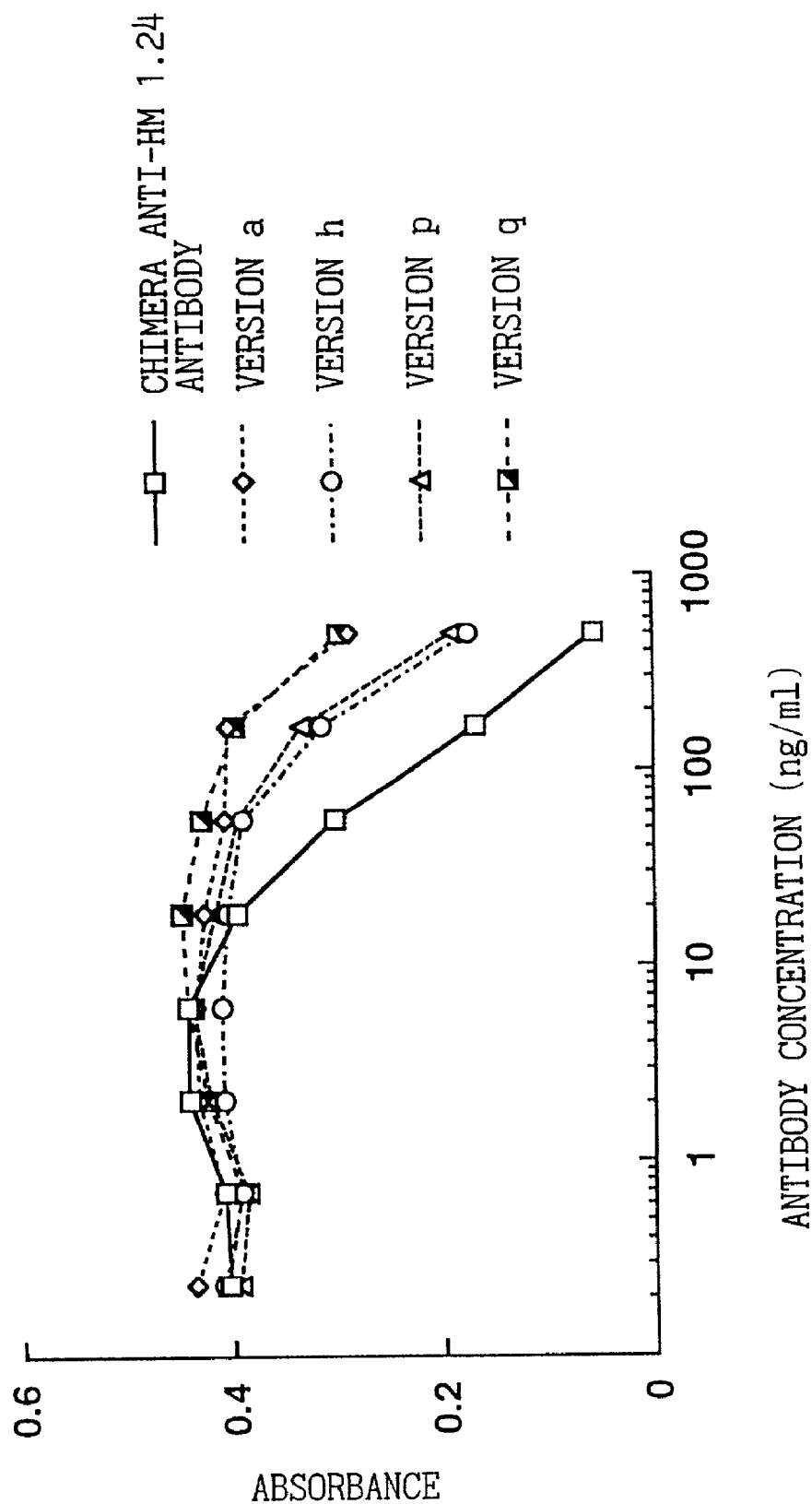
FIG. 27 is a graph showing the binding inhibition activity of the H chain versions a, h, p, and q of reshaped human anti-HM1.24 antibody and chimeric anti-HM1.24 antibody.

Version q of the H chain of the reshaped human anti-HM1.24 antibody was evaluated as mentioned above for measurement of antigen binding activity and of binding inhibition activity. The result, as shown in FIGS. 25 and 27, indicated that this version was weaker for both activities as compared to the above version h or version p and was similar to that of the above-mentioned a at most, suggesting that substitution of the amino acid at position 78 is essential for the increase in the activity of the reshaped human antibody.

Figure 15:
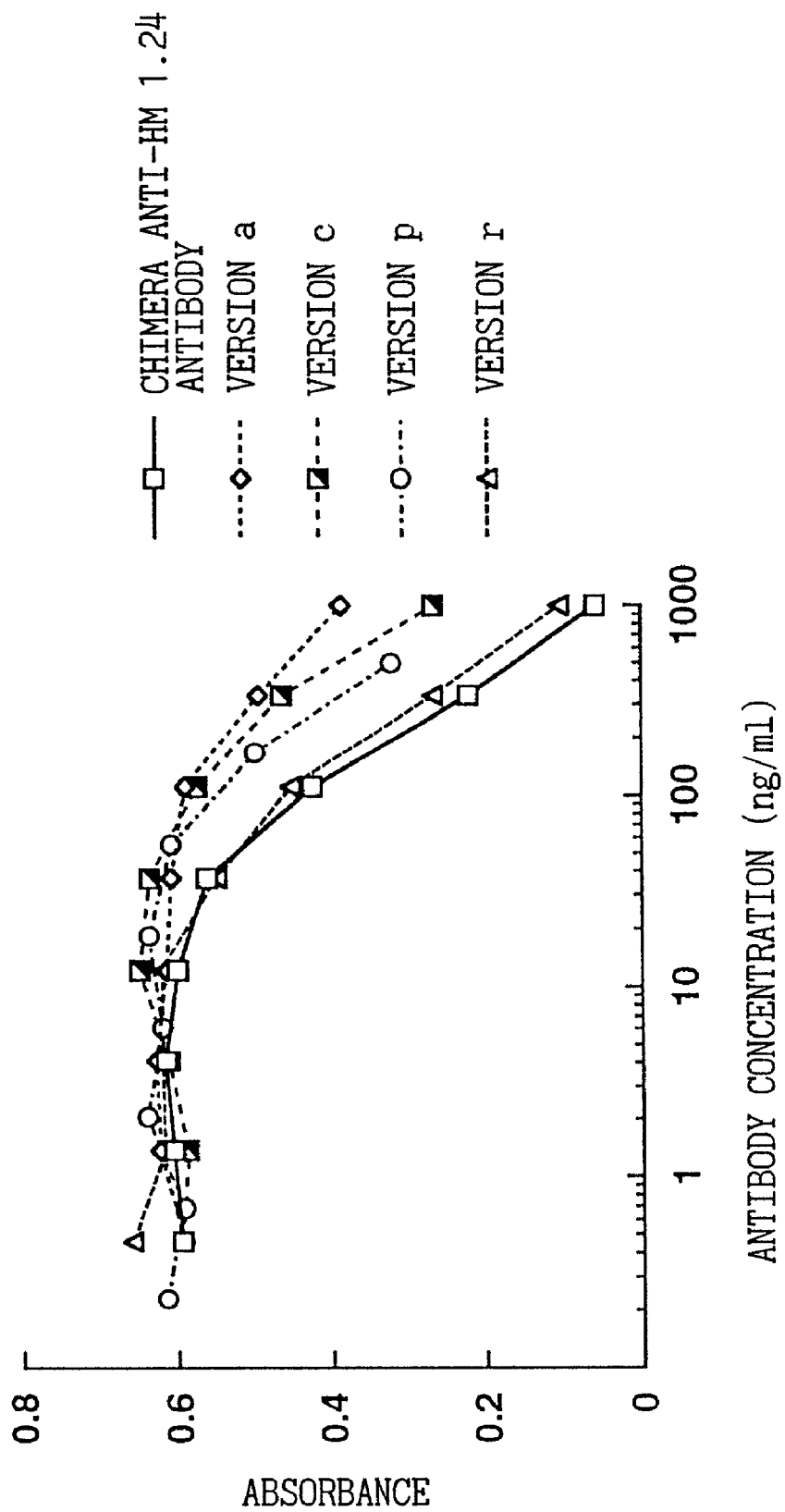
FIG. 15 is a graph showing the binding inhibition activity of the H chain versions a, c, p, and r of reshaped human anti-HM1.24 antibody and chimeric anti-HM1.24 antibody.
Figure 28:
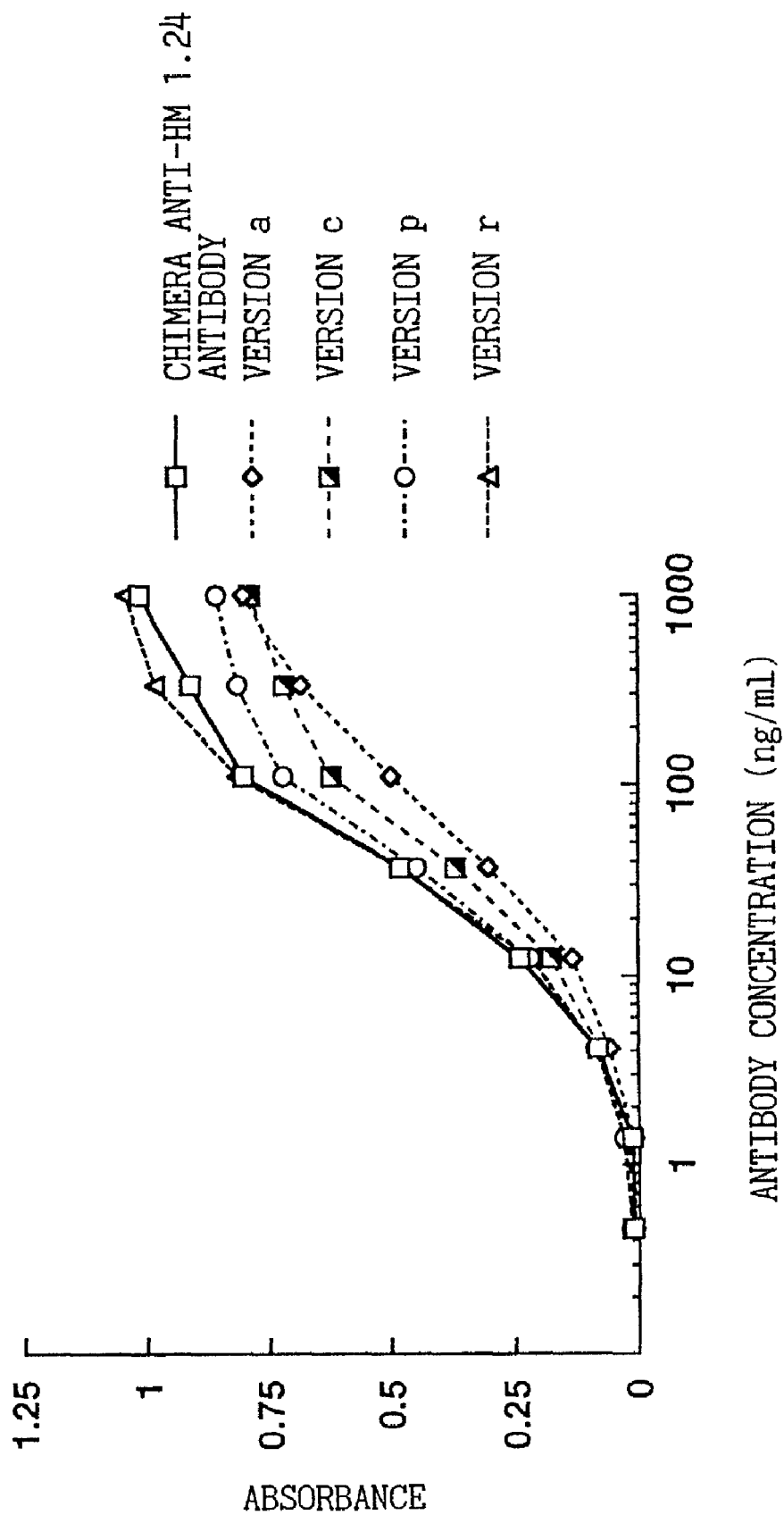
FIG. 28 is a graph showing the antigen binding activity of the H chain versions a, c, p, and r of reshaped human anti-HM1.24 antibody and chimeric anti-HM1.24 antibody.

Version r of the H chain of the reshaped human anti-HM1.24 antibody were evaluated by the method mentioned above. The result, as shown in FIGS. 15 and 28, indicated that version r has a similar level of antigen binding activity and the binding inhibition activity to that of the chimera anti-HM1.24 antibody.

The above results indicated that the minimum conversion required for the reshaped human anti-HM1.24 antibody to have a similar level of antigen binding activity to that of the mouse anti-HM1.24 antibody or the chimera anti-HM1.24 antibody is the amino acids at positions 30, 71, and 78 and, furthermore, 73.

The antigen binding activity and the binding inhibition activity for H chain versions a to r of the reshaped human anti-HM1.24 antibody are summarized in Table 2.

TABLE 2

| H chain version | Antigen binding activity | Binding inhibition activity |
|---|---|---|
| a | + | + |
| b | + | + |
| c | + | + |
| d | + | not measured |
| e | + | not measured |
| f | ++ | ++ |
| g | + | + |
| h | ++ | ++ |
| i | ++ | ++ |
| j | ++ | ++ |
| k | ++ | ++ |
| l | ++ | ++ |
| m | ++ | ++ |
| n | ++ | ++ |
| o | ++ | ++ |
| p | ++ | ++ |
| q | + | + |
| r | +++ | +++ |

Furthermore, the amino acid sequences of the reshaped human anti-HM1.24 antibody and versions a and b of the L chain are shown in Table 3, and those of versions a to r of the H chain of the reshaped human anti-HM1.24 antibody are shown in Tables 4 to 6.

TABLE 3

```
The amino acid sequence of the L chain V region

FR1                              CDR1          FR2
                1         2                3            4
        12345678901234567890123 45678901234 56789012
AHM     DIVMTQSHKFMSTSVGDRVSITC KASQDVNTAVA WYQQKPGQ
HuSG I  DIQMTQSPSSLSASVGDRVTITC             WYQQKPGK
REI     DIQMTQSPSSLSASVGDRVTITC             WYQQKPGK
RVLa    ----------------------- ----------- --------
RVLb    ----------------------- ----------- --------
                                                      3456789
                                                      SPKLLIY
                                                      APKLLIY
                                                      APKLLIY
                                                      -------
                                                      -------

CDR2        FR3
         5           6           7           8
        0123456 789012345678901234567890123456789012345678
AHM     SASNRYT GVPDRITGSGSGTDFTFTISSVQAEDLALYYC
HuSG I          GVPSRFSGSGSGTDFTLTISSLQPEDFATYYC
REI             GVPSRFSGSGSGTDFTFTISSLQPEDIATYYC
RVLa    ------- --------------------------------
RVLb    ------- ---------------Y----------------

CDR3         FR4
         9            10
        901234567    8901234567
AHM     QQHYSTPFT    FGSGTKLEIK
HuSG I               FGQGTKVEIK
REI                  FGQGTKVEIK
RVLa    ---------    ----------
RVLb    ---------    ----------
```

TABLE 4

The amino acid sequence of the H chain V region (1)

```
              FR1                                   CDR1    FR2
                    1         2         3                    4
              1234567890123456789012345678901   12345   6789012
                                                        3456789
AHM    QVQLQQSGAELARPGASVKLSCKASGYTFT           PYWMQ   WVKQRPG
                                                        QGLEWIG

HuSGI  EVQLVQSGADVKKPGXSVXVSCKASGYTFS                   WVRQAPG
                                                        XGLDWVG

HG3    QVQLVQSGAEVKKPGASVKVSCKASGYTFN                   WVRQAPG
                                                        QGLEWMG

RVHa   ------------------------------T           -----   -------
       -------
RVHb   ------------------------------T           -----   -------
       -------
RVHc   ------------------------------T           -----   -------
       -------
RVHd   ------------------------------T           -----   -------
       -------
RVHe   ------------------------------T           -----   -------
       -------
RVHf   ------------------------------T           -----   -------
       -------
RVHg   ------------------------------T           -----   ---R---
       -------
RVHh   ------------------------------T           -----   -------
       -------
RVHi   ------------------------------T           -----   -------
       -------
RVHj   ------------------------------T           -----   -------
       -------
RVHk   ------------------------------T           -----   -------
       -------
RVHl   ------------------------------T           -----   -------
       -------
RVHm   ------------------------------T           -----   -------
       -------
RVHn   ------------------------------T           -----   -------
       -------
RVHo   ------------------------------T           -----   -------
       -------
RVHp   ------------------------------T           -----   -------
       -------
RVHq   ------------------------------T           -----   -------
       -------
RVHr   ------------------------------T           -----   -------
       -------
```

TABLE 5

The amino acid sequence of the H chain V region (2)

```
  CDR2                    FR3
5             6              7              8              9
012A3456789012345  67890123456789012ABC345678901234
AHM
SIFPGDGDTRYSQKFKG  KATLTADKSSSTAYMQLSILAFEDSAVYYCAR

HuSGI
                   RVTXTXDXSXNTAYMELSSLRSEDTAVYYCAR

HG3
                   RVTMTRDTSTSTVYMELSSLRSEDTAVYYCAR

RVHa
-----------------  -----A--------------------------
```

TABLE 5-continued

The amino acid sequence of the H chain V region (2)

```
RVHb
-----------------  K----A--------------------------
RVHc
-----------------  -----A-K------------------------
RVHd
-----------------  K----A-K------------------------
RVHe
-----------------  -A-L-A--------------------------
RVHf
-----------------  -A-L-A---S--A-------------------
RVHg
-----------------  -----A--------------------------
RVHh
-----------------  K----A---S--A-------------------
RVHi
-----------------  K----A---S--A-------AF----------
RVHj
-----------------  KA-L-A---S--A-------------------
RVHk
-----------------  K----A---S--A--Q----------------
RVHl
-----------------  K----A---S--A--Q--I-------------
RVHm
-----------------  K----A---S--A--Q--I-----S-------
RVHn
-----------------  K----A---S--A-----I-------------
RVHo
-----------------  K----A---S--A----------S-------
RVHp
-----------------  -----A------A-------------------
RVHq
-----------------  -----A---S----------------------
RVHr
-----------------  -----A-K----A-------------------
```

TABLE 6

The amino acid sequence of the H chain V region

```
          CDR3           FR4
           10            11
       57890ABJK12   34567890123
AHM    GLRRGGYYFDY   WGQGTTLTVSS

HuSGI                WGQGTLVTVSS

JH6                  WGQGTTVTVSS

RVHa   -----------   -----------
RVHb   -----------   -----------
RVHc   -----------   -----------
RVHd   -----------   -----------
RVHe   -----------   -----------
RVHf   -----------   -----------
RVHg   -----------   -----------
RVHh   -----------   -----------
RVHi   -----------   -----------
RVHj   -----------   -----------
RVHk   -----------   -----------
RVHl   -----------   -----------
RVHm   -----------   -----------
RVHn   -----------   -----------
RVHo   -----------   -----------
RVHp   -----------   -----------
RVHq   -----------   -----------
RVHr   -----------   -----------
```

3. Evaluation of the Purified Reshaped Human Anti-HM1.24 Antibody

Figure 31:
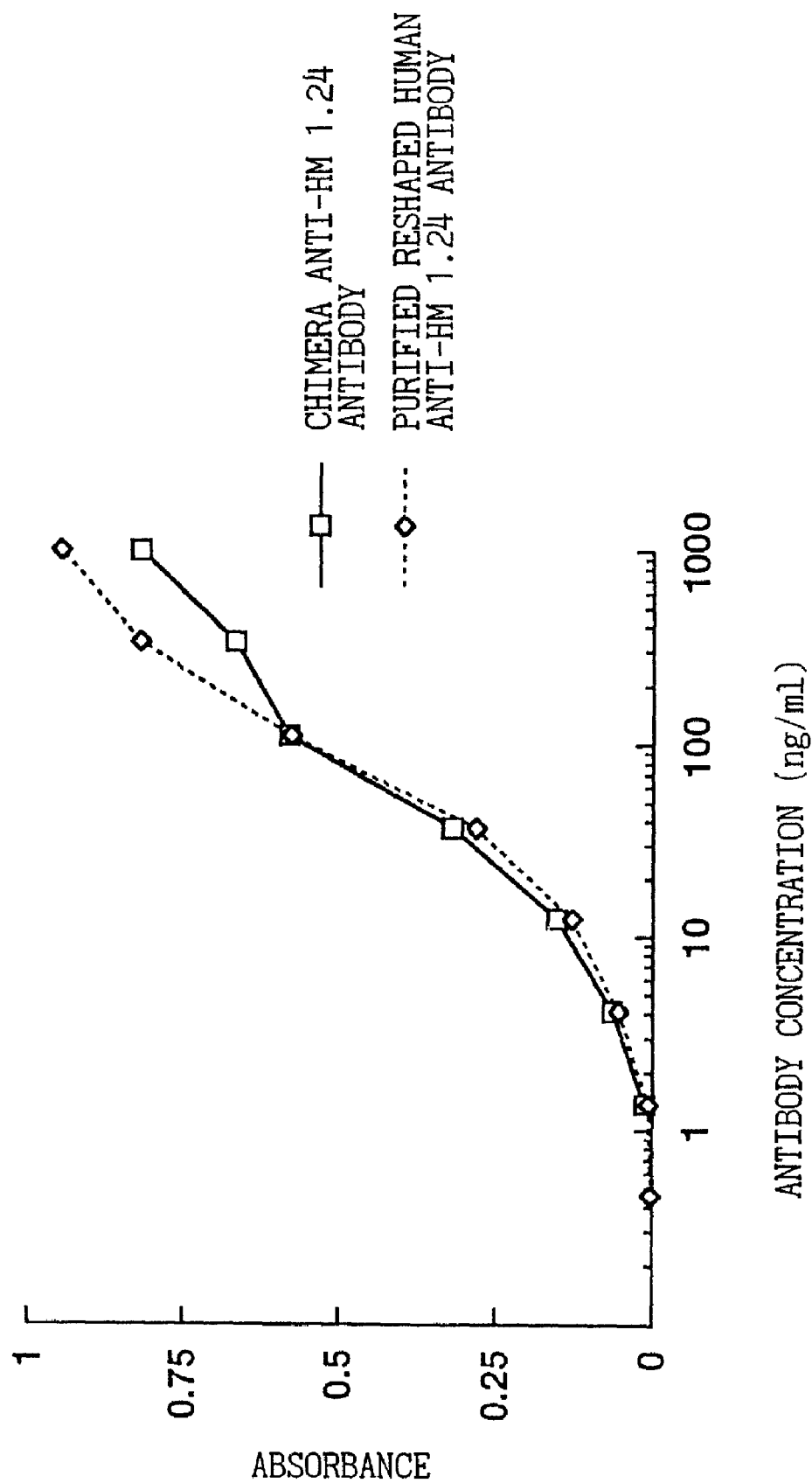
FIG. 31 is a graph showing that purified reshaped human anti-HM1.24 antibody has an antigen binding activity of a similar degree to that of chimeric human anti-HM1.24 antibody.
Figure 32:
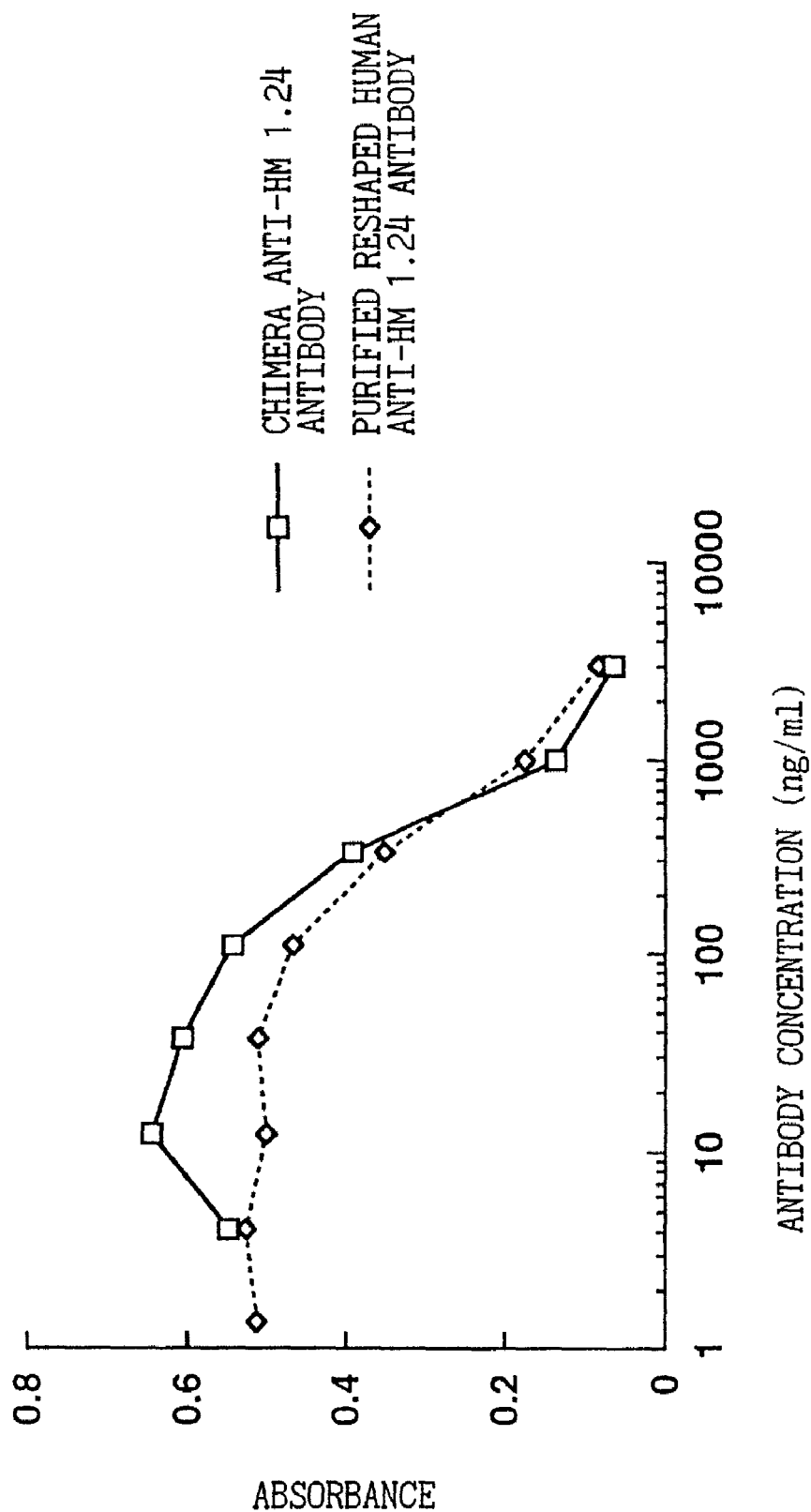
FIG. 32 is a graph showing that purified reshaped human anti-HM1.24 antibody has an binding inhibition activity of a similar degree to that of chimeric human anti-HM1.24 antibody.

The purified reshaped human anti-HM1.24 antibody was evaluated for the above-mentioned antigen binding activity and binding inhibition activity. The result, as shown in FIGS. 31 and 32, indicated that the reshaped human anti-HM1.24 antibody has a similar level of antigen binding activity and binding inhibition activity to that of the chimera anti-HM1.24 antibody. This fact indicated that the reshaped human anti-HM1.24 antibody has the same antigen binding activity as the mouse anti-HM1.24 antibody.

Reference Example 12

Construction of the Hybridoma that Produces the Mouse Anti-HM1.24 Monoclonal Antibody The hybridoma that produces the mouse anti-HM1.24 monoclonal antibody was prepared according to the method described in Goto, T. et al., Blood (1994) 84, 1992–1930.

The Epstein-Barr virus nuclear antigen (EBNA)-negative plasma cell line KPC-32 ($1 \times 10^7$ cells) derived from the bone marrow of human patients with multiple myeloma (Goto, T. et al., Jpn. J. Clin. Hematol. (11991) 32, 1400) was intraperitoneally given twice to BALB/c mice (manufactured by Charles River) every six weeks.

In order to further elevate the titer of antibody production, $1.5 \times 10^6$ KPC-32 cells were injected into the spleen of the mice three days before sacrificing the animals (Goto, T. et al., Tokushima J. Exp. Med. (1990) 37, 89). After sacrificing the mice, the spleen was removed, and the spleen cells removed according to the method of Groth, de St. & Schreidegger (Cancer Research (1981) 41, 3465) were subjected to cell fusion with the myeloma cells SP2/0.

Antibody in the supernatant of the hybridoma culture was screened by the ELISA (Posner, M. R. et al., J. Immunol. Methods (1982) 48, 23) using the KPC-32 cell-coated plates. $5 \times 10^4$ KPC-32 cells were suspended in 50 ml of PBS and dispensed into 96-well plates (U-bottomed, Corning, manufactured by Iwaki). After blocking with PBS containing 1% bovine serum albumin (BSA), the supernatant of the hybridoma was added and incubated at 4° C. for 2 hours. Subsequently, peroxidase-labeled anti-mouse IgG goat antibody (manufactured by Zymed) was reacted at 4° C. for 1 hour, washed once, and was reacted with the o-phenylenediamine substrate solution (manufactured by Sumitomo Bakelite) at room temperature for 30 minutes.

After stopping the reaction with 2N sulfuric acid, absorbance at 492 nm was measured using the ELISA reader (manufactured by Bio-Rad). In order to remove the hybridoma that produces antibody against human immunoglobulin, the positive hybridoma culture supernatant had previously been adsorbed to human serum, and the reactivity to other sub-cellular components was screened. Positive hybridomas were selected and their reactivity to various cell lines and human samples was investigated using flow cytometry. The finally selected hybridoma clones were cloned twice, were injected into the abdominal cavity of the pristane-treated BALB/c mice and then the ascitic fluid was obtained therefrom.

Monoclonal antibody was purified from the mouse ascites by ammonium sulfate precipitation and Protein A affinity chromatography kit (Ampure Pa., manufactured by Amersham). The purified antibody was conjugated to fluorescein isocyanate (FITC) using the Quick Tag FITC conjugation kit (manufactured by Boehringer Mannheim).

As a result, the monoclonal antibody produced by 30 hybridoma clones reacted with KPC-32 and RPMI 8226 cells. After cloning, the reactivity of the supernatant of these hybridomas with other cell lines and peripheral blood-derived monocytes was investigated.

Of them, three clones were monoclonal antibodies that specifically react with plasma cells. Out of these three clones, the hybridoma clone having the clone that is most useful for flow cytometry analysis and that has complement-dependent cytotoxicity was selected and termed HM1.24. The subclass of monoclonal antibody produced by this hybridoma was determined by ELISA using subclass-specific anti-mouse rabbit antibody (manufactured by Zymed). Anti-HM1.24 antibody had a subclass of IgG2a κ. The hybridoma that produces the anti-HM1.24 antibody was internationally deposited on Sep. 14, 1995, with the National Institute of Bioscience and Human-Technology, Agency of Industrial Science and Technology, MITI (Higashi 1-Chome 1-3, Tsukuba city, Ibaraki prefecture, Japan) under the accession number FERM BP-5233 under the provisions of the Budapest Treaty.

Reference Example 13

Cloning of cDNA Encoding the HM1.24 Antigen Polypeptide

1. Construction of cDNA Library

1) Preparation of Total RNA

The cDNA that encodes the HM1.24 antigen which is an antigen polypeptide specifically recognized by mouse monoclonal antibody HM1.24 was isolated as follows.

From the human multiple myeloma cell line KPMM2, total RNA was prepared according to the method of Chirgwin et al. (Biochemistry, 18, 5294 (1979)). Thus, $2.2 \times 10^8$ KPMM2 cells were completely homogenized in 20 ml of 4 M guanidine isocyanate (manufactured by Nacalai Tesque Inc.).

The homogenate was layered on the 5.3 M cesium chloride layer in the centrifuge tube, which was then centrifuged using Beckman SW40 rotor at 31,000 rpm at 20° C. for 24 hours to precipitate RNA. The RNA precipitate was washed with 70% ethanol, and dissolved in 300 μl of 10 mM Tris-HCl (pH 7.4) containing 1 mM EDTA and 0.5% SDS. After adding Pronase (manufactured by Boehringer) thereto to a concentration of 0.5 mg/ml, it was incubated at 37° C. for 30 minutes. The mixture was extracted with phenol and chloroform to precipitate RNA. Then, the RNA precipitate was dissolved in 200 μl of 10 mM Tris-HCl (pH 7.4) containing 1 mM EDTA.

2) Preparation of Poly(A)+RNA

Using about 500 μg of the total RNA prepared as above as a raw material, poly(A)+RNA was purified using the Fast Track 2.0 m RNA Isolation Kit (manufactured by Invitrogen) according to the instructions attached to the kit.

3) Construction of cDNA Library

Using 10 μg of the above poly(A)+RNA as a raw material, double strand cDNA was synthesized using the cDNA synthesizing kit TimeSaver cDNA Synthesis Kit (manufactured by Pharmacia) according to the instructions attached to the kit and, using the Directional Cloning Toolbox (manufactured by Pharmacia), EcoRI adapter was linked thereto according to the instructions attached to the kit. Kination and restriction enzyme NotI treatment of the EcoRI adapter were carried out according to the instructions attached to the kit. Furthermore, the adapter-attached double strand cDNA having a size of about 500 bp or higher was isolated and purified using 1.5% agarose gel (manufactured by SIGMA) to obtain about 40 µl of adapter-attached double strand cDNA.

The adapter-attached double strand cDNA thus prepared was linked using pCOS1 vector (Japanese Unexamined Patent Publication (Kokai) No. 8(1996)-255196) and T4 DNA ligase (manufactured by GIBCO BRL) that had previously been treated with restriction enzymes EcoRI and NotI and alkaline phosphatase (manufactured by Takara Shuzo) to construct a cDNA library. The constructed cDNA library was transduced into Escherichia coli strain DH5 (manufactured by GIBCO BRL) and the total size was estimated to be about $2.5 \times 10^6$ independent cells.

2. Cloning by Direct Expression

1) Transfection into COS-7 Cells cDNA was amplified by culturing about $5 \times 10^5$ clones of the above transduced Escherichia coli in the 2-YT medium (Molecular Cloning: A Laboratory Manual, Sambrook et al., Cold Spring Harbor Laboratory Press, (1989)) containing 50 µg/ml of ampicillin, and plasmid DNA was recovered from the Escherichia coli by the alkali method (Molecular Cloning: A Laboratory Manual, Sambrook et al., Cold Spring Harbor Laboratory Press, (1989)). The plasmid DNA obtained was transfected into COS-7 cells by electroporation using the Gene Pulser instrument (manufactured by Bio-Rad).

Thus, 10 µg of the purified plasmid DNA was added to 0.8 ml of COS-7 cells that were suspended into PBS at a concentration of $1 \times 10^7$ cells/ml, and was subjected to pulses at 1500 V and a capacity of 25 µF. After 10 minutes of recovery period at room temperature, the electroporated cells were cultured in the DMEM medium (manufactured by GIBCO BRL) supplemented with 10% bovine fetal serum under the condition of 37° C. and 5% $CO_2$ for three days.

2) Preparation of the Panning Dish

A panning dish coated with the mouse anti-HM1.24 antibody was prepared by the method of B. Seed et al. (Proc. Natl. Acad. Sci. USA, 84, 3365–3369 (1987)). Thus, the mouse anti-HM1.24 antibody was added to 50 mM Tris-HCl, pH 9.5, to a concentration of 10 µg/ml. Three ml of the antibody solution thus prepared was added to a tissue culture plate with a diameter of 60 mm and incubated at room temperature for 2 hours. After washing three times with PBS containing 0.15 M NaCl, 5% bovine fetal serum, 1 mM EDTA, and 0.02% $NaN_3$ was added, and after blocking, it was used for the following cloning.

3) Cloning of cDNA Library

The COS-7 cells transfected as described above were detached by PBS containing 5 mM EDTA, and then washed once with PBS containing 5% bovine fetal serum. It was then suspended in PBS containing 5% bovine fetal serum and 0.02% $NaN_3$ to a concentration of about $1 \times 10^6$ cells/ml, which was added to the panning dish prepared as above and incubated at room temperature for 2 hours. After washing three times with PBS containing 5% bovine fetal serum and 0.02% $NaN_3$, plasmid DNA was recovered from the cells bound to the panning dish using a solution containing 0.6% SDS and 10 mM EDTA.

The recovered plasmid DNA was transduced again to Escherichia coli DH5α. After amplifying the plasmid DNA as above, it was recovered by the alkali method. The recovered plasmid DNA was transfected into COS-7 cells by the electroporation method to recover plasmid DNA from the bound cells as described above. The same procedure was repeated one more time, and the recovered plasmid DNA was digested with restriction enzymes EcoRI and NotI. As a result, concentration of the insert with a size of about 0.9 kbp was confirmed. Fifty µg of Escherichia coli transduced with part of the recovered plasmid DNA was inoculated to the 2-YT agar plate containing 50 µg/ml of ampicillin. After culturing overnight, plasmid DNA containing a single colony was recovered. It was digested with restriction enzymes EcoRI and NotI and clone p3.19 having an insert of 0.9 kbp was obtained.

The base sequence of this clone was determined by reacting using PRISM, Terminater Cycle Sequencing kit (manufactured by Perkin Elmer) according to the instructions attached to the kit. The amino acid sequence and the base sequence thereof are shown in SEQ ID NO: 128.

The cDNA encoding the polypeptide having the amino acid sequence as set forth in SEQ ID NO: 128 was inserted into the XbaI cleavage site of pUC19 vector, and has been prepared as plasmid pRS38-pUC19. The Escherichia coli that contains this plasmid pRS38-pUC19 has been internationally deposited on Oct. 5, 1993, as Escherichia coli DH5α (pRS38-pUC19), with the National Institute of Bioscience and Human-Technology, Agency of Industrial Science and Technology, MITI (Higashi 1-Chome 1-3, Tsukuba city, Ibaraki prefecture, Japan) under the accession number FERM BP-4434 under the provisions of the Budapest Treaty (see Japanese Unexamined Patent Publication (Kokai) No. 7(1995)-196694).

EXAMPLES

As an example of natural humanized antibodies composed of the natural FR sequences of the present invention, a preparation example of a natural humanized antibody based on humanized anti-HM1.24 antibody is described.

Example 1

Mouse monoclonal anti-HM1.24 antibody was humanized as the reshaped human anti-HM1.24 antibody by CDR-grafting as described in Reference Examples. Each FR of human antibody HG3 for FR1 to FR3 and the FR4 of human antibody JH6 for FR4 were selected for the construction of the humanized H chain. The result on the study of the FR amino acid residues indicated that amino acid substitution was required at four sites (FR1/30, FR3/71, 73, 78) (Tables 7 and 8). This humanized antibody had an antigen binding activity similar to that of the original antibody. This humanized antibody (humanized antibody comprising RVLa/RVHr) was used as the primary design antibody.

Design of V region of Natural Humanized Antibody

A) L chain

```
                        FR1                      CDR1         FR2              CDR2
                    1           2            3            4                5
                    1234567890123456789 0123 45678901234 567890123456789 0123456
HM1.24              DIVMTQSHKFMSTSVGDRVSITC KASQDVNTAVA WYQQKPGQSPKLLIY SASNRYT

HUSG I              DIQMTQSPSSLSASVGDRVTITC                 WYQQKPGKAPKLLIY

REI                 DIQMTQSPSSLSASVGDRVTITC                 WYQQKPGKAPKLLIY

Primary design (RVLa   ----------------------- ----------- --------------- -------
Secondary design       ----------------------- ----------- --------------- -------

FR3                                           CDR3        FR4
                      6         7         8                   9            10
                    78901234567890123456789012345678 901234567 8901234567
HM1.24              GVPDRITGSGSGTDFTFTISSVQAEDLALYYC QQHYSTPFT FGSGTKLEIK

HUSG I              GVPSRFSGSGSGTDFTLTISSLQPEDFATYYC           FGQGTKVEIK

REI                 GVPSRFSGSGSGTDFTFTISSLQPEDIATYYC           FGQGTKVEIK

Primary design (RVLa) -------------------------------- --------- ----------
Secondary design      -------------------------------- --------- ----------
```

Design of V region of Natural Humanized Antibody

B) H chain

```
                        FR1                                        CDR1   FR2              CDR2
                    1          2         3                       4                 5           6
                    1234567890123456789012345678 90 12345 67890123456789 012A3456789012345
HM1.24              QVQLQQSGAELARPGASVKLSCKASGYTFT PYWMQ WVKQRPGQGLEWIG SIFPGDGDTRYSQKFKG

HuSGI               EVQLVQSGADVKKPGXSVXVSCKASGYTFS       WVRQAPGXGLDWVG

HG3                 QVQLVQSGAEVKKPGASVKVSCKASGYTFN       WVRQAPGQGLEWMG

Primary design (RVHr)   ------------------------------T ----- --------------- -----------------
Secondary design (2ndRVH) ----------------------------T ----- --------------- -----------------

FR3                                        CDR3         FR4
                      7         8         9                  10             11
                    67890123456789012ABC345678901234 57890ABJK12 34567890123
HM1.24              KATLTADKSSSTAYMQLSILAFEDSAVYYCAR GLRRGGYYFDY WGQGTTLTVSS

HuSGI               RVTXTXDXSXNTAYMELSSLRSEDTAVYYCAR             WGQGTLVTVSS

HG3 JH6             RVTMTRDTSTSTVYMELSSLRSEDTAVYYCAR             WGQGTTVTVSS

Primary design (RVHr)   -----A-K----A-------------------- ----------- -----------
Secondary design (2ndRVH) ---I-A-K----A-------------------- ----------- -----------
```

(1) The Construction of H Chain

For the FR of the primary design antibody, homology search on human FRs found in nature was carried out using such databases as SeissPlot, GenBank, PRF, PIR, and Gen-Pept. First, 50 human FRs were found that have completely matching amino acid sequences for FR1. Thus, the FR1 of the primary design antibody already had a natural sequence. Since no amino acid substitution has been made for FR2 and FR4, 50 and 100 natural FRs including HG3 and JH6 respectively of natural human body were found.

On the other hand, no complete matches were found for FR3. As the FR3 that had the highest homology, S46463 having a homology of 96.875%, 1921296C, HUMIGHRF 1, U00583 1 and the like were found (symbols are all accession numbers for the database).

Thus, in the primary design antibody, FR3 was the FR containing artificial amino acid residues that are not found in nature. The amino acid sequence is compared with that of the human antibody S46463 that had the highest homology in Table 9.

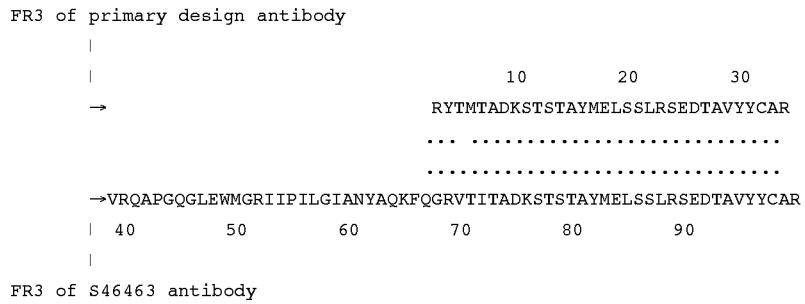

The amino acid residue at position 70 was methionine in the FR3 of the primary design antibody and was isoleucine in the FR3 of the human antibody S46463. The other amino acid sequences have shown complete matches. Thus, the amino acid residue at position 70 in the primary design antibody was replaced with isoleucine to convert it to a naturally occurring FR3. Accordingly, the secondary design antibody obtained is a CDR-grafting antibody comprising the natural human FR of the human antibody S46463. The secondary design antibody thus constructed comprises FRs that are all found in nature.

(2) Construction of the H Chain V Region of Natural Humanized Anti-HM1.24 Antibody The H chain V region of the natural humanized anti-HM 1.24 antibody was constructed by mutagenesis using PCR. The mutagen primers SS (SEQ ID NO: 124) and SA (SEQ ID NO: 125) were designed to mutate methionine at position 69 to isoleucine.

After the above primer was amplified using plasmid HEF-RVHr-AHM-gγ1 as a template, the final product was purified, digested with BamHI and HindIII, and the DNA fragment obtained was cloned into an expression vector HEF-VH-gγ1 to obtain a plasmid HEF-RVHs-AHM-gγ1. The amino acid sequence and the nucleotide sequence of the V region of the H chain contained in this plasmid HEF-RVHs-AHM-gγ1 are shown in SEQ ID NO: 126.

The region encoding the variable region of the above-mentioned plasmid HEF-RVHs-AHM-gγ1 was digested with restriction enzymes HindIII and BamHI to make a restriction fragment. This was inserted into the BamHI and HindIII sites of plasmid vector pUC19. The plasmid obtained was termed pUC19-RVHs-AHM-gγ1.

*Escherichia coli* that contains pUC19-RVHs-AHM-gγ1 was designated as *Escherichia coli* DH5α (pUC19-RVHs-AHM-gγ1) and has been internationally deposited on Sep. 29, 1997, with the National Institute of Bioscience and Human-Technology, Agency of Industrial Science and Technology, MITI (Higashi 1-Chome 1-3, Tsukuba city, Ibaraki prefecture, Japan) under the accession number FERM BP-6127 under the provisions of the Budapest Treaty.

2) Analysis of L Chain

Although amino acids of the FRs were not substituted in the construction of the L chain of the primary design antibody, homology search was conducted also for these FRs, since the human antibody REI used was a Reshaped FR (Riechmann, L. et al., Nature (1988) 332, 323–327) that had already been subjected to amino acid substitution. The result confirmed the presence of natural sequences corresponding to the reshaped FRs. Thus, it was demonstrated that no amino acid substitution is required for FRs of L chain.

Example 2

Production of Natural Humanized Anti-HM1.24 Antibody (1) Expression of Natural Humanized Anti-HM1.24 Antibody Ten μg each of the expression vector (HEF-RVHs-AHM-gγ1) for H chain of natural humanized anti-HM1.24 antibody and the expression vector (HEF-RVLa-AHM-gκ) for L chain of reshaped human anti-HM1.24 antibody was cotransformed into COS cells by electroporation using the Gene Pulser instrument (manufactured by BioRad). Each DNA (10 μg) was added to 0.8 ml aliquots of $1\times10^7$ cells/ml in PBS, and was subjected to pulses at 1500 V and a capacity of 25 μF.

After a recovery period of 10 minutes at room temperature, the electroporated cells were added to 30 ml of DHEM culture liquid (manufactured by GIBCO) containing 10% γ-globulin-free bovine fetal serum. After incubation of 72 hours in a $CO_2$-incubator BNA120D (manufactured by TABAI) under the condition of 37° C. and 5% $CO_2$, the culture supernatant was collected, and the cell debris was removed by centrifugation at 1000 rpm for 5 minutes in a centrifuge 505PR-22 (manufactured by HITACHI) equipped with a centrifuge rotor 03 (manufactured by HITACHI). Then ultrafiltration was carried out with a microconcentrator (Centricon 100, manufactured by Amicon) using a centrifuge J2-21 (manufactured by BECKMAN) equipped with a centrifuge rotor JA-20.1 (manufactured by BECKMAN), at a condition of 2000 rpm, and filter-sterilization was carried out using a filter Milex GV13 mm (manufactured by Millipore) to obtain a product which was used for Cell-ELISA.

(2) Measurement of Antibody Concentration

Concentration of the antibody obtained was measured by ELISA. To each well of a 96-well ELISA plate (Maxisorp, manufactured by NUNC) was added 100 μl of goat anti-human IgG antibody (manufactured by BIO SOURCE) prepared to a concentration of 1 μg/ml with the coating buffer (0.1 M $NaHCO_3$, 0.02% $NaN_3$, pH 9.6) and the plate was incubated at room temperature for one hour. After blocking with 100 μl of the dilution buffer (50 mM Tris-HCl, 1 MM $MgCl_2$, 0.15 M NaCl, 0.05% Tween 20, 0.02% $NaN_3$, 1% bovine serum albumin (BSA), pH 8.1), 100 μl each of serial dilutions of the natural humanized anti-HM1.24 antibody was added to each well and the plate was incubated at room temperature for one hour. Then after washing, 100 μl of alkaline phosphatase-labeled goat anti-human IgG antibody (manufactured by DAKO) was added.

After incubating at room temperature for one hour and washing, 100 μl of 1 mg/ml substrate solution (Sigma 104, p-nitrophenyl phosphate, manufactured by SIGMA) dissolved in substrate buffer (50 mM NaHCO$_3$, 10 mM MgCl$_2$, pH 9.8) was added, and then the absorbance at 405 nm was measured using the MICROPLATE READER Model 3550 (manufactured by Bio Rad). As a standard for measurement of concentration, human IgG1κ (manufactured by The Binding Site) was used.

(3) Establishment of the CHO Cell Line that Stably Produces the Natural Humanized Anti-HM1.24 Antibody The CHO cell line that stably produces the natural humanized anti-HM1.24 antibody can be established according to the following method.

(3)-1. Construction of an Expression Vector for an H Chain of a Natural Humanized Anti-HM1.24 Antibody By digesting plasmid HEF-RVHs-AHM-gγ1 with restriction enzymes PvuI and BamHI, an about 2.8 kbp fragment containing DNA encoding an EF1 promoter and a V region of the H chain of natural humanized anti-HM1.24 antibody was purified using 1.5% low melting point agarose gel. Then, the above DNA fragment is inserted into an about 6 kbp fragment that was prepared by digesting with PvuI and BamHI the expression vector used for a human H chain expression vector, DHFR-ΔE-RVh-PM1f (International Patent Publication No. WO 92-19759), containing a DHFR gene and a gene encoding a constant region of a human H chain, so as to construct an expression vector, DHFR-ΔE-HEF-RVHs-AHM-gγ1, for the H chain of the natural humanized anti-HM1.24 antibody.

(3)-2. Gene Introduction into CHO Cells

In order to establish a stable production system of the natural humanized anti-HM1.24 antibody, the genes of the above-mentioned expression vectors, DHFR-ΔE-RVHs-AHM-gγ1 and HEF-RVLa-AHM-gκ, that were linearized by digestion with PvuI, were simultaneously introduced into the CHO cell DXB-11 by the electroporation method under the condition similar to the above-mentioned one (transfection into the above-mentioned COS-7 cells).

(3)-3. Gene Amplification by MTX

Of the gene-introduced CHO cells, only those CHO cells in which both of L chain and H chain expression vectors have been introduced can survive in the nucleoside-free α-MEM culture liquid (manufactured by GIBCO-BRL) to which 500 μg/ml G418 (manufactured by GIBCO-BRL) and 10% bovine fetal serum were added, and so they were selected. Subsequently, 10 nM MTX (manufactured by Sigma) is added to the above culture. Of the clones that propagated, those that produce a natural humanized anti-HM1.24 antibody in large amount were selected.

(3)-4. Construction of the Natural Humanized Anti-HM1.24 Antibody

The natural humanized anti-HM1.24 antibody was produced in the following method. The above CHO cells that produce the natural humanized anti-HM1.24 antibody were cultured for 10 days using a nucleoside-free α-MEM culture medium (manufactured by GIBCO-BRL) to which 500 μg/ml G418 (manufactured by GIBCO-BRL) containing 10% γ-globulin-free bovine fetal serum (manufactured by GIBCO-BRL) had been added, using a CO$_2$ incubator BNAS120D (manufactured by TABAI) under the condition of 37° C. and 5% CO$_2$. On day 8 and 10 after starting the culture the culture medium was recovered, the cell debris was removed by centrifuging for 10 minutes at 2000 rpm using the centrifuge RL-500SP (manufactured by Tomy Seiko) equipped with the TS-9 rotor, and then filter-sterilized using a bottle top filter (manufactured by FALCON) having a membrane with pores of 0.45 μm in diameter.

After an equal amount of PBS(−) was added to the culture liquid of the CHO cells that produce the natural humanized anti-HM1.24 antibody, then the natural humanized anti-HM1.24 antibody was affinity-purified using the high-speed antibody purification system ConSep LC100 (manufactured by MILLIPORE) and Hyper D Protein A column (manufactured by Nippon Gaishi) using PBS(−) as an absorption buffer and 0.1 M sodium citrate buffer (pH 3) as an elution buffer, according to the attached instructions. The eluted fractions were adjusted to about pH 7.4 by immediately adding 1 M Tris-HCl (pH 8.0) and then using the centrifuging ultrafiltration concentrator Centriprep 10 (manufactured by MILLIPORE), concentration and substitution to PBS(−) were carried out and the product was filter-sterilized using a membrane filter MILLEX-GV (manufactured by MILLIPORE) with a pore size of 0.22 μm to obtain the purified natural humanized anti-HM1.24 antibody. Concentration of purified antibody was measured by absorbance at 280 nm and calculated as 1 μg/ml per 1.35 OD.

Example 3

Determination of Activity of the Natural Humanized Anti-HM1.24 Antibody

The natural humanized anti-HM1.24 antibody was evaluated for the following antigen binding activity, binding inhibition activity, and ADCC activity.

(1) The Method of Measurement of Antigen Binding Activity and Binding Inhibition Activity (1)-1. Measurement of Antigen Binding Activity Antigen binding activity was measured by Cell-ELISA using WICH cells. Cell-ELISA plates were prepared as described in the above Reference Example 7.1-2.

After blocking, 100 μl of serial dilutions of the natural humanized anti-HM1.24 antibody that was obtained from a concentrate of a culture supernatant of COS-7 cells was added to each well. After it was incubated for 2 hours at room temperature and washed, peroxidase-labeled rabbit anti-human IgG antibody (manufactured by DAKO) was added. After incubating for 2 hours at room temperature and washing, a substrate solution was added and incubated. Then the reaction was stopped by adding 50 μl of 6N sulfuric acid, and absorbance at 490 nm was measured using the MICROPLATE READER Model 3550 (manufactured by Bio-Rad).

(1)-2. Measurement of Binding Inhibition Activity

The binding inhibition activity by the biotin-labeled mouse anti-HM1.24 antibody was measured by the Cell-ELISA using WISH cells. Cell-ELISA plates were prepared as described above. After blocking, 50 μl of serial dilutions of the natural humanized anti-HM1.24 antibody that was obtained from the concentrate of the culture supernatant of COS-7 cells was added to each well, and 50 μl of 2 μg/ml biotin-labeled mouse anti-HM1.24 antibody was added simultaneously. After incubating at room temperature for two hours and washing, peroxidase-labeled streptoavidin (manufactured by DAKO) was added. After incubating at room temperature for one hour and washing, the reaction was stopped by adding 50 μl of 6N sulfuric acid, and absorbance at 490 nm was measured using the MICROPLATE READER Model 3550 (manufactured by Bio-Rad).

(2) Antigen Binding Activity and Binding Inhibition Activity

Figure 29:
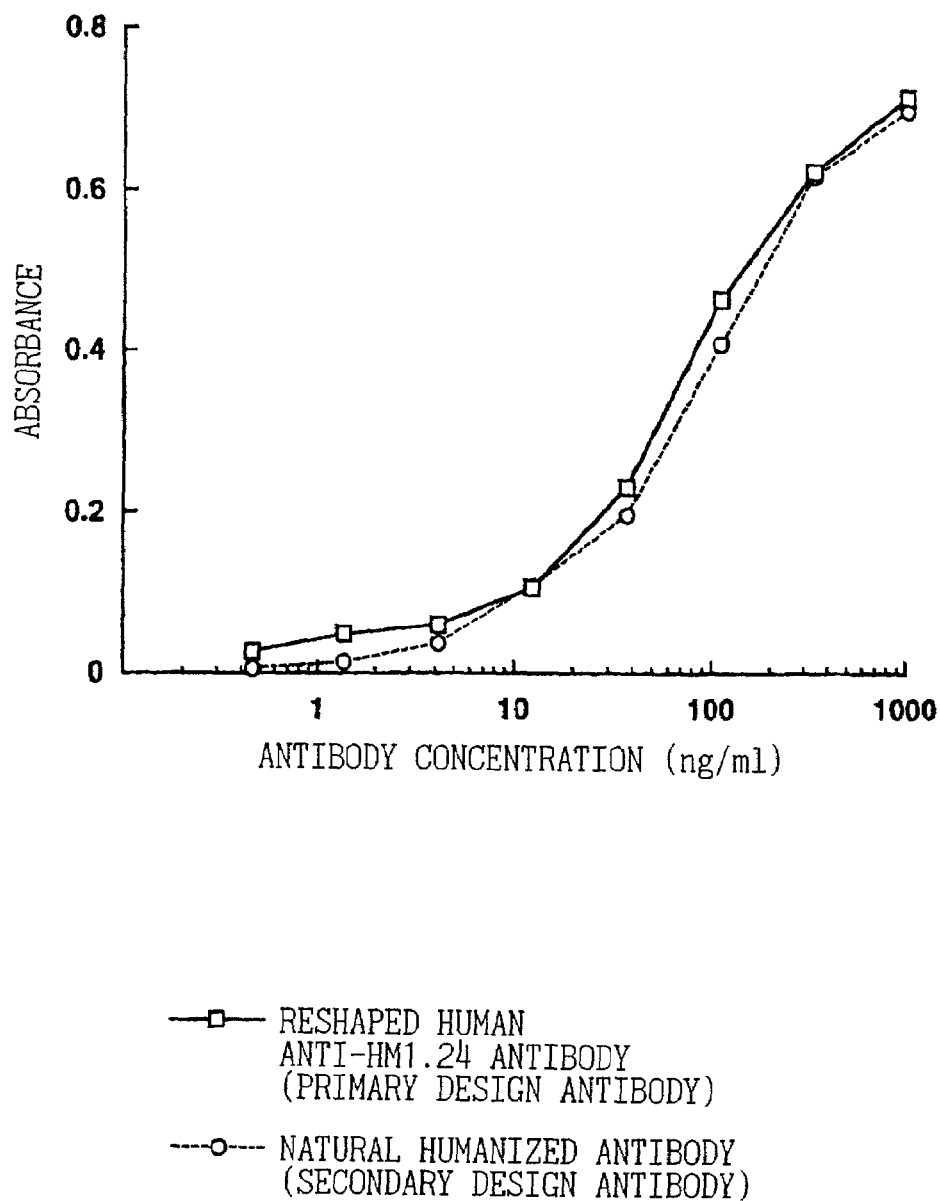
FIG. 29 is a graph showing that natural humanized anti-HM1.24 antibody (the secondary design antibody) has an antigen binding activity of a similar degree to that of reshaped human anti-HM1.24 antibody (the primary design antibody).
Figure 30:
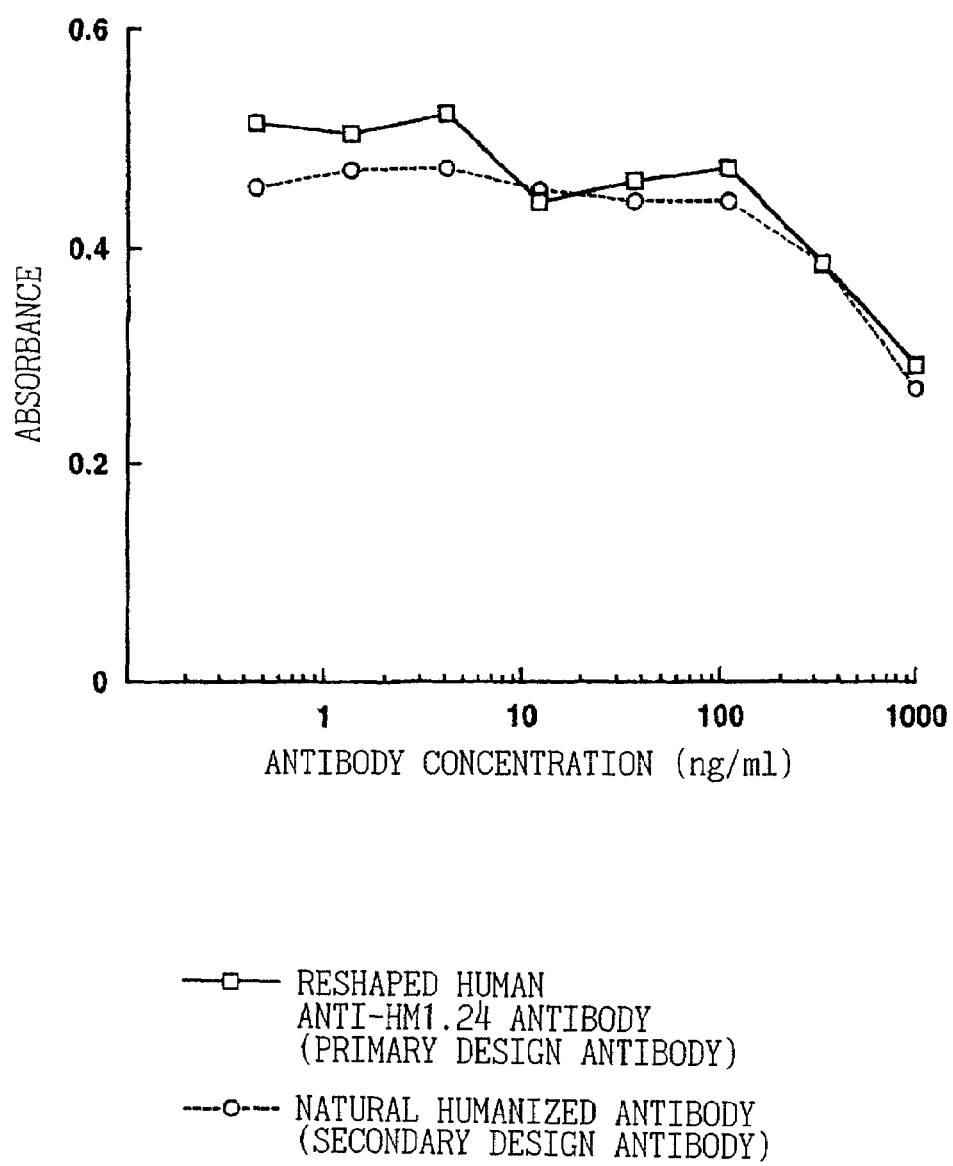
FIG. 30 is a graph showing that natural humanized anti-HM1.24 antibody (the secondary design antibody) has a binding inhibition activity of a similar degree to that of reshaped human anti-HM1.24 antibody (the primary design antibody).

The evaluation of the H chain of natural humanized anti-HM1.24 antibody was conducted by measurement of the above-mentioned antigen binding activity and binding inhibition activity in combination with the L chain version a. The result, as shown in FIGS. 29 and 30, indicated that natural humanized anti-HM1.24 antibody (the secondary design antibody) has antigen binding activity and binding inhibition activity of a similar degree to the primary design antibody (reshaped human anti-HM1.24 antibody: the H chain version r).

(3) Measurement of the ADCC Activity

ADCC (Antibody-dependent Cellular Cytotoxicity) activity was measured according to the method described in Reference Example 8.

1. Preparation of Effector Cells

To the peripheral blood of healthy human subject was added an equal amount of PBS(−), onto which Ficoll-Paque (manufactured by Pharmacia) was layered, and was centrifuged at 500 g for 30 minutes. The monocyte layer was taken therefrom and was washed twice with RPMI 1640 (manufactured by GIBCO BRL) supplemented with 10% bovine fetal serum (manufactured by GIBCO BRL), and was adjusted to a cell density of $5 \times 10^6$/ml with the same culture liquid.

2. Preparation of Target Cells

The human myeloma cell line KPMM2 (Deposit No. P-14170, Patent application No. 6-58082) was radiolabeled by incubating in RPMI 1640 (manufactured by GIBCO BRL) supplemented with 10% bovine fetal serum (manufactured by GIBCO BRL) together with 0.1 mCi of $^{51}$Cr-sodium chromate at 37° C. for 60 minutes. After radiolabeling, cells were washed three times with the same buffer and adjusted to a concentration of $2 \times 10^5$/ml.

3. Measurement of ADCC Assay

Into a 96-well U-bottomed plate (manufactured by Corning) were added 50 µl of $2 \times 10^5$ target cells/ml, 50 µl of the antibody solution previously prepared at 4 µg/ml, 0.4 µg/ml, 0.04 µg/ml, and 0.004 µg/ml, and reacted at 4° C. for 15 minutes. A solution that does not contain natural humanized anti-HM1.24 antibody (the secondary design antibody) was similarly prepared and used as a control.

Then, 100 µl of $5 \times 10^5$ effector cells/ml was added thereto, and cultured in a $CO_2$-incubator for 4 hours, wherein the ratio (E:T) of the effector cells (E) to the target cells (T) was set at 0:1, 20:1, and 50:1. Since the final concentration of each antibody was diluted by four-fold, they were 1 µg/ml, 0.1 µg/ml, 0.01 µg/ml, and 0.001 µg/ml as well as no antibody addition control.

One hundred µl of the supernatant was taken and the radioactivity released into the culture supernatant was measured by a gamma counter (ARC361, manufactured by Aloka). For measurement of the maximum radioactivity, 1% NP-40 (manufactured by Nacalai Tesque Inc.) was used. Cytotoxicity (%) was calculated by $(A-C)/(B-C) \times 100$, wherein A is radioactivity (cpm) released in the presence of antibody, B is radioactivity (cpm) released by NP-40, and C is radioactivity (cpm) released by the culture medium alone without antibody.

4. Result

Figure 33:
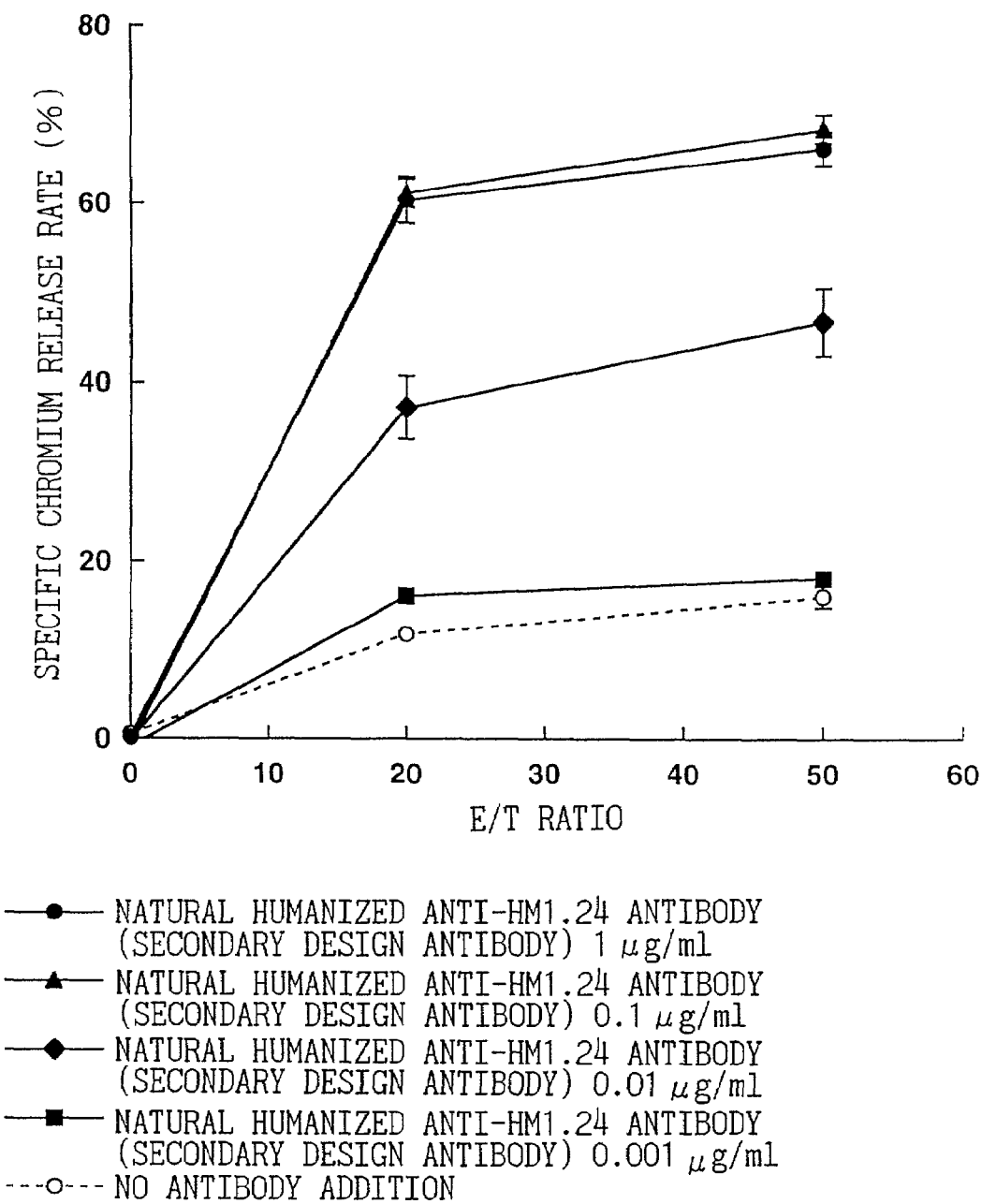
FIG. 33 is a graph showing that natural humanized anti-HM1.24 antibody (the secondary design antibody) has an increased cytotoxic activity to the KPMM2 cells with increasing E/T ratios.

As shown in FIG. 33, when the natural humanized anti-HM1.24 antibody (the secondary design antibody) was added, specific chromium release rate increased with the increase in the E:T ratio depending on antibody concentration as compared to the no antibody added control. This, therefore, indicated that this natural humanized anti-HM1.24 antibody (the secondary design antibody) has ADCC activity.

The present invention relates to a method of preparing natural humanized antibody and the natural humanized antibody obtained by said method of preparation. This is a highly excellent humanization technology that has solved the problems associated with CDR-grafting (Jones, P. T. et al., Nature (1986) 321, 522–525) created by G. Winter.

Construction of the primary design antibody may be considered as an intermediate stage for the construction of humanized antibody comprising natural human FRs. When antibody is developed as a pharmaceutical product comprising recombinant protein, natural humanized antibody that comprises naturally occurring human FRs is more excellent in terms of antigenicity and safety.

Effects of the Invention

Since the natural humanized antibody obtained by the method of preparation of the present invention does not contain the amino acid residues of non-naturally occurring artificial FRs that are contained in the humanized antibody produced by the conventional humanizzation technology, it is expected to have low antigenicity. Furthermore, it was shown that the natural humanized antibody obtained by the method of preparation of the present invention has an activity similar to that of antibody derived from a non-human mammal that was used as a template for humanization. Therefore, the natural humanized antibody obtained by the method of preparation of the present invention is useful for therapeutic administration to humans.

Reference to the microorganisms deposited under the Patent Cooperation Treaty, Rule 13-2, and the name of the Depository Institute Depository Institute Name: the National Institute of Bioscience and Human Technology, Agency of Industrial Science and Technology Address: 1-3, Higashi 1-chome, Tsukuba-shi, Ibaraki, Japan Organism (1)

Indication: *Escherichia coli* DH5α (pRS38-pUC19)

Accession number: FERM BP-4434

Deposition Date: Oct. 5, 1993

Organism (2)

Indication: Hybridoma HM1.24

Accession number: FERM BP-5233

Deposition Date: Sep. 14, 1995

Organism (3)

Indication: *Escherichia coli* DH5α (pUC19-RVHr-AHM-gγ1)

Accession number: FERM BP-5643

Deposition Date: Aug. 29, 1996

Organism (4)

Indication: *Escherichia coli* DH5α (pUC19-1.24H-gγ1)

Accession number: FERM BP-5644

Deposition Date: Aug. 29, 1996

Organism (5)

Indication: *Escherichia coli* DH5α (pUC19-RVLa-AHM-gκ)

Accession number: FERM BP-5645

Deposition Date: Aug. 29, 1996

Organism (6)

Indication: *Escherichia coli* DH5α (pUC19-RVHs-AHM-gγ1)

Accession number: FERM BP-6127

Deposition Date: Sep. 29, 1997

What is claimed is:

1. A method for preparing a humanized antibody, wherein a framework region ("FR") in the humanized antibody is a FR naturally occurring in human antibodies, comprising the steps of:
   (1) obtaining a humanized antibody, wherein the humanized antibody has:
      i) six complementary determining regions ("CDRs") of a first animal species; and
      ii) eight FRs of a second animal species, wherein one or more amino acid residues in one or more of the FRs have been substituted to retain antigen binding ability, with corresponding amino acid residues in FRs of the first animal species, and wherein said second animal species is human;
   (2) conducting a homology search using a database of amino acid sequence of FRs naturally occurring in human antibodies ("natural FRs") in comparison with the amino acid sequence of the humanized antibody obtained in step (1), wherein the homology search is conducted over all 8FRs;
   (3) preparing a list of amino acid sequences of the natural FRs having the same as or at least 80% homology with the amino acid sequence of the FR, of the humanized antibody obtained in step (1),
   (4) selecting, from the list of step (3), a natural FR which has
      i) at corresponding positions the same amino acid residues as the amino acid residues introduced by the substitution in step (1); and
      ii) comprises an amino acid sequence that is the same as or has at least 80% homology with the FR sequence of the humanized antibody obtained in step (1);
   (5) if the amino acid sequence of the FR, in which amino acid residues have been substituted in step (1), of the humanized antibody obtained in step (1) has one or more amino acid residues that are different from amino acid residues at corresponding positions of the natural FR selected in step (4), replace said different amino acid residues in the FR sequence of the humanized antibody obtained in step (1) with corresponding amino acid residues in the natural FR;
   (6) constructing an expression vector expressing an amino acid sequence of the antibody obtained via steps (1) to (5);
   (7) culturing cells comprising an expression vector constructed in step (6); and
   (8) recovering from the culture the humanized antibody comprising the natural FR and 6 CDRs from the first animal species and wherein the recovered humanized antibody binds the same antigen that the antibody from the first animal species binds.

2. The method according to claim 1, wherein the first animal species is a non-human mammal.

3. The method according to claim 2, wherein the non-human mammal is selected from a mouse, rat, hamster, rabbit and monkey.

4. The method according to claim 1, wherein all natural FRs belong to the same subgroup.

5. The method according to claim 1, wherein the number of the substituted amino acid residues of the FR in step (1) is from one to ten.

6. The method according to claim 1, wherein the number of the different amino acid residues in the FR in step (5) is from one to ten.

7. The method according to claim 1, wherein the substituted amino acid residues in the FR in step (1) comprise an amino acid residue selected from amino acid residues responsible for canonical structure of the antibody, amino acid residues involved in the maintenance of the structure of CDRs, and the amino acid residues that directly interact with an antigen.

8. The method according to claim 5, wherein the substituted amino acid residues in the FR in step (1) comprise an amino acid residue selected from an amino acid residue at position 71 of the heavy chain or at position 94 of the heavy chain.

* * * * *